(12) United States Patent
Zhang et al.

(10) Patent No.: US 12,410,196 B2
(45) Date of Patent: Sep. 9, 2025

(54) BENZOPYRIMIDINE COMPOUNDS AND USE THEREOF

(71) Applicant: USYNOVA PHARMACEUTICALS LTD., Shanghai (CN)

(72) Inventors: Yang Zhang, Shanghai (CN); Wentao Wu, Shanghai (CN); Kaijun Geng, Shanghai (CN); Jikui Sun, Shanghai (CN); Yangyang Xu, Shanghai (CN); Jian Li, Shanghai (CN); Shuhui Chen, Shanghai (CN)

(*) Notice: Subject to any disclaimer, the term of this patent is extended or adjusted under 35 U.S.C. 154(b) by 0 days.

(21) Appl. No.: 18/768,367

(22) Filed: Jul. 10, 2024

(65) Prior Publication Data

US 2024/0383924 A1 Nov. 21, 2024

Related U.S. Application Data

(63) Continuation of application No. PCT/CN2023/073182, filed on Jan. 19, 2023.

(30) Foreign Application Priority Data

| Jan. 21, 2022 | (CN) | 202210072243 |
| Jan. 29, 2022 | (CN) | 202210113080 |
| Feb. 9, 2022 | (WO) | PCT/CN2022/075732 |
| Mar. 11, 2022 | (CN) | 202210239568 |
| Jun. 17, 2022 | (CN) | 202210693538 |
| Jul. 15, 2022 | (CN) | 202210837790 |
| Aug. 17, 2022 | (CN) | 202210989455 |

(51) Int. Cl.
- C07D 519/00 (2006.01)
- A61K 31/517 (2006.01)
- A61P 35/00 (2006.01)

(52) U.S. Cl.
CPC .......... C07D 519/00 (2013.01); A61K 31/517 (2013.01); A61P 35/00 (2018.01)

(58) Field of Classification Search
CPC ...... C07D 519/00; A61K 31/517; A61P 35/00
See application file for complete search history.

(56) References Cited

U.S. PATENT DOCUMENTS

2024/0174692 A1* 5/2024 Zhang .................. C07D 519/00

FOREIGN PATENT DOCUMENTS

| CN | 112442030 A | 3/2021 | |
| CN | 115385938 A | 11/2022 | |
| WO | WO-2017172979 A1 * | 10/2017 | .......... A61K 31/517 |
| WO | 2021041671 A1 | 3/2021 | |
| WO | 2021106231 A1 | 6/2021 | |
| WO | 2021107160 A1 | 6/2021 | |
| WO | 2022002102 A1 | 1/2022 | |
| WO | 2022015375 A1 | 1/2022 | |
| WO | 2022031678 A1 | 2/2022 | |
| WO | 2022061251 A1 | 3/2022 | |
| WO | 2022066646 A1 | 3/2022 | |
| WO | 2022068921 A1 | 4/2022 | |
| WO | 2022098625 A1 | 5/2022 | |
| WO | 2022105859 A1 | 5/2022 | |
| WO | 2022148422 A1 | 7/2022 | |
| WO | 2022173033 A1 | 8/2022 | |
| WO | 2022177917 A2 | 8/2022 | |
| WO | WO-2022171147 A1 * | 8/2022 | .......... A61K 31/517 |
| WO | 2022187528 A1 | 9/2022 | |
| WO | 2022192794 A1 | 9/2022 | |
| WO | 2022193871 A1 | 9/2022 | |
| WO | 2022221739 A1 | 10/2022 | |
| WO | 2022228568 A1 | 11/2022 | |
| WO | 2022247760 A1 | 12/2022 | |

OTHER PUBLICATIONS

International Search Report and Written Opinion for International Application No. PCT/CN2023/073182, mailed Apr. 13, 2023, 11 Pages.

* cited by examiner

*Primary Examiner* — Joseph K Mckane
*Assistant Examiner* — Meghan C Heasley

(57) ABSTRACT

Disclosed are a series of benzopyrimidine compounds and a use thereof, and specifically disclosed are compounds represented by formula (II) and pharmaceutically acceptable salts thereof.

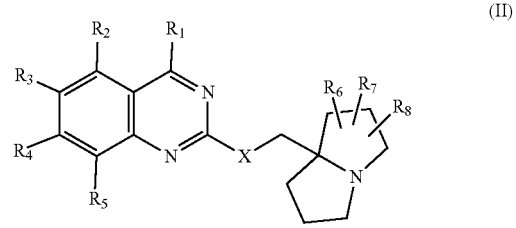

(II)

14 Claims, No Drawings

BENZOPYRIMIDINE COMPOUNDS AND USE THEREOF

CROSS-REFERENCE TO RELATED APPLICATION

This application is a continuation of International Application No. PCT/CN2023/073182 filed on Jan. 19, 2023; which claims the benefit of Chinese Application No. CN202210072243.0 filed on Jan. 21, 2022; Chinese Application No. CN202210113080.6 filed on Jan. 29, 2022; International Application No. PCT/CN2022/075732 filed on Feb. 9, 2022; Chinese Application No. CN202210239568.3 filed on Mar. 11, 2022; Chinese Application No. CN202210693538.X filed on Jun. 17, 2022; Chinese Application No. CN202210837790.3 filed on Jul. 15, 2022; and Chinese Application No. CN202210989455.5 filed on Aug. 17, 2022. Each of the above-listed applications is incorporated by reference herein in its entirety.

FIELD OF THE INVENTION

The present disclosure relates to a series of benzopyrimidine compounds and use thereof, in particular to a compound represented by formula (II) and a pharmaceutically acceptable salt thereof.

BACKGROUND OF THE INVENTION

RAS oncogene mutations are the most common activating mutations in human cancers, and RAS mutations are present in about 30% of human tumors. The RAS gene family includes three subtypes (KRAS, HRAS, and NRAS), of which 85% of RAS-driven cancers are caused by mutations in the KRAS subtype.

KRAS is a rat sarcoma viral oncogene and an important member of the RAS protein. KRAS is like a molecular switch, once it is turned on, it will activate a variety of division and proliferation factors, such as c-RAF, PI3K and so on. Under normal circumstances, KRAS binds to GTP, and cuts off one phosphate group at the end of GTP to turn GTP into GDP. After GTP is turned into GDP, KRAS is closed. Under normal circumstances, KRAS can regulate the path of cell growth; after KRAS gene mutation, KRAS protein continues to remain activated, and can independently transmit growth and proliferation signals to downstream pathways independent of upstream growth factor receptor signals, resulting in uncontrolled cell growth and tumor progression.

KRAS mutations are commonly found in solid tumors such as lung adenocarcinoma, pancreatic ductal carcinoma, and colorectal cancer, etc. In KRAS-mutated tumors, 80% of oncogenic mutations occur at codon 12, with the most common mutations including: p. G12D (41%), p. G12V (28%), and p.G12C (14%). At the same time, whether the KRAS gene has mutation or not is also an important indicator of tumor prognosis.

At present, small molecules that directly target KRAS mutations are mainly focused in the field of $KRAS^{G12C}$, including Amgen's AMG510 and Mirati Therapeutics' MRTX849. Clinical results show that these two compounds have shown good therapeutic effects on patients with $KRAS^{G12C}$-mutated tumor. Among drugs targeting $KRAS^{G12D}$, only HRS-4642 from Jiangsu Hengrui Pharmaceutical Co., Ltd. has entered a clinical stage and is an injection. Currently, no orally administered $KRAS^{G12D}$ small molecule has entered a clinical research stage, and there is a huge unmet clinical need for inhibitors of $KRAS^{G12D}$ mutations.

SUMMARY OF THE INVENTION

The present disclosure provides a compound represented by formula (II) and a pharmaceutically acceptable salt thereof,

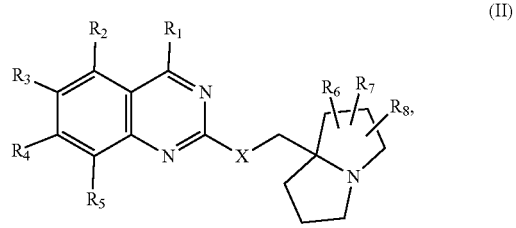

wherein
X is selected from O and S;
$R_1$ is selected from

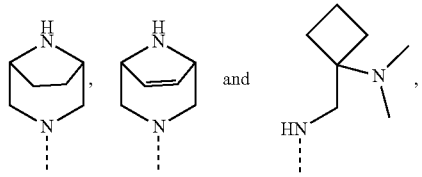

wherein the

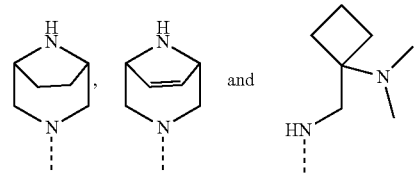

are optionally substituted with 1, 2 or 3 $R_a$;

$R_2$ is selected from H, halogen, $C_{1-3}$ alkoxy and $C_{3-4}$ cycloalkyl-O—, wherein the $C_{1-3}$ alkoxy and $C_{3-4}$ cycloalkyl-O— are optionally substituted with 1, 2, 3, 4 or 5 halogens;

$R_3$ is selected from H, halogen and $C_{1-3}$ alkyl, wherein the $C_{1-3}$ alkyl is optionally substituted with 1, 2 or 3 $R_b$;

$R_4$ is selected from phenyl and naphthyl, wherein the phenyl and naphthyl are each independently optionally substituted with 1, 2, 3, 4 or 5 $R_c$;

$R_5$ is selected from H, halogen and $C_{1-3}$ alkyl, wherein the $C_{1-3}$ alkyl is optionally substituted with 1, 2, or 3 halogens;

$R_6$, $R_7$ and $R_8$ are each independently selected from H, halogen, CN, $C_{1-3}$ alkyl, $C_{1-3}$ alkoxy, $C_{1-3}$ alkylamino, $C_{2-3}$ alkenyl and phenyl, wherein the $C_{1-3}$ alkyl, $C_{1-3}$ alkoxy, $C_{1-3}$ alkylamino, $C_{2-3}$ alkenyl and phenyl are optionally substituted with 1, 2, or 3 halogens;

alternatively, $R_6$ and $R_7$ are taken together with atoms to which they are attached to form phenyl,

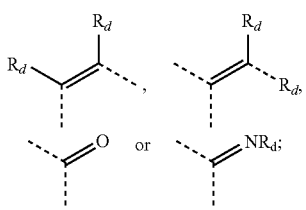

each $R_a$ is independently selected from H, halogen, OH, $NH_2$, $C_{1-3}$ alkyl and $C_{1-3}$ alkoxy, wherein the $C_{1-3}$ alkyl and $C_{1-3}$ alkoxy are optionally substituted with 1, 2, 3, 4 or 5 halogens;

each $R_b$ is independently selected from H, halogen and OH;

each $R_c$ is independently selected from H, halogen, OH, $NH_2$, CN and $C_{2-3}$ alkynyl;

$R_a$ is absent, or each $R_d$ is independently selected from H, halogen, OH, CN, $C_{1-3}$ alkyl and $C_{1-3}$ alkylamino, wherein the $C_{1-3}$ alkyl and $C_{1-3}$ alkylamino are optionally substituted with 1, 2, or 3 halogens;

when $R_1$ is selected from

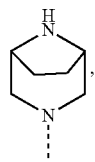

X is selected from S, alternatively, $R_4$ is selected from naphthyl, wherein the naphthyl is substituted with 5 $R_c$.

In some embodiments of the present disclosure, provided herein is a compound or a pharmaceutically acceptable salt thereof, wherein the compound is selected from (P-1)

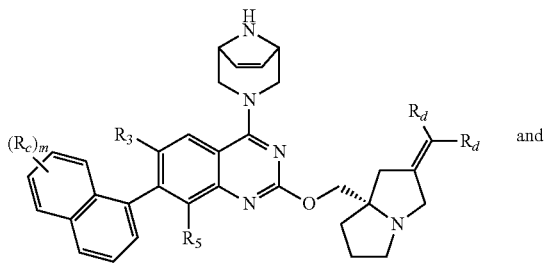

and (P-2)

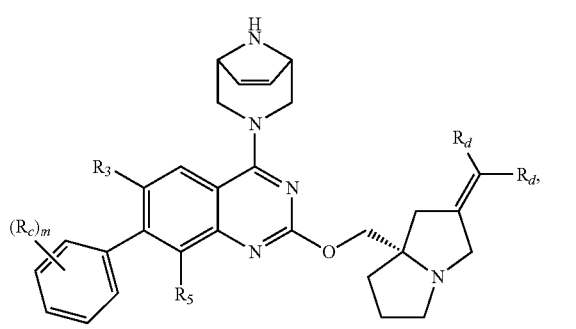

wherein $R_3$, $R_5$ and $R_c$ are as defined herein;
m is selected from 0, 1, 2, 3, 4 and 5.

In some embodiments of the present disclosure, provided herein is a compound, wherein the compound is selected from (P-3)

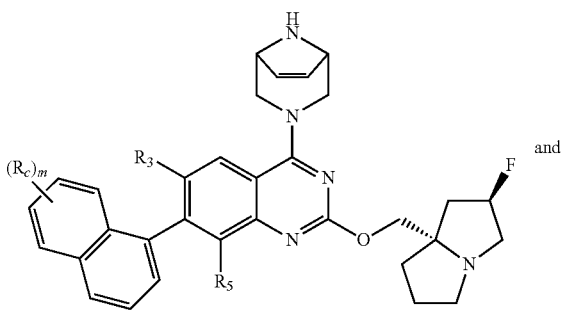

and (P-4)

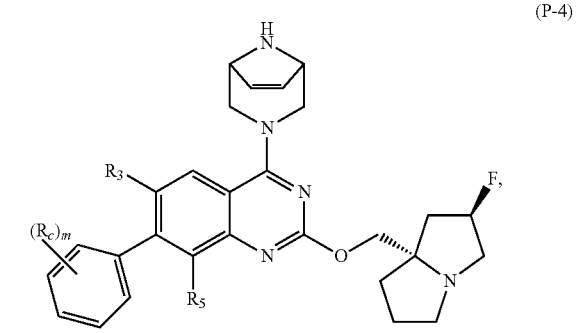

wherein $R_3$, $R_5$ and $R_c$ are as defined herein;
m is selected from 0, 1, 2, 3, 4 and 5.

In some embodiments of the present disclosure, provided herein is a compound or a pharmaceutically acceptable salt thereof, wherein the compound is selected from (P-3-1)

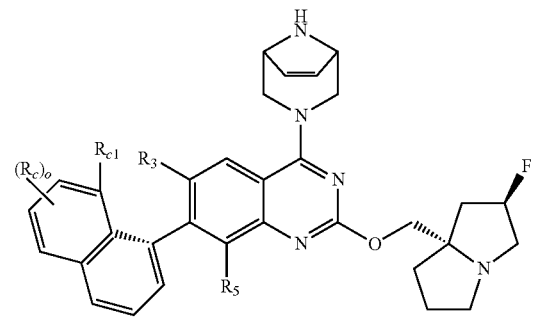

-continued (P-3-2)

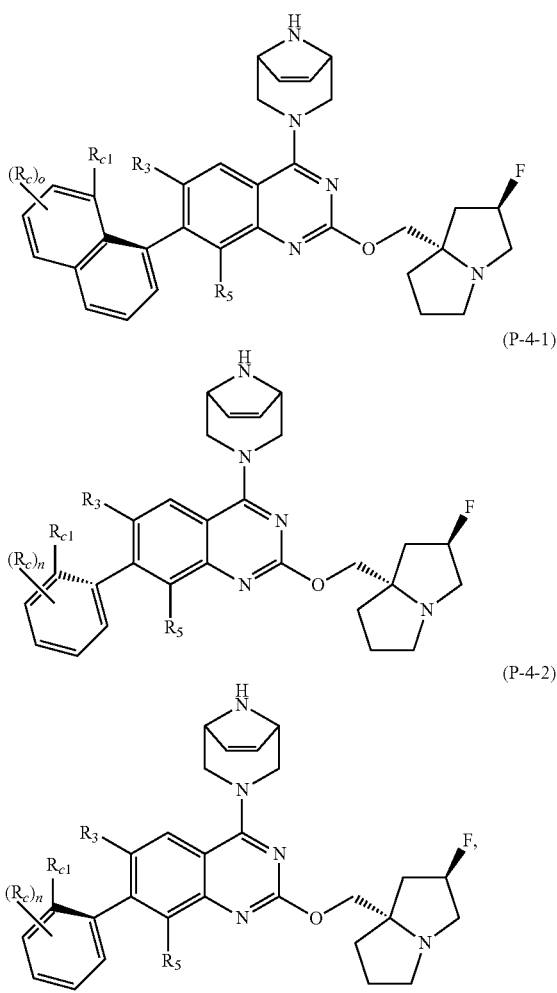

(P-4-1)

(P-4-2)

wherein
R$_3$ is selected from halogen and C$_{1-3}$ alkyl, wherein the C$_{1-3}$ alkyl is optionally substituted with 1, 2 or 3 R$_b$;
R$_5$ is selected from halogen and C$_{1-3}$ alkyl, wherein the C$_{1-3}$ alkyl is optionally substituted with 1, 2, or 3 halogens;
each R$_b$ is independently selected from H, halogen and OH;
each R$_c$ is independently selected from H, halogen, OH, NH$_2$, CN and C$_{2-3}$ alkynyl;
R$_{c1}$ is selected from halogen, OH, NH$_2$, CN and C$_{2-3}$ alkynyl;
o is selected from 0, 1, 2, 3, 4 and 5;
n is selected from 0, 1, 2, 3 and 4.

In some embodiments of the present disclosure, the R$_2$ is selected from H, OCH$_3$, OCH$_2$CH$_3$, OCH(CH$_3$)$_2$,

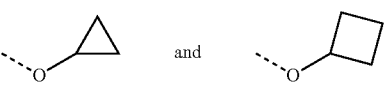

wherein the OCH$_3$, OCH$_2$CH$_3$, OCH(CH$_3$)$_2$, are optionally substituted with 1, 2, 3, 4 or 5 halogens, and other variables are as defined herein.

In some embodiments of the present disclosure, the R$_2$ is selected from H, F and OCH$_3$, and other variables are as defined herein.

In some embodiments of the present disclosure, the R$_3$ is selected from H, F, Cl and CH$_2$OH, and other variables are as defined herein.

In some embodiments of the present disclosure, the each R$_c$ is independently selected from H, F, OH, NH$_2$ and —C≡CH, and other variables are as defined herein.

In some embodiments of the present disclosure, the R$_4$ is selected from

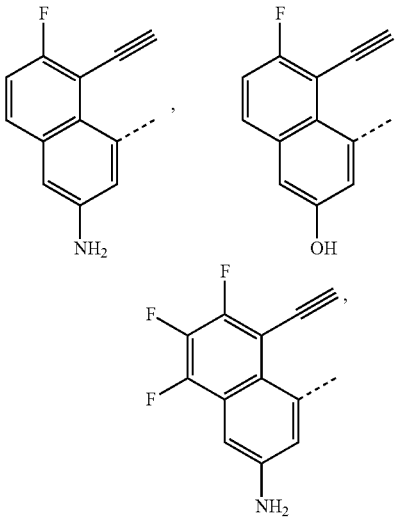

and other variables are as defined herein.

In some embodiments of the present disclosure, the R$_5$ is selected from H, F, Cl, Br, CH$_3$, CH$_2$CH$_3$ and CH(CH$_3$)$_2$, wherein the CH$_3$, CH$_2$CH$_3$ and CH(CH$_3$)$_2$ are optionally substituted with 1, 2, or 3 halogens, and other variables are as defined herein.

In some embodiments of the present disclosure, the R$_5$ is selected from F, CH$_2$F and CHF$_2$, and other variables are as defined herein.

In some embodiments of the present disclosure, the R$_6$, R$_7$ and R$_8$ are each independently selected from H, F, Cl, Br, I, CN, CH$_3$, CH$_2$CH$_3$, CH(CH$_3$)$_2$, OCH$_3$, OCH$_2$CH$_3$, OCH(CH$_3$)$_2$, NHCH$_3$, NHCH$_2$CH$_3$, N(CH$_3$)$_2$, CH═CH$_2$, CH$_2$CH═CH$_2$, CH═CH$_2$CH$_3$ and phenyl, wherein the CH$_3$, CH$_2$CH$_3$, CH(CH$_3$)$_2$, OCH$_3$, OCH$_2$CH$_3$, OCH(CH$_3$)$_2$, NHCH$_3$, NHCH$_2$CH$_3$, N(CH$_3$)$_2$, CH═CH$_2$, CH$_2$CH═CH$_2$, CH═CH$_2$CH$_3$ and phenyl are optionally substituted with 1, 2, or 3 halogens, and other variables are as defined herein.

In some embodiments of the present disclosure, the R$_6$, R$_7$ and R$_8$ are each independently selected from H, F, Cl, Br, I, CN, CH$_3$, CH$_2$F, CHF$_2$, CF$_3$, CH$_2$CH$_3$, CH$_2$CF$_3$, CF$_2$CF$_3$, OCH$_3$, OCH$_2$F, OCHF$_2$, OCF$_3$, OCH$_2$CH$_3$, OCH$_2$CF$_3$, OCF$_2$CF$_3$, NHCH$_3$, N(CH$_3$)$_2$, CH═CH$_2$, CF═CH$_2$, CH═CHF, CH═CF$_2$ and phenyl, and other variables are as defined herein.

In some embodiments of the present disclosure, the $R_6$ is selected from H, F, Cl, Br, I, CN, $CH_3$, $CH_2F$, $CHF_2$, $CF_3$, $CH_2CH_3$, $CH_2CF_3$, $CF_2CF_3$, $OCH_3$, $OCH_2F$, $OCHF_2$, $OCF_3$, $OCH_2CH_3$, $OCH_2CF_3$, $OCF_2CF_3$, $NHCH_3$, $N(CH_3)_2$, $CH=CH_2$, $CF=CH_2$, $CH=CHF$, $CH=CF_2$ and phenyl, and other variables are as defined herein.

In some embodiments of the present disclosure, the $R_7$ is selected from H, F, Cl, Br, I, CN, $CH_3$, $CH_2F$, $CHF_2$, $CF_3$, $CH_2CH_3$, $CH_2CF_3$, $CF_2CF_3$, $OCH_3$, $OCH_2F$, $OCHF_2$, $OCF_3$, $OCH_2CH_3$, $OCH_2CF_3$, $OCF_2CF_3$, $NHCH_3$, $N(CH_3)_2$, $CH=CH_2$, $CF=CH_2$, $CH=CHF$, $CH=CF_2$ and phenyl, and other variables are as defined herein.

In some embodiments of the present disclosure, the $R_8$ is selected from H, F, Cl, Br, I, CN, $CH_3$, $CH_2F$, $CHF_2$, $CF_3$, $CH_2CH_3$, $CH_2CF_3$, $CF_2CF_3$, $OCH_3$, $OCH_2F$, $OCHF_2$, $OCF_3$, $OCH_2CH_3$, $OCH_2CF_3$, $OCF_2CF_3$, $NHCH_3$, $N(CH_3)_2$, $CH=CH_2$, $CF=CH_2$, $CH=CHF$, $CH=CF_2$ and phenyl, and other variables are as defined herein.

In some embodiments of the present disclosure, the $R_6$ is selected from H, and other variables are as defined herein.

In some embodiments of the present disclosure, the $R_7$ is selected from H, F, CN, $OCH_3$, $OCHF_2$, $OCF_3$, $CH=CHF$ and phenyl, and other variables are as defined herein.

In some embodiments of the present disclosure, the $R_7$ is selected from H, and other variables are as defined herein.

In some embodiments of the present disclosure, the each $R_a$ is independently selected from H, F, Cl, Br, I, OH, CN, $CH_3$, $CH_2CH_3$, $CH(CH_3)_2$, $NHCH_3$, $NHCH_2CH_3$ and $N(CH_3)_2$, wherein the $CH_3$, $CH_2CH_3$, $CH(CH_3)_2$, $NHCH_3$, $NHCH_2CH_3$ and $N(CH_3)_2$ are optionally substituted with 1, 2, or 3 halogens, and other variables are as defined herein.

In some embodiments of the present disclosure, the each $R_a$ is independently selected from H, F, OH, CN, and $CH_3$, and other variables are as defined herein.

In some embodiments of the present disclosure, the $R_6$ and $R_7$ are taken together with atoms to which they are attached to form phenyl,

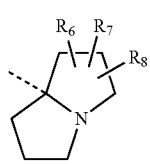

and other variables are as defined herein.

In some embodiments of the present disclosure, the $R_8$ is selected from H, F, CN, $OCH_3$, $OCHF_2$, $OCF_3$, $CH=CHF$ and phenyl, and other variables are as defined herein.

In some embodiments of the present disclosure, the structural moiety is selected from

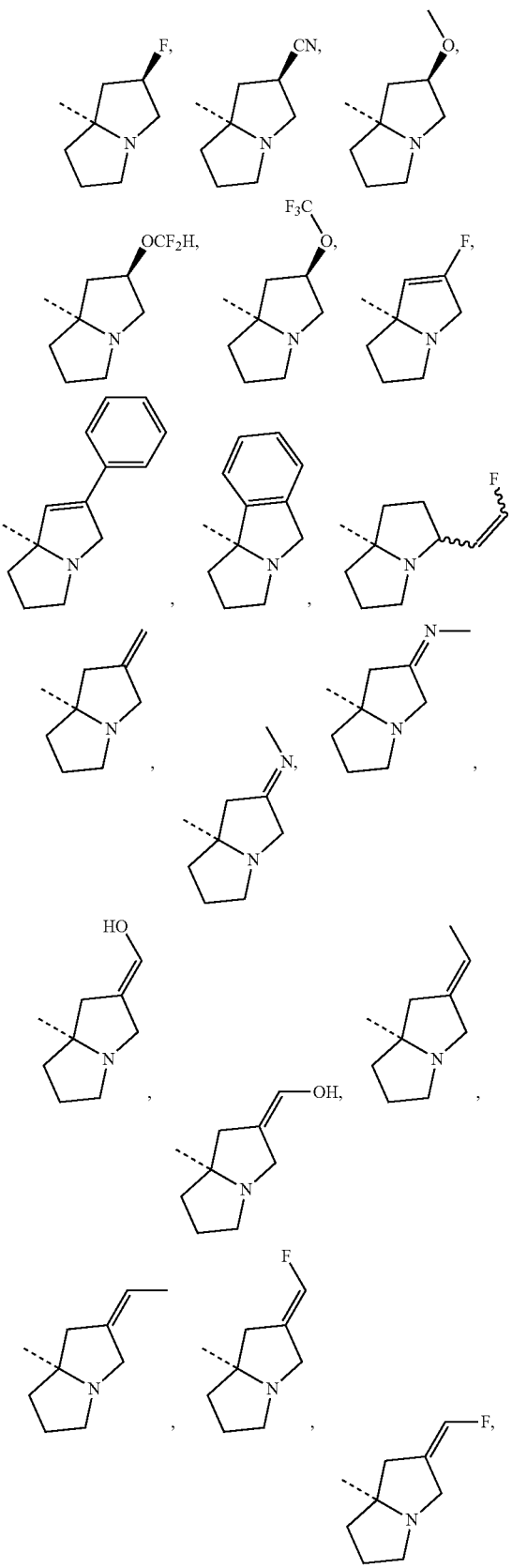

-continued

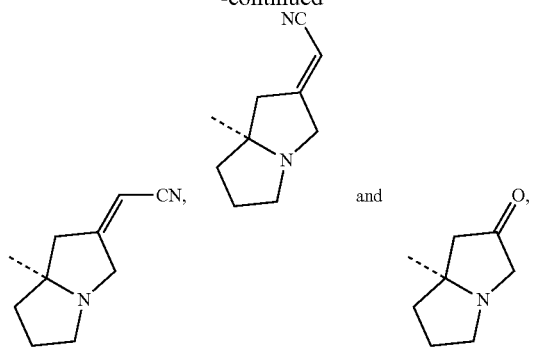

and other variables are as defined herein.

The present disclosure also provides a compound represented by formula (II) and a pharmaceutically acceptable salt thereof

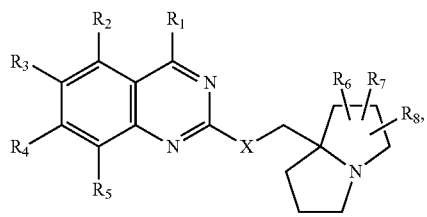
(II)

wherein
X is selected from O and S;
R₁ is selected from

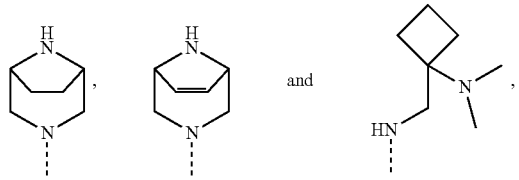

wherein the

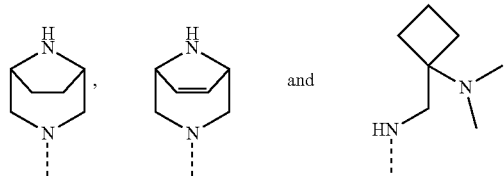

are optionally substituted with 1, 2 or 3 $R_a$;

$R_2$ is selected from H, halogen, $C_{1-3}$ alkoxy and $C_{3-4}$ cycloalkyl-O—, wherein the $C_{1-3}$ alkoxy and $C_{3-4}$ cycloalkyl-O— are optionally substituted with 1, 2, 3, 4 or 5 halogens;

$R_3$ is selected from H, halogen and $C_{1-3}$ alkyl, wherein the $C_{1-3}$ alkyl is optionally substituted with 1, 2 or 3 $R_b$;

$R_4$ is selected from phenyl and naphthyl, wherein the phenyl and naphthyl are each independently optionally substituted with 1, 2, 3, 4 or 5 $R_c$;

$R_5$ is selected from H, halogen and $C_{1-3}$ alkyl, wherein the $C_{1-3}$ alkyl is optionally substituted with 1, 2, or 3 halogens;

$R_6$, $R_7$ and $R_8$ are each independently selected from H, halogen, CN, $C_{1-3}$ alkyl, $C_{1-3}$ alkoxy, $C_{1-3}$ alkylamino, $C_{2-3}$ alkenyl and phenyl, wherein the $C_{1-3}$ alkyl, $C_{1-3}$ alkoxy, $C_{1-3}$ alkylamino, $C_{2-3}$ alkenyl and phenyl are optionally substituted with 1, 2, or 3 halogens;

alternatively, $R_6$ and $R_7$ are taken together with atoms to which they are attached to form phenyl,

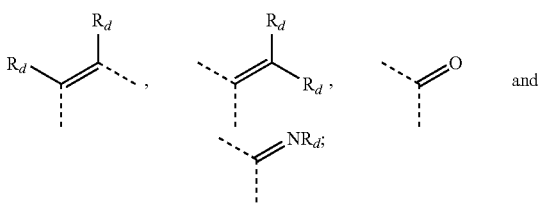

each $R_a$ is independently selected from H, halogen, OH, $NH_2$, $C_{1-3}$ alkyl and $C_{1-3}$ alkoxy, wherein the $C_{1-3}$ alkyl and $C_{1-3}$ alkoxy are optionally substituted with 1, 2, 3, 4 or 5 halogens;

each $R_b$ is independently selected from H, halogen and OH;

each $R_c$ is independently selected from H, halogen, OH, $NH_2$, CN and $C_{2-3}$ alkynyl;

$R_d$ is absent, or each $R_d$ is independently selected from H, halogen, $C_{1-3}$ alkyl and $C_{1-3}$ alkylamino, wherein the $C_{1-3}$ alkyl and $C_{1-3}$ alkylamino are optionally substituted with 1, 2, or 3 halogens;

when $R_1$ is selected from

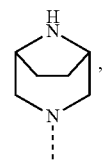

X is selected from S, alternatively, $R_4$ is selected from naphthyl, wherein the naphthyl is substituted with 5 $R_c$.

In some embodiments of the present disclosure, the $R_2$ is selected from H, $OCH_3$, $OCH_2CH_3$, $OCH(CH_3)_2$,

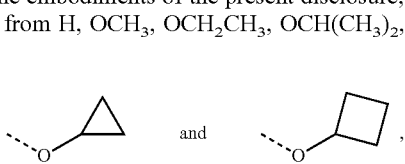

wherein the $OCH_3$, $OCH_2CH_3$, $OCH(CH_3)_2$,

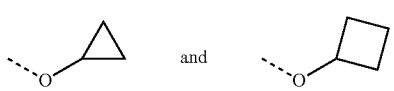

are optionally substituted with 1, 2, 3, 4 or 5 halogens, and other variables are as defined herein.

In some embodiments of the present disclosure, the $R_2$ is selected from H, F and $OCH_3$, and other variables are as defined herein.

In some embodiments of the present disclosure, the $R_3$ is selected from H, F, Cl and $CH_2OH$, and other variables are as defined herein.

In some embodiments of the present disclosure, the each $R_e$ is independently selected from H, F, OH, $NH_2$ and —C≡CH, and other variables are as defined herein.

In some embodiments of the present disclosure, the $R_4$ is selected from

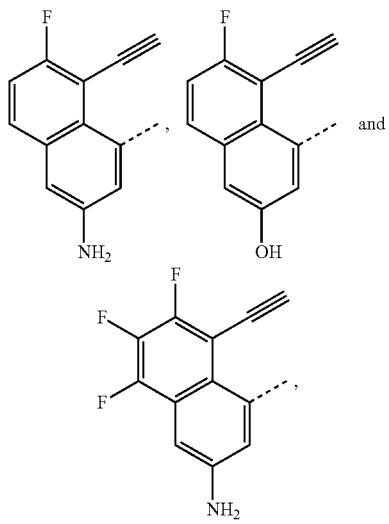

and other variables are as defined herein.

In some embodiments of the present disclosure, the $R_5$ is selected from H, F, Cl, Br, $CH_3$, $CH_2CH_3$ and $CH(CH_3)_2$, wherein the $CH_3$, $CH_2CH_3$ and $CH(CH_3)_2$ are optionally substituted with 1, 2, or 3 halogens, and other variables are as defined herein.

In some embodiments of the present disclosure, the $R_5$ is selected from F, $CH_2F$ and $CHF_2$, and other variables are as defined herein.

In some embodiments of the present disclosure, the $R_6$, $R_7$ and $R_5$ are each independently selected from H, F, Cl, Br, I, CN, $CH_3$, $CH_2CH_3$, $CH(CH_3)_2$, $OCH_3$, $OCH_2CH_3$, $OCH(CH_3)_2$, $NHCH_3$, $NHCH_2CH_3$, $N(CH_3)_2$, $CH=CH_2$, $CH_2CH=CH_2$, $CH=CH_2CH_3$ and phenyl, wherein the $CH_3$, $CH_2CH_3$, $CH(CH_3)_2$, $OCH_3$, $OCH_2CH_3$, $OCH(CH_3)_2$, $NHCH_3$, $NHCH_2CH_3$, $N(CH_3)_2$, $CH=CH_2$, $CH_2CH=CH_2$, $CH=CH_2CH_3$ and phenyl are optionally substituted with 1, 2, or 3 halogens, and other variables are as defined herein.

In some embodiments of the present disclosure, the $R_6$, $R_7$ and $R_5$ are each independently selected from H, F, Cl, Br, I, CN, $CH_3$, $CH_2F$, $CHF_2$, $CF_3$, $CH_2CH_3$, $CH_2CF_3$, $CF_2CF_3$, $OCH_3$, $OCH_2F$, $OCHF_2$, $OCF_3$, $OCH_2CH_3$, $OCH_2CF_3$, $OCF_2CF_3$, $NHCH_3$, $N(CH_3)_2$, $CH=CH_2$, $CF=CH_2$, $CH=CHF$, $CH=CF_2$ and phenyl, and other variables are as defined herein.

In some embodiments of the present disclosure, the $R_6$ is selected from H, and other variables are as defined herein.

In some embodiments of the present disclosure, the $R_7$ is selected from H, F, CN, $OCH_3$, $OCHF_2$, $OCF_3$, $CH=CHF$ and phenyl, and other variables are as defined herein.

In some embodiments of the present disclosure, the $R_7$ is selected from H, and other variables are as defined herein.

In some embodiments of the present disclosure, the each $R_a$ is independently selected from H, F, Cl, Br, I, CN, $CH_3$, $CH_2CH_3$, $CH(CH_3)_2$, $NHCH_3$, $NHCH_2CH_3$ and $N(CH_3)_2$, wherein the $CH_3$, $CH_2CH_3$, $CH(CH_3)_2$, $NHCH_3$, $NHCH_2CH_3$ and $N(CH_3)_2$ are optionally substituted with 1, 2, or 3 halogens, and other variables are as defined herein.

In some embodiments of the present disclosure, the each $R_a$ is independently selected from H, F and $CH_3$, and other variables are as defined herein.

In some embodiments of the present disclosure, the $R_6$ and $R_7$ are taken together with atoms to which they are attached to form phenyl,

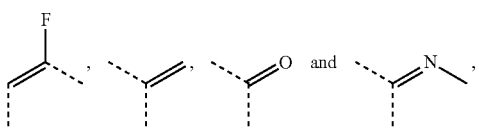

and other variables are as defined herein.

In some embodiments of the present disclosure, the $R_8$ is selected from H, F, CN, $OCH_3$, $OCHF_2$, $OCF_3$, $CH=CHF$ and phenyl, and other variables are as defined herein.

In some embodiments of the present disclosure, the structural moiety

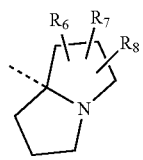

is selected from

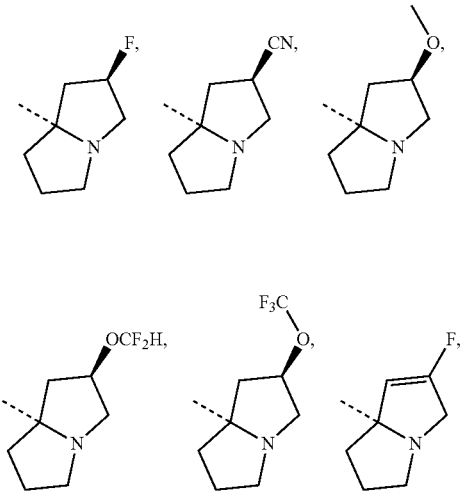

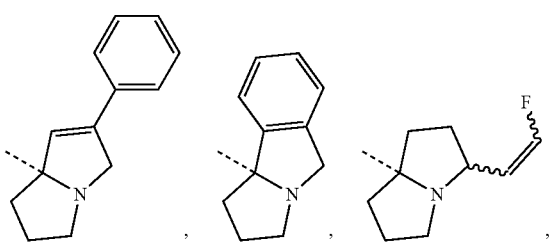

-continued

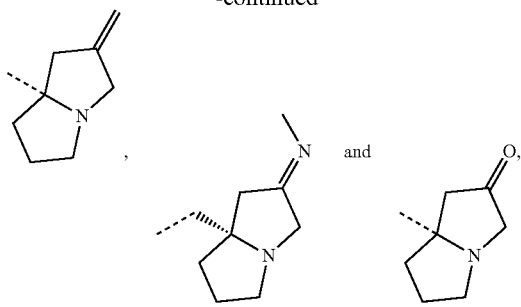

and other variables are as defined herein.

The present disclosure also provides a compound represented by formula (I) and a pharmaceutically acceptable salt thereof

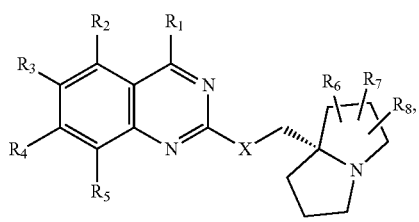
(I)

wherein
X is selected from O and S;
$R_1$ is selected from

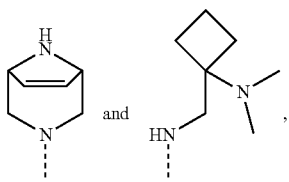

wherein the

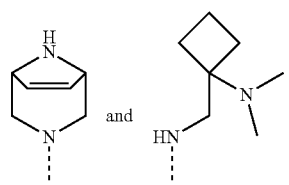

are optionally substituted with 1, 2 or 3 $R_a$;
$R_2$ is selected from H, $C_{1-3}$ alkoxy and $C_{3-4}$ cycloalkyl-O—, wherein the $C_{1-3}$ alkoxy and $C_{3-4}$ cycloalkyl-O— are optionally substituted with 1, 2, 3, 4 or 5 halogens;
$R_3$ is selected from H, halogen and $C_{1-3}$ alkyl, wherein the $C_{1-3}$ alkyl is optionally substituted with 1, 2 or 3 $R_b$;
$R_4$ is selected from phenyl and naphthyl, wherein the phenyl and naphthyl are each independently optionally substituted with 1, 2, 3, 4 or 5 $R_c$;
$R_5$ is selected from H, halogen and $C_{1-3}$ alkyl, wherein the $C_{1-3}$ alkyl is optionally substituted with 1, 2, or 3 halogens;
$R_6$, $R_7$ and $R_8$ are each independently selected from H, halogen, CN, $C_{1-3}$ alkyl, $C_{1-3}$ alkoxy, $C_{1-3}$ alkylamino, $C_{2-3}$ alkenyl and phenyl, wherein the $C_{1-3}$ alkyl, $C_{1-3}$ alkoxy, $C_{1-3}$ alkylamino, $C_{2-3}$ alkenyl and phenyl are optionally substituted with 1, 2, or 3 halogens;
alternatively, $R_6$ and $R_7$ are taken together with atoms to which they are attached to form phenyl,

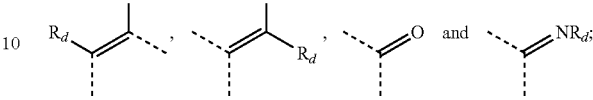

each $R_a$ is independently selected from H, halogen, OH, $NH_2$, $C_{1-3}$ alkyl and $C_{1-3}$ alkoxy, wherein the $C_{1-3}$ alkyl and $C_{1-3}$ alkoxy are optionally substituted with 1, 2, 3, 4 or 5 halogens;
each $R_b$ is independently selected from H, halogen and OH;
each $R_c$ is independently selected from H, halogen, OH, $NH_2$, CN and $C_{2-3}$ alkynyl;
$R_d$ is absent, or each $R_d$ is independently selected from H, halogen, $C_{1-3}$ alkyl and $C_{1-3}$ alkylamino, wherein the $C_{1-3}$ alkyl and $C_{1-3}$ alkylamino are optionally substituted with 1, 2, or 3 halogens.

In some embodiments of the present disclosure, the $R_2$ is selected from H and $OCH_3$, and other variables are as defined herein.

In some embodiments of the present disclosure, the $R_3$ is selected from H, F, Cl and $CH_2OH$, and other variables are as defined herein.

In some embodiments of the present disclosure, the each $R_b$ is independently selected from H, F, OH, $NH_2$ and —C≡CH, and other variables are as defined herein.

In some embodiments of the present disclosure, the $R_4$ is selected from

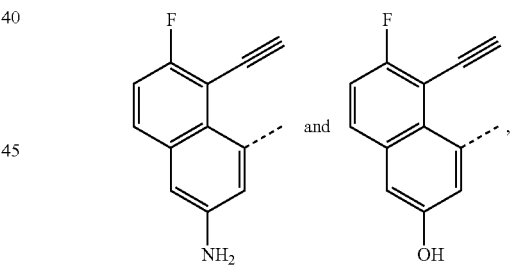

and other variables are as defined herein.

In some embodiments of the present disclosure, the $R_5$ is selected from H, F, Cl, Br, $CH_3$, $CH_2CH_3$ and $CH(CH_3)_2$, wherein the $CH_3$, $CH_2CH_3$ and $CH(CH_3)_2$ are optionally substituted with 1, 2, or 3 halogens, and other variables are as defined herein.

In some embodiments of the present disclosure, the $R_5$ is selected from F, $CH_2F$ and $CHF_2$, and other variables are as defined herein.

In some embodiments of the present disclosure, the $R_6$, $R_7$ and $R_8$ are each independently selected from H, F, Cl, Br, I, CN, $CH_3$, $CH_2CH_3$, $CH(CH_3)_2$, $OCH_3$, $OCH_2CH_3$, $OCH(CH_3)_2$, $NHCH_3$, $NHCH_2CH_3$, $N(CH_3)_2$, $CH=CH_2$, $CH_2CH=CH_2$, $CH=CHCH_3$ and phenyl, wherein the $CH_3$, $CH_2CH_3$, $CH(CH_3)_2$, $OCH_3$, $OCH_2CH_3$, $OCH(CH_3)_2$, $NHCH_3$, $NHCH_2CH_3$, $N(CH_3)_2$, $CH=CH_2$, $CH_2CH=CH_2$, CH=CH$_2$CH$_3$ and phenyl are optionally substituted with 1, 2, or 3 halogens, and other variables are as defined herein.

In some embodiments of the present disclosure, the R$_6$, R$_7$ and R$_8$ are each independently selected from H, F, Cl, Br, I, CN, CH$_3$, CH$_2$F, CHF$_2$, CF$_3$, CH$_2$CH$_3$, CH$_2$CF$_3$, CF$_2$CF$_3$, OCH$_3$, OCH$_2$F, OCHF$_2$, OCF$_3$, OCH$_2$CH$_3$, OCH$_2$CF$_3$, OCF$_2$CF$_3$, NHCH$_3$, N(CH$_3$)$_2$, CH=CH$_2$, CF=CH$_2$, CH=CHF, CH=CF$_2$ and phenyl, and other variables are as defined herein.

In some embodiments of the present disclosure, the R$_6$ is selected from H, and other variables are as defined herein.

In some embodiments of the present disclosure, the R$_7$ is selected from H, F, CN, OCH$_3$, OCHF$_2$, OCF$_3$, CH=CHF and phenyl, and other variables are as defined herein.

In some embodiments of the present disclosure, the R$_7$ is selected from H, and other variables are as defined herein.

In some embodiments of the present disclosure, the each R$_a$ is independently selected from H, F, Cl, Br, I, CN, CH$_3$, CH$_2$CH$_3$, CH(CH$_3$)$_2$, NHCH$_3$, NHCH$_2$CH$_3$ and N(CH$_3$)$_2$, wherein the CH$_3$, CH$_2$CH$_3$, CH(CH$_3$)$_2$, NHCH$_3$, NHCH$_2$CH$_3$ and N(CH$_3$)$_2$ are optionally substituted with 1, 2, or 3 halogens, and other variables are as defined herein.

In some embodiments of the present disclosure, the each R$_a$ is independently selected from H, F and CH$_3$, and other variables are as defined herein.

In some embodiments of the present disclosure, the R$_6$ and R$_7$ are taken together with atoms to which they are attached to form phenyl,

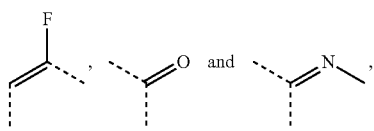

and other variables are as defined herein.

In some embodiments of the present disclosure, the R$_8$ is selected from H, F, CN, OCH$_3$, OCHF$_2$, OCF$_3$, CH=CHF and phenyl, and other variables are as defined herein.

In some embodiments of the present disclosure, the structural moiety

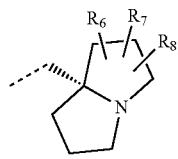

is selected from

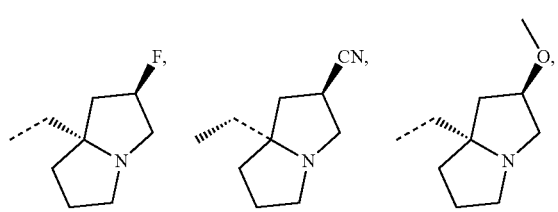

-continued

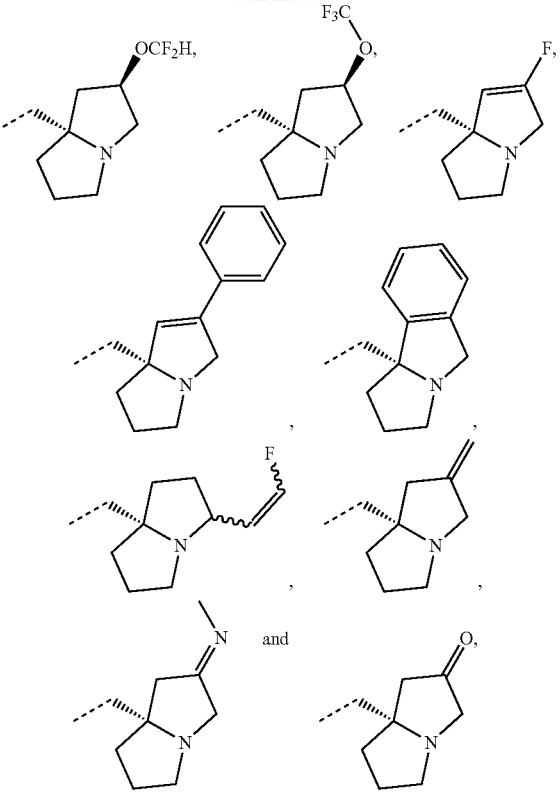

and other variables are as defined herein.

The present disclosure also provides a compound represented by formula (IX) and a pharmaceutically acceptable salt thereof (IX)

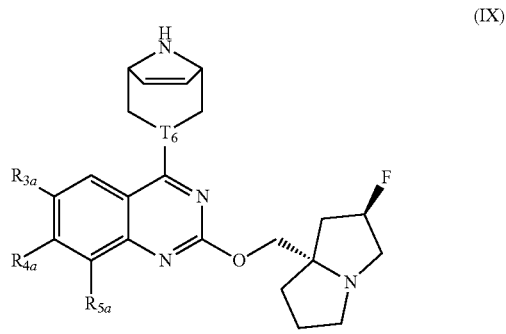

wherein
T$_6$ is selected from CH and N;
R$_{4a}$ is selected from C$_{6-10}$ aryl and 5- to 10-membered heteroaryl, wherein the C$_{6-10}$ aryl and 5- to 10-membered heteroaryl are optionally substituted with 1, 2, 3, 4 or 5 R$_e$;
R$_{5a}$ is selected from H, F, Cl, CN, NH$_2$, C$_{1-3}$ alkyl and C$_{1-3}$ alkoxy, wherein the C$_{1-3}$ alkyl and C$_{1-3}$ alkoxy are optionally substituted with 1, 2, or 3 halogens;
R$_{3a}$ is selected from H, F, Cl, C$_{1-3}$ alkyl, C$_{1-3}$ alkoxy, C$_{2-4}$ alkenyl and cyclopropyl, wherein the C$_{1-3}$ alkyl, C$_{1-3}$ alkoxy, C$_{2-4}$ alkenyl and cyclopropyl are optionally substituted with 1, 2, or 3 halogens;
each R$_e$ is independently selected from F, Cl, Br, I, OH, NH$_2$, CN, C$_{1-3}$ alkyl, C$_{1-3}$ alkoxy, C$_{2-4}$ alkenyl and C$_{2-4}$ alkynyl, wherein the $C_{1-3}$ alkyl, $C_{1-3}$ alkoxy, $C_{2-4}$ alkenyl and $C_{2-4}$ alkynyl are optionally substituted with 1, 2, or 3 halogens.

In some embodiments of the present disclosure, provided herein is a compound or a pharmaceutically acceptable salt thereof, wherein the compound is selected from

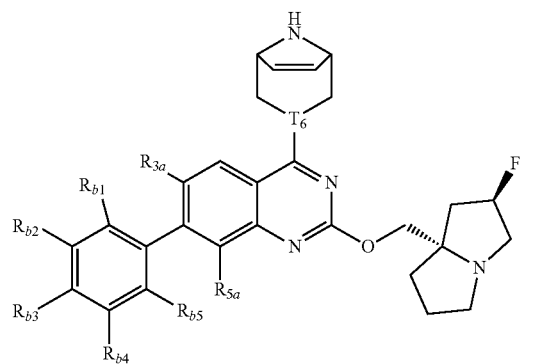

(IX-1)

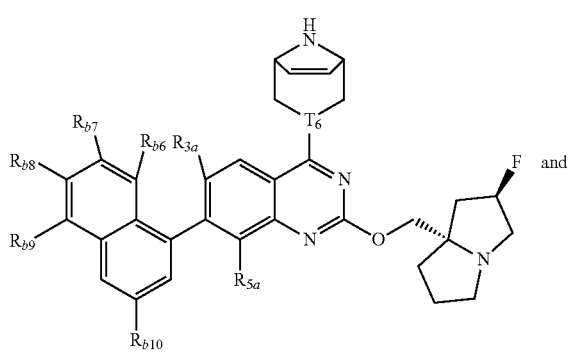

(IX-2)

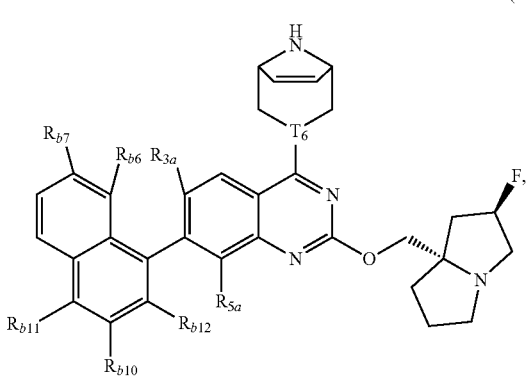

(IX-3)

wherein $T_6$ is selected from CH and N;

$R_{5a}$ is selected from H, F, Cl, CN, $NH_2$, $C_{1-3}$ alkyl and $C_{1-3}$ alkoxy, wherein the $C_{1-3}$ alkyl and $C_{1-3}$ alkoxy are optionally substituted with 1, 2, or 3 halogens;

$R_{5a}$ is selected from H, F, Cl, $C_{1-3}$ alkyl, $C_{1-3}$ alkoxy, $C_{2-4}$ alkenyl and cyclopropyl, wherein the $C_{1-3}$ alkyl, $C_{1-3}$ alkoxy, $C_{2-4}$ alkenyl and cyclopropyl are optionally substituted with 1, 2, or 3 halogens;

$R_{b1}$, $R_{b2}$, $R_{b3}$, $R_{b4}$, $R_{b5}$, $R_{b6}$, $R_{b7}$, $R_{b8}$, $R_{b9}$, $Rb_{10}$ and $Rb_{11}$ are each independently selected from H, F, Cl, Br, I, OH, $NH_2$, CN, $C_{1-3}$ alkyl, $C_{1-3}$ alkoxy, $C_{2-4}$ alkenyl and $C_{2-4}$ alkynyl, wherein the $C_{1-3}$ alkyl, $C_{1-3}$ alkoxy, $C_{2-4}$ alkenyl and $C_{2-4}$ alkynyl are optionally substituted with 1, 2, or 3 halogens.

In some embodiments of the present disclosure, the $R_{b1}$, $R_{b2}$, $R_{b3}$, $R_{b4}$, $R_{b5}$, $R_{b6}$, $R_{b7}$, $R_{b8}$, $R_{b9}$, $R_{b10}$ and $R_{b11}$ are each independently selected from F, Cl, Br, I, OH, $NH_2$, CN, $CH_3$, $CH_2CH_3$, $OCH_3$, $OCH_2CH_3$, $-CH=CH_2$, $-CH_2-CH=CH_2$ and $-C\equiv CH$, wherein the $CH_3$, $CH_2CH_3$, $OCH_3$, $OCH_2CH_3$, $-CH=CH_2$, $-CH_2-CH=CH_2$ and $-C\equiv CH$ are optionally substituted with 1, 2, or 3 halogens, and other variables are as defined herein.

In some embodiments of the present disclosure, the $R_{b1}$, $R_{b2}$, $R_{b3}$, $R_{b4}$, $R_{b5}$, $R_{b6}$, $R_{b7}$, $R_{b8}$, $R_{b9}$, $R_{b10}$ and $R_{b11}$ are each independently selected from F, Cl, OH, $NH_2$, CN, $CH_3$, $CF_3$, $CH_2CH_3$ and $-C\equiv CH$, and other variables are as defined herein.

The present disclosure also provides compounds shown below and pharmaceutically acceptable salts thereof,

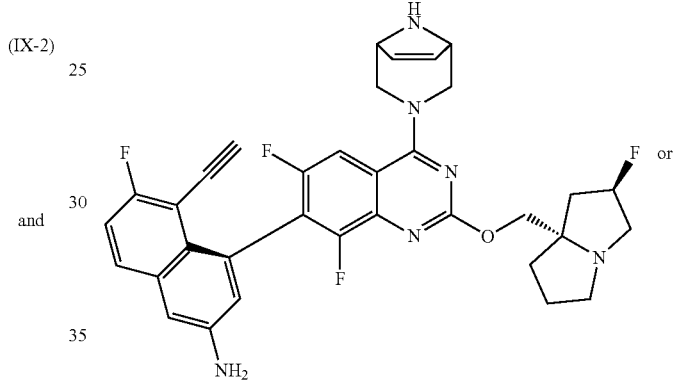

or

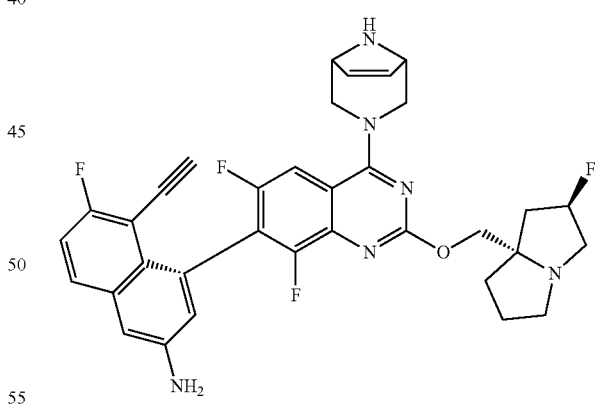

wherein the compound had a retention time Rt of 1.801 min after SFC analysis;

The analytical conditions for the SFC method were column: Chiralcel OD-3, 50×4.6 mm I.D., 3 μm; mobile phases: A (supercritical $CO_2$), B: (ethanol with 0.1% isopropylamine); gradient: B %=5~50% for 3 min; flow rate: 3.4 mL/min; wavelength: 220 nm; pressure: 1800 psi.

The present disclosure also provides compounds shown below and pharmaceutically acceptable salts thereof,

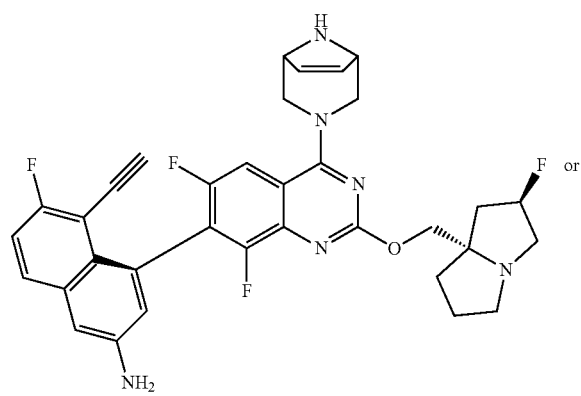

or

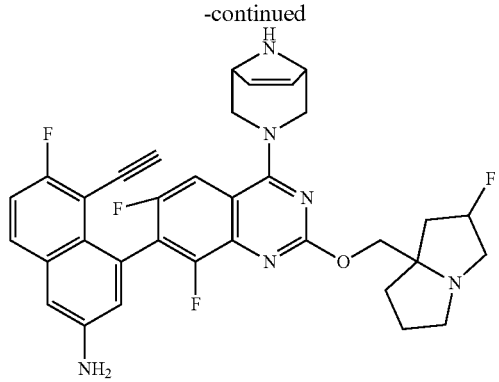

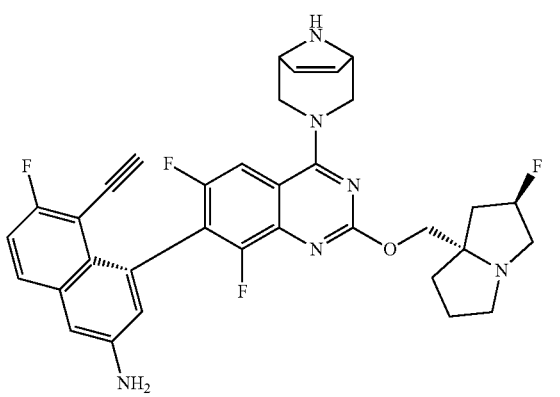

wherein the compound had a retention time Rt of 2.233 min after SFC analysis;

The analytical conditions for the SFC method were column: Chiralcel OD-3, 50×4.6 mm I.D., 3 μm; mobile phases: A (supercritical $CO_2$), B: (ethanol with 0.1% isopropylamine); gradient: B %=5~50% for 3 min; flow rate: 3.4 mL/min; wavelength: 220 nm; pressure: 1800 psi.

The present disclosure also includes some embodiments obtained by any combination of the above variables.

The present disclosure also provides compounds shown below and pharmaceutically acceptable salts thereof,

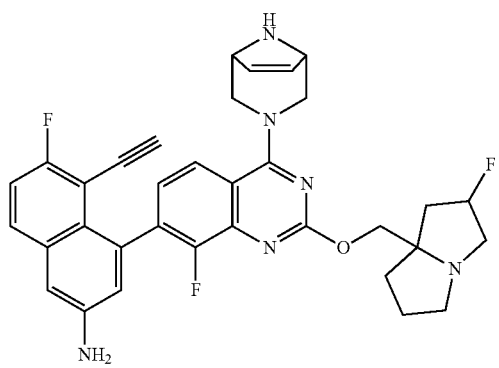

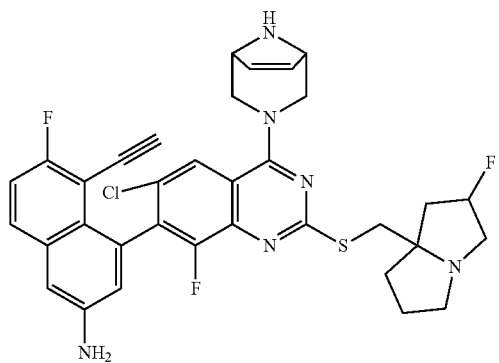

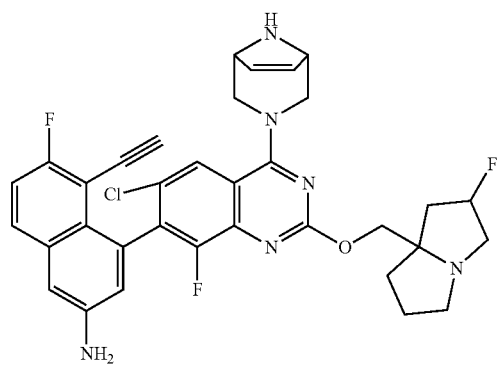

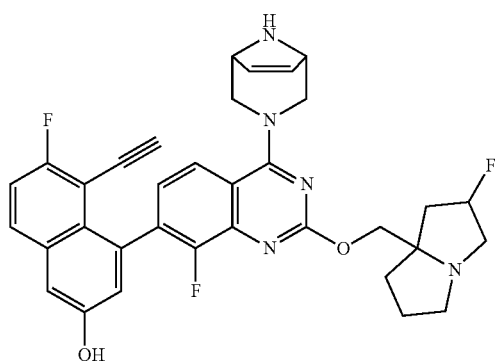

-continued

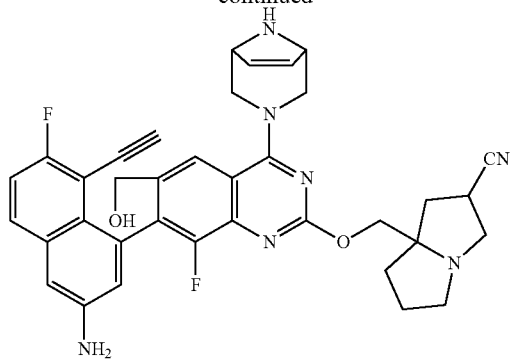
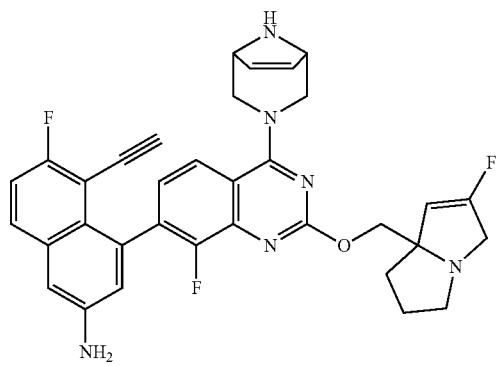
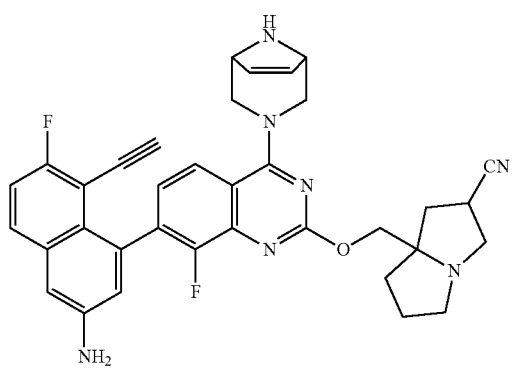
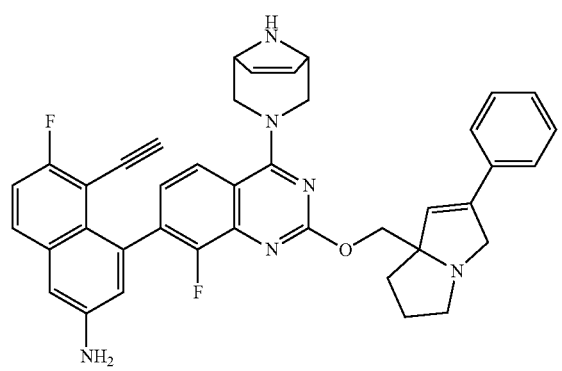
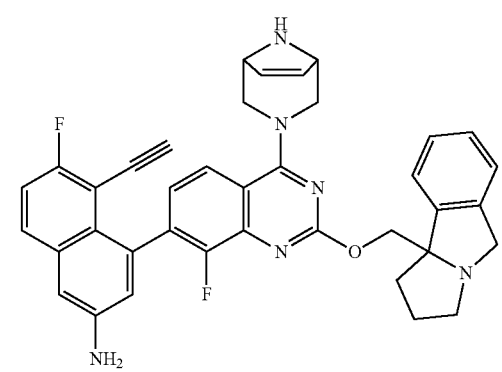
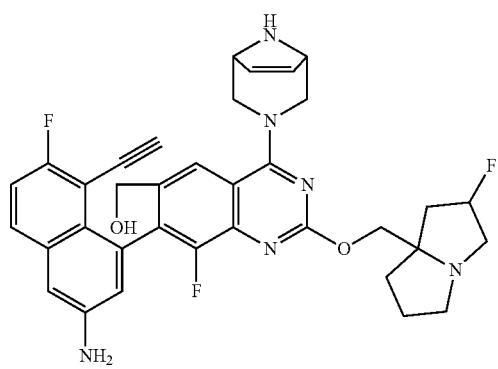
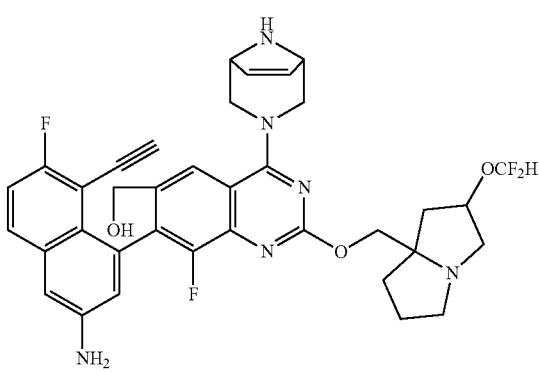

-continued
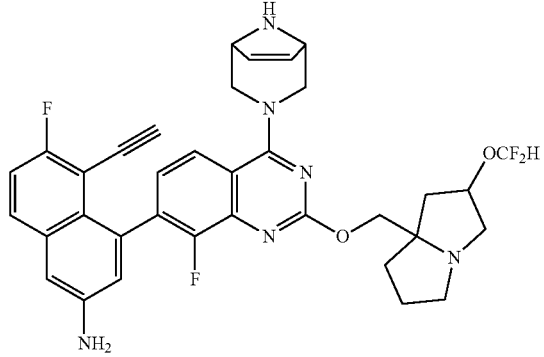
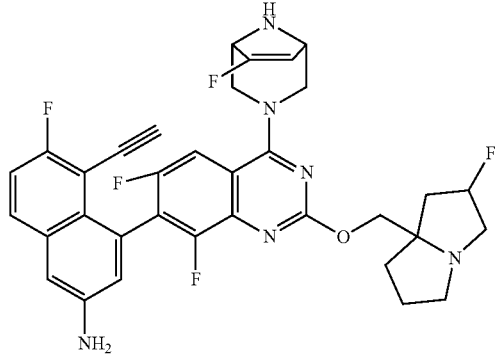
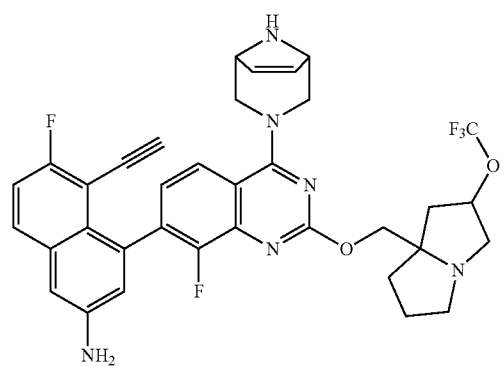
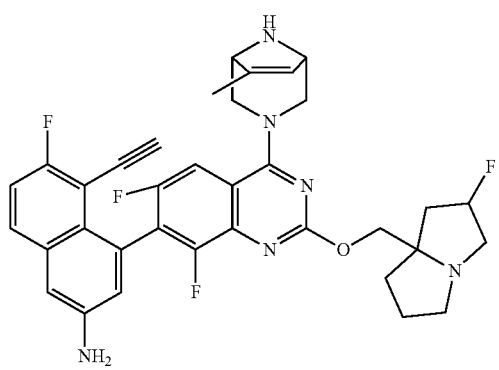
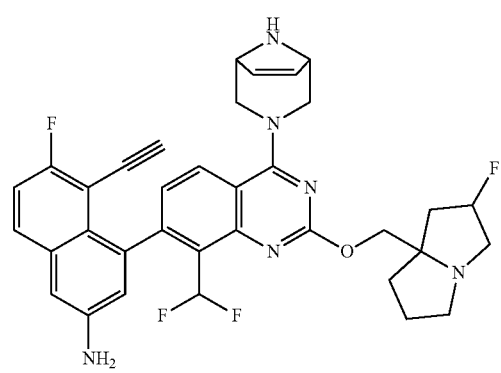
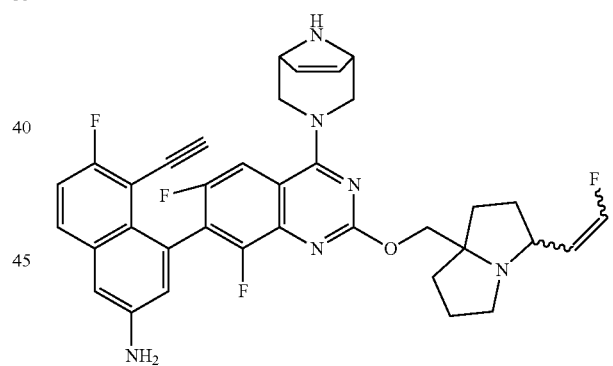
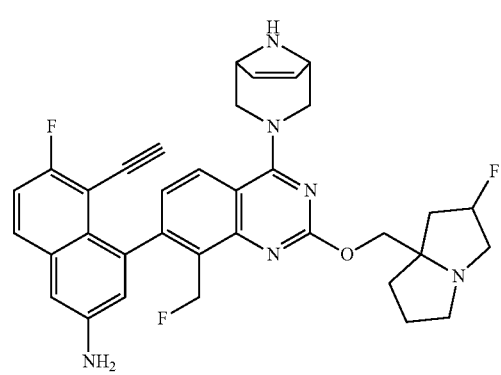
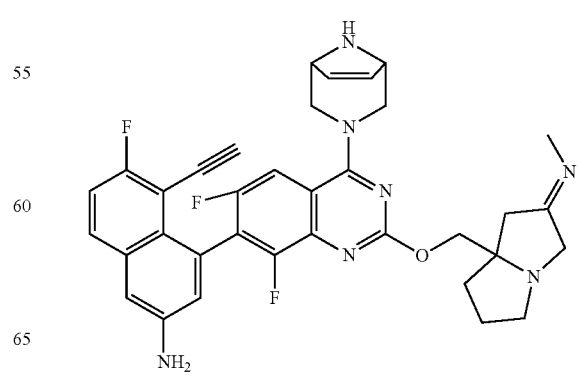

25
-continued
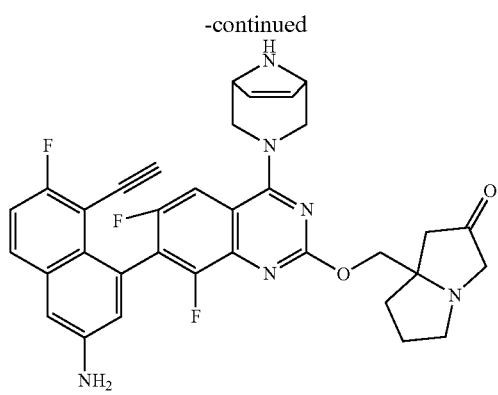
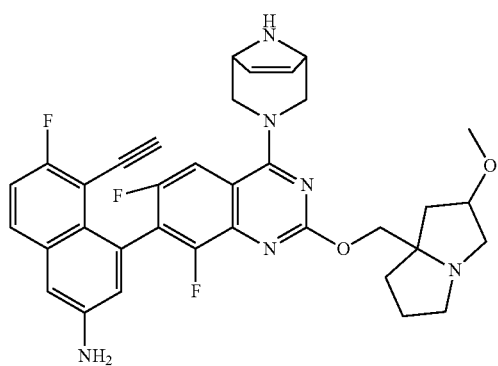
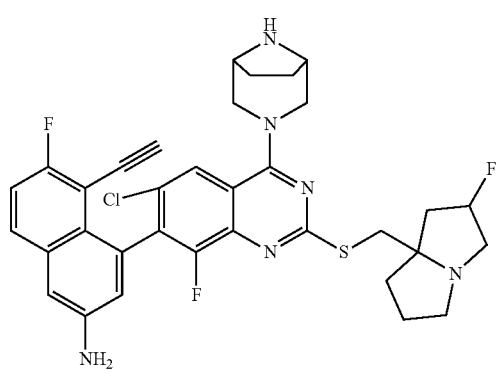
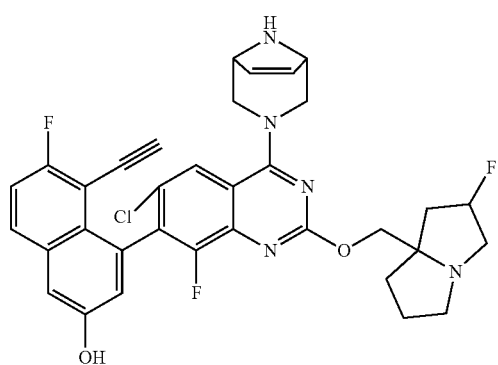
26
-continued
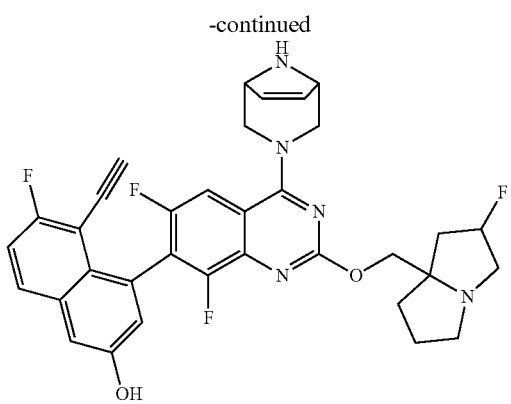
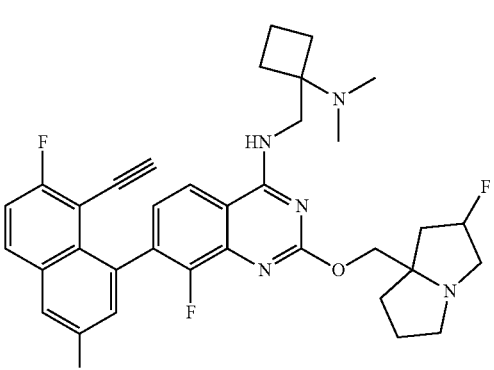
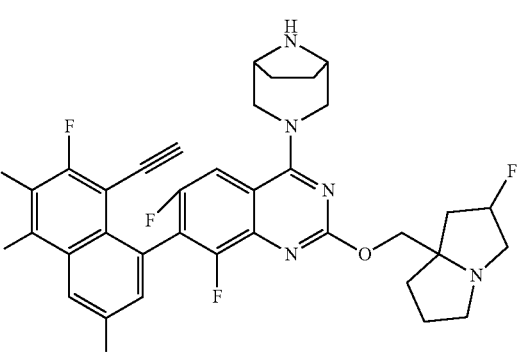
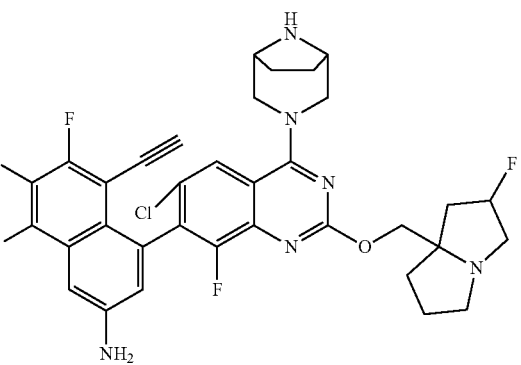

27
-continued
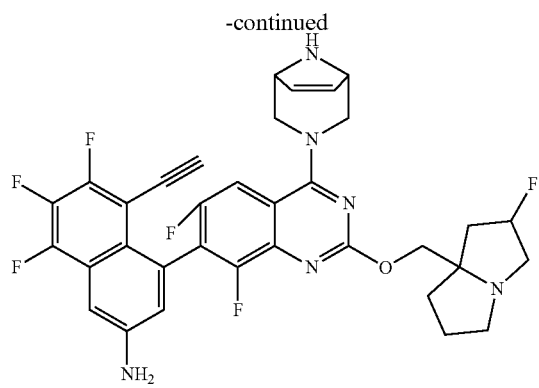
28
-continued
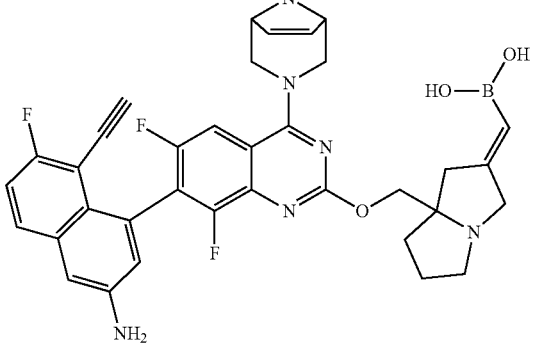
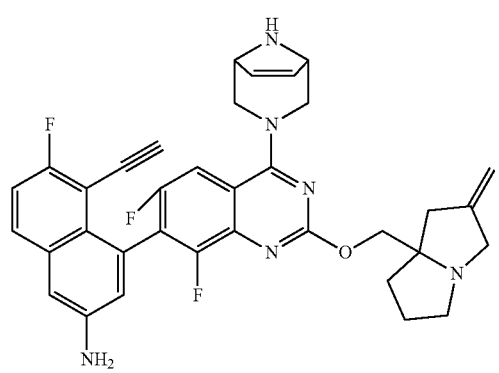
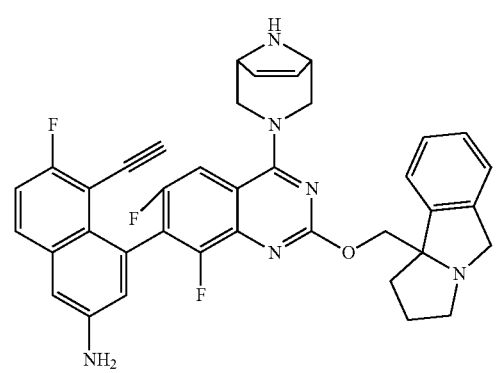
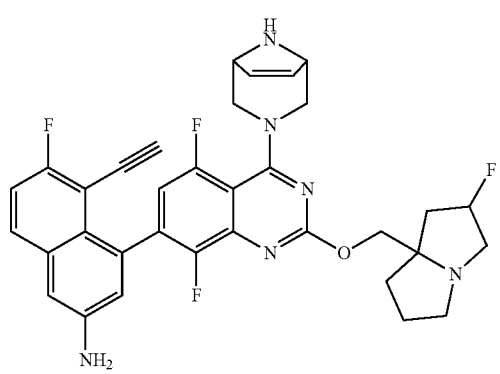

29
-continued
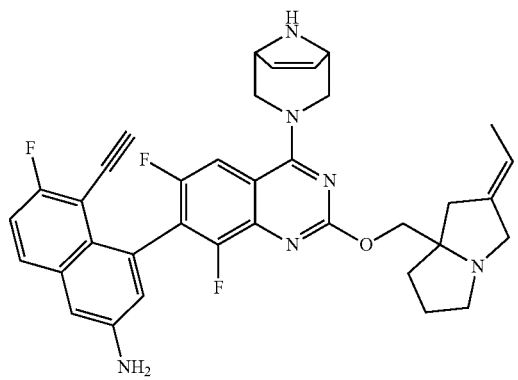
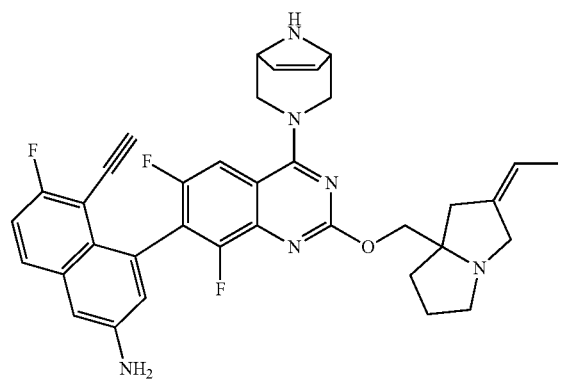
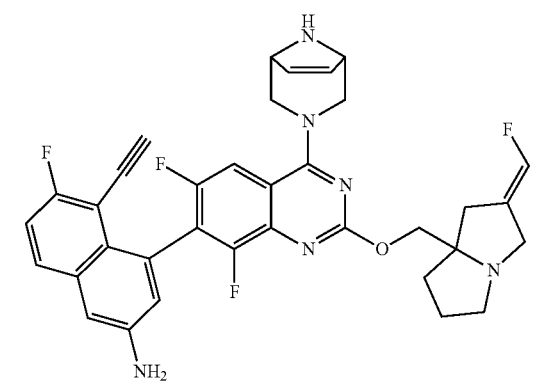
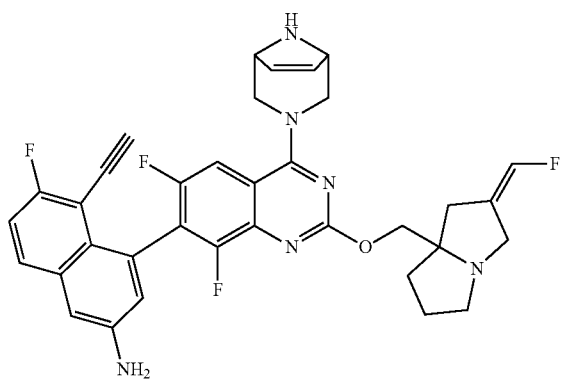
30
-continued
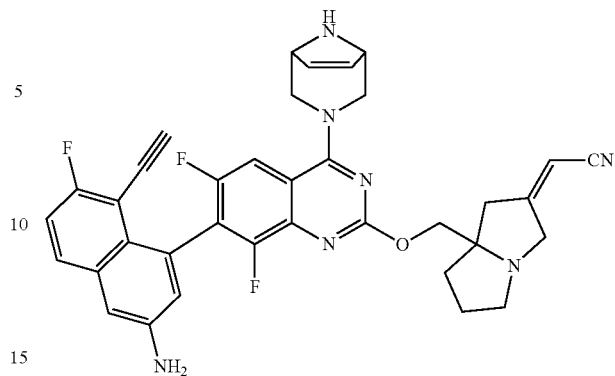
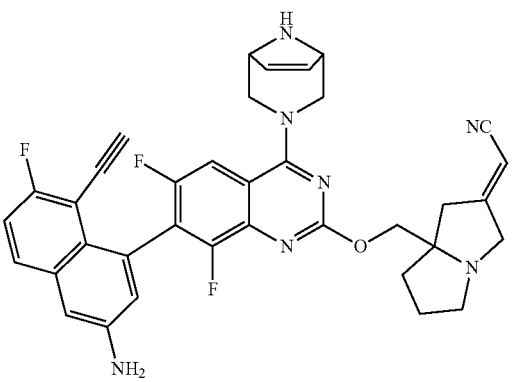
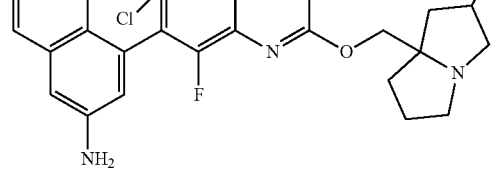
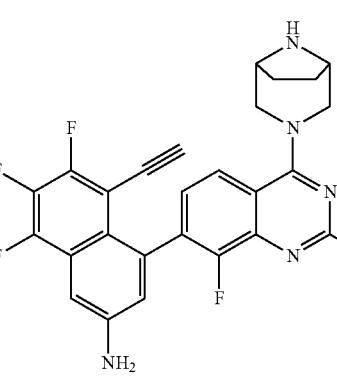

31
-continued
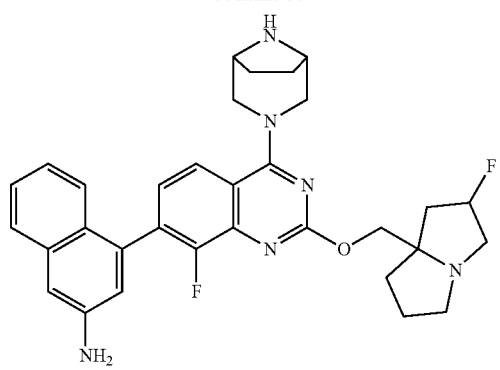
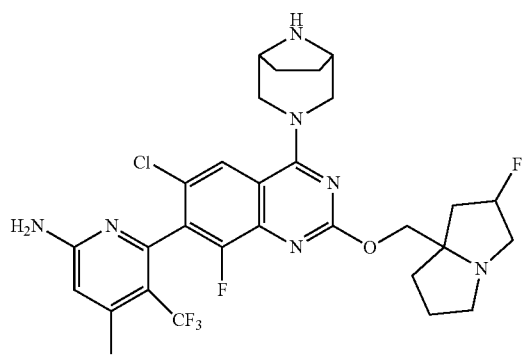
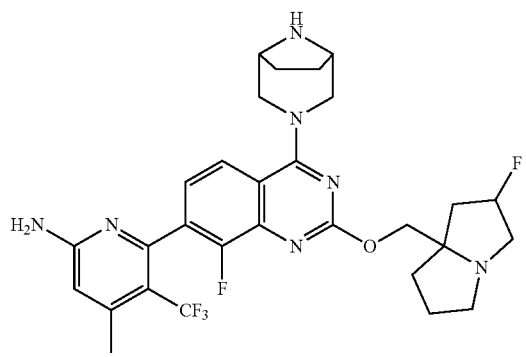
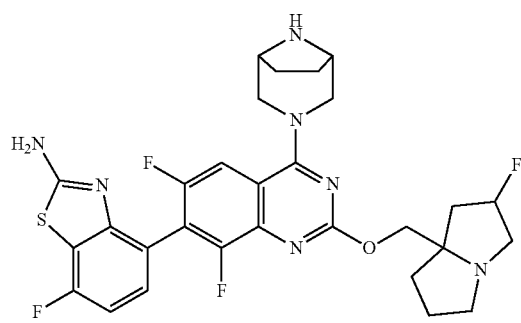
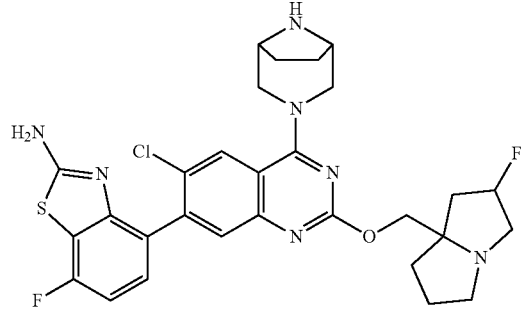
32
-continued
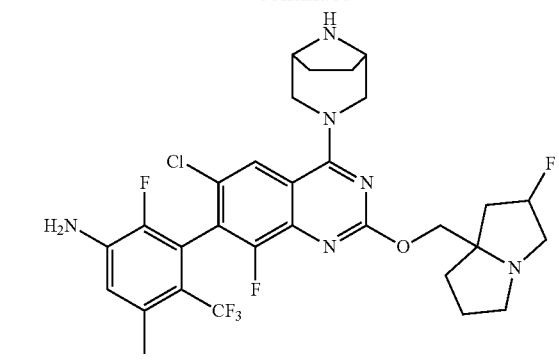
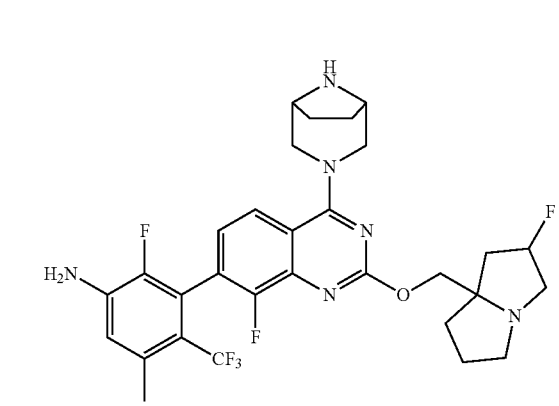
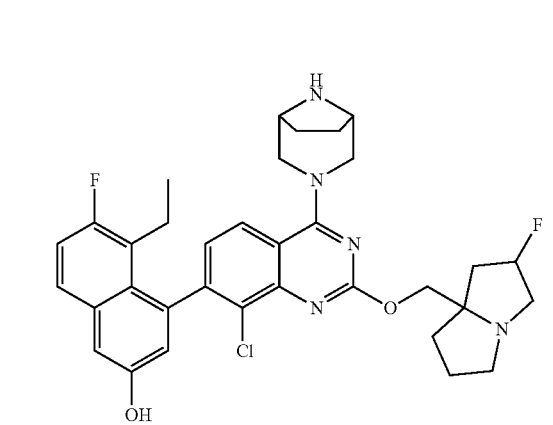
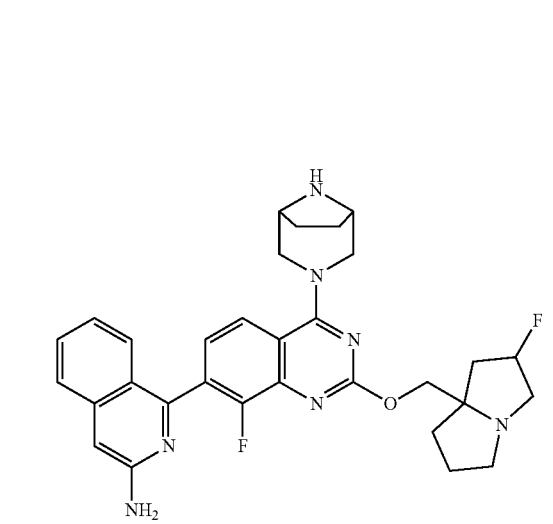

33
-continued
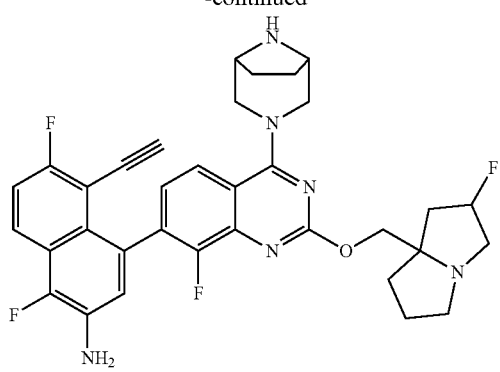
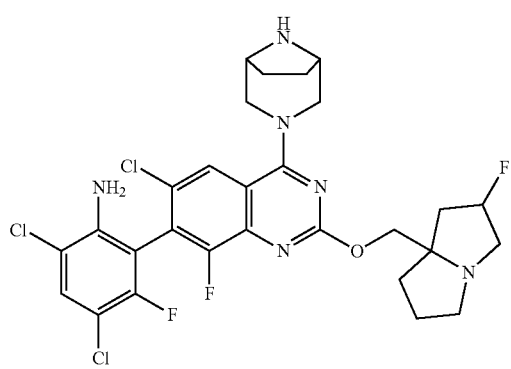
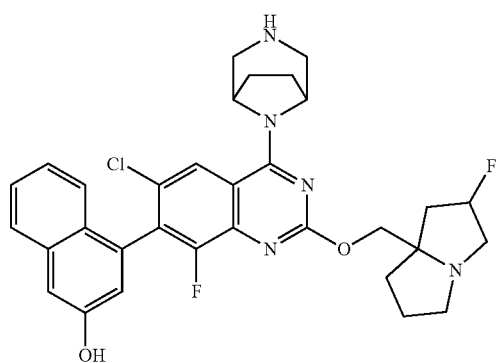
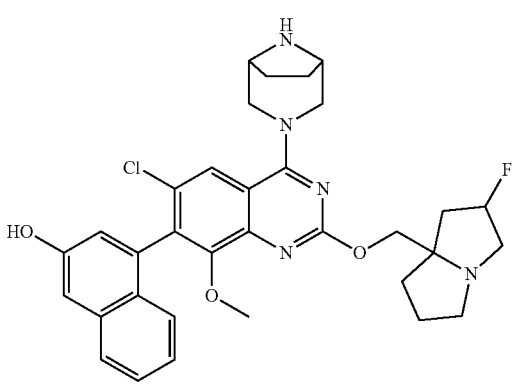
34
-continued
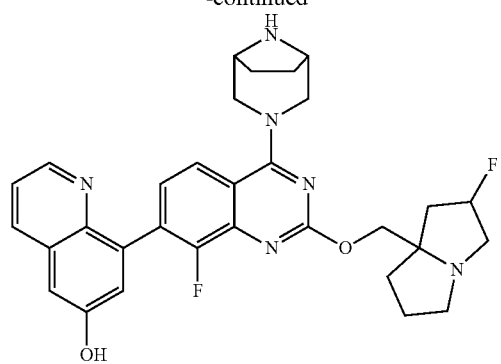
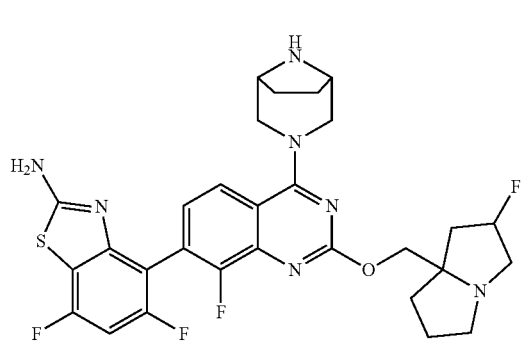
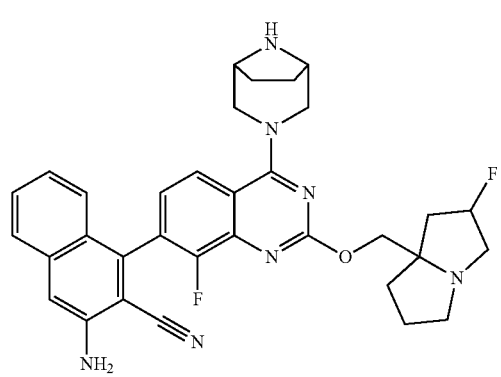
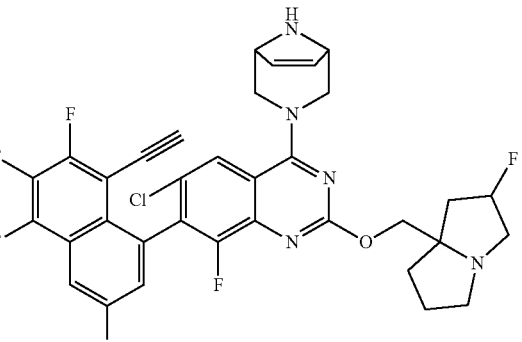

35
-continued
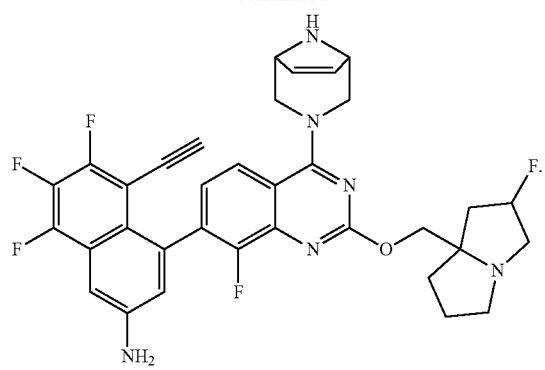
In some embodiments of the present disclosure, provided herein is a compound or a pharmaceutically acceptable salt thereof, wherein the compound is selected from
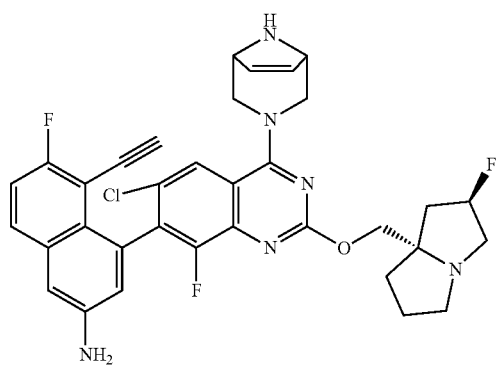
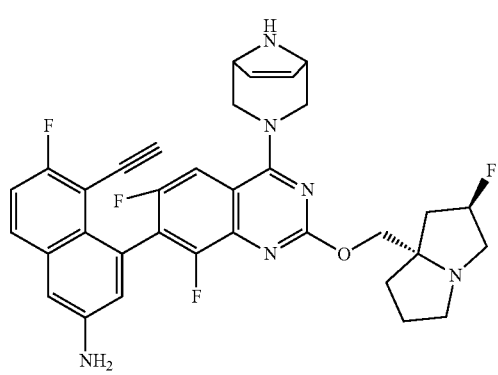
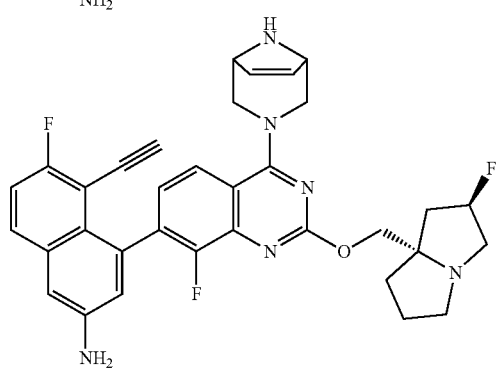
36
-continued
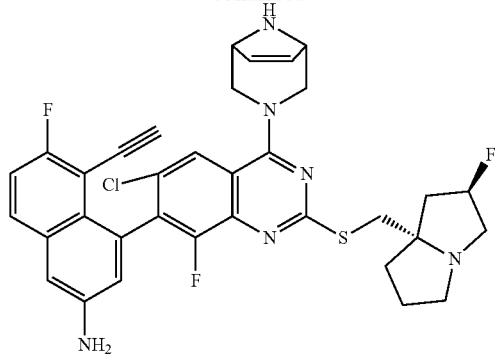
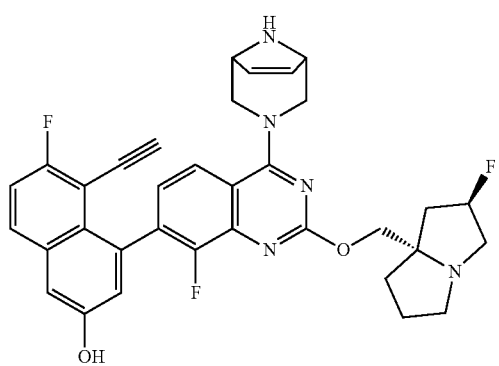
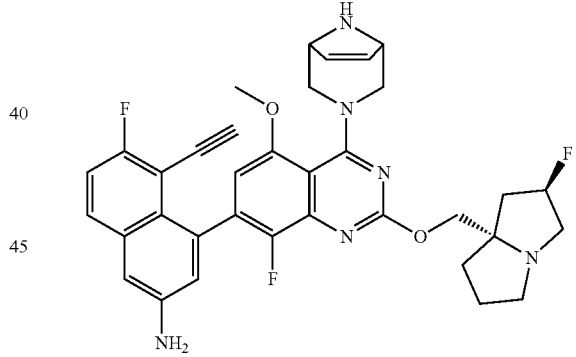
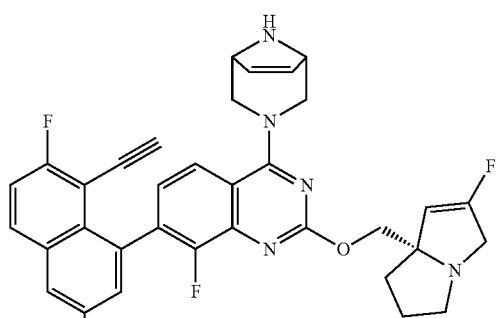

37
-continued
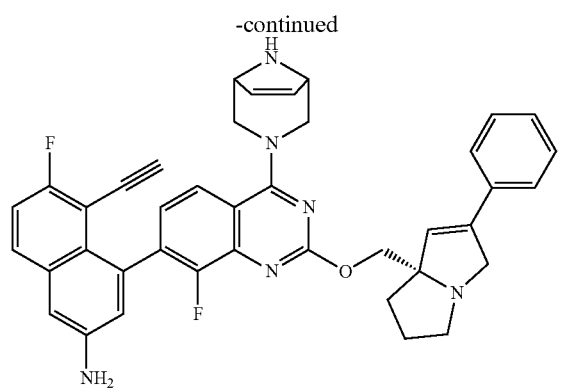
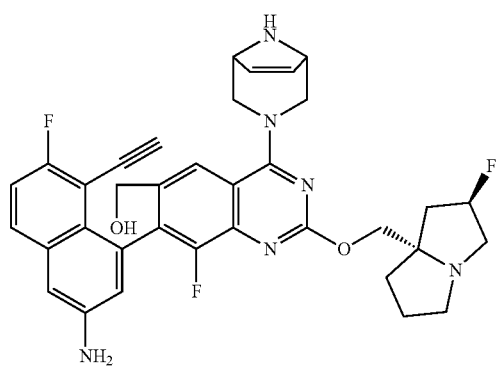
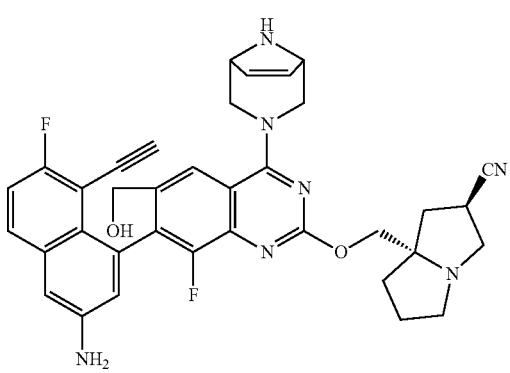
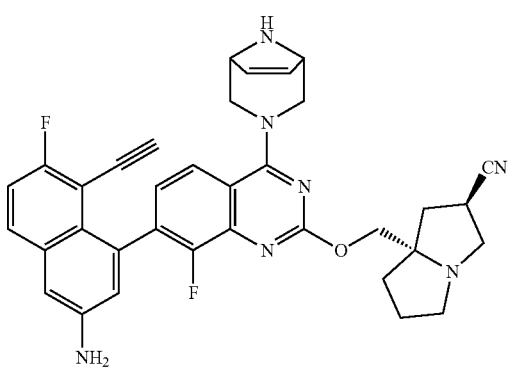
38
-continued
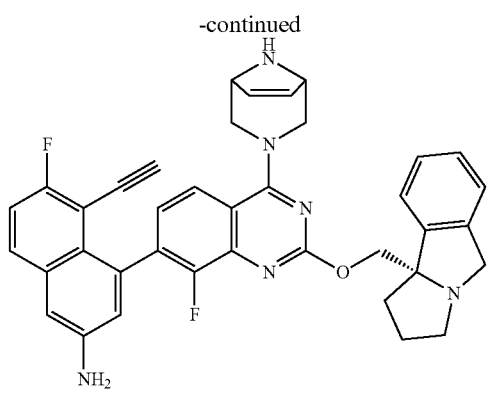
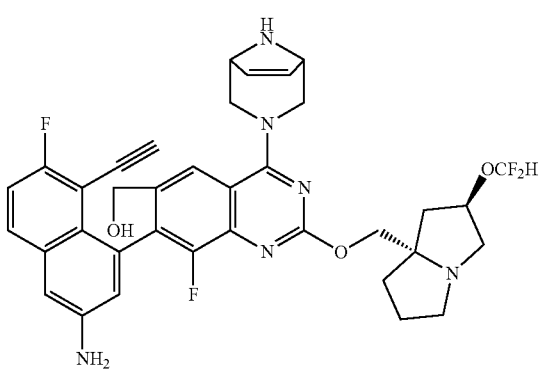
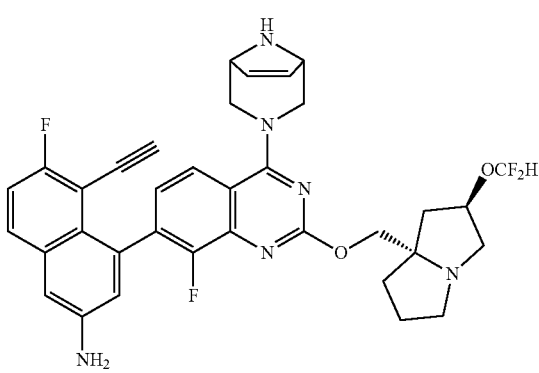
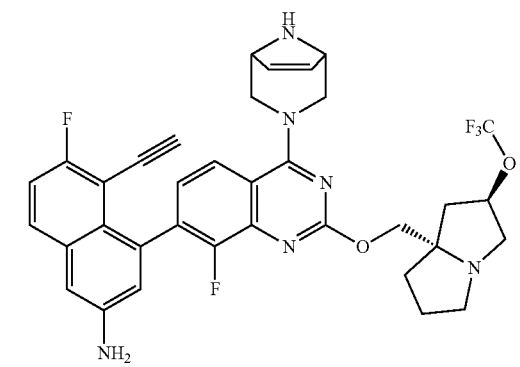

39
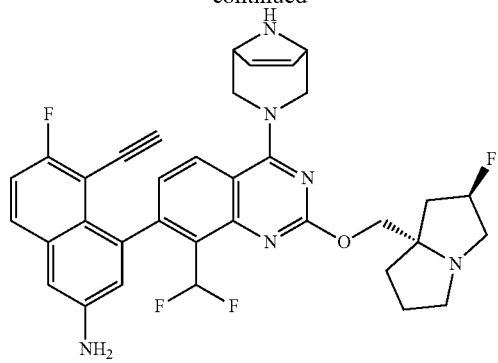
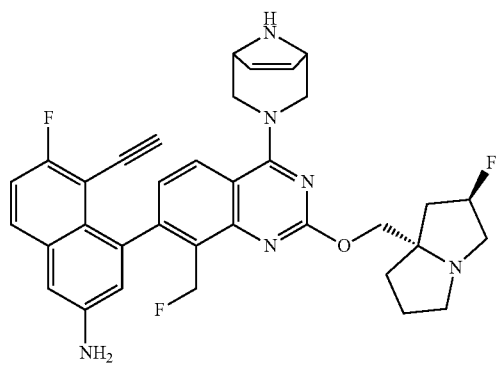
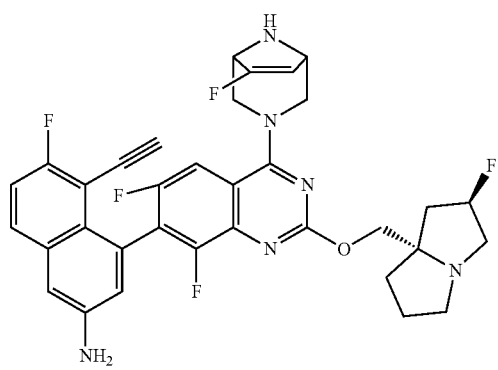
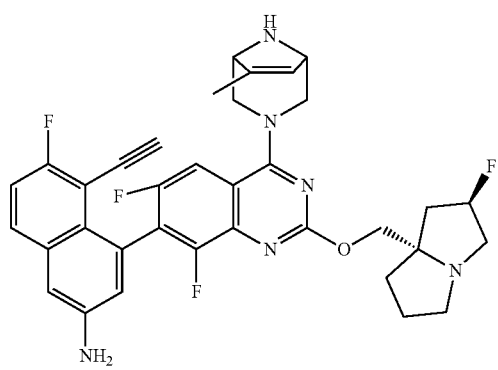
40
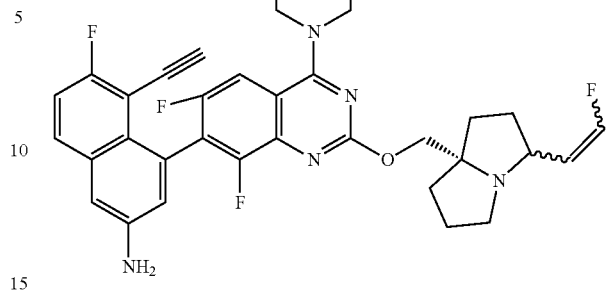
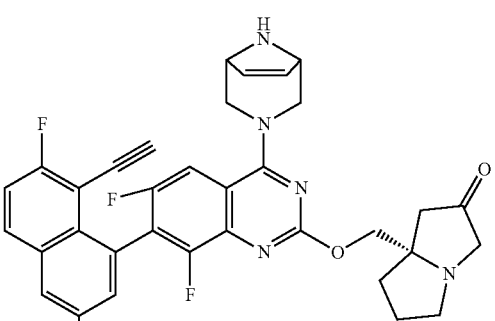
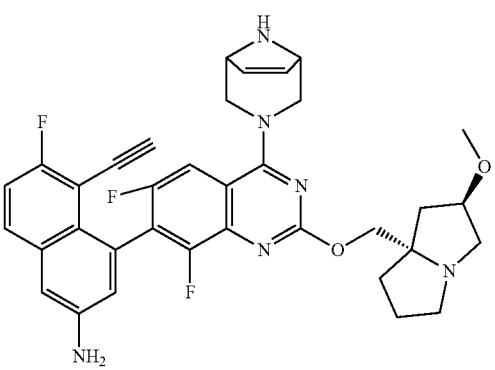

41
-continued
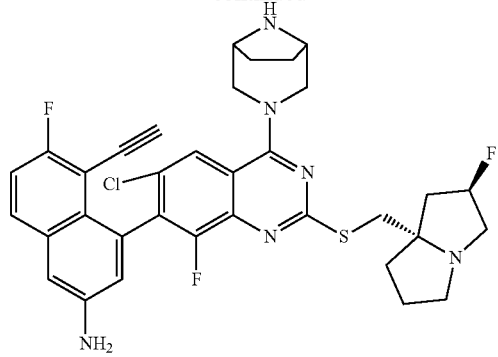
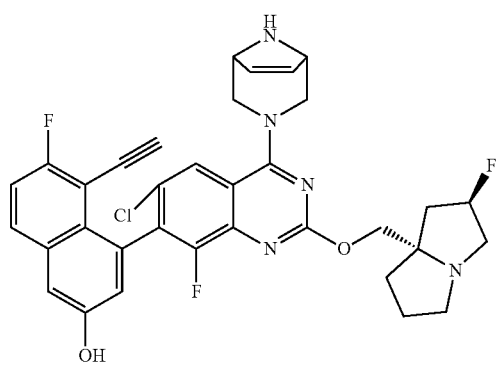
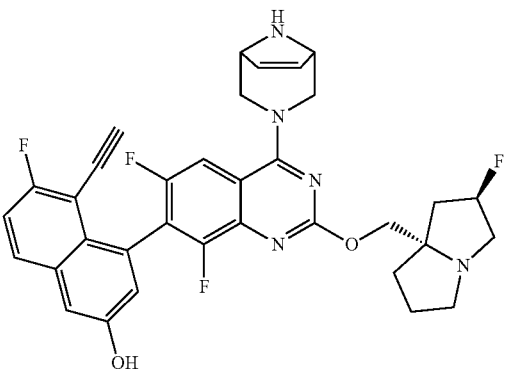
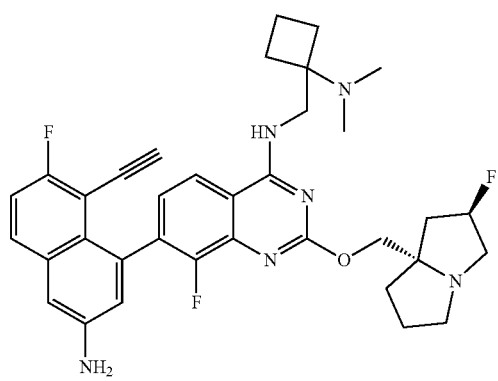
42
-continued
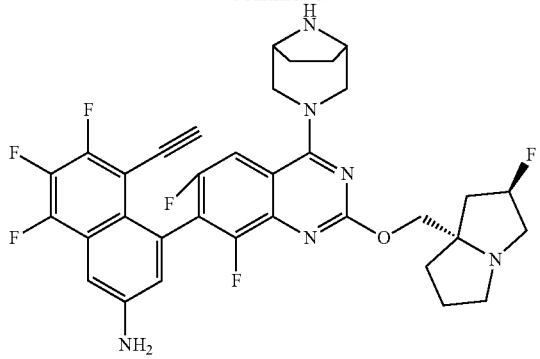
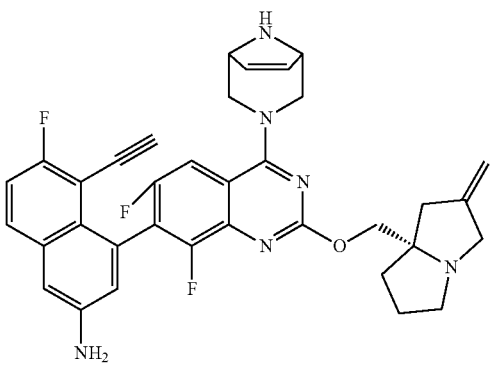

-continued
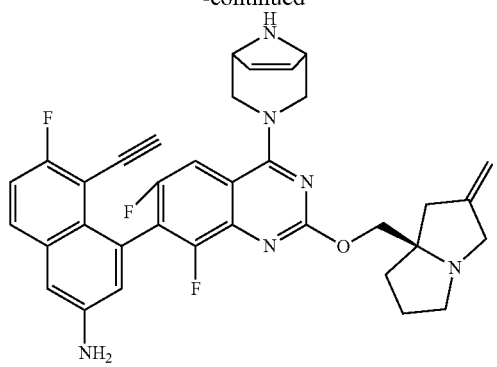
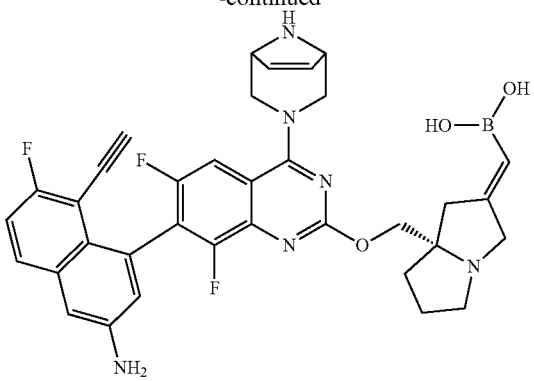
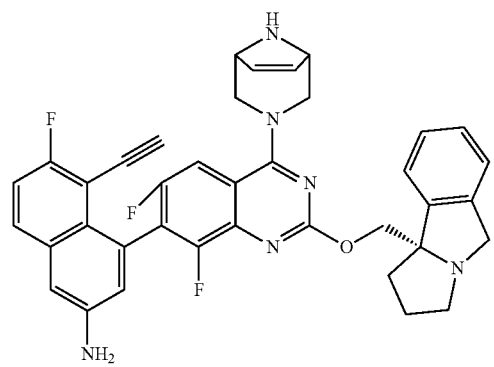
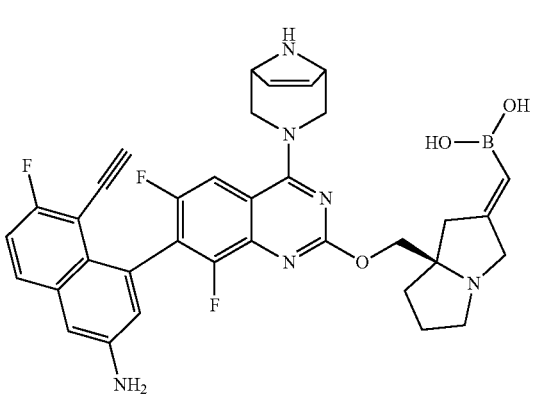
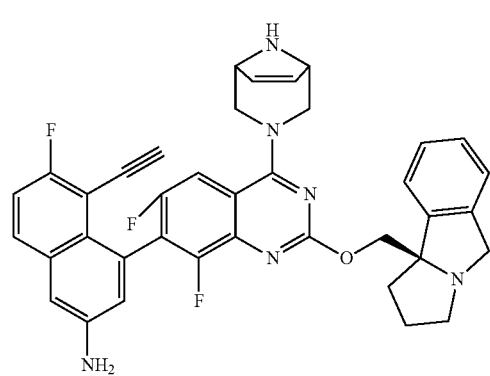
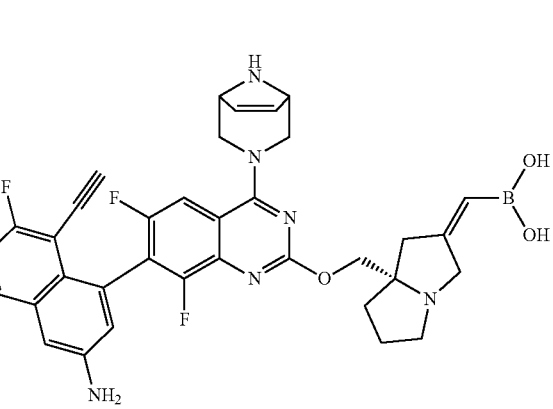
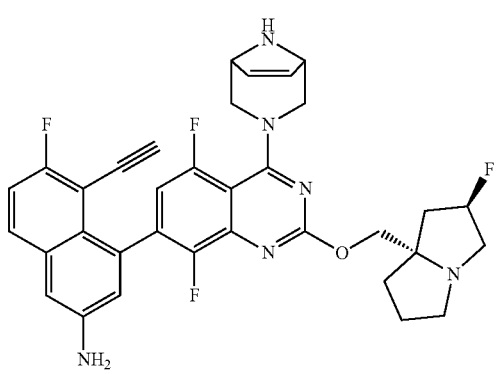
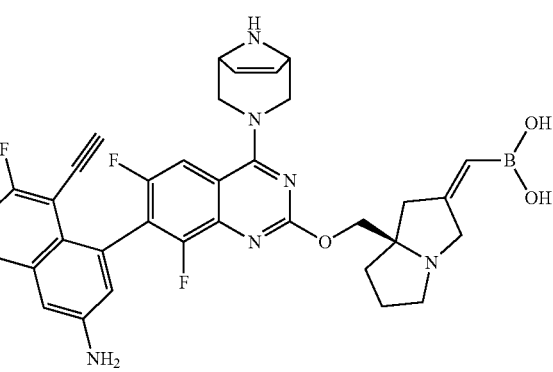

-continued
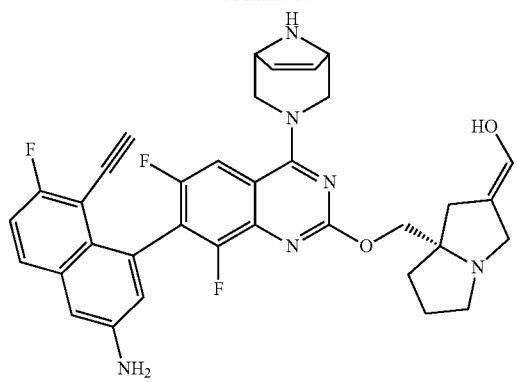
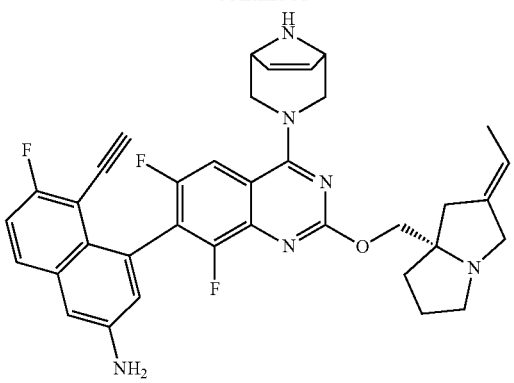
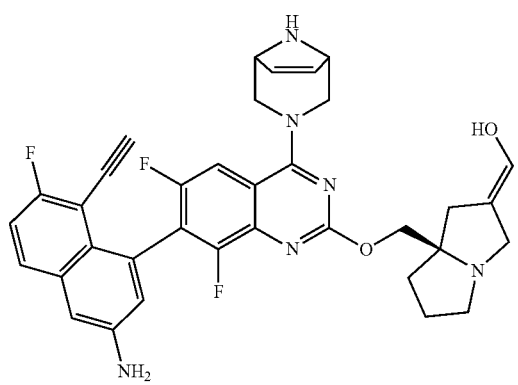
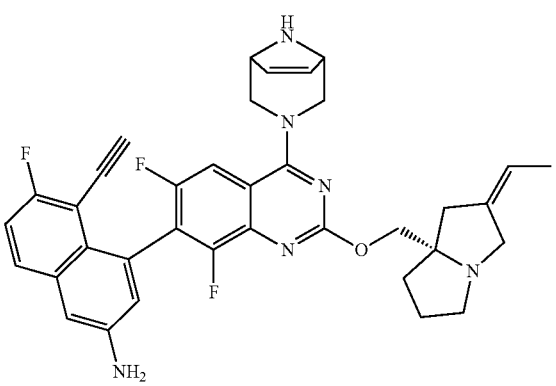
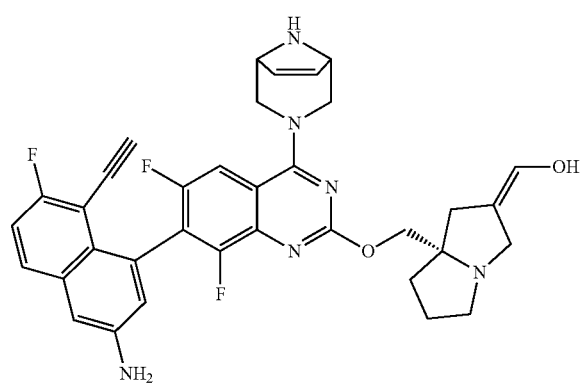
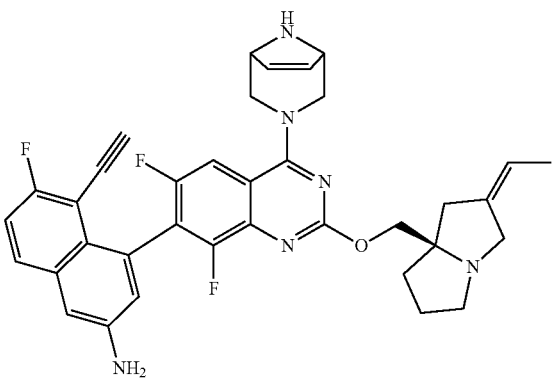
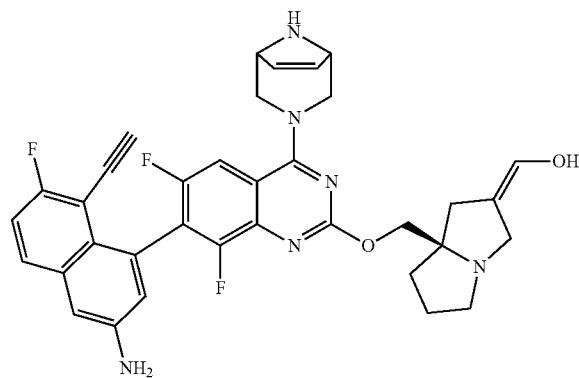

-continued
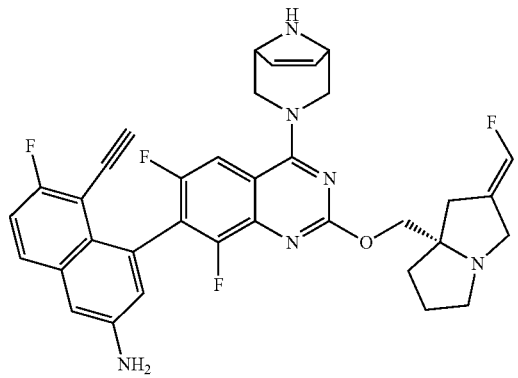
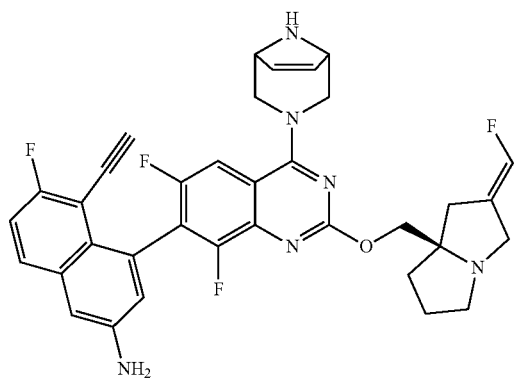
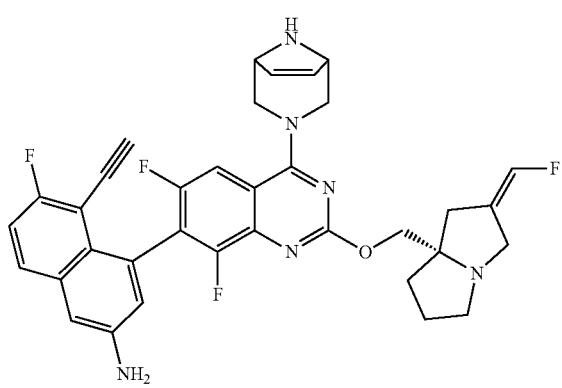
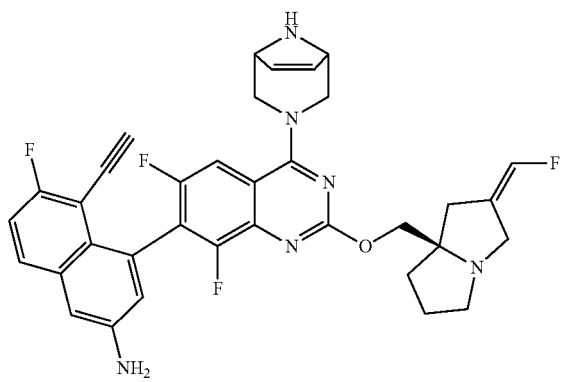
-continued
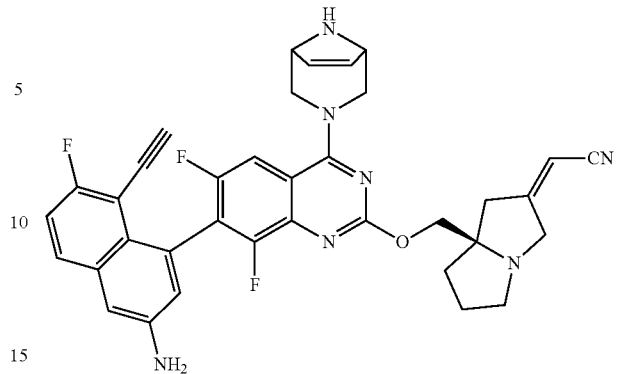
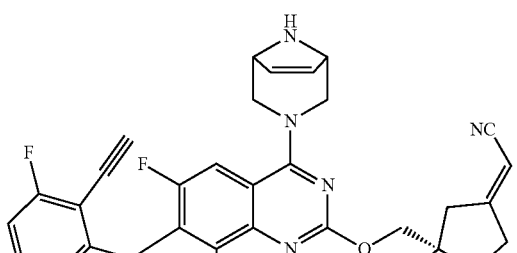
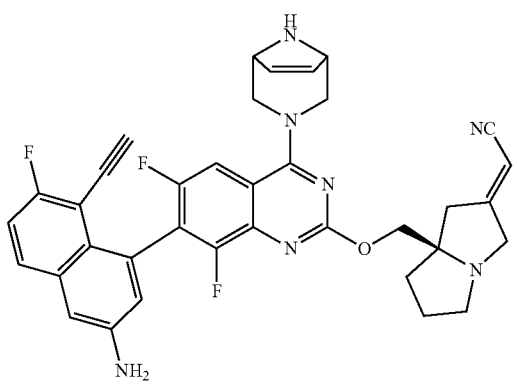

-continued
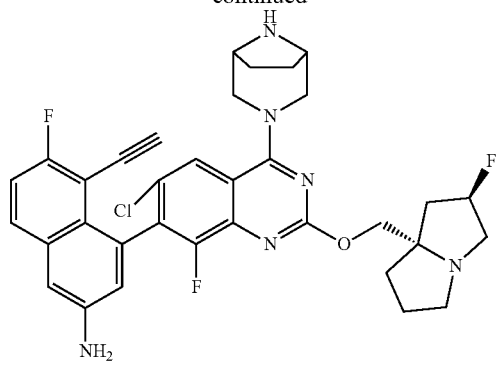
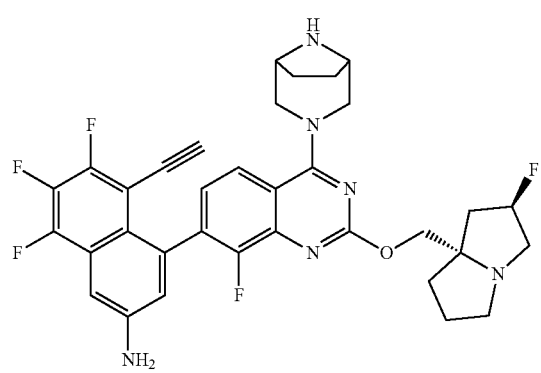
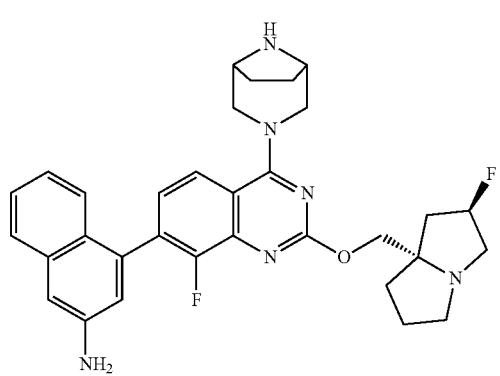
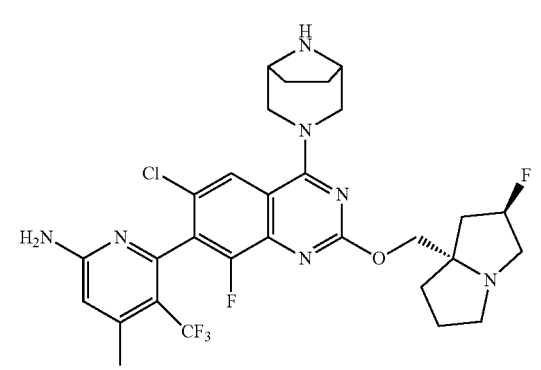
-continued
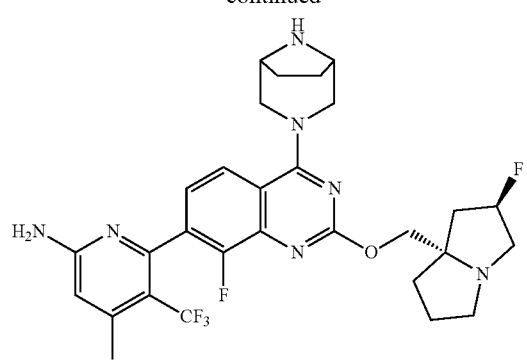
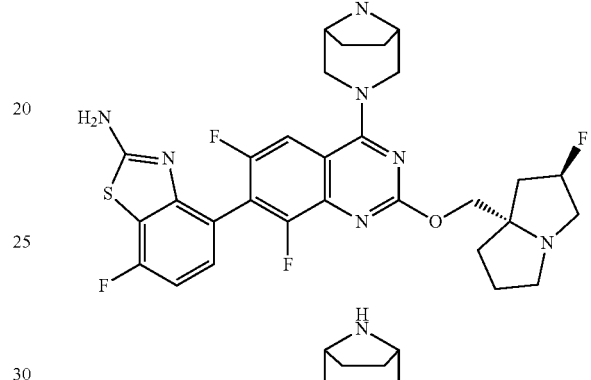
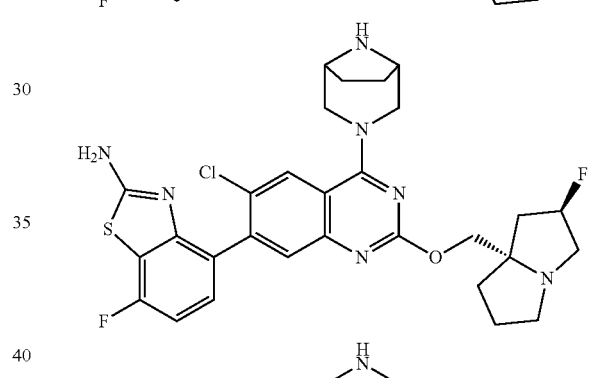
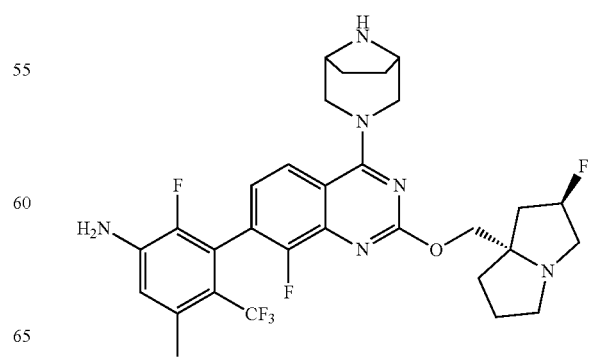

51
-continued
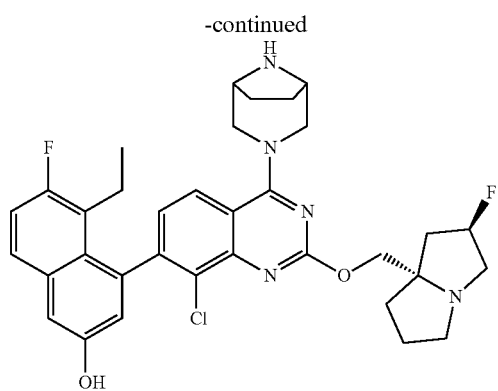
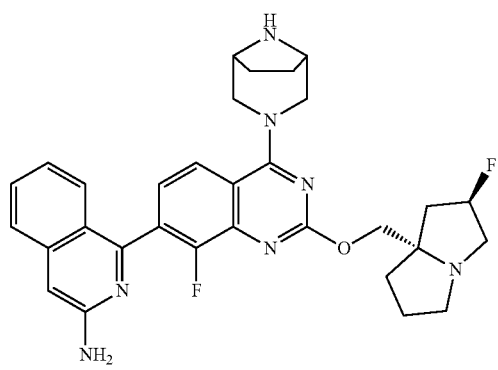
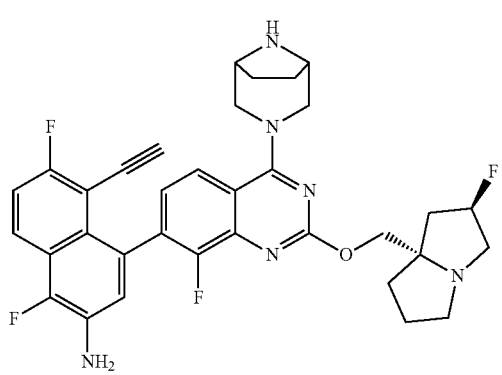
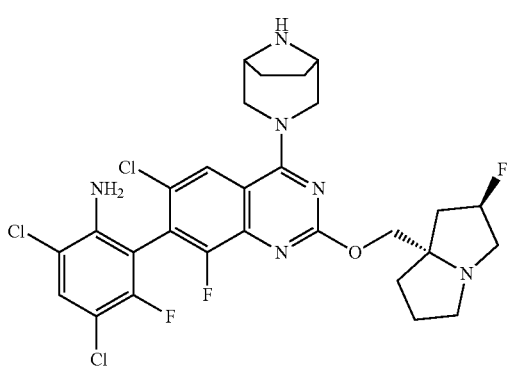
52
-continued
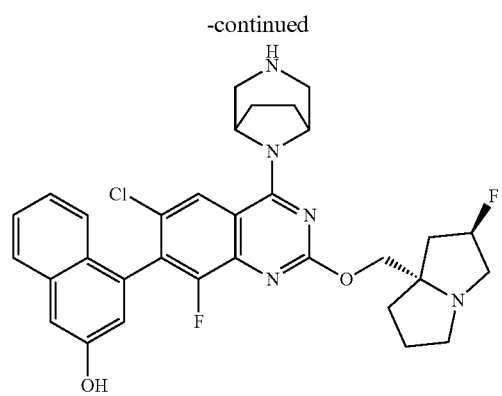
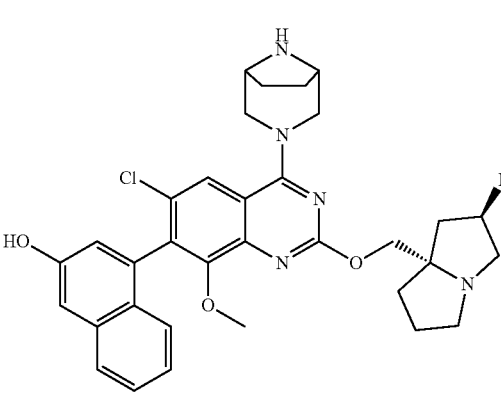
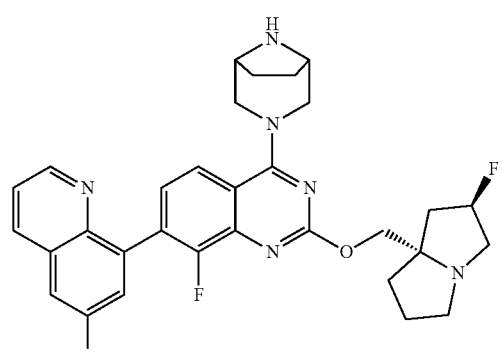
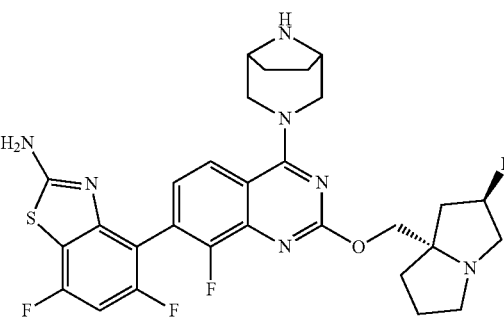

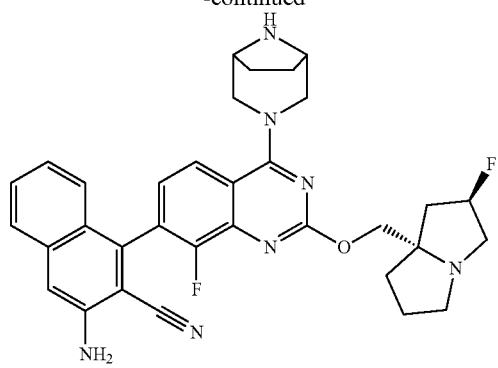
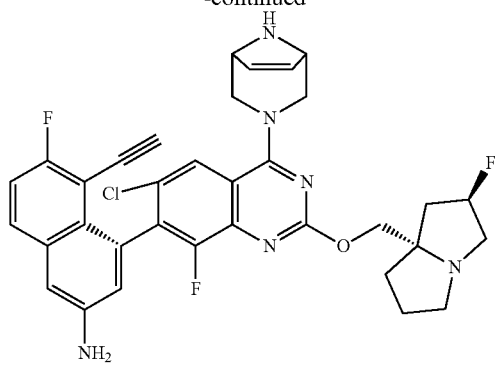
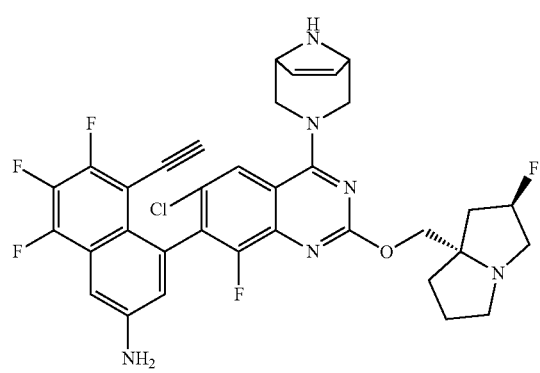
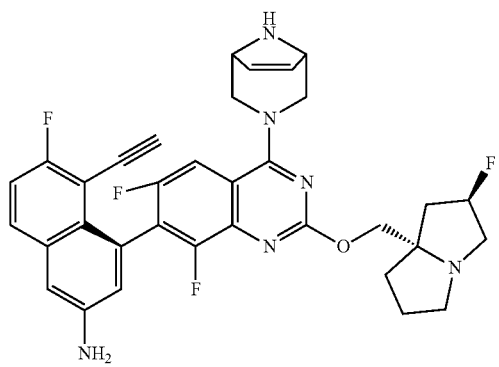
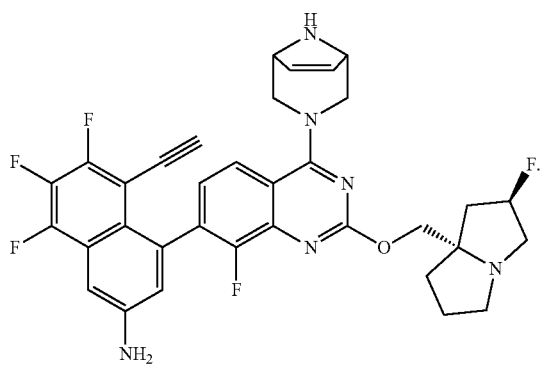 [SMILES: C#Cc1c(F)c(F)c(F)c2cc(N)cc(-c3ccc4c(N5CC6C=CC(C5)N6)nc(OC[C@@]56CCCN5C[C@H](F)C6)nc4c3F)c12]
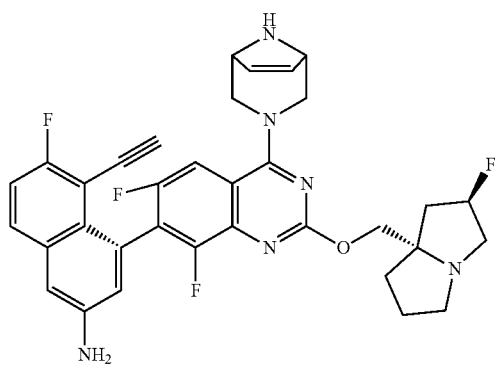
In some embodiments of the present disclosure, provided herein is a compound or a pharmaceutically acceptable salt thereof, wherein the compound is selected from
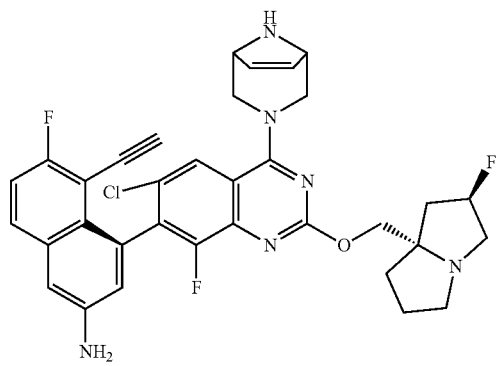
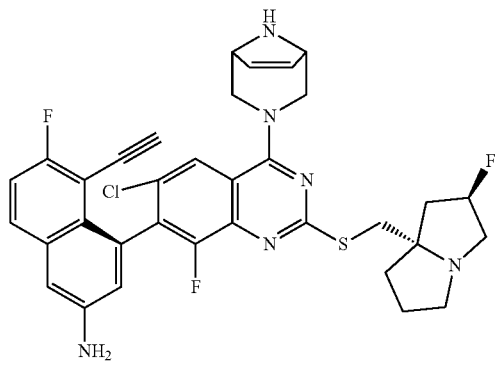

55
-continued
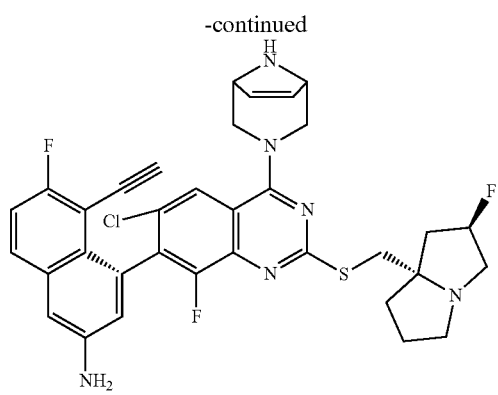
56
-continued
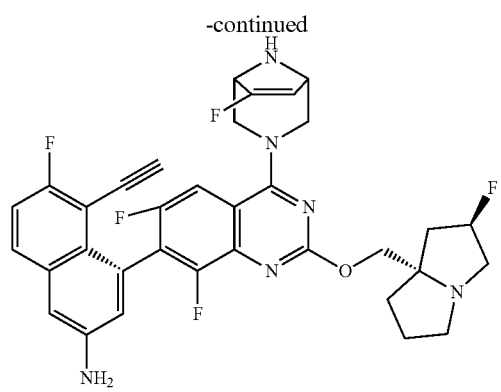
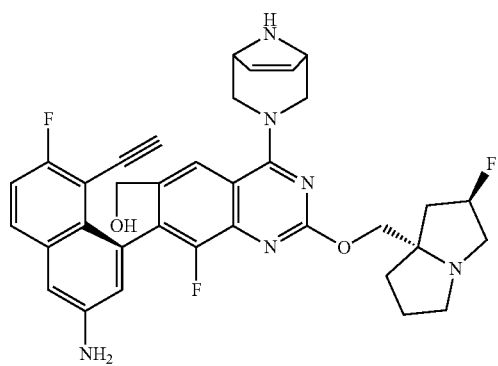
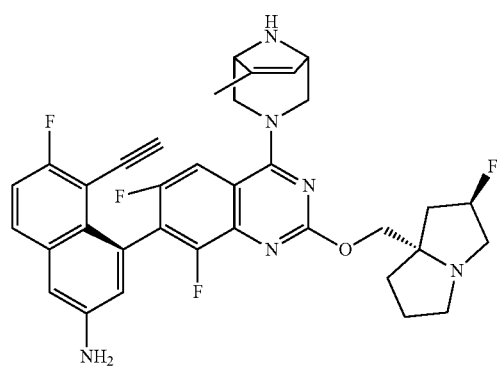
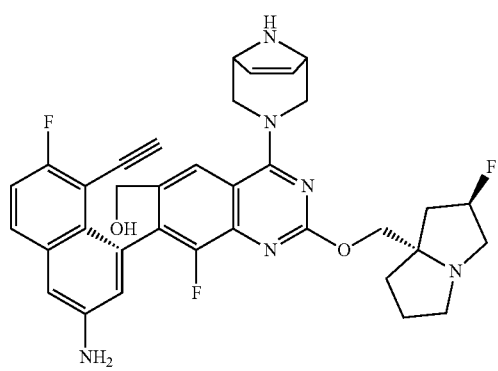
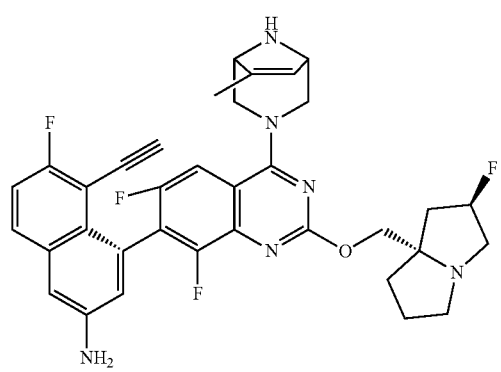
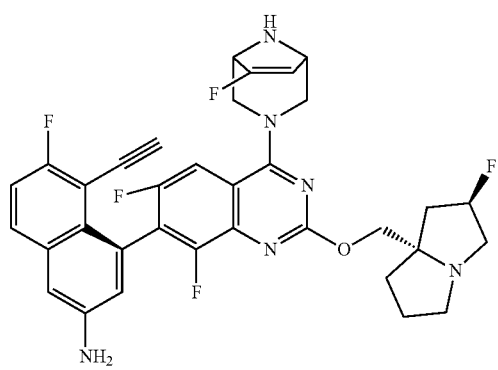
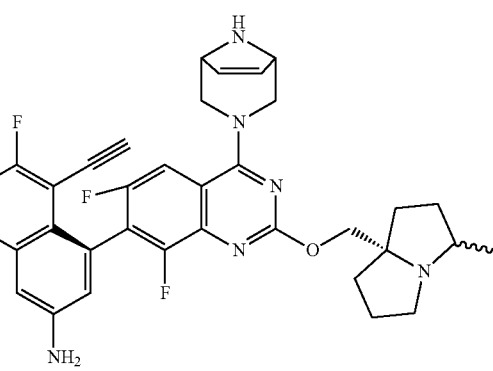

-continued
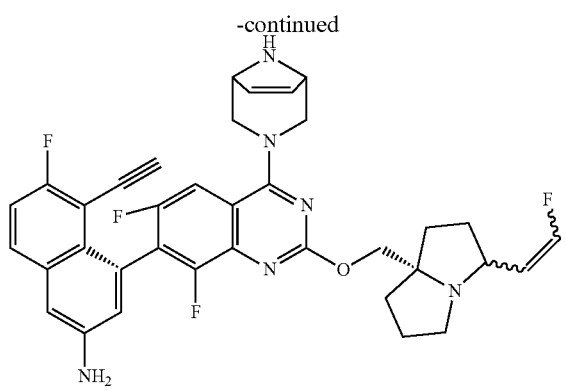
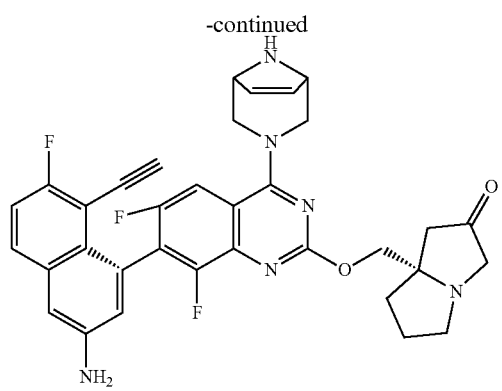
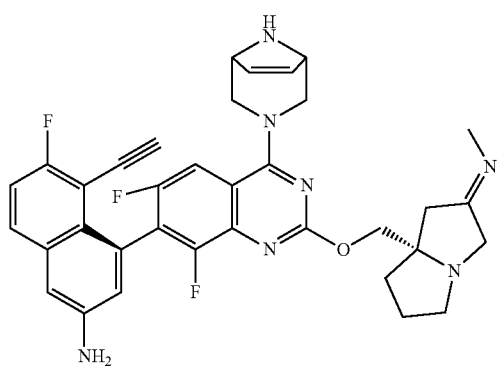
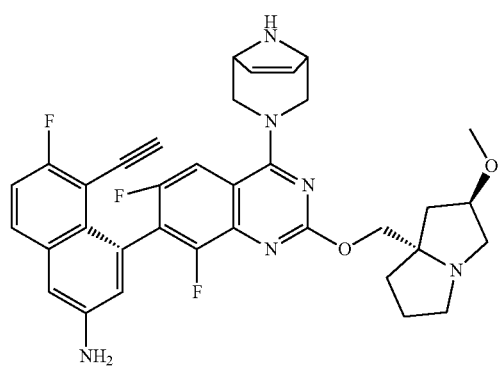
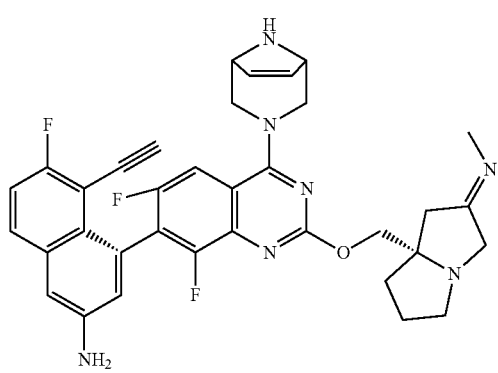
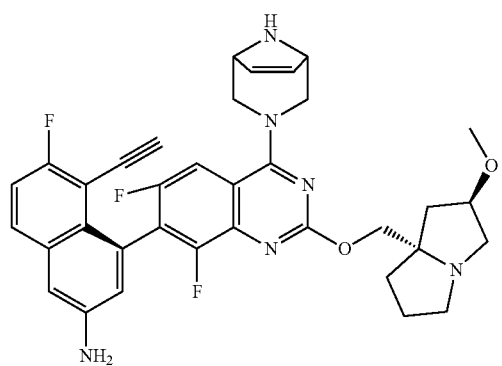
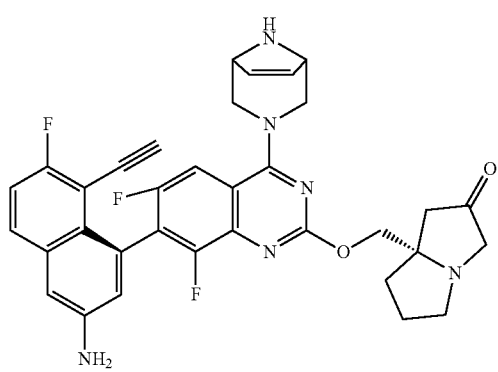
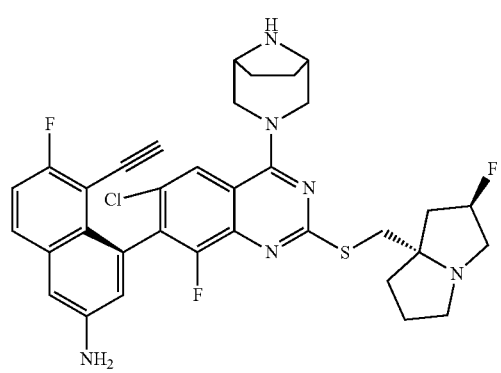

-continued
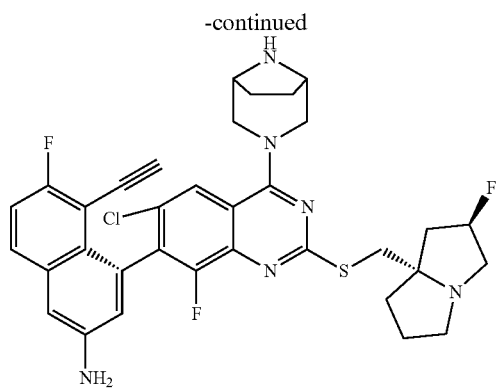
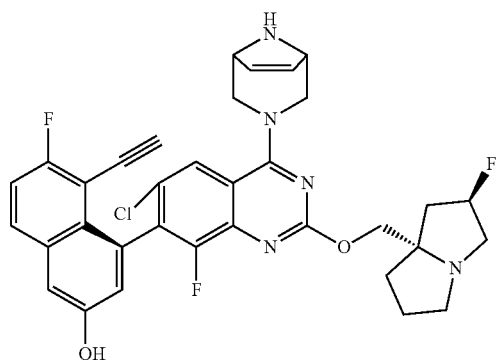
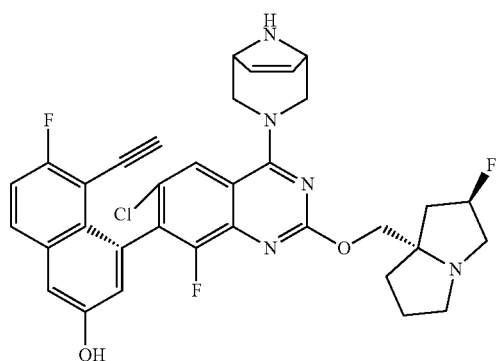
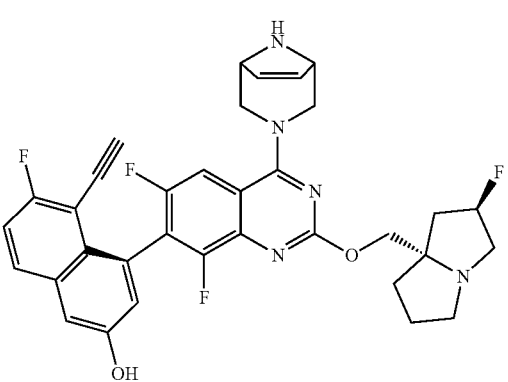
-continued
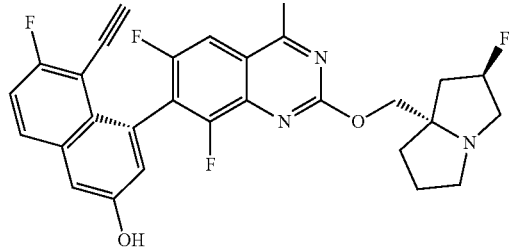
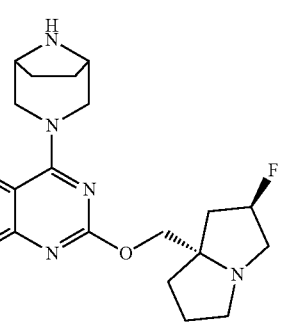
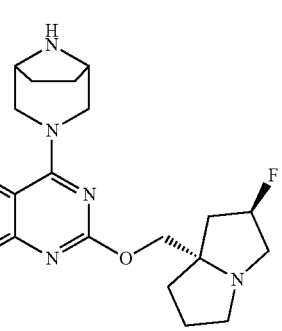
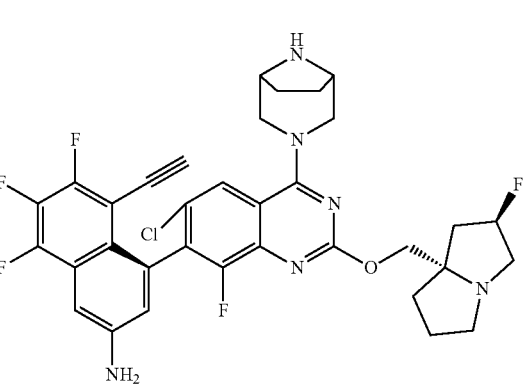

61
-continued
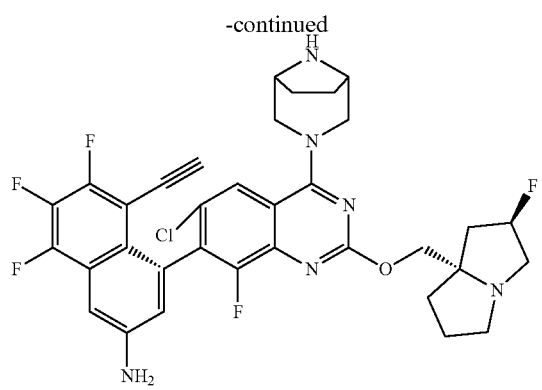
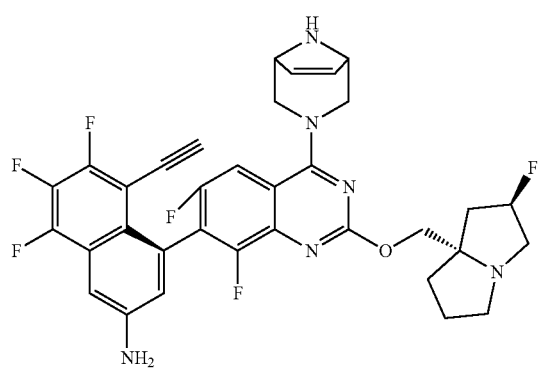
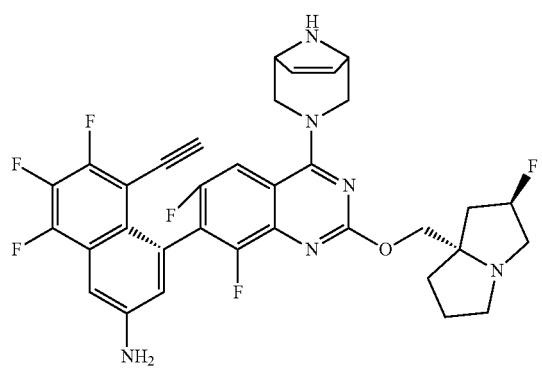
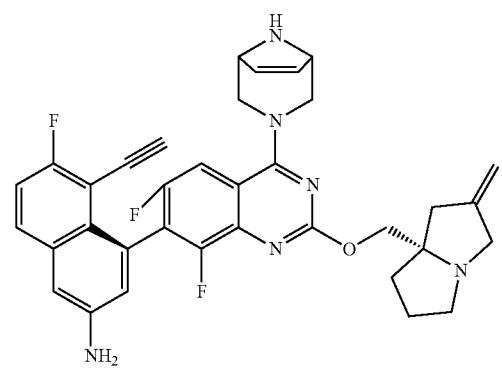
62
-continued
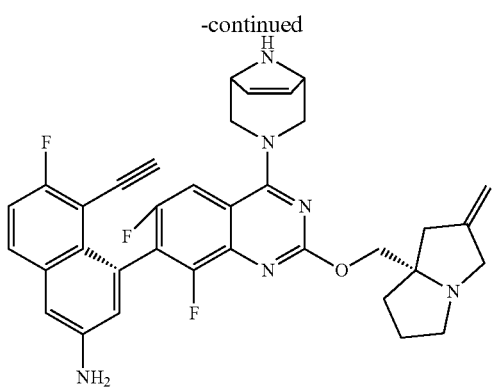
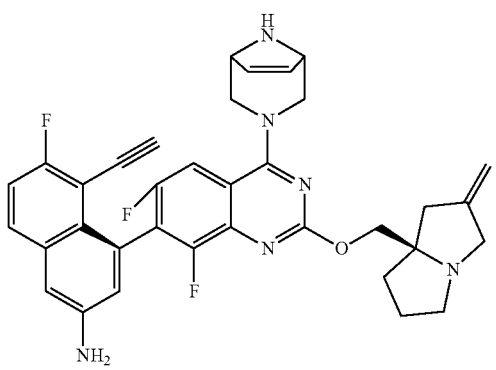
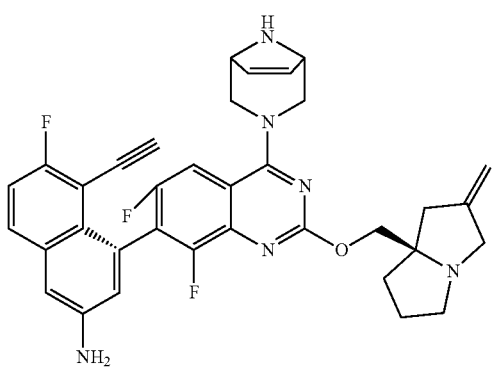
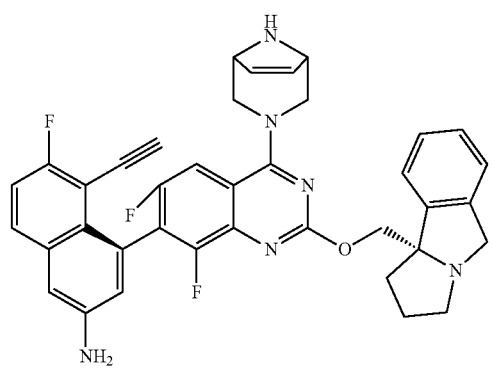

63
-continued
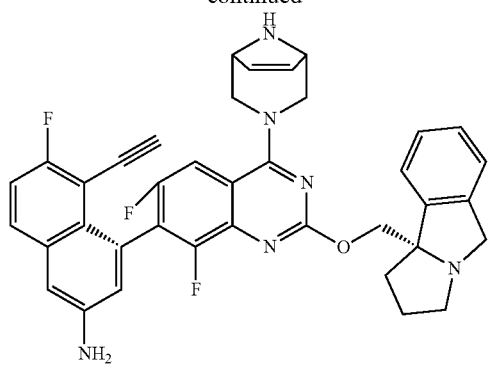
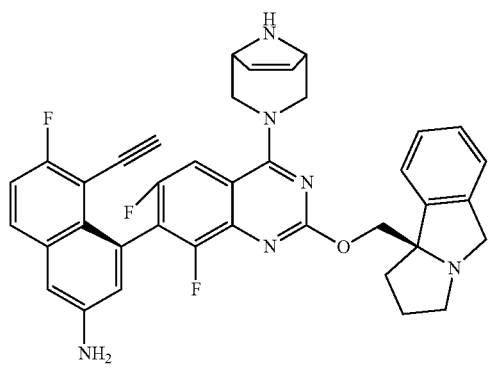
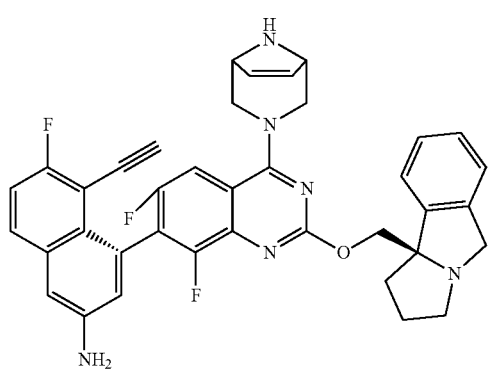
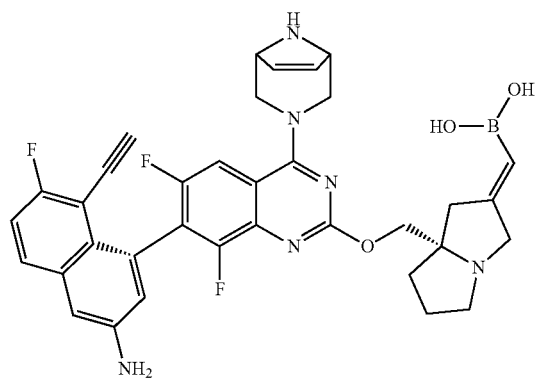
64
-continued
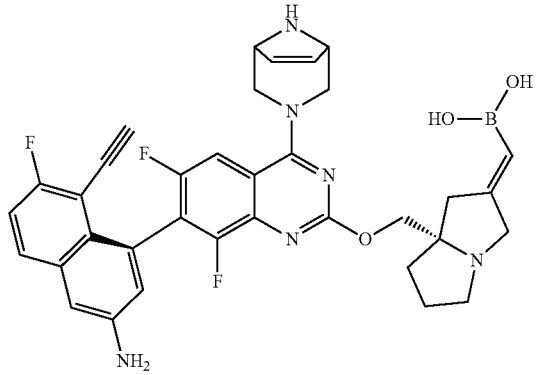
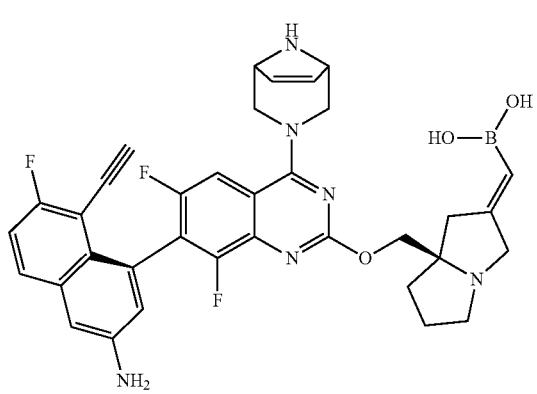
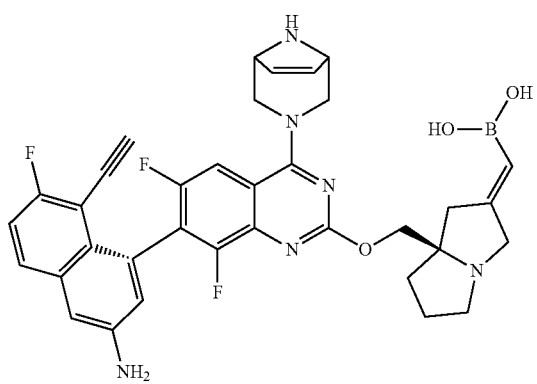
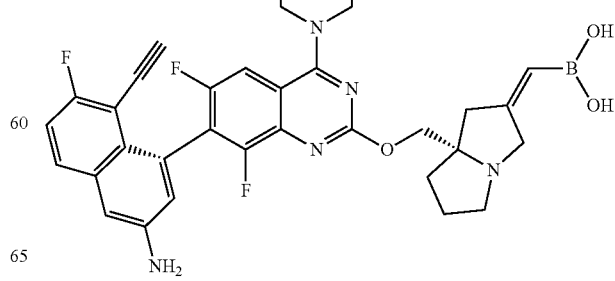

65
-continued
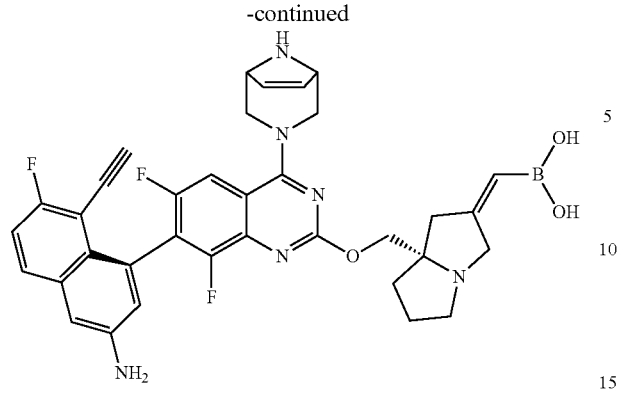
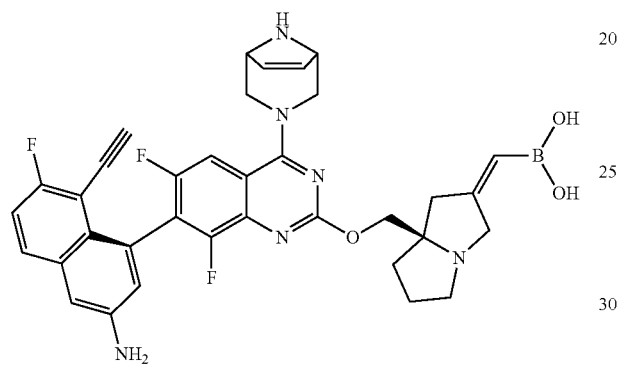
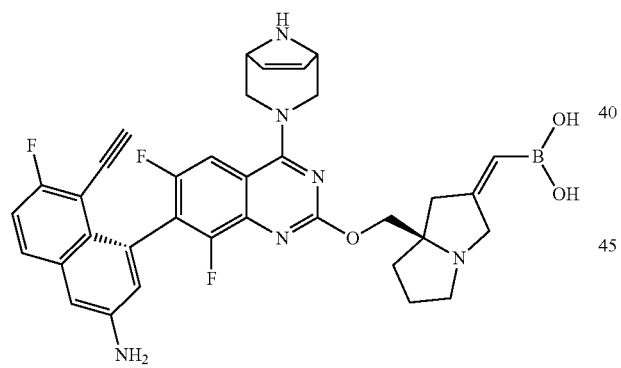
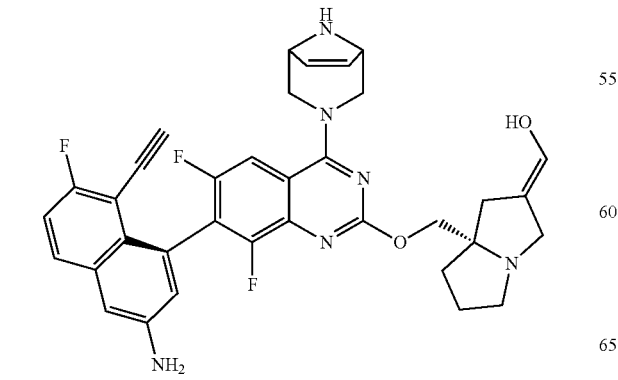
66
-continued
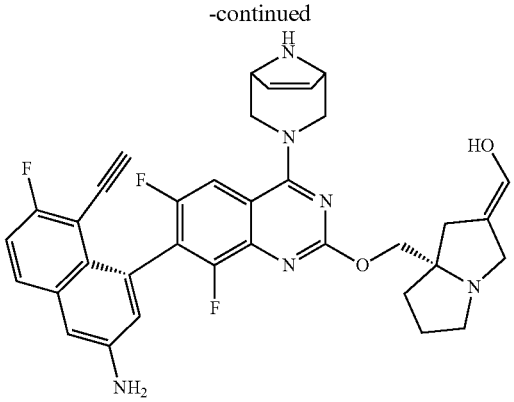
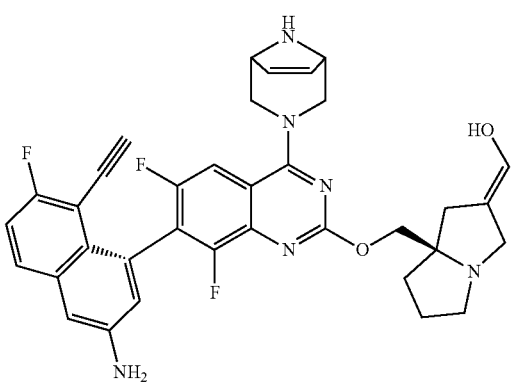
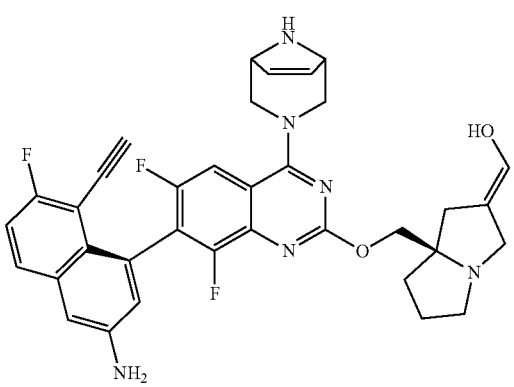
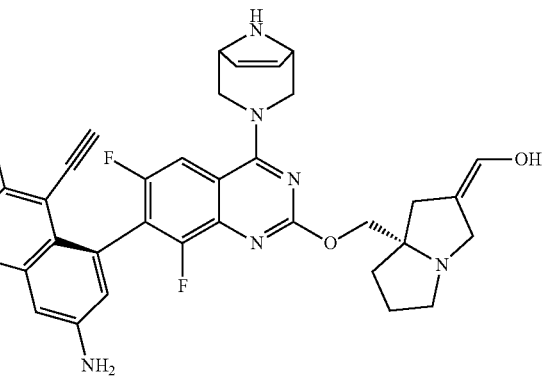

67
-continued
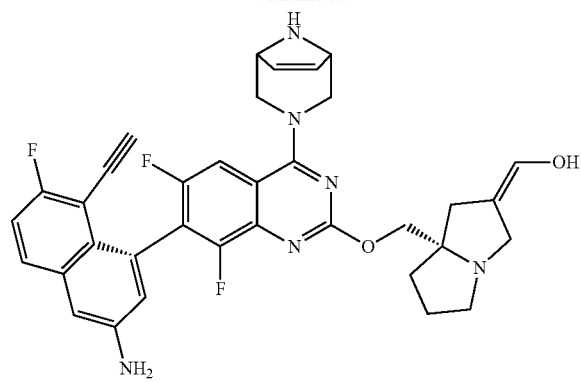
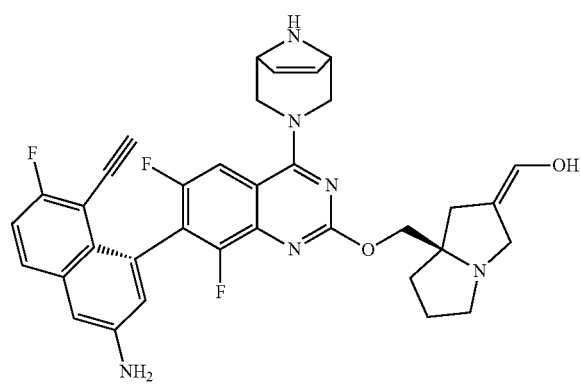
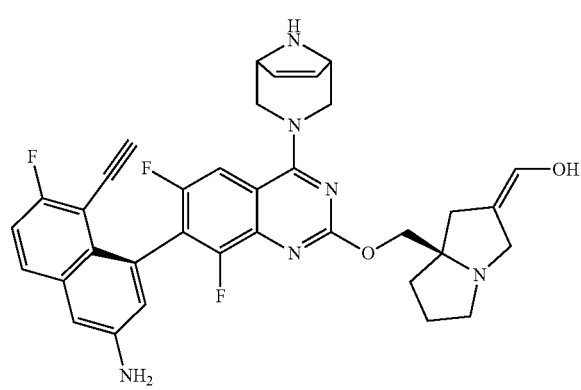
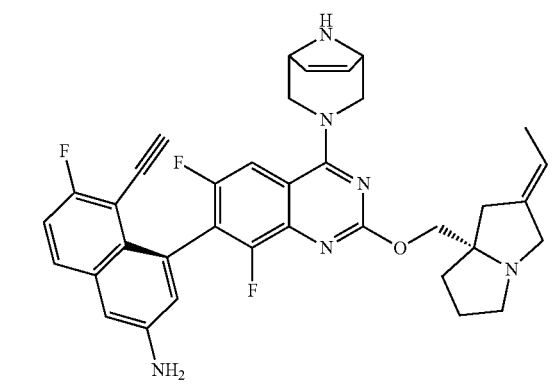
68
-continued
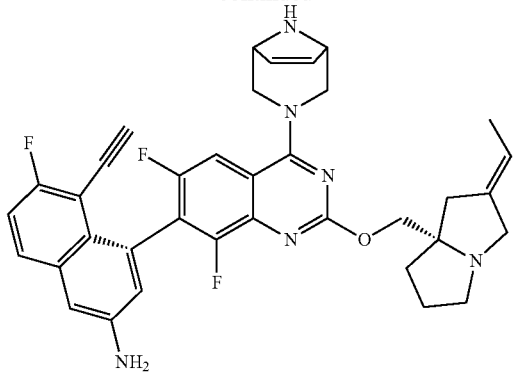
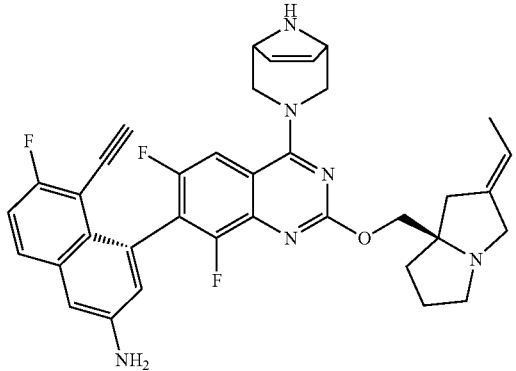
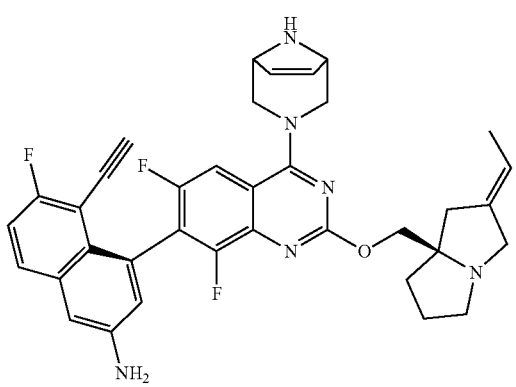
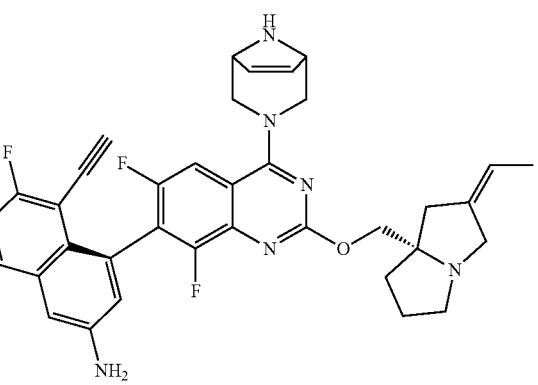

69
-continued
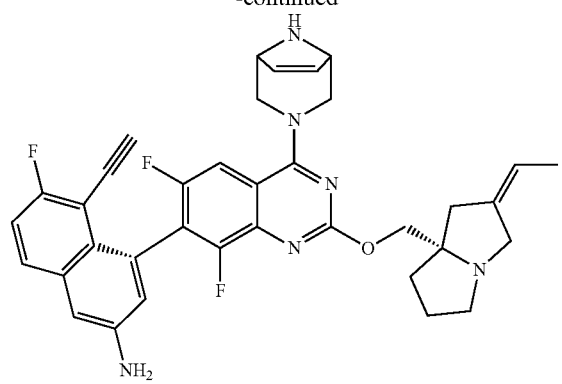
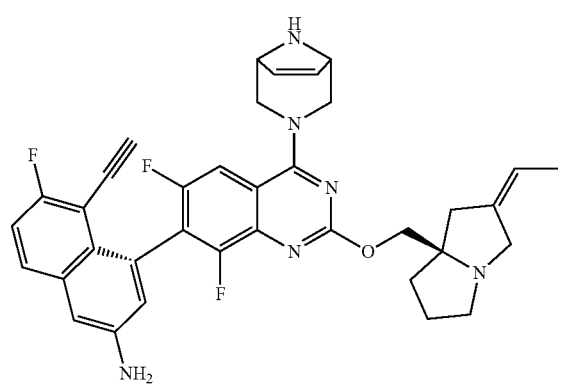
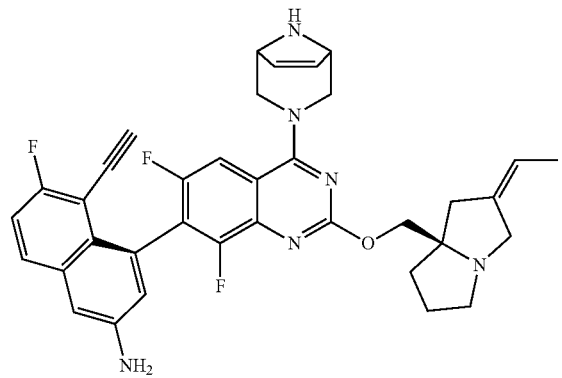
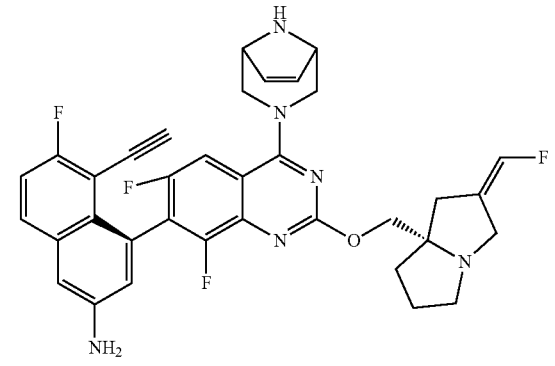
70
-continued
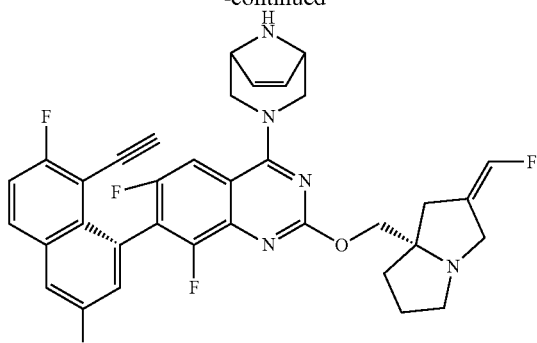
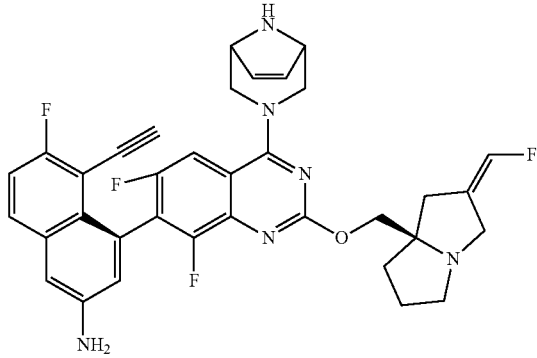
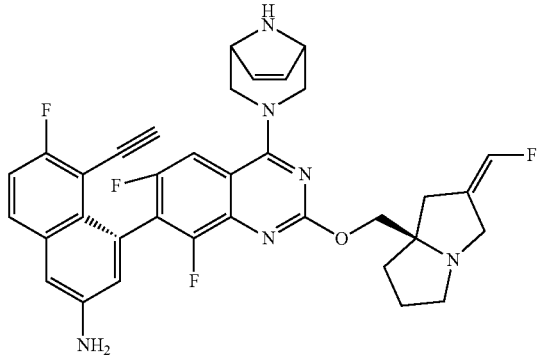
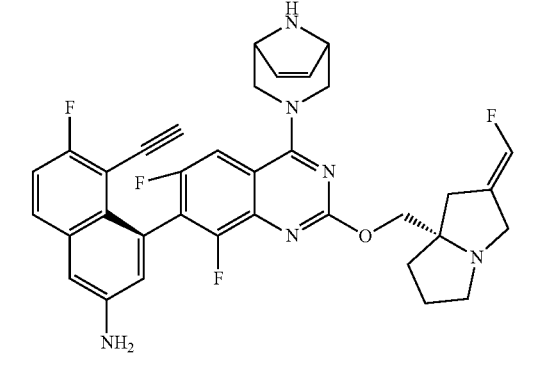

71
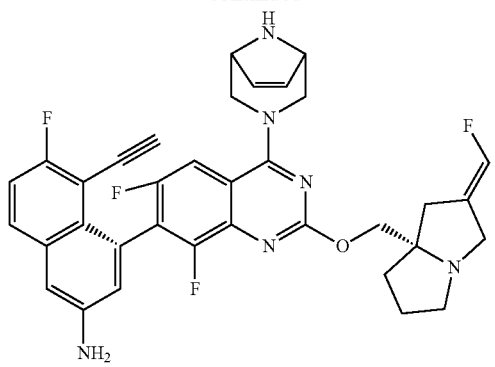
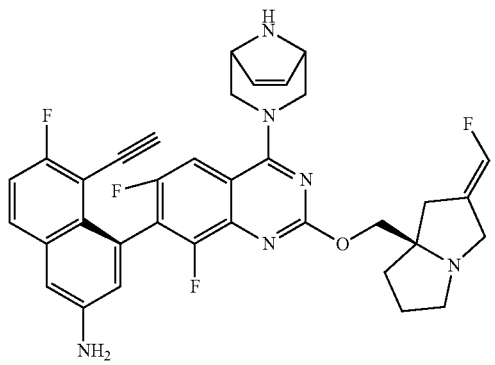
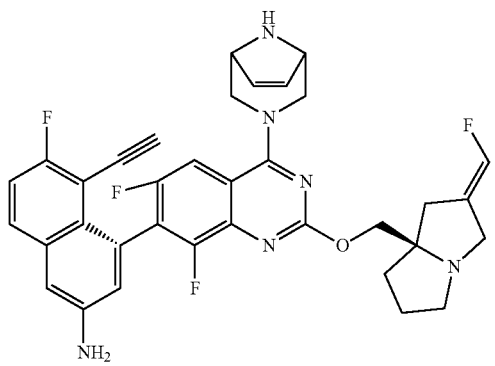
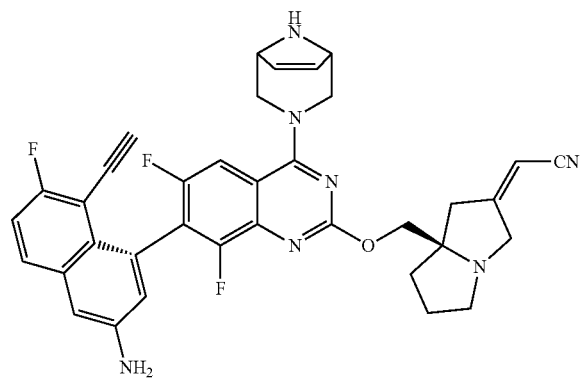
72
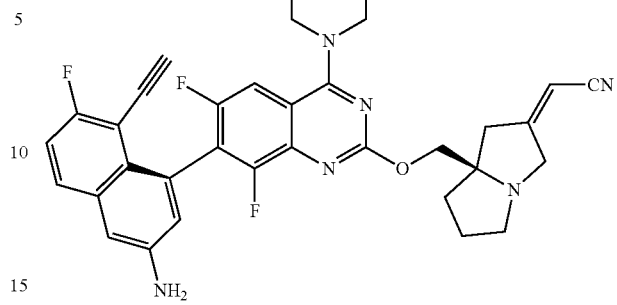
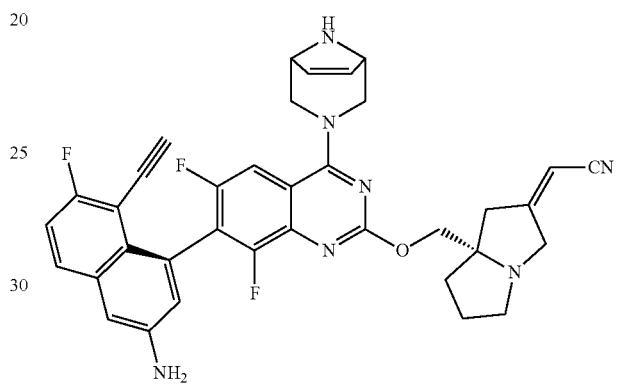
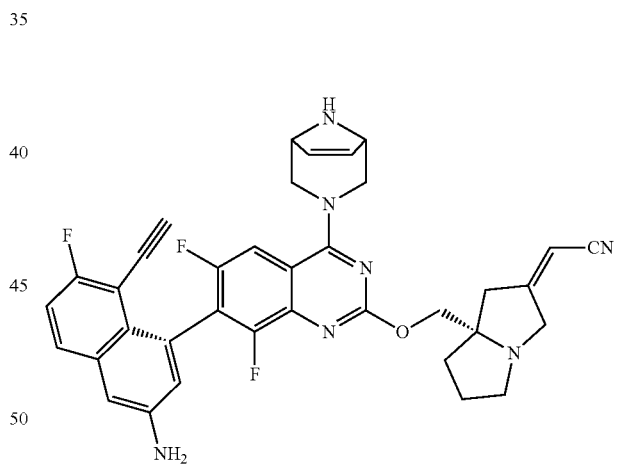
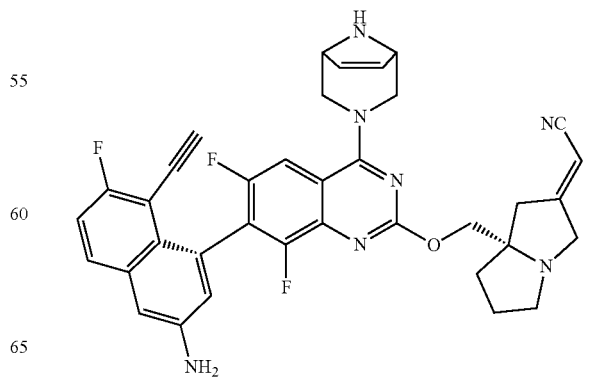

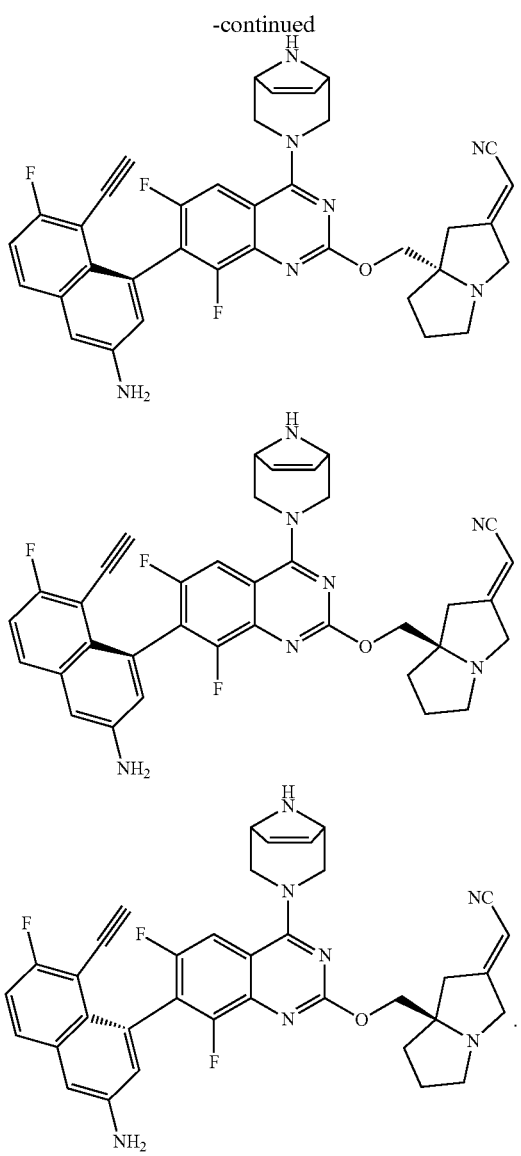

The present disclosure also provides use of the compound and a pharmaceutically acceptable salt thereof in the manufacture of a medicament for treating KRAS$^{G12D}$ mutation-related tumors.

In some embodiments of the present disclosure, the tumors refer to colorectal cancer and pancreatic cancer.

Technical Effect

The compounds of the present disclosure have good inhibitory effect on KRAS$^{G12D}$ protein, can effectively inhibit the downstream signal p-ERK, and have good activity of inhibiting cell proliferation on KRAS$^{G12D}$ mutated cells. In addition, the compounds of the present disclosure have good pharmacokinetic properties and good oral bioavailability.

Related Definitions

Unless otherwise specified, the following terms and phrases used herein are intended to have the following meanings. A specific term or phrase should not be considered indefinite or unclear in the absence of a particular definition, but should be understood in the conventional sense. When a trade name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" means a salt of compounds disclosed herein that is prepared by reacting the compound having a specific substituent disclosed herein with a relatively non-toxic acid or base. When compounds disclosed herein contain a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium or similar salts. When compounds disclosed herein contain a relatively basic functional group, an acid addition salt can be obtained by bringing the compound into contact with a sufficient amount of acid in a pure solution or a suitable inert solvent. Certain specific compounds disclosed herein contain both basic and acidic functional groups and can be converted to any base or acid addition salt.

The pharmaceutically acceptable salt disclosed herein can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

Compounds disclosed herein may be present in a specific geometric or stereoisomeric form. The present disclosure contemplates all such compounds, including cis and trans isomers, (−)- and (+)-enantiomers, (R)- and (S)-enantiomers, diastereoisomer, (I))-isomer, (L)-isomer, and a racemic mixture and other mixtures, for example, a mixture enriched in enantiomer or diastereoisomer, all of which are encompassed within the scope disclosed herein. The substituent such as alkyl may have an additional asymmetric carbon atom. All these isomers and mixtures thereof are encompassed within the scope disclosed herein.

Compounds disclosed herein may contain an unnatural proportion of atomic isotopes at one or more of the atoms that make up the compounds. For example, a compound may be labeled with a radioisotope such as tritium ($^3$H), iodine-125 ($^{125}$I) or C-14 ($^{14}$C). For another example, hydrogen can be replaced by heavy hydrogen to form a deuterated drug. The bond between deuterium and carbon is stronger than that between ordinary hydrogen and carbon. Compared with undeuterated drugs, deuterated drugs have advantages of reduced toxic side effects, increased drug stability, enhanced efficacy, and prolonged biological half-life of drugs. All changes in the isotopic composition of compounds disclosed herein, regardless of radioactivity, are included within the scope of the present disclosure.

The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted by a substituent, including deuterium and hydrogen variants, as long as the valence of the specific atom is normal and the substituted compound is stable. When the substituent is oxo (i.e., =O), it means two hydrogen atoms are substituted. Positions on an aromatic ring cannot be substituted by oxo. The term "optionally substituted" means an atom can be substituted by a substituent or not, unless otherwise specified, the species and number of the substituent may be arbitrary so long as being chemically achievable.

When any variable (such as R) occurs in the constitution or structure of the compound more than once, the definition of the variable at each occurrence is independent. Thus, for example, if a group is substituted by 0 to 2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When one of variables is a single bond, it means that the two groups linked by the single bond are connected directly. For example, when L in A-L-Z represents a single bond, the structure of A-L-Z is actually A-Z.

Unless otherwise specified, when a group has one or more connectable sites, any one or more sites of the group can be connected to other groups through chemical bonds. Where the connection position of the chemical bond is variable, and there is H atom(s) at a connectable site(s), when the connectable site(s) having H atom(s) is connected to the chemical bond, the number of H atom(s) at this site will correspondingly decrease as the number of the connected chemical bond increases, and the group will become a group of corresponding valence. The chemical bond between the site and other groups can be represented by a straight solid bond (╱), a straight dashed bond (╱), or a wavy line ($\sim\!\!\xi$—). For example, the straight solid bond in —OCH$_3$ indicates that the group is connected to other groups through the oxygen atom in the group; the straight dashed bond in

indicates that the group is connected to other groups group; the straight dashed bond in through two ends of the nitrogen atom in the group; the wavy line in

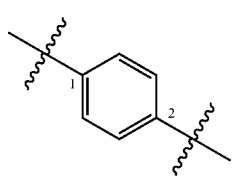 [SMILES: *c1ccc(*)cc1]

indicates that the group is connected to other groups through the 1- and 2-carbon atoms in the phenyl group;

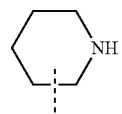

indicates that any connectable site on the piperidinyl group can be connected to other groups through one chemical bond, including at least four connection ways:

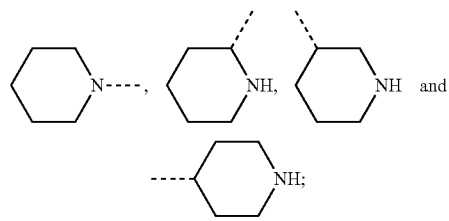

even if a H atom is drawn on —N—,

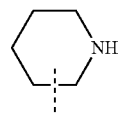

still includes the connection way:

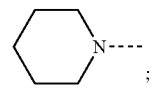

it's just that when one chemical bond is connected, the H at this site will be reduced by one, and the group will become the corresponding monovalent piperidinyl group.

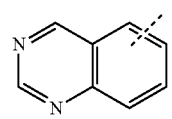

indicates that any connectable site on this quinazolinyl group can be connected to other groups through one chemical bond, including several connection ways:

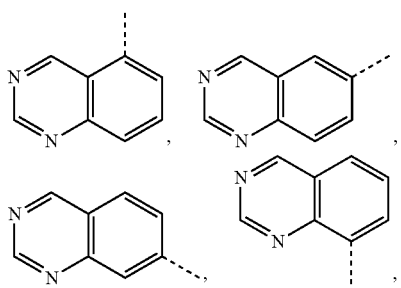

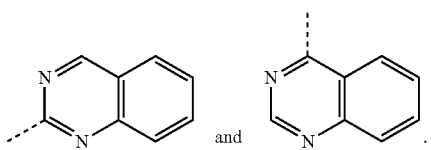

Unless otherwise specified, a wedged solid bond (⫽) and a wedged dashed bond (⫽) indicate the absolute configuration of a stereocenter; a straight solid bond (⫽) and a straight dashed bond (⫽) indicate the relative configuration of a stereocenter; a wavy line (⫽) indicates a wedged solid bond (⫽) or a wedged dashed bond (⫽); or a wavy line (⫽) indicates a straight solid bond (⫽) or a straight dashed bond (⫽).

Unless otherwise specified, when a double bond structure such as a carbon-carbon double bond, a carbon-nitrogen double bond, and a nitrogen-nitrogen double bond is present in a compound, and each atom on the double bond is attached to two different substituents (in the double bond containing a nitrogen atom, a pair of lone pair electrons on the nitrogen atom is considered as one of the substituents to which it is attached), the compound represents (Z) isomer, (E) isomer, if the atoms on the double bond in the compound are attached to their substituents by a wavy line (⫽). For example, the compound having following formula (A) means that the compound is present as a single isomer of formula (A-1) or formula (A-2) or as a mixture of two isomers of formula (A-1) and formula (A-2); and the compound having following formula (B) means that the compound is present as a single isomer of formula (B-1) or formula (B-2) or as a mixture of two isomers of formula (B-1) and formula (B-2). The compound having following formula (C) means that the compound is present as a single isomer of formula (C-1) or formula (C-2) or as a mixture of two isomers of formula (C-1) and formula (C-2).

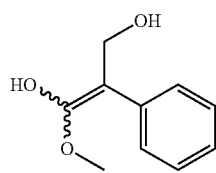

(A)

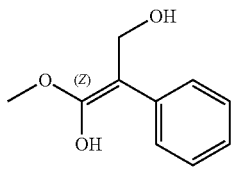

(A-1)

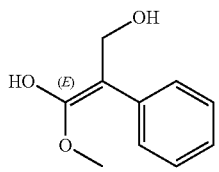

(A-2)

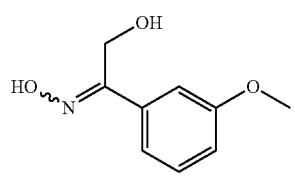

(B)

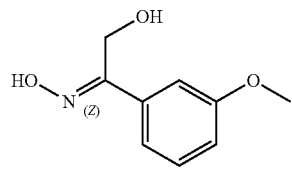

(B-1)

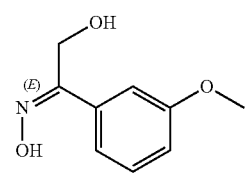

(B-2)

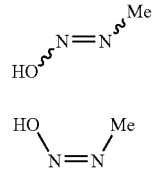

(C)

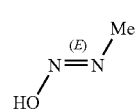

(C-1)

(C-2)

Unless otherwise specified, the term "atropisomer (or atropoisomer)" is a stereoisomer which has a particular spatial configuration, resulting from a restricted rotation about a single bond due to large steric hindrance. Certain compounds of the present disclosure may exist as atropisomers. The compounds disclosed herein include all atropisomers, which may be a pure individual atropisomer, enriched in one of atropisomers, or non-specific mixtures thereof. If the rotational potential energy around a single bond is high enough and the interconversion between conformations is slow enough, isomers are allowed to be isolated. For example,

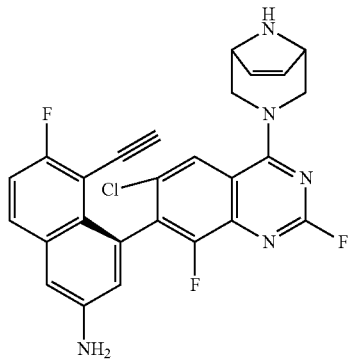

and

-continued

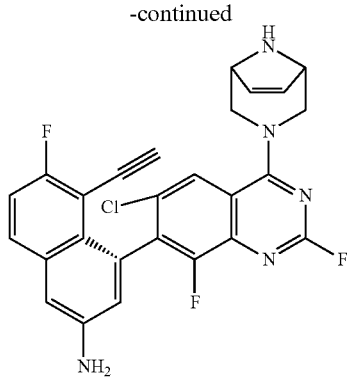

are a pair of atropisomers, in which ⟋ on the naphthalene ring indicates that the stereo orientation of this side is outward, and indicates that the stereo orientation of this side is inward.

Unless otherwise specified, the term "halo" or "halogen" by itself or as part of another substituent represents a fluorine (F), chlorine (Cl), bromine (Br) or iodine (I) atom.

Unless otherwise specified, the term "$C_{1-3}$ alkyl" is used to indicate a linear or branched saturated hydrocarbon group consisting of 1 to 3 carbon atoms. The $C_{1-3}$ alkyl group includes $C_{1-2}$ and $C_{2-3}$ alkyl groups and the like. It may be monovalent (e.g., methyl), divalent (e.g., methylene) or multivalent (e.g., methenyl). Examples of $C_{1-3}$ alkyl group include, but are not limited to, methyl (Me), ethyl (Et), propyl (including n-propyl and isopropyl), and the like.

Unless otherwise specified, the term "$C_{1-3}$ alkoxy" means an alkyl group containing 1 to 3 carbon atoms and attached to the remainder of a molecule by an oxygen atom. The $C_{1-3}$ alkoxy group includes $C_{1-2}$, $C_{2-3}$, $C_3$ and $C_2$ alkoxy groups, and the like. Examples of $C_{1-3}$ alkoxy groups include, but are not limited to, methoxy, ethoxy, propoxy (including n-propoxy and isopropoxy), and the like.

Unless otherwise specified, the term "$C_{1-3}$ alkylamino" means an alkyl group containing 1 to 3 carbon atoms and attached to the remainder of a molecule by an amino group. The $C_{1-3}$ alkylamino group includes $C_{1-2}$, $C_3$ and $C_2$ alkylamino groups and the like. Examples of $C_{1-3}$ alkylamino groups include, but are not limited to —NHCH$_3$, —N(CH$_3$)$_2$, —NHCH$_2$CH$_3$, —N(CH$_3$) CH$_2$CH$_3$, —NHCH$_2$CH$_2$CH$_3$, —NHCH$_2$ (CH$_3$)$_2$, and the like.

Unless otherwise specified, "$C_{2-3}$ alkenyl" is used to represent a linear or branched hydrocarbon group composed of 2 to 3 carbon atoms containing at least one carbon-carbon double bond, wherein the carbon-carbon double bond can be located at any position of the group. The $C_{2-3}$ alkenyl includes $C_3$ and $C_2$ alkenyl. The $C_{2-3}$ alkenyl may be monovalent, divalent or multivalent. Examples of the $C_{2-3}$ alkenyl include, but are not limited to, vinyl, propenyl, and the like.

Unless otherwise specified, "$C_{2-3}$ alkynyl" is used to represent a linear or branched hydrocarbon group composed of 2 to 3 carbon atoms containing at least one carbon-carbon triple bond, wherein the carbon-carbon triple bond can be located at any position of the group. It may be monovalent, divalent or multivalent. The $C_{2-3}$ alkynyl includes $C_3$ and $C_2$ alkynyl. Examples of the $C_{2-3}$ alkynyl include, but are not limited to, ethynyl, propynyl, and the like.

Unless otherwise specified, "$C_{3-4}$ cycloalkyl" means a saturated cyclic hydrocarbon group composed of 3 to 4 carbon atoms, which is a single ring system. The $C_{3-4}$ cycloalkyl includes $C_3$ and $C_4$ cycloalkyl, etc.; it may be monovalent, divalent or polyvalent. Examples of $C_{3-4}$ cycloalkyl include, but are not limited to, cyclopropyl, cyclobutyl, and the like.

Unless otherwise specified, "$C_{2-4}$ alkenyl" is used to represent a linear or branched hydrocarbon group composed of 2 to 4 carbon atoms containing at least one carbon-carbon double bond, wherein the carbon-carbon double bond can be located at any position of the group. The $C_{2-4}$ alkenyl includes $C_{2-3}$, $C_4$, $C_3$ and $C_2$ alkenyl, etc. The $C_{2-4}$ alkenyl may be monovalent, divalent or multivalent. Examples of the $C_{2-4}$ alkenyl include, but are not limited to, vinyl, propenyl, butenyl, butadienyl and the like.

Unless otherwise specified, "$C_{2-4}$ alkynyl" is used to represent a linear or branched hydrocarbon group composed of 2 to 4 carbon atoms containing at least one carbon-carbon triple bond, wherein the carbon-carbon triple bond can be located at any position of the group. The $C_{2-4}$ alkynyl includes $C_{2-3}$, $C_4$, $C_3$ and $C_2$ alkynyl, etc. It may be monovalent, divalent or multivalent. Examples of the $C_{2-4}$ alkynyl include, but are not limited to, ethynyl, propynyl, butynyl, and the like.

Unless otherwise specified, the terms "$C_{6-10}$ aromatic ring" and "$C_{6-10}$ aryl" may be used interchangeably in this disclosure. The term "$C_{6-10}$ aromatic ring" or "$C_{6-10}$ aryl" means a cyclic hydrocarbon group having a conjugated pi electron system and composed of 6 to 10 carbon atoms. It may be a monocyclic, fused bicyclic or fused tricyclic ring system, wherein each ring is aromatic. It may be monovalent, divalent or multivalent. The $C_{6-10}$ aryl includes $C_{6-9}$, $C_9$, $C_{10}$ and $C_6$ aryl, etc. Examples of $C_{6-10}$ aryl include, but are not limited to, phenyl, naphthyl (including 1-naphthyl and 2-naphthyl, etc.).

Unless otherwise specified, the terms "5- to 10-membered heteroaromatic ring" and "5- to 10-membered heteroaryl" may be used interchangeably. The term "5- to 10-membered heteroaryl" means a cyclic group having a conjugated pi electron system and composed of 5 to 10 ring atoms, in which 1, 2, 3 or 4 ring atoms are heteroatoms independently selected from O, S and N, and the remainder is carbon atoms. It may be a monocyclic, fused bicyclic or fused tricyclic ring system, wherein each ring is aromatic, and wherein the nitrogen atom is optionally quaternized and the nitrogen and sulfur heteroatoms are optionally oxidized (i.e., NO and S(O) p, p is 1 or 2). A 5- to 10-membered heteroaryl can be attached to the remainder of the molecule through a heteroatom or a carbon atom. The 5- to 10-membered heteroaryl group includes 5- to 8-membered, 5- to 7-membered, 5- to 6-membered, 5-membered and 6-membered heteroaryl groups. Examples of the 5-10 membered heteroaryl include, but are not limited to, pyrrolyl (including N-pyrrolyl, 2-pyrrolyl, 3-pyrrolyl, and the like), pyrazolyl (including 2-pyrazolyl and 3-pyrazolyl, and the like), imidazolyl (including N-imidazolyl, 2-imidazolyl, 4-imidazolyl, and 5-imidazolyl, and the like), oxazolyl (including 2-oxazolyl, 4-oxazolyl, and 5-oxazolyl, and the like), triazolyl (1H-1,2,3-triazolyl, 2H-1,2,3-triazolyl, 1H-1,2,4-triazolyl and 4H-1,2,4-triazolyl, and the like), tetrazolyl, isoxazolyl (3-isoxazolyl, 4-isoxazolyl and 5-isoxazolyl, and the like), thiazolyl (including 2-thiazolyl, 4-thiazolyl and 5-thiazolyl, and the like), furyl (including 2-furyl and 3-furyl, and the like), thienyl (including 2-thienyl and 3-thienyl, and the like), pyridyl (including 2-pyridyl, 3-pyridyl and 4-pyridyl, and the like), pyrazinyl or pyrimidinyl (including 2-pyrimidinyl and 4-pyrimidinyl, and the like), benzothiazolyl (including 5-benzothiazolyl, and the like), purinyl, benzimidazolyl (including 2-benzimidazolyl, and the like), benzoxazolyl, indolyl (including 5-indolyl, and the like), isoquinolyl (including 1-isoquinolyl, 5-isoquinolyl, and the like), quinoxalinyl (including 2-quinoxalinyl, 5-quinoxalinyl, and the like) or quinolyl (including 3-quinolyl, 6-quinolyl, and the like).

Unless otherwise specified, $C_{n-n+m}$ or $C_n-C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, also includes any range from n to n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$ and $C_{9-12}$, etc.; similarly, n membered to n+m membered indicates that the number of atoms on a ring is n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, also includes any range from n to n+m, for example, 3-12 membered ring includes 3-6 membered ring, 3-9 membered ring, 5-6 membered ring, 5-7 membered ring, 6-7 membered ring, 6-8 membered ring, and 6-10 membered ring, and the like.

Compounds disclosed herein can be prepared by a variety of synthetic methods well known to those skilled in the art, including the following enumerated embodiment, the embodiment formed by the following enumerated embodiment in combination with other chemical synthesis methods, and equivalent replacement well known to those skilled in the art. Alternative embodiments include, but are not limited to the embodiment disclosed herein.

The structures of compounds disclosed herein can be confirmed by conventional methods well known to those skilled in the art. If the present disclosure relates to an absolute configuration of a compound, the absolute configuration can be confirmed by conventional techniques in the art, such as single crystal X-Ray diffraction (SXRD). In the single crystal X-Ray diffraction (SXRD), the diffraction intensity data of the cultivated single crystal is collected using a Bruker D8 venture diffractometer with a light source of CuKα radiation in a scanning mode of φ/ω scan; after collecting the relevant data, the crystal structure is further analyzed by the direct method (Shelxs97) to confirm the absolute configuration.

Solvents used in the present disclosure are commercially available. Hr represents hour; the ratio of eluents in column chromatography purification is volume ratio; HCl represents hydrochloric acid; NaOH represents sodium hydroxide; EtOH represents ethanol; Boc represents tert-butoxycarbonyl; TIPS represents triisopropylsilyl; PMB represents p-methoxybenzyl; Tf represents trifluoromethanesulfonyl; MOM represents methylene methyl ether; Fmoc represents fluorenylmethyloxycarbonyl.

Compounds are named according to general naming principles in the art or by ChemDraw® software, and commercially available compounds are named with their vendor directory names.

DETAILED DESCRIPTION OF THE INVENTION

The present disclosure is described in detail below by means of examples. However, it is not intended that these examples have any disadvantageous limitations to the present disclosure. The present disclosure has been described in detail herein, and embodiments are also disclosed herein. It will be apparent to those skilled in the art that various changes and modifications may be made to the embodiments disclosed herein without departing from the spirit and scope disclosed herein.

Example 1

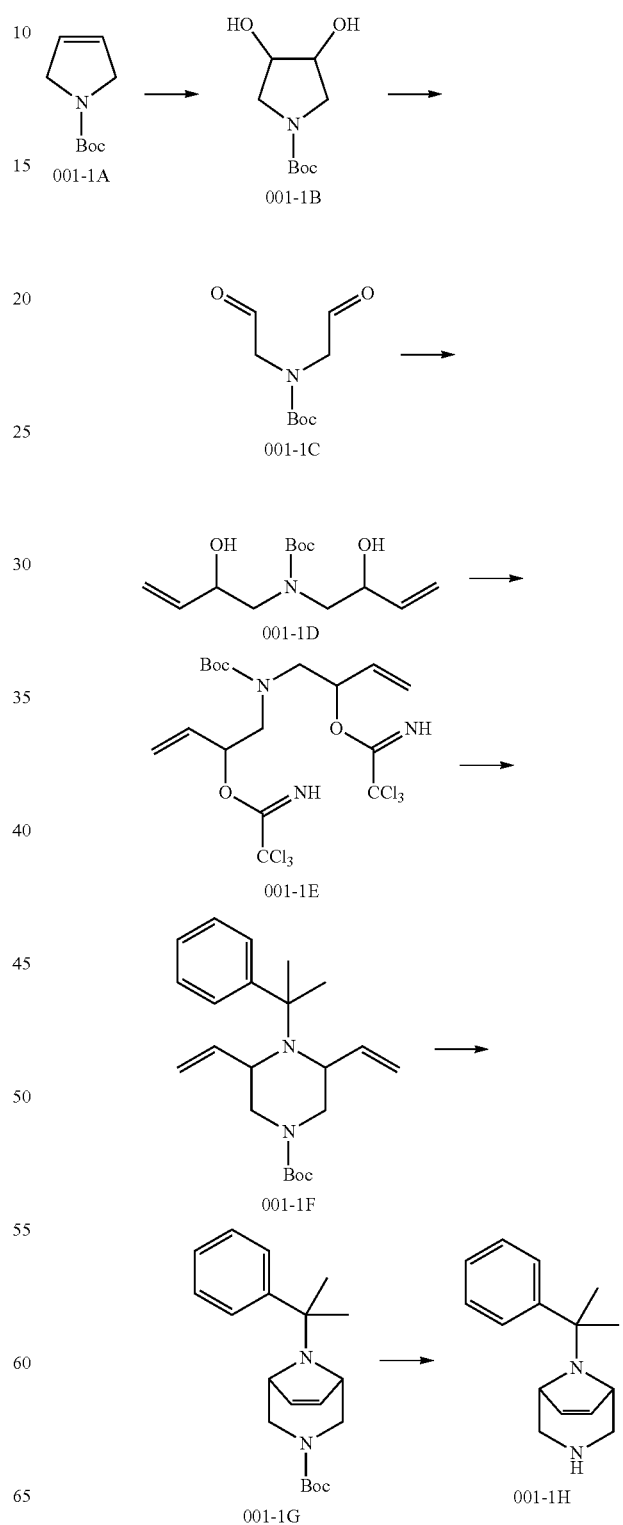

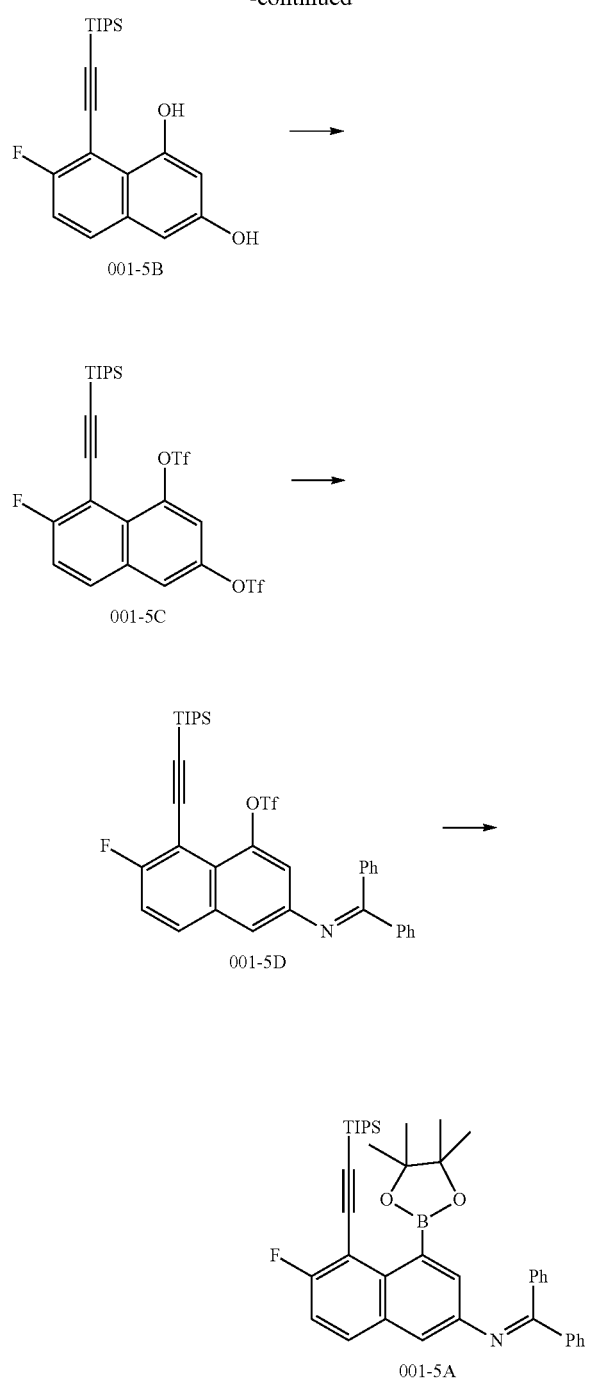
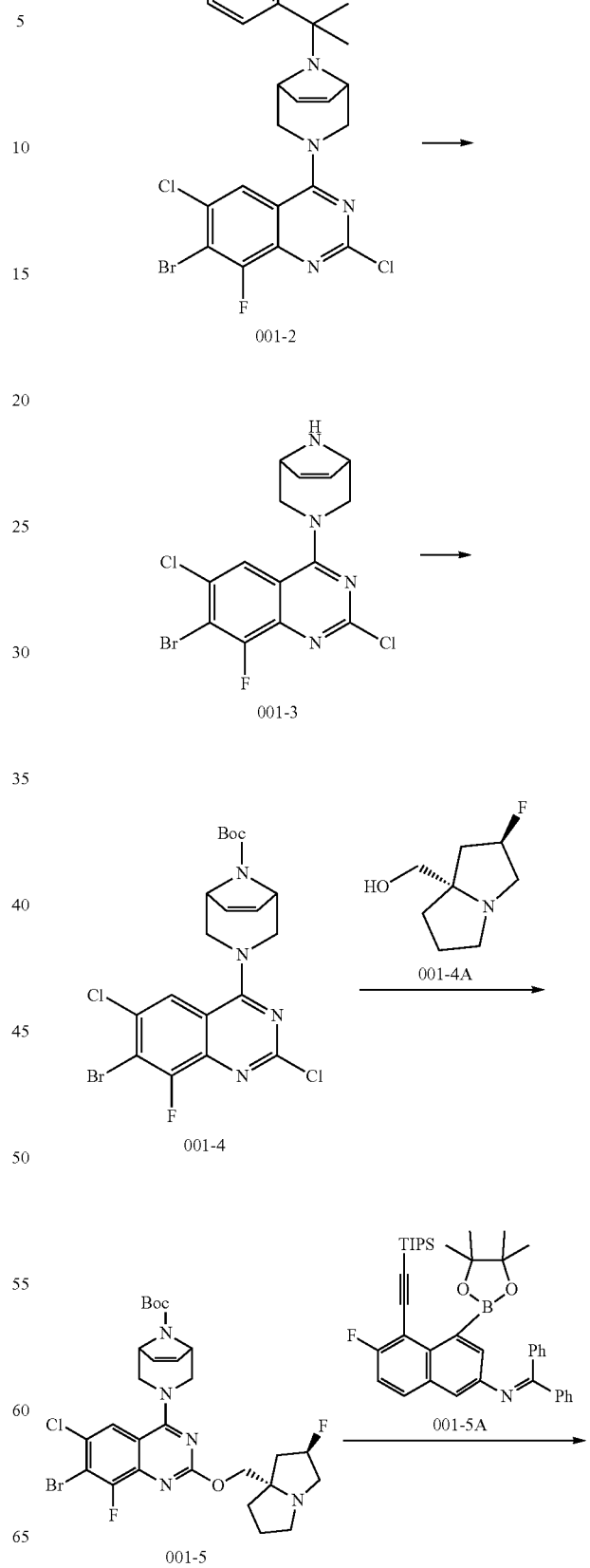

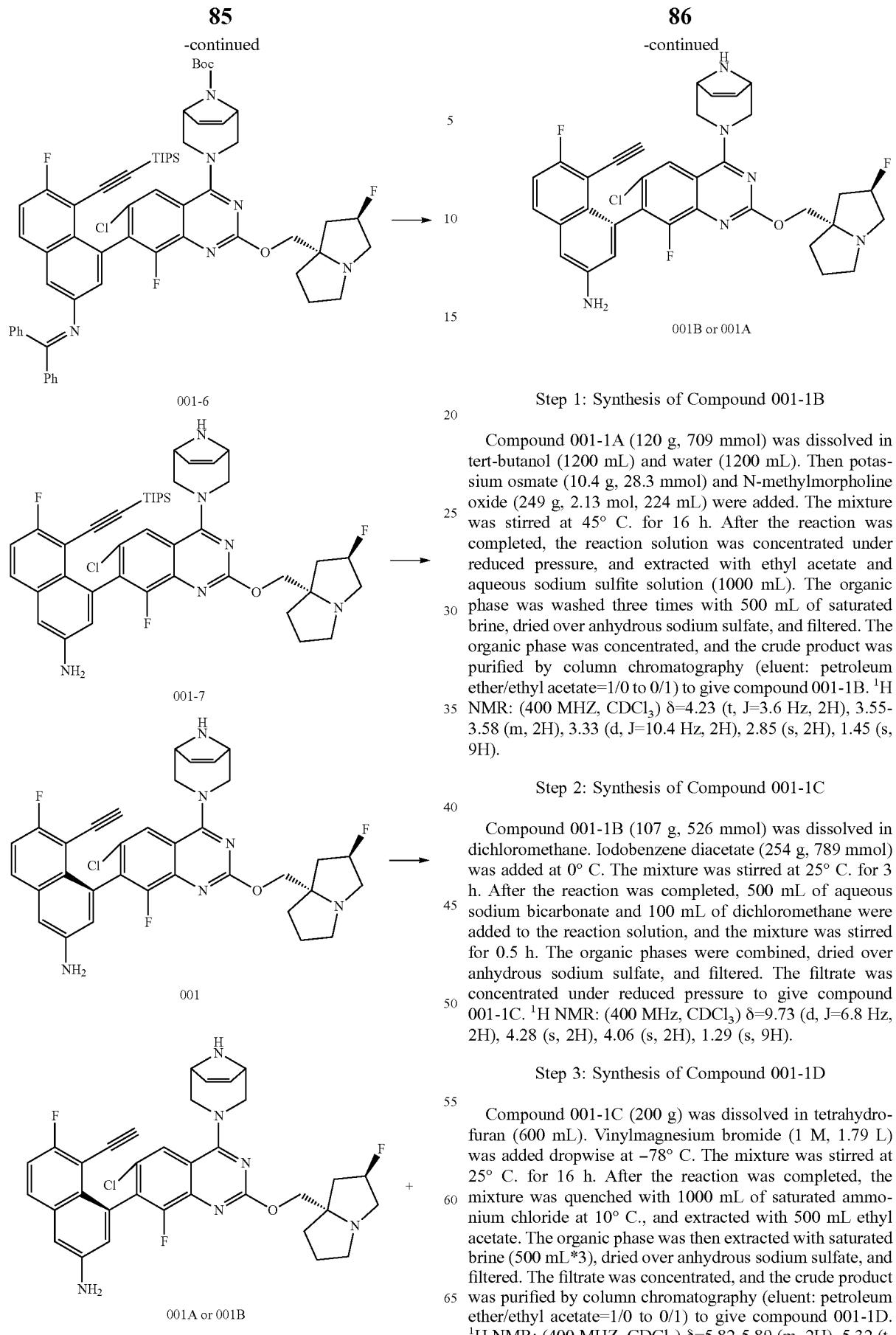

Step 1: Synthesis of Compound 001-1B

Compound 001-1A (120 g, 709 mmol) was dissolved in tert-butanol (1200 mL) and water (1200 mL). Then potassium osmate (10.4 g, 28.3 mmol) and N-methylmorpholine oxide (249 g, 2.13 mol, 224 mL) were added. The mixture was stirred at 45° C. for 16 h. After the reaction was completed, the reaction solution was concentrated under reduced pressure, and extracted with ethyl acetate and aqueous sodium sulfite solution (1000 mL). The organic phase was washed three times with 500 mL of saturated brine, dried over anhydrous sodium sulfate, and filtered. The organic phase was concentrated, and the crude product was purified by column chromatography (eluent: petroleum ether/ethyl acetate=1/0 to 0/1) to give compound 001-1B. $^1$H NMR: (400 MHZ, CDCl$_3$) δ=4.23 (t, J=3.6 Hz, 2H), 3.55-3.58 (m, 2H), 3.33 (d, J=10.4 Hz, 2H), 2.85 (s, 2H), 1.45 (s, 9H).

Step 2: Synthesis of Compound 001-1C

Compound 001-1B (107 g, 526 mmol) was dissolved in dichloromethane. Iodobenzene diacetate (254 g, 789 mmol) was added at 0° C. The mixture was stirred at 25° C. for 3 h. After the reaction was completed, 500 mL of aqueous sodium bicarbonate and 100 mL of dichloromethane were added to the reaction solution, and the mixture was stirred for 0.5 h. The organic phases were combined, dried over anhydrous sodium sulfate, and filtered. The filtrate was concentrated under reduced pressure to give compound 001-1C. $^1$H NMR: (400 MHz, CDCl$_3$) δ=9.73 (d, J=6.8 Hz, 2H), 4.28 (s, 2H), 4.06 (s, 2H), 1.29 (s, 9H).

Step 3: Synthesis of Compound 001-1D

Compound 001-1C (200 g) was dissolved in tetrahydrofuran (600 mL). Vinylmagnesium bromide (1 M, 1.79 L) was added dropwise at −78° C. The mixture was stirred at 25° C. for 16 h. After the reaction was completed, the mixture was quenched with 1000 mL of saturated ammonium chloride at 10° C., and extracted with 500 mL ethyl acetate. The organic phase was then extracted with saturated brine (500 mL*3), dried over anhydrous sodium sulfate, and filtered. The filtrate was concentrated, and the crude product was purified by column chromatography (eluent: petroleum ether/ethyl acetate=1/0 to 0/1) to give compound 001-1D. $^1$H NMR: (400 MHZ, CDCl$_3$) δ=5.82-5.89 (m, 2H), 5.32 (t, J=11.6 Hz, 2H), 5.16-5.19 (m, 2H), 4.45 (s, 2H), 3.60-3.70 (m, 1H), 3.37 (s, 2H), 3.25 (s, 1H), 2.95 (d, J=8.8 Hz, 1H), 1.48 (s, 9H).

Step 4: Synthesis of Compound 001-1E

Compound 001-1D (80.0 g, 310 mmol) was dissolved in dichloromethane (1000 mL). Diazabicycle (23.6 g, 155 mmol, 23.4 mL) and trichloroacetonitrile (269 g, 1.87 mol, 187 mL) were added at 0° C. The mixture was stirred at 25° C. for 16 h. After the reaction was completed, the mixture was filtered and the filtrate was concentrated to give a crude product. The crude product was purified by column chromatography (eluent: petroleum ether/ethyl acetate=5/1) to give compound 001-1E. $^1$H NMR: (400 MHZ, CDCl$_3$) δ=8.37 (s, 2H), 5.81-5.87 (m, 2H), 5.45 (s, 2H), 5.39-5.43 (m, 2H), 5.25-5.30 (m, 2H), 3.61-3.81 (m, 4H), 1.48 (s, 9H).

Step 5: Synthesis of Compound 001-1F

Compound α,α-dimethylbenzylamine (32.1 g, 238 mmol) was dissolved in 1,2-dichloroethane. Then chloro(1,5-cyclooctadiene) iridium (I) dimer (12.3 g, 18.3 mmol) was added. Compound 001-1E was dissolved in 1,2-dichloroethane (1.00 L), and then added dropwise to the reaction solution at 0° C. The mixture was stirred at 25° C. for 16 h. After the reaction was completed, the mixture was filtered, and the filtrate was concentrated under reduced pressure to give a crude product. The crude product was purified by column chromatography (eluent: petroleum ether/ethyl acetate=10:1) to give compound 001-1F. 1H NMR: (400 MHZ, CDCl$_3$) δ=7.52-7.55 (m, 2H), 7.30 (t, J=7.2 Hz, 2H), 7.22 (t, J=7.2 Hz, 1H), 5.94-6.03 (m, 2H), 5.10 (t, J=19.2 Hz, 2H), 4.99 (d, J=10.4 Hz, 2H), 3.51-3.61 (m, 4H), 3.33 (t, J=13.6 Hz, 2H), 1.48 (s, 15H).

Step 6: Synthesis of Compound 001-1G

Compound 001-1F (36.0 g, 50.4 mmol) was dissolved in toluene (900 mL). 1,3-Bis(2,4,6-trimethylphenyl)-2-(imidazolidinylidene) (dichlorophenylmethylene) (tricyclohexylphosphine) ruthenium (2.14 g, 2.52 mmol) was added. The mixture was stirred at 125° C. for 16 h. After the reaction was completed, the mixture was filtered, and the filtrate was concentrated to give a crude product. The crude product was purified by column chromatography (eluent: petroleum ether/ethyl acetate=10:1) to give compound 001-1G. LCMS: (ESI) m/z=329.2 [M+H]$^+$0.1H NMR: (400 MHZ, CDCl$_3$) δ=7.60 (t, J=1.2 Hz, 2H), 7.31 (t, J=7.2 Hz, 2H), 7.22 (s, 1H), 5.96 (t, J=9.2 Hz, 2H), 3.60-3.65 (m, 2H), 3.46-3.53 (m, 2H), 3.09-3.14 (m, 2H), 1.42 (s, 9H), 1.25 (d, J=6.0 Hz, 6H).

Step 7: Synthesis of Compound 001-1H

Compound 001-1G (26.8 g, 81.6 mmol) was dissolved in methanol (201 mL). Hydrochloric acid/methanol (4 M, 67.3 mL) was added. The mixture was reacted at 35° C. for 16 h. After the reaction was completed, the mixture was adjusted to pH 12 with 4M sodium hydroxide, and extracted with 30 mL of ethyl acetate. The organic phase was dried over anhydrous sodium sulfate, and filtered. The filtrate was concentrated to give compound 001-1H. LCMS: (ESI) m/z=229.2 [M+H]$^+$. $^1$H NMR: (400 MHZ, CDCl$_3$) δ=7.62 (t, J=7.2 Hz, 2H), 7.31 (t, J=7.6 Hz, 2H), 7.21 (s, 1H), 6.01 (s, 2H), 3.42 (s, 2H), 2.89-2.93 (m, 2H), 2.30-2.34 (m, 2H), 1.23 (s, 6H).

Step 8: Synthesis of Compound 001-5C

To a pre-dried reaction flask were added compound 001-5B (2 g, 5.58 mmol), dichloromethane, and N,N-diisopropylethylamine (4.33 g, 33.47 mmol, 5.83 mL). Trifluoromethanesulfonic anhydride (6.30 g, 22.31 mmol, 3.68 mL) was added at 0° C. The mixture was stirred at 0° C. for 1 hr. After the reaction was completed, water (5 mL) was added. The mixture was extracted with dichloromethane (5 mL×4). The combined organic phase was washed with saturated brine (5 mL), dried over anhydrous sodium sulfate, and filtered. The filtrate was concentrated under reduced pressure, and the crude product was purified by silica gel column chromatography (gradient elution:petroleum ether:ethyl acetate=10:1) to give compound 001-5C.

Step 9: Synthesis of Compound 001-5D

To the reaction flask were added compound 001-5C (3.2 g, 5.14 mmol), diphenylimine (1.86 g, 10.28 mmol, 1.72 mL), and anhydrous toluene (64 mL), followed by cesium carbonate (5.02 g, 15.42 mmol) and 4,5-bis(diphenylphosphino)-9,9-dimethylxanthene (594.75 mg, 1.03 mmol) under nitrogen. Tris(dibenzylideneacetone) dipalladium (470.62 mg, 513.94 μmol, 0.1 eq) was added and the mixture was stirred at 100° C. for 2 hr. After the reaction was completed, the reaction solution was cooled to room temperature and concentrated under reduced pressure. The crude product was purified by column chromatography (gradient elution:petroleum ether:ethyl acetate=10:1) to give compound 001-5D. LCMS: (ESI) m/z=654.2 [M+H]$^+$. $^1$H NMR (400 MHZ, CDCl$_3$) δ ppm 7.83~7.78 (m, 5H), 7.60~7.49 (m, 9H), 1.20~1.16 (m, 21H).

Step 10: Synthesis of Compound 001-5A

Compound 001-5D (2.4 g, 3.67 mmol), bis(pinacolato)diboron (1.86 g, 7.34 mmol), and potassium acetate (1.08 g, 11.01 mmol) were dissolved in anhydrous toluene (48 mL). 1,1'-Bis(diphenylphosphino) ferrocene palladium dichloride (537.20 mg, 734.17 μmol) was added. Under nitrogen, the mixture was stirred at 130° C. for 12 h. After the reaction was completed, the mixture was concentrated under reduced pressure and the crude product was purified by column chromatography (gradient elution:petroleum ether:ethyl acetate=10:1) to give compound 001-5A. LCMS: (ESI) m/z=632.3 [M+H]$^+$. $^1$H NMR (400 MHZ, DMSO) δ ppm 7.80-7.87 (m, 1H), 7.68-7.74 (m, 2H), 7.55-7.62 (m, 1H), 7.47-7.53 (m, 2H), 7.39-7.47 (m, 1H), 7.27-7.35 (m, 4H), 7.18-7.23 (m, 2H), 7.10-7.15 (m, 1H), 1.26 (s, 12H), 1.07-1.15 (m, 21H).

Step 11: Synthesis of Compound 001-2

Compound 001-1 (138.23 mg, 605.38 μmol) and 001-1H (0.2 g, 605.38 μmol) were dissolved in N,N-dimethylformamide (2 mL). N,N-diisopropylethylamine (234.72 mg, 1.82 mmol, 316.34 μL) was added. The mixture was stirred to react at 25° C. for 2 h. After the reaction was completed, 10 mL of water was added, and a solid was precipitated. The solid was filtered to give compound 001-2. LCMS: (ESI) m/z=521.02 [M+H]$^+$. $^1$H NMR (400 MHZ, CDCl$_3$) δ ppm 1.23 (s, 6H) 3.58-3.74 (m, 4H) 4.22 (br d, J=11.04 Hz, 2H) 5.91 (s, 2H) 7.16-7.23 (m, 2H) 7.26-7.34 (m, 2H) 7.54 (s, 1H) 7.69 (d, J=2.01 Hz, 1H).

Step 12: Synthesis of Compound 001-3 Trifluoroacetate

Compound 001-2 (300 mg, 574.45 µmol) was dissolved in trifluoroacetic acid (2 mL). The mixture was stirred at 75° C. for 1 h. After the reaction was completed, the mixture was concentrated to give compound 001-3 trifluoroacetate. LCMS: (ESI) m/z=402.92 [M+H].

Step 13: Synthesis of Compound 001-4

Compound 001-3 (220 mg, 544.47 µmol, trifluoroacetate) was dissolved in tetrahydrofuran (2 mL). Then di-tert-butyl dicarbonate (142.60 mg, 653.36 µmol, 150.10 µL) and triethylamine (165.28 mg, 1.63 mmol, 227.35 µL) were added. The mixture was reacted at 25° C. for 2 h. After the reaction was completed, the mixture was concentrated under reduced pressure. The crude product was purified by column chromatography (eluent: petroleum ether/ethyl acetate=10: 1-3:1) to give compound 001-4. LCMS: (ESI) m/z=502.92 [M+H]$^+$. $^1$H NMR (400 MHZ, CDCl$_3$) δ=1.55 (s, 9H) 3.62-3.90 (m, 2H) 4.27-4.52 (m, 2H) 4.60-4.82 (m, 2H) 6.19 (s, 2H) 7.75 (d, J=2.01 Hz, 1H).

Step 14: Synthesis of Compound 001-5

Compound 001-4 (250 mg, 495.86 µmol) was dissolved in N,N-dimethylformamide (5 mL) and tetrahydrofuran (5 mL). Then triethylenediamine (5.56 mg, 49.59 µmol, 5.45 µL), 001-4A (94.73 mg, 595.03 µmol) and cesium carbonate (242.34 mg, 743.78 µmol) were added. The mixture was stirred at 25° C. for 2 h. After the reaction was completed, the mixture was concentrated under reduced pressure to give a crude product. The crude product was purified by column chromatography (eluent: dichloromethane/methanol=10:1-5:1) to give compound 001-5. LCMS: (ESI) m/z=626.12 [M+H]$^+$. $^1$H NMR (400 MHZ, DMSO-d$_6$) δ ppm 1.47 (s, 9H) 1.77-1.92 (m, 2H) 1.96-2.16 (m, 3H) 2.74 (s, 1H) 2.79-2.90 (m, 2H) 3.04-3.19 (m, 2H) 3.66 (br d, J=10.54 Hz, 2H) 3.90-4.11 (m, 2H) 4.30 (br s, 2H) 4.60 (br s, 2H) 5.15-5.38 (m, 1H) 6.06-6.22 (m, 1H) 6.16 (br s, 1H) 7.92-8.05 (m, 1H).

Step 15: Synthesis of Compound 001-6

Compound 001-5 (0.25, 398.78 µmol), compound 001-5A (327.48 mg, 518.41 µmol) and potassium phosphate (253.94 mg, 1.20 mmol) were added to 1,4-dioxane and water (0.4 mL). The atmosphere was replaced with nitrogen three times, and chloro [(bis(1-adamantyl)-n-butylphosphine)-2-(2-aminobiphenyl)]palladium (II) (26.66 mg, 39.88 µmol) was added under nitrogen. The mixture was reacted at 80° C. for 12 h. After the reaction was completed, 3 mL of water was added to the reaction solution, and the mixture was extracted with ethyl acetate (2 mL*2). The combined organic phase was washed with 5 mL of saturated brine, dried over anhydrous sodium sulfate, and filtered. The filtrate was concentrated to give a crude product. The crude product was purified by column chromatography (petroleum ether:ethyl acetate=100:0-1:2, dichloromethane:methanol=10:1) to give compound 001-6. LCMS: (ESI) m/z=1051.4 [M+H]$^+$.

Step 16: Synthesis of Compound 001-7 Hydrochloride

Compound 001-6 (0.13 g, 123.60 µmol) was added to hydrochloric acid/methanol (2 mL). The mixture was reacted at 18° C. for 2 h. After the reaction was completed, the reaction solution was concentrated. The crude product was stirred with 5 mL of ethyl acetate for 1 h, and then filtered. The filter cake was rinsed with 2 mL of ethyl acetate and concentrated under reduced pressure to give compound 001-7 hydrochloride. LCMS: (ESI) m/z=787.3 [M+H]$^+$.

Step 17: Synthesis of Compound 001A and Compound 001B

Compound 001-7 (0.2 g, 242.75 µmol, hydrochloride) was added to N,N-dimethylformamide (3 mL). Potassium carbonate (335.51 mg, 2.43 mmol) and cesium fluoride (73.75 mg, 485.50 µmol, 17.90 µL) were added. The mixture was reacted at 60° C. for 16 h. After the reaction was completed, 5 mL of water was added to the reaction solution. The mixture was extracted with ethyl acetate (3 mL*2). The combined organic phase was washed with saturated brine (10 mL*3), dried over anhydrous sodium sulfate, and filtered. The filtrate was concentrated to give a crude compound. The crude product was purified by preparative high performance liquid chromatography (column: Phenomenex Luna 80*30 mm*3 µm; mobile phase A: water (0.05% HCl), mobile phase B: acetonitrile; running gradient: B %; 5%-30%, running for 8 min) to give compound 001 hydrochloride. The fraction solution was adjusted to a pH of 7 by adding ammonia water, and then purified by supercritical fluid chromatography (SFC) (column: DAICEL CHIRALPAK IC (250 mm*30 mm, 10 µm); mobile phase: A (supercritical CO$_2$) and B (ethanol with 0.1% ammonia); gradient: B %=60%-60%, running for 20 min) to give compound 001A and compound 001B.

The analysis and characterization of compound 001A were as follows:

SFC analysis method (column: Chiralpak IC-3, 50×4.6 mm I.D., 3 µm; mobile phase: A (supercritical CO$_2$), B: (ethanol with 0.1% isopropylamine); gradient: B %=50~50%, 4 min; flow rate: 4 mL/min; wavelength: 220 nm; pressure: 1800 psi, Rt=1.059 min, 100% ee. LCMS: MS m/z (ESI)=631.1 [M+H]$^+$. $^1$H NMR (400 MHZ, CD$_3$OD) δ=7.79 (s, 1H), 7.71 (dd, J=6.0, 9.2 Hz, 1H), 7.21 (t, J=8.8 Hz, 1H), 7.16 (d, J=2.4 Hz, 1H), 6.96 (d, J=2.4 Hz, 1H), 6.30-6.22 (m, 2H), 5.38-5.20 (m, 1H), 4.51-4.37 (m, 2H), 4.26-4.19 (m, 1H), 4.15-4.10 (m, 1H), 3.98 (dd, J=1.2, 11.6 Hz, 2H), 3.84-3.71 (m, 2H), 3.29-3.15 (m, 4H), 3.05-2.95 (m, 1H), 2.37-2.17 (m, 2H), 2.15-2.08 (m, 1H), 2.02-1.84 (m, 3H).

The analysis and characterization of compound 001B were as follows:

SFC analysis method (column: Chiralpak IC-3, 50×4.6 mm I.D., 3 µm; mobile phase: A (supercritical CO$_2$), B: (ethanol with 0.1% isopropylamine); gradient: B %=50~50%, 4 min; flow rate: 4 mL/min; wavelength: 220 nm; pressure: 1800 psi, Rt=1.917 min, 96.54% ee. LCMS: MS m/z (ESI)=631.1 [M+H]$^+$. $^1$H NMR (400 MHZ, CD$_3$OD) δ=7.80 (d, J=1.2 Hz, 1H), 7.72 (dd, J=5.6, 8.8 Hz, 1H), 7.22 (t, J=8.8 Hz, 1H), 7.16 (d, J=2.4 Hz, 1H), 6.96 (d, J=2.4 Hz, 1H), 6.33-6.23 (m, 2H), 5.40-5.21 (m, 1H), 4.44 (t, J=12.0 Hz, 2H), 4.24-4.12 (m, 2H), 4.02-3.95 (m, 2H), 3.83-3.73 (m, 2H), 3.29-3.27 (m, 1H), 3.26-3.16 (m, 3H), 3.05-2.95 (m, 1H), 2.38-2.09 (m, 3H), 2.04-1.85 (m, 3H).

Example 2
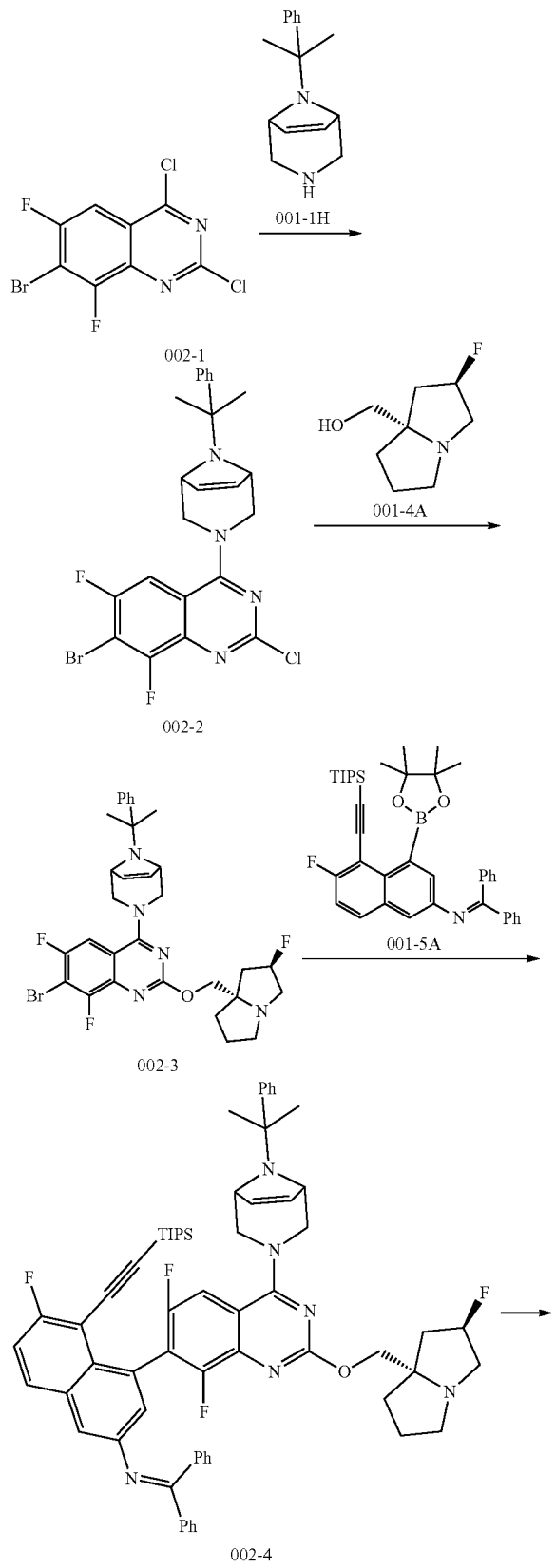
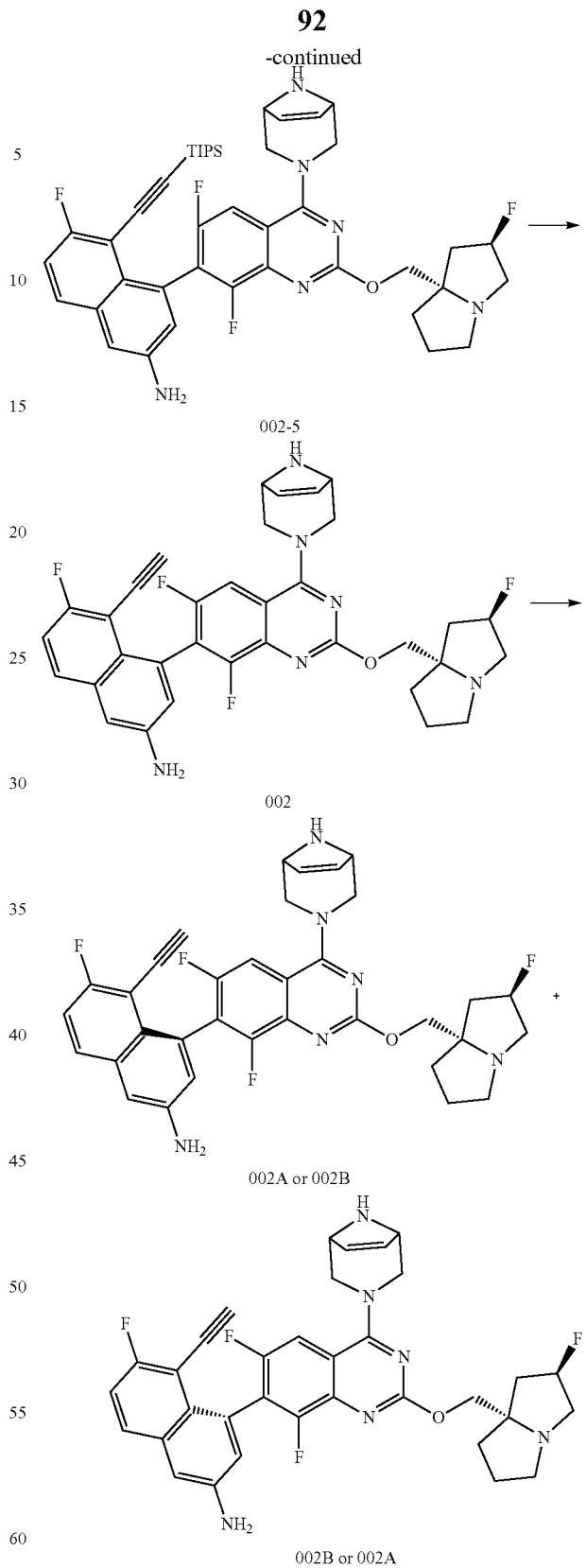
Step 1: Synthesis of Compound 002-2
Compound 002-1 (0.5 g, 1.59 mmol) was added to anhydrous dichloromethane (10 mL). Compound 001-1H (400.05 mg, 1.75 mmol) and triethylamine (322.35 mg, 3.19 mmol, 443.40 μL) were added. The mixture was reacted at 18° C. for 1 h. After the reaction was completed, the mixture was washed twice with 10 mL of saturated ammonium chloride and washed with 10 mL of saturated brine, dried over anhydrous sodium sulfate, and filtered. The filtrate was concentrated under reduced pressure, and the crude product was stirred with a mixed solvent (petroleum ether:methyl tert-butyl ether=3:1, 10 mL) for 1 h and filtered. The filter cake was rinsed with 10 mL of solvent at the same ratio to give compound 002-2 as a filter cake. LCMS: (ESI) m/z=505.1 [M+H]$^+$. $^1$H NMR (400 MHZ, CDCl$_3$) δ=7.63 (d, J=7.6 Hz, 2H), 7.44-7.34 (m, 3H), 7.30-7.25 (m, 1H), 5.99 (s, 2H), 4.29 (d, J=11.2 Hz, 2H), 3.78 (s, 2H), 3.70 (d, J=11.6 Hz, 2H), 1.31 (s, 6H).

Step 2: Synthesis of Compound 002-3

Compound 002-2 (0.35 g, 691.99 μmol) was added to anhydrous tetrahydrofuran (2 mL) and N,N-dimethylformamide (2 mL). Cesium carbonate (676.40 mg, 2.08 mmol), compound 001-4A (132.20 mg, 830.39 μmol) and triethylenediamine (23.29 mg, 207.60 μmol, 22.83 μL) were added. The mixture was reacted at 25° C. for 17 h. After the reaction was completed, the reaction solution was added to 10 mL of methyl tert-butyl ether, washed twice using 10 mL of saturated ammonium chloride followed by 10 mL of saturated brine, dried over anhydrous sodium sulfate, and filtered. The filtrate was concentrated under reduced pressure to give compound 002-3. LCMS: (ESI) m/z=628.0 [M+H]$^+$. $^1$H NMR (400 MHZ, CDCl$_3$) δ=7.65-7.60 (m, 2H), 7.40-7.32 (m, 3H), 7.30-7.28 (m, 1H), 5.97-5.93 (m, 2H), 5.40-5.15 (m, 1H), 4.34-4.22 (m, 2H), 4.16 (d, J=10.0 Hz, 1H), 4.02 (d, J=10.4 Hz, 1H), 3.75-3.71 (m, 2H), 3.69-3.60 (m, 2H), 3.30-3.17 (m, 2H), 3.15-3.08 (m, 1H), 3.01-2.92 (m, 1H), 2.33-2.06 (m, 3H), 1.98-1.80 (m, 3H), 1.30 (s, 6H).

Step 3: Synthesis of Compound 002-4

Compound 002-3 (0.3 g, 477.31 μmol), compound 001-5A (452.27 mg, 715.96 μmol) and potassium phosphate (303.95 mg, 1.43 mmol) were added to toluene (3 mL) and water (0.6 mL). The atmosphere was replaced with nitrogen three times, and chloro [(bis(1-adamantyl)-n-butylphosphine)-2-(2-aminobiphenyl)]palladium (II) (31.91 mg, 47.73 μmol) was added under nitrogen. The mixture was reacted at 80° C. for 4.5 h. Then, 20 mL of water was added to the reaction solution. The mixture was extracted with ethyl acetate (20 mL*2). The organic phases were combined, washed with 30 mL of saturated brine, dried over anhydrous sodium sulfate, and filtered. The filtrate was concentrated under reduced pressure, and the crude product was purified by column chromatography (petroleum ether:ethyl acetate=1:0-0:1, dichloromethane:methanol=10:1) to give compound 002-4. LCMS: (ESI) m/z=1053.5 [M+H]$^+$. $^1$H NMR (400 MHZ, CDCl$_3$) δ=7.81-7.76 (m, 2H), 7.67-7.62 (m, 3H), 7.52-7.47 (m, 1H), 7.46-7.31 (m, 5H), 7.30-7.28 (m, 1H), 7.26-7.22 (m, 3H), 7.21-7.17 (m, 2H), 7.15-7.10 (m, 2H), 6.96-6.90 (m, 1H), 6.12-6.06 (m, 1H), 5.98-5.94 (m, 1H), 5.36-5.18 (m, 1H), 4.65-4.58 (m, 1H), 4.22-4.08 (m, 1H), 4.06-3.97 (m, 1H), 3.94-3.87 (m, 1H), 3.85-3.77 (m, 2H), 3.70-3.68 (m, 1H), 3.50-3.43 (m, 1H), 3.30-3.13 (m, 3H), 3.02-2.92 (m, 1H), 2.33-2.13 (m, 3H), 1.94-1.85 (m, 3H), 1.25 (s, 6H), 0.93-0.81 (m, 18H), 0.59-0.51 (m, 3H).

Step 4: Synthesis of Compound 002-5

Compound 002-4 (0.23 g, 218.35 μmol) was added to trifluoroacetic acid (2 mL). The mixture was heated to 70° C. and reacted for 0.5 h. After the reaction was completed, the reaction solution was concentrated under reduced pressure and diluted with 5 mL of ethyl acetate. The mixture was washed twice with 5 mL of water, washed with 10 mL of saturated sodium bicarbonate solution, and washed with 10 mL of saturated brine. The organic phase was dried over anhydrous sodium sulfate, and filtered. The filtrate was concentrated to give compound 002-5. LCMS: (ESI) m/z=771.3 [M+H]$^+$.

Step 5: Synthesis of Compound 002A and Compound 002B

Compound 002-5 (0.27 g, 350.21 μmol) was added to N,N-dimethylformamide (3 mL). Potassium carbonate (242.01 mg, 1.75 mmol) and cesium fluoride (106.39 mg, 700.41 μmol, 25.82 μL) were added. The mixture was reacted at 60° C. for 5 h. After the reaction was completed, the reaction solution was diluted with 10 mL of ethyl acetate and washed with 10 mL of water. The aqueous phase was further extracted with 5 mL of ethyl acetate. The organic phases were combined, washed 3 times with 10 mL of saturated brine, dried over anhydrous sodium sulfate, and filtered. The filtrate was concentrated under reduced pressure to give a crude product. The crude product was stirred with a mixed solvent (n-heptane:ethyl acetate=5:1) for 1 hr, and filtered. The filter cake was washed three times with 3 mL of a mixed solvent at the same ratio, dried and purified by preparative high performance liquid chromatography (column: Phenomenex Luna 80*30 mm*3 μm; mobile phase A: water (0.04% hydrochloric acid), mobile phase B: acetonitrile; running gradient: acetonitrile %: 10%-35%, running for 8 min). The fractions were adjusted to pH 8 with 10 mL of saturated sodium bicarbonate solution, and the mixture was extracted with ethyl acetate (20 mL*2). The organic phases were combined, washed with 20 mL of saturated brine, dried over anhydrous sodium sulfate, and filtered. The filtrate was concentrated under reduced pressure to give compound 002, which is purified by supercritical fluid chromatography (SFC) (column: DAICEL CHIRALCEL OD (250 mm*30 mm, 10 μm); mobile phase: A (supercritical CO$_2$) and B (ethanol with 0.1% ammonia); gradient: B %=50%-50%, running for 20 min) to give 002A and 002B.

The analysis and characterization of compound 002A were as follows:

SFC analysis method (column: Chiralcel OD-3, 50×4.6 mm I.D., 3 μm; mobile phase: A (supercritical CO$_2$), B: (ethanol with 0.1% isopropylamine); gradient: B %=5~50%, 3 min; flow rate: 3.4 mL/min; wavelength: 220 nm; pressure: 1800 psi), Rt=1.801 min, enantiomeric excess: 100%. LCMS: MS m/z (ESI)=615.2 [M+H]$^+$. $^1$H NMR (400 MHZ, CD$_3$OD) δ=7.81-7.71 (dd, J=6.0, 8.8 Hz, 1H), 7.56 (d, J=10.0 Hz, 1H), 7.29-7.21 (m, 2H), 7.06 (s, 1H), 6.48-6.35 (m, 2H), 5.67-5.48 (m, 1H), 4.69-4.64 (m, 4H), 4.18-4.00 (m, 3H), 3.98-3.77 (m, 3H), 3.53-3.40 (m, 3H), 2.77-2.55 (m, 2H), 2.51-2.41 (m, 1H), 2.37-2.28 (m, 2H), 2.25-2.13 (m, 1H).

The analysis and characterization of compound 002B were as follows:

SFC analysis method (column: Chiralcel OD-3, 50×4.6 mm I.D., 3 μm; mobile phase: A (supercritical CO$_2$), B: (ethanol with 0.1% isopropylamine); gradient: B %=5~50%, 3 min; flow rate: 3.4 mL/min; wavelength: 220 nm; pressure: 1800 psi), Rt=2.233 min, enantiomeric excess: 93.58%. LCMS: MS m/z (ESI)=615.2 [M+H]$^+$. $^1$H NMR (400 MHZ, CD$_3$OD) δ=7.75 (dd, J=6.0, 9.2 Hz, 1H), 7.51 (dd, J=1.6, 10.0 Hz, 1H), 7.25 (t, J=8.8 Hz, 1H), 7.19 (d, J=2.4 Hz, 1H), 7.05 (d, J=2.4 Hz, 1H), 6.33-6.30 (m, 1H), 6.28-6.26 (m, 1H), 5.4-5.25 (m, 1H), 4.51 (d, J=11.6 Hz, 1H), 4.42 (d, J=12.4 Hz, 1H), 4.32-4.27 (m, 1H), 4.21-4.16 (m, 1H), 4.02 (dd, J=2.0, 12.0 Hz, 2H), 3.85-3.69 (m, 2H), 3.29-3.20 (m, 4H), 3.07-3.00 (m, 1H), 2.44-2.24 (m, 2H), 2.23-2.14 (m, 1H), 2.09-1.99 (m, 2H), 1.98-1.88 (m, 1H).
Example 3
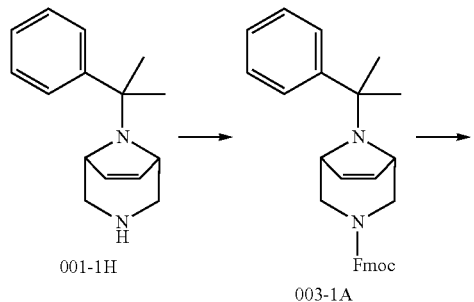
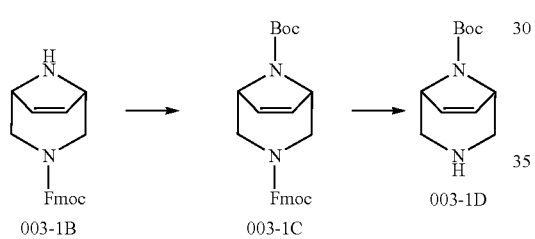
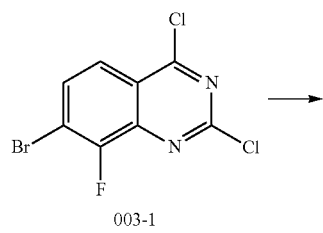
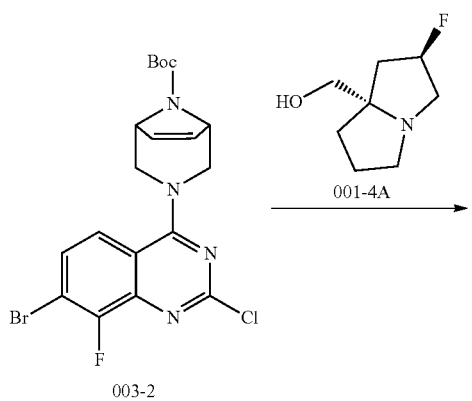
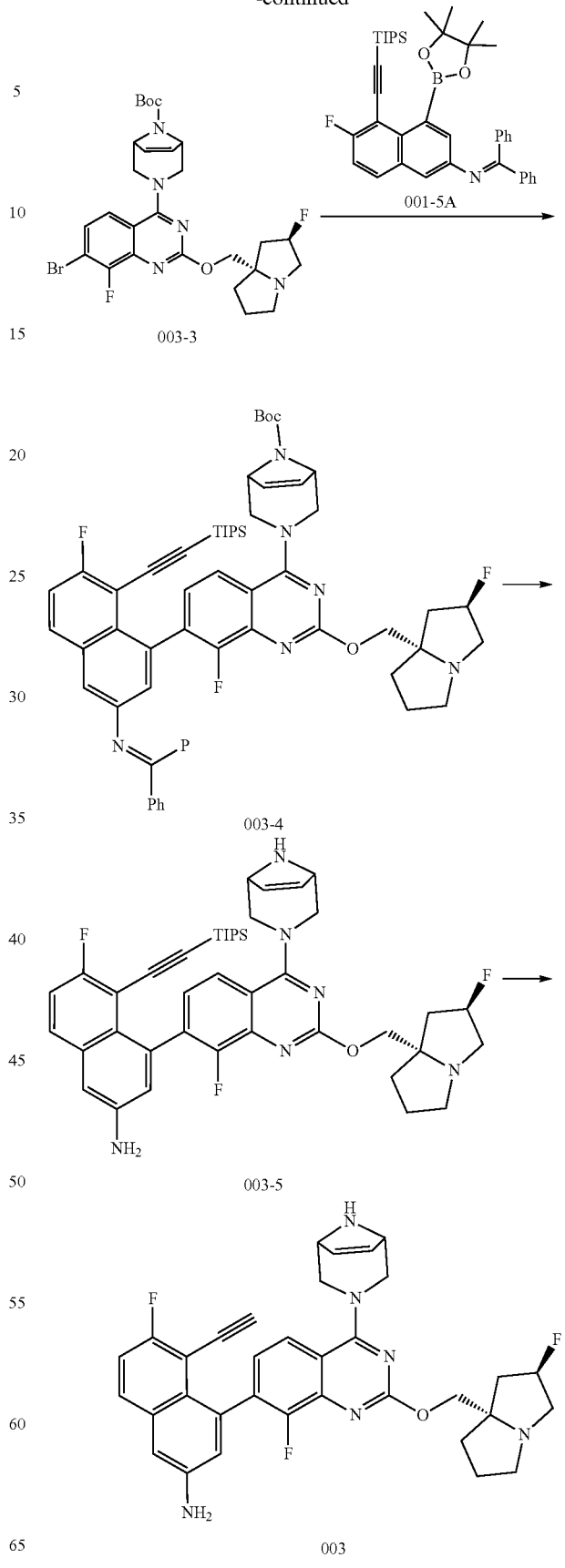

Step 1: Synthesis of Compound 003-1A

Compound 001-1H (18.6 g) was dissolved in tetrahydrofuran (190 mL). Then 9-fluorenylmethyl chloroformate (20.5 g, 79.4 mmol) and sodium carbonate (25.2 g, 238.2 mmol) were added. The mixture was stirred at 0° C. for 1 h. After the reaction was completed, 100 mL of ethyl acetate and 200 mL of water were added to the reaction solution for extraction. The organic phase was washed with saturated brine, dried over anhydrous sodium sulfate, and filtered. The filtrate was concentrated to give compound 003-1A. LCMS: (ESI) m/z=451.3 [M+H]$^+$. $^1$H NMR: (400 MHZ, CDCl$_3$) δ=7.76 (d, J=13.6 Hz, 2H), 7.54-7.61 (m, 4H), 7.24-7.40 (m, 7H), 5.93-6.01 (m, 2H), 4.34-4.40 (m, 2H), 4.21 (s, 1H), 3.70 (t, J=2 Hz, 2H), 3.55-3.59 (m, 2H), 3.15-3.23 (m, 2H), 1.27 (d, J=2.4 Hz, 6H).

Step 2: Synthesis of Compound 003-1B

Compound 003-1A (9.52 g, 21.1 mmol) was dissolved in trifluoroacetic acid (192 mL). The solution was stirred at 75° C. for 16 h. After the reaction was completed, 20 mL of water was added to the reaction solution and the reaction solution was adjusted to pH 9 with 2M sodium hydroxide. Then the mixture was extracted with 20 mL of dichloromethane. The organic phase was dried over anhydrous sodium sulfate, and filtered. The filtrate was concentrated to give a crude product. The crude product was stirred with 6 mL of n-heptane at 25° C. for 2 h, and filtered to give compound 003-1B. LCMS: (ESI) m/z=333.3 [M+H]$^+$. 1H NMR: (400 MHZ, CDCl$_3$) δ=7.77 (d, J=7.6 Hz, 2H), 7.56 (d, J=7.2 Hz, 2H), 7.41 (t, J=7.6 Hz, 2H), 7.33 (t, J=6 Hz, 2H), 6.18-6.27 (m, 2H), 4.38-4.42 (m, 2H), 4.23 (s, 1H), 3.88 (d, J=2.0 Hz, 2H), 3.82 (d, J=2.4 Hz, 1H), 3.72 (d, J=2.0 Hz, 1H), 3.21-3.60 (m, 2H).

Step 3: Synthesis of Compound 003-1C

Compound 003-1B (1.00 g) was dissolved in tetrahydrofuran (10.0 mL). Then di-tert-butyl dicarbonate (764 mg, 3.50 mmol, 804 μL), and triethylamine (885 mg, 8.75 mmol, 1.22 mL) were added. The mixture was stirred at 25° C. for 1 h. After the reaction was completed, the mixture was extracted with 10 mL of ethyl acetate and 10 mL of water. The organic phase was washed with 15 mL of saturated brine, dried over anhydrous sodium sulfate, and concentrated. The crude product was purified by column chromatography (petroleum ether:ethyl acetate=3:1) to give compound 003-1C. LCMS: (ESI) m/z=433.2 [M+H]$^+$.

Step 4: Synthesis of Compound 003-1D

Compound 003-1C (5.69 g) was dissolved in ethanol (60.0 mL). Then dimethylamine (34.4 g, 251.8 mmol, 33% content) was added. The mixture was stirred at 25° C. for 3 h. After the reaction was completed, the mixture was extracted with 40 mL of ethyl acetate and 40 mL of citric acid. The aqueous phase was adjusted to pH 9 with 2M sodium hydroxide, and filtered. The filtrate was extracted with 40 mL of ethyl acetate. The organic phases were combined, dried over anhydrous sodium sulfate, and filtered. The filtrate was concentrated to give compound 003-1D. LCMS: (ESI) m/z=211.2 [M+H]$^+$. $^1$H NMR: (400 MHZ, CDCl$_3$) δ=6.22 (d, J=10 Hz, 2H), 4.40 (d, J=38.8 Hz, 2H), 2.89-3.01 (m, 2H), 2.40 (d, J=13.2 Hz, 2H), 1.49 (s, 9H).

Step 5: Synthesis of Compound 003-2

Compound 003-1 (0.5 g, 1.69 mmol) was dissolved in anhydrous dichloromethane (5 mL). Triethylamine (512.92 mg, 5.07 mmol, 705.53 μL) and 003-1D (426.34 mg, 2.03 mmol) were added. The mixture was stirred at 15° C. for 1 h. After the reaction was completed, the mixture was concentrated. The residue was dissolved with 20 mL of dichloromethane, then washed once with 10 mL of water, dried over anhydrous sodium sulfate, and filtered. The filtrate was concentrated to give compound 003-2. LCMS: (ESI) m/z=468.9 [M+H]$^+$ 1H NMR (400 MHZ, CDCl$_3$) δ ppm 7.55-7.39 (m, 2H), 6.17 (s, 2H), 4.80-4.60 (m, 2H), 4.51-4.25 (m, 2H), 3.88-3.58 (m, 2H), 1.57-1.51 (m, 9H).

Step 6: Synthesis of Compound 003-3

Compound 003-2 (0.9 g, 1.92 mmol) was dissolved in N,N-dimethylformamide (9 mL) and anhydrous tetrahydrofuran (9 mL). Then compound 001-4A (366.03 mg, 2.30 mmol), cesium carbonate (1.87 g, 5.75 mmol), and triethylenediamine (64.47 mg, 574.79 μmol, 63.21 μL) were added. The mixture was stirred at 30° C. for 12 h. After the reaction was completed, 10 ml of water and 15 mL of ethyl acetate were added to the reaction solution. The mixture was stirred for 5 min, and then left to stand. The layers were separated. The aqueous phase was extracted once with 15 mL of ethyl acetate. The organic phases were combined, washed with saturated brine (20 mL*2), dried over anhydrous sodium sulfate, and filtered. The filtrate was concentrated and purified by silica gel column chromatography (gradient elution:petroleum ether:ethyl acetate=100:0~50:50, with 5 parts per thousand of triethylamine in ethyl acetate) to give compound 003-3. LCMS: (ESI) m/z=592.1 [M+H]$^+$. $^1$H NMR (400 MHZ, CDCl$_3$) δ ppm 7.37 (d, J=9.2 Hz, 1H), 7.29-7.23 (m, 1H), 6.13 (s, 2H), 5.38-5.17 (m, 1H), 4.76-4.56 (m, 2H), 4.45-4.25 (m, 2H), 4.24-4.04 (m, 2H), 3.81-3.53 (m, 2H), 3.30-3.11 (m, 3H), 3.02-2.92 (m, 1H), 2.32-2.09 (m, 3H), 2.00-1.81 (m, 3H), 1.56-1.48 (m, 9H).

Step 7: Synthesis of Compound 003-4

To a pre-dried reaction flask were added compound 003-3 (0.8 g, 1.35 mmol), anhydrous tetrahydrofuran (8 mL), anhydrous potassium phosphate (859.87 mg, 4.05 mmol) and water (4 mL). The atmosphere was replaced with nitrogen three times, and [(n-butylbis(1-adamantyl)phosphine)-2-(2-aminobiphenyl)]palladium (II) chloride (98.34 mg, 135.03 μmol) was added. The atmosphere was replaced with nitrogen three times, and the mixture was heated to 60° C. A solution of compound 001-5A (1.19 g, 1.89 mmol) in anhydrous tetrahydrofuran (8 mL) was added, and then the mixture was reacted at 60° C. for 3 h. After the reaction was completed, the reaction solution was cooled down to room temperature, and concentrated under reduced pressure to remove tetrahydrofuran. 20 mL of ethyl acetate was added. The organic phase was washed with saturated brine (20 mL*3), dried over anhydrous sodium sulfate, and filtered. The filtrate was concentrated to give a crude product. The crude product was purified by silica gel column chromatography (gradient elution:petroleum ether:ethyl acetate=100:0~50:50 with 5 parts per thousand of triethylamine in ethyl acetate) to give compound 003-4. LCMS: (ESI) m/z=1017.5 [M+H]$^+$. $^1$H NMR (400 MHz, CDCl$_3$) δ ppm 7.83-7.71 (m, 2H), 7.65 (dd, J=9.0, 5.8 Hz, 1H), 7.53-7.40 (m, 4H), 7.36-7.10 (m, 8H), 6.93 (t, J=7.0 Hz, 1H), 6.89-6.86 (m, 1H), 6.25 (br s, 1H), 6.18-6.12 (m, 1H), 5.39-5.12 (m, 1H), 4.85-4.49 (m, 3H), 4.26-4.00 (m, 2H), 3.96-3.68 (m, 1H), 3.66-3.38 (m, 1H), 3.32-3.11 (m, 3H), 3.05-2.90 (m, 1H), 2.36-2.14 (m, 3H), 2.00-1.80 (m, 3H), 1.59 (s, 9H), 0.90-0.76 (m, 18H), 0.59-0.43 (m, 3H).

Step 8: Synthesis of Compound 003-5 Hydrochloride

To compound 003-4 (0.8 g, 786.39 μmol) was added hydrochloric acid/methanol (4 M, 8.00 mL). The mixture was stirred at 15° C. for 1 h. After the reaction was completed, the reaction solution was concentrated under reduced pressure. A mixed solution (ethyl acetate:dichloromethane=5:1, 20 mL) was added and the mixture was stirred for 0.5 h. The mixture was filtered and the filter cake was dried under vacuum to give compound 003-5 hydrochloride. LCMS: (ESI) m/z=753.3 [M+H]$^+$.

Step 9: Synthesis of Compound 003

Compound 003-5 (0.7 g, 847.56 μmol, hydrochloride) was dissolved in N,N-dimethylformamide (7 mL). Anhydrous potassium carbonate (2.34 g, 16.95 mmol) and cesium fluoride (643.73 mg, 4.24 mmol) were added. The mixture was stirred at 65° C. for 4 h. After the reaction was completed, the reaction solution was cooled down to room temperature, and then filtered. The filter cake was rinsed with 20 mL of ethyl acetate. The mother liquor was washed with saturated brine (20 mL*3), dried over anhydrous sodium sulfate, and filtered. The filtrate was concentrated to give a crude product. The crude product was purified by preparative high performance liquid chromatography (column: Phenomenex Luna 80*30 mm*3 μm; mobile phase: [water (0.04% hydrochloric acid)-acetonitrile]; acetonitrile %: 5%-25%, 8 min). The fractions were adjusted to a pH of 9 by adding ammonia dropwise, and then concentrated under reduced pressure to remove acetonitrile. The residue was extracted with ethyl acetate (50 mL*2), and concentrated under reduced pressure to give compound 003. LCMS: (ESI) m/z=597.2 [M+H]$^+$. $^1$H NMR (400 MHZ, CDCl$_3$) δ ppm 7.65 (dd, J=9.0, 5.8 Hz, 1H), 7.52 (d, J=9.2 Hz, 1H), 7.21 (t, J=8.8 Hz, 1H), 7.12-7.01 (m, 2H), 6.95 (d, J=2.4 Hz, 1H), 6.29-6.22 (m, 2H), 5.38-5.18 (m, 1H), 4.48-4.38 (m, 2H), 4.29-4.18 (m, 1H), 4.00-3.93 (m, 2H), 3.90 (s, 1H), 3.79-3.72 (m, 2H), 3.31-3.22 (m, 2H), 3.17 (s, 1H), 3.01-2.94 (m, 1H), 2.72 (d, J=2.0 Hz, 1H), 2.34-2.15 (m, 3H), 2.03-1.84 (m, 3H).

Example 4

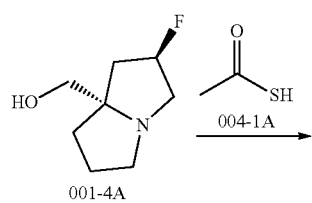

001-4A    004-1A

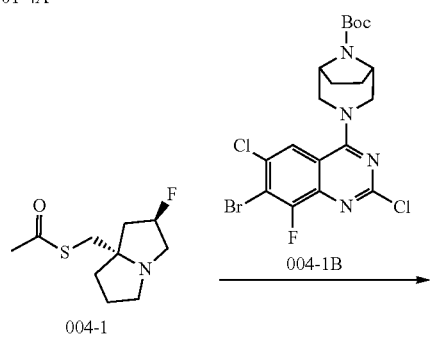

004-1    004-1B

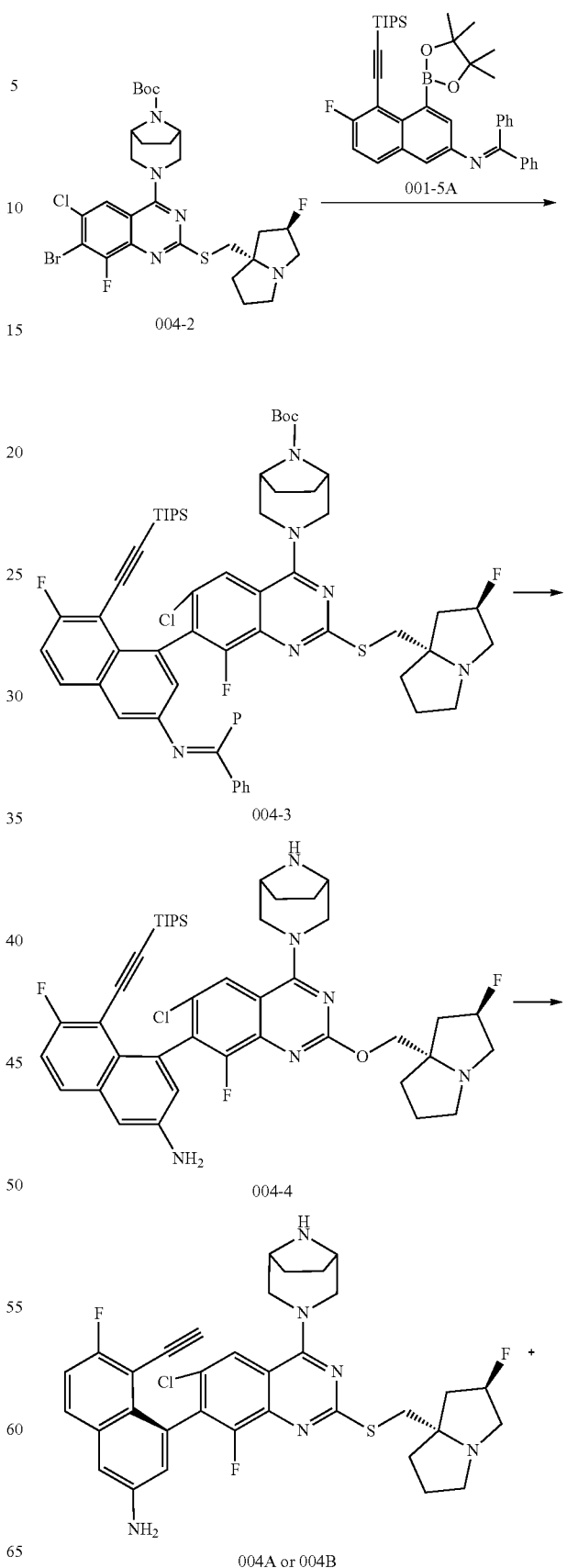

004-2    001-5A 004-3

004-4

004A or 004B

-continued

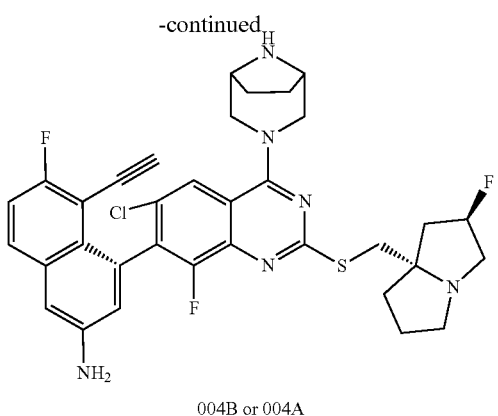

004B or 004A

Step 1: Synthesis of Compound 004-1

To a pre-dried reaction flask was added anhydrous tetrahydrofuran (20 mL). Diisopropyl azodicarboxylate (2.54 g, 12.56 mmol, 2.44 mL) and triphenylphosphine (3.30 g, 12.56 mmol) were added at 0° C. The mixture was stirred at 0° C. for 0.5 h, and a solid was precipitated. Compound 001-4A (1 g, 6.28 mmol) and compound 004-1A (634.24 mg, 8.17 mmol, 592.75 μL) dissolved in anhydrous tetrahydrofuran (10 mL) were added, and the mixture was stirred at 0-15° C. for 2 h. After the reaction was completed, the reaction was quenched by adding 5 mL of water to the reaction solution. 20 mL of ethyl acetate was added, and the mixture was stirred for several minutes. The mixture was left to stand, and the layers were separated. The organic phase was dried over anhydrous sodium sulfate, and filtered. The filtrate was concentrated, and then 20 mL of n-heptane was added. The mixture was stirred for 1 h. The mixture was filtered. The mother liquor was collected, and concentrated under reduced pressure to give a crude compound. The crude compound was purified by silica gel column chromatography (gradient elution:petroleum ether:ethyl acetate=100: 0~30:70, with 5 parts per thousand of triethylamine in ethyl acetate) to give 004-1. LCMS m/z=217.9 [M+H]$^+$. $^1$H NMR (400 MHZ, CDCl$_3$) δ ppm 5.28-5.08 (m, 1H), 3.26-3.06 (m, 4H), 2.99-2.83 (m, 2H), 2.34 (s, 3H), 2.20-2.04 (m, 1H), 1.96-1.76 (m, 5H).

Step 2: Synthesis of Compound 004-2

To a reaction flask were added compound 004-1 (180 mg, 828.34 μmol) and dimethyl sulfoxide (8 mL). Sodium hydroxide (2 M, 753.03 μL) was added at 15° C. The mixture was stirred at 15° C. for 2 hours. Then compound 004-1B (381.18 mg, 753.03 μmol) and dimethyl sulfoxide (8 mL) were added. The mixture was stirred at 60° C. for 48 h. After the reaction was completed, the reaction solution was allowed to cool down to room temperature. 20 mL of ethyl acetate was added. The mixture was washed with saturated brine (20 ml*2), dried over anhydrous sodium sulfate, and filtered. The filtrate was concentrated, and then purified by silica gel column chromatograph (gradient elution:petroleum ether:ethyl acetate=100:0~60:40) to give compound 004-2. LCMS m/z=644.0 [M+H]$^+$.

Step 3: Synthesis of Compound 004-3

To a pre-dried reaction flask were added compound 004-2 (170 mg, 263.57 μmol), anhydrous toluene (2.5 mL), anhydrous potassium phosphate (167.84 mg, 790.70 μmol), water (0.5 mL), and compound 001-5A (249.74 mg, 395.35 μmol). The atmosphere was replaced with nitrogen three times, and [(n-butylbis(1-adamantyl)phosphine)-2-(2-aminobiphenyl)] palladium (II) chloride (17.62 mg, 26.36 μmol) was added. The atmosphere was replaced with nitrogen three times again. The mixture was heated to 80° C. and reacted for 12 h. After the reaction was completed, the reaction solution was cooled down to room temperature. 10 mL of water and 20 mL of ethyl acetate were added. The mixture was stirred for 5 min, and then left to stand. The layers were separated. The aqueous phase was extracted once with 10 mL of ethyl acetate. The organic phases were combined, dried over anhydrous sodium sulfate, and filtered. The filtrate was concentrated to give a crude product. The crude compound was purified by silica gel column chromatography (gradient elution:petroleum ether:ethyl acetate=100:0~60:40, with 5 parts per thousand of triethylamine in ethyl acetate) to give compound 004-3. LCMS m/z=1069.4 [M+H]$^+$.

Step 4: Synthesis of Compound 004-4 hydrochloride

To compound 004-3 (40 mg, 37.39 μmol) was added hydrochloric acid/methanol (4 M, 2.00 mL). The mixture was stirred at 15° C. for 1 h. After the reaction was completed, the reaction solution was concentrated under reduced pressure to give a crude product of compound 004-4 hydrochloride. LCMS m/z=805.2 [M+H]$^+$.

Step 5: Synthesis of Compound 004A and Compound 004B

Compound 004-4 (30 mg, 34.15 μmol, hydrochloride) was added to N,N-dimethylformamide (1 mL). Anhydrous potassium carbonate (94.40 mg, 683.04 μmol) and cesium fluoride (25.94 mg, 170.76 μmol, 6.30 μL) were added. The mixture was stirred at 65° C. for 2 h. After the reaction was completed, the reaction solution was cooled down to room temperature, and then filtered. The filter cake was rinsed with 20 mL of ethyl acetate. The mother liquor was washed with saturated brine (20 mL*3), dried over anhydrous sodium sulfate, and filtered. The filtrate was concentrated to give a crude product. The crude product was purified by supercritical fluid chromatography (column: DAICEL CHIRALPAK IC (250 mm*30 mm, 10 μm); mobile phase:A: supercritical CO$_2$,B: [0.1% ammonia-isopropyl alcohol]; B %: 60%-60%, 16 min). The fractions were adjusted to a pH of 9 by adding ammonia dropwise, and then concentrated under reduced pressure to remove acetonitrile. The residue was extracted with ethyl acetate (20 mL*2), and concentrated under reduced pressure to give compound 004A and compound 004B.

Characterization of compound 004A was as follows:

SFC analysis method: column: Chiralpak IC-3, 3 μm, 50×4.6 mm I.D; mobile phase: A (supercritical CO$_2$) and B (isopropyl alcohol with 0.1% isopropylamine); gradient: B %=5~40%, 5 min; flow rate: 4.0 mL/min; wavelength: 220 nm; pressure: 124.14 bar, Rt=2.13 min, enantiomeric excess: 83.48%. LCMS m/z=649.2 [M+H]$^+$. $^1$H NMR (400 MHZ, CD$_3$OD) δ ppm 7.82 (s, 1H), 7.74 (dd, J=9.2, 6.0 Hz, 1H), 7.23 (t, J=9.2 Hz, 1H), 7.18 (d, J=2.4 Hz, 1H), 6.98 (d, J=2.4 Hz, 1H), 5.39-5.19 (m, 1H), 4.51 (br d, J=13.6 Hz, 1H), 4.41 (br d, J=13.6 Hz, 1H), 3.71-3.64 (m, 2H), 3.57 (br t, J=14.0 Hz, 2H), 3.50-3.41 (m 2H), 3.29-3.26 (m, 1H), 3.08 (s, 1H), 2.42-2.19 (m, 4H), 2.14-2.01 (m, 3H), 1.93-1.74 (m, 6H).

103

Characterization of compound 004B was as follows:

SFC analysis method: column: Chiralpak IC-3, 3 μm, 50×4.6 mm I.D; mobile phase: A (supercritical CO₂) and B (isopropyl alcohol with 0.1% isopropylamine); gradient: B %=5~40%, 5 min; flow rate: 4.0 mL/min; wavelength: 220 nm; pressure: 124.14 bar, Rt=1.38 min, enantiomeric excess: 91.90%. LCMS m/z=649.2 [M+H]⁺. ¹H NMR (400 MHZ, CD₃OD) δ ppm 7.82 (s, 1H), 7.74 (dd, J=9.2, 6.0 Hz, 1H), 7.24 (t, J=8.8 Hz, 1H), 7.18 (d, J=2.8 Hz, 1H), 6.98 (d, J=2.4 Hz, 1H), 5.44-5.19 (m, 1H), 4.58-4.50 (m, 1H), 4.42-4.36 (m, 1H), 3.70-3.63 (m, 2H), 3.56 (br d, J=11.8 Hz, 2H), 3.48-3.40 (m, 2H), 3.27 (s, 1H), 3.16-3.02 (m, 1H), 2.46-2.18 (m, 4H), 2.14-1.94 (m, 3H), 1.93-1.69 (m, 6H).

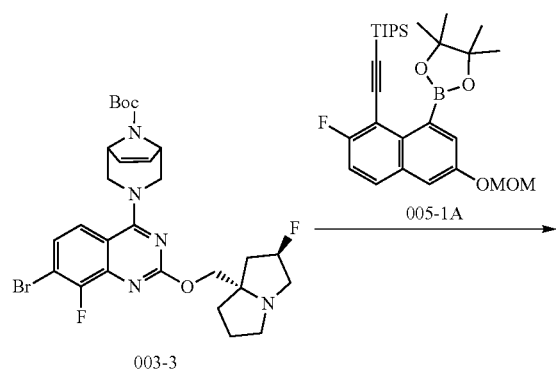

003-3

005-1A

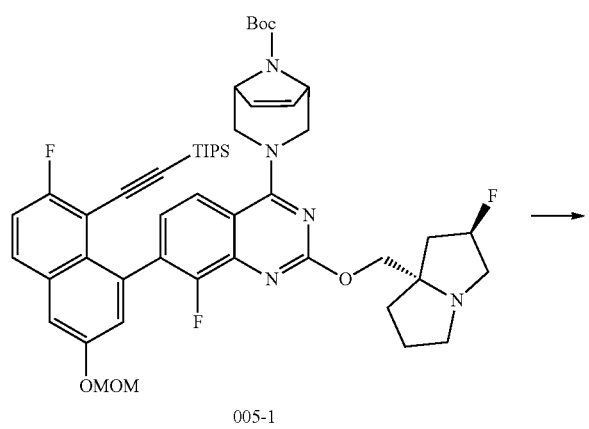

005-1

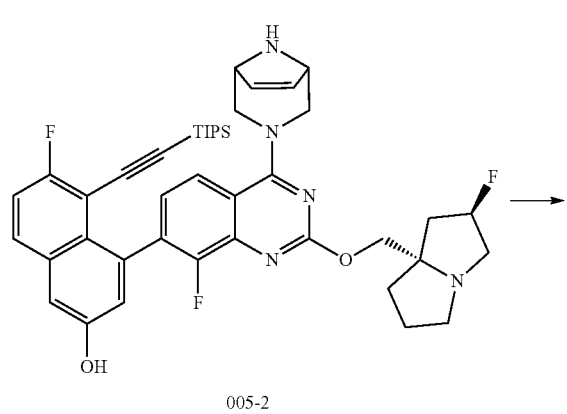

005-2

104

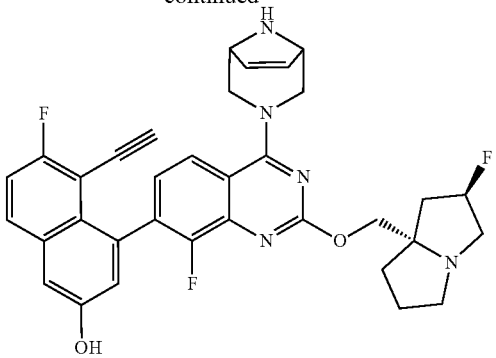

005

Step 1: Synthesis of Compound 005-1

To a reaction flask were added compound 003-3 (0.3 g, 506.35 μmol), anhydrous tetrahydrofuran (3 mL) and water (1 mL), followed by anhydrous potassium phosphate (322.45 mg, 1.52 mmol). The atmosphere was replaced with nitrogen three times, and CataCXium® A Pd G3 (CAS: 1651823-59-4) (36.88 mg, 50.64 μmol) was added. The atmosphere was replaced with nitrogen three times, and the mixture was heated to 60° C. Then a solution of compound 005-1A (519.04 mg, 1.01 mmol) in anhydrous tetrahydrofuran (3 mL) was added dropwise with stirring and the mixture was stirred at 60° C. for 3 hours. After the reaction was completed, the reaction solution was concentrated under reduced pressure, and the crude product was purified by column chromatography (ethyl acetate/petroleum ether=0~45%, with 5 parts per thousand of triethylamine in ethyl acetate) to give compound 005-1. LCMS m/z=898.4 [M+H]⁺.

Step 2: Synthesis of Compound 005-2 hydrochloride

To a pre-dried reaction flask were added compound 005-1 (0.4 g, 445.37 μmol) and hydrochloric acid/methanol (4 M, 4.00 mL). The mixture was stirred under nitrogen at 15° C. for 1 h. After the reaction was completed, the reaction solution was concentrated under reduced pressure to give a crude product of compound 005-2 hydrochloride, which was used directly in the next step. LCMS m/z=754.3 [M+H]⁺.

Step 3: Synthesis of Compound 005

Compound 005-2 (0.2 g, 241.87 μmol, hydrochloride) was added to N,N-dimethylformamide (4 mL). Anhydrous potassium carbonate (668.56 mg, 4.84 mmol) and cesium fluoride (183.70 mg, 1.21 mmol, 44.59 μL) were added. The mixture was stirred at 65° C. for 4 h. After the reaction was completed, the reaction solution was cooled down to room temperature, and then filtered. The filter cake was rinsed with 20 mL of ethyl acetate. The mother liquor was washed with saturated brine (20 mL*3), dried over anhydrous sodium sulfate, and filtered. The filtrate was concentrated to give a crude product. The crude product was purified by preparative high performance liquid chromatography (column: Phenomenex Luna 80*30 mm*3 μm; mobile phase: [water (0.05% hydrochloric acid)-acetonitrile]; acetonitrile %: 1%-25%, 8 min). The fractions were adjusted to a pH of 9 by adding ammonia dropwise, and then concentrated under reduced pressure to remove acetonitrile. The residue was extracted with ethyl acetate (20 mL*2), and concentrated under reduced pressure to give compound 005. LCMS m/z=598.2 [M+H]$^+$. $^1$H NMR (400 MHZ, CD$_3$OD) δ=7.82 (dd, J=9.2, 6.0 Hz, 1H), 7.75 (d, J=8.8 Hz, 1H), 7.32-7.26 (m, 2H), 7.19 (dd, J=8.6, 7.0 Hz, 1H), 7.06 (d, J=2.6 Hz, 1H), 6.34-6.25 (m, 2H), 5.24 (br s, 1H), 4.56-4.45 (m, 2H), 4.27-4.13 (m, 2H), 4.01-3.96 (m, 2H), 3.81-3.73 (m, 2H), 3.38-3.33 (m, 1H), 3.29-3.14 (m, 3H), 3.08-2.96 (m, 1H), 2.40-2.11 (m, 3H), 2.07-1.83 (m, 3H).

Example 6

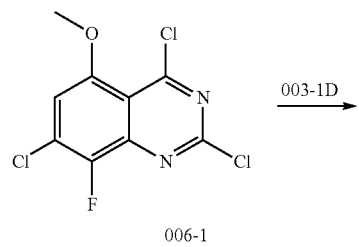

006-1

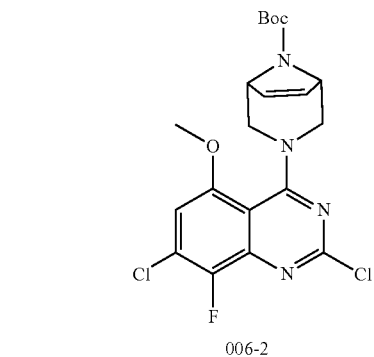

006-2

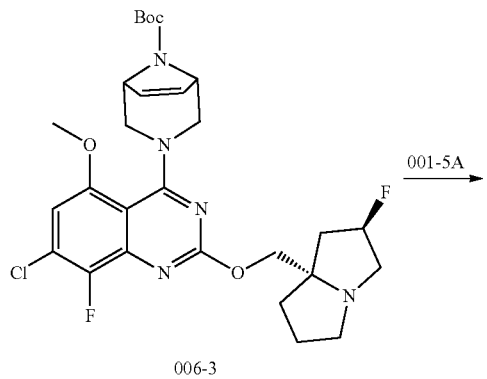

006-3

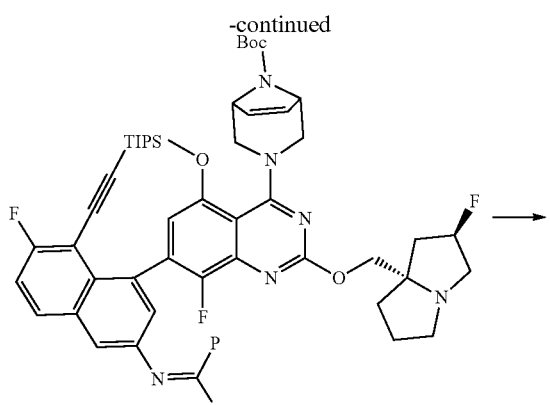

006-4

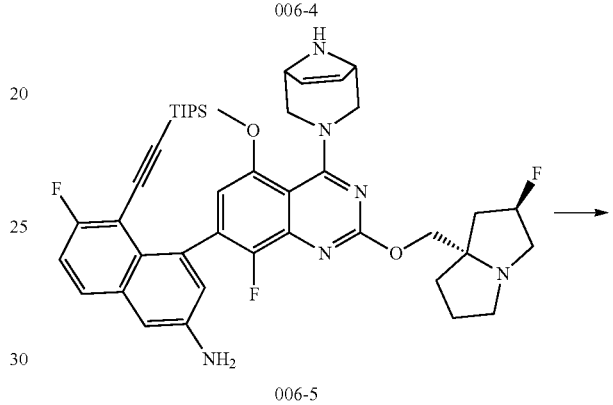

006-5

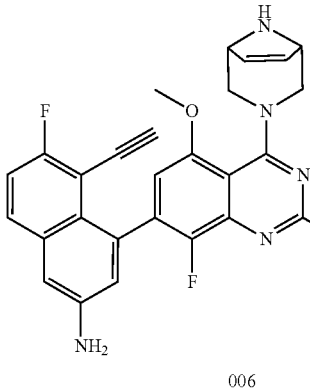

006

Step 1: Synthesis of Compound 006-2

Compound 006-1 (0.3 g, 1.07 mmol) and compound 003-1D (246.50 mg, 1.17 mmol) were added to anhydrous dichloromethane (5 mL). Triethylamine (323.52 mg, 3.20 mmol, 445.01 µL) was added. The mixture was reacted at 18° C. for 1 hr. After the reaction was completed, the reaction solution was diluted with 5 mL of dichloromethane. The mixture was washed with saturated ammonium chloride (10 mL*2) followed by 10 mL of saturated brine, dried over anhydrous sodium sulfate, and filtered. The filtrate was concentrated to give a crude product. The crude product was stirred with a mixed solvent (petroleum ether: methyl tert-butyl ether=4:1, 10 mL) for 1 h and filtered. The filter cake was rinsed with a mixed solvent at the same ratio (3 mL*2) and dried to give compound 006-2. LCMS m/z (ESI)=455.0 [M+H]$^+$. $^1$H NMR (400 MHZ, CDCl$_3$) δ=6.69 (d, J=5.6 Hz, 1H), 6.04 (s, 2H), 4.60 (s, 2H), 3.92 (s, 3H), 3.83-3.43 (m, 3H), 3.19-2.89 (m, 1H), 1.52 (s, 9H).

Step 2: Synthesis of Compound 006-3

Compound 006-2 (0.3 g, 658.89 µmol) was added to anhydrous tetrahydrofuran (1.5 mL) and N,N-dimethylformamide (1.5 mL). Cesium carbonate (644.04 mg, 1.98 mmol), compound 001-4A (125.88 mg, 790.67 µmol) and triethylenediamine (22.17 mg, 197.67 µmol, 21.74 µL) were added. The mixture was reacted at 25° C. for 17 h. After the reaction was completed, the reaction solution was added to 10 mL of methyl tert-butyl ether. The mixture was washed with 10 mL of water followed by 10 mL of saturated brine, dried over anhydrous sodium sulfate, and filtered. The filtrate was concentrated to give a crude product. The crude product was purified by column chromatography (petroleum ether:ethyl acetate=1:0-1:2, dichloromethane:methanol=10:1) to give compound 006-3. LCMS m/z (ESI)=578.2 [M+H]$^+$. $^1$H NMR (400 MHz, CDCl$_3$) δ=6.49 (d, J=5.2 Hz, 1H), 5.99 (s, 2H), 5.37-5.16 (m, 1H), 4.57 (s, 2H), 4.16 (d, J=10.4 Hz, 1H), 4.00 (d, J=10.0 Hz, 1H), 3.88 (s, 4H), 3.70-3.57 (m, 1H), 3.54-3.41 (m, 1H), 3.30-3.18 (m, 3H), 3.18-3.09 (m, 1H), 3.02-2.95 (m, 1H), 2.32-2.07 (m, 3H), 1.98-1.79 (m, 3H), 1.52 (s, 9H).

Step 3: Synthesis of Compound 006-4

Compound 006-3 (0.3 g, 518.99 µmol), compound 001-5A (393.41 mg, 622.78 µmol) and potassium phosphate (220.33 mg, 1.04 mmol) were added to 1,4-dioxane (3 mL) and water (0.6 mL). The atmosphere was replaced with nitrogen three times, and (2-dicyclohexylphosphino-2',6'-dimethoxy-1,1'-biphenylyl) [2-(2'-amino-1,1'-biphenylyl)] palladium (II) chloride (37.40 mg, 51.90 µmol) was added under nitrogen. The mixture was heated to 100° C. and reacted for 1.5 hours. After the reaction was completed, the reaction solution was diluted with 10 mL of ethyl acetate, washed respectively with 10 ml of water and 10 mL of saturated brine, dried over anhydrous sodium sulfate, and filtered. The filtrate was concentrated, and the crude product was purified by column chromatography (petroleum ether:ethyl acetate=1:0-1:2, dichloromethane:methanol=10:1) to give compound 006-4. LCMS m/z (ESI)=1047.5 [M+H]$^+$.

Step 4: Synthesis of Compound 006-5 hydrochloride

Compound 006-4 (0.3 g, 286.44 µmol) was added to hydrochloric acid/methanol (5 mL). The mixture was reacted at 18° C. for 3 hours. After the reaction was completed, the reaction solution was concentrated directly. The crude product was stirred with 10 mL of ethyl acetate for 1 h, and then filtered. The filter cake was rinsed with ethyl acetate (2 mL*2) and dried to give compound 006-5 hydrochloride. LCMS m/z (ESI)=783.3 [M+H]$^+$.

Step 5: Synthesis of Compound 006

Compound 006-5 (0.16 g, 195.25 µmol, hydrochloride) was added to N,N-dimethylformamide (2 mL). Potassium carbonate (269.85 mg, 1.95 mmol) and cesium fluoride (59.32 mg, 390.50 µmol, 14.40 µL) were added. The mixture was reacted at 60° C. for another 16 hours. After the reaction was completed, 20 mL of water was added to the reaction solution. The solution was extracted with ethyl acetate (10 mL*2). The combined organic phase was washed with saturated brine (20 mL*3), dried over anhydrous sodium sulfate, and filtered. The filtrate was concentrated to give a crude compound. The crude product was purified by preparative high performance liquid chromatography (column: P Phenomenex Luna 80*30 mm*3 µm; mobile phase A: water (0.05% hydrochloric acid), mobile phase B: acetonitrile; running gradient: B %: 1%-35%, running for 8 min). The fractions were adjusted to a pH of about 9 by adding ammonia dropwise, and then concentrated under reduced pressure to remove acetonitrile. The residue was extracted with ethyl acetate (20 mL*2), and concentrated under reduced pressure to give compound 006. LCMS m/z (ESI) =627.2 [M+H]$^+$. $^1$H NMR (400 MHZ, CD$_3$OD) δ=7.76 (dd, J=5.8, 9.2 Hz, 1H), 7.30-7.20 (m, 2H), 7.08 (d, J=2.4 Hz, 1H), 6.84 (d, J=5.2 Hz, 1H), 6.40-6.28 (m, 2H), 5.65-5.44 (m, 1H), 4.72-4.50 (m, 5H), 4.49-4.33 (m, 1H), 4.07-4.00 (m, 1H), 3.98 (s, 4H), 3.94-3.78 (m, 3H), 3.48-3.38 (m, 1H), 3.35-3.381 (m, 1H), 2.75-2.54 (m, 2H), 2.50-2.40 (m, 1H), 2.37-2.27 (m, 2H), 2.21-2.08 (m, 1H).

Example 7

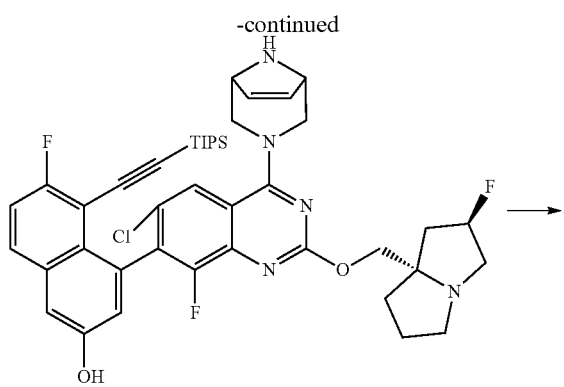

007-3

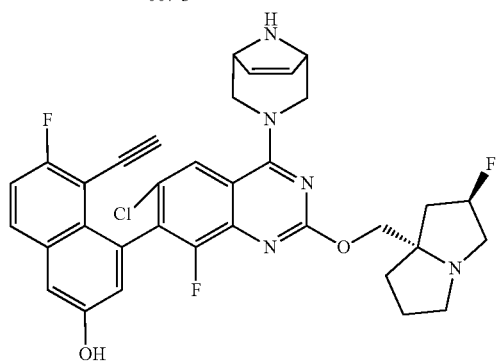

007

Step 1: Synthesis of Compound 007-2

Compound 001-5 (0.05 g, 79.76 μmol), compound 005-1A (53.14 mg, 103.68 μmol) and potassium phosphate (50.79 mg, 239.27 μmol) were added to 1,4-dioxane (1.5 mL) and water (0.3 mL). The atmosphere was replaced with nitrogen three times, and chloro [(bis(1-adamantyl)-n-butylphosphine)-2-(2-aminobiphenyl)]palladium (II) (5.33 mg, 7.98 μmol) was added under nitrogen. The mixture was reacted at 100° C. under nitrogen for 1 hour. The reaction solution was diluted with 5 mL of ethyl acetate and washed with 10 mL of water. The aqueous phase was extracted with 5 mL of ethyl acetate. The organic phases were combined, washed with 10 mL of saturated brine, dried over anhydrous sodium sulfate, and filtered. The filtrate was concentrated to give compound 007-2. LCMS m/z (ESI)=932.4 [M+H]⁺.

Step 2: Synthesis of Compound 007-3

Compound 007-2 (0.06 g, 64.34 μmol) was added to HCl/methanol (3 mL, 4M). The mixture was reacted at 18° C. for 2 hours. The reaction solution was concentrated. The crude product was stirred with 5 mL of ethyl acetate for 16 h, and then filtered. The filter cake was rinsed with 2 mL of ethyl acetate and dried to give compound 007-3 hydrochloride. LCMS m/z (ESI)=788.3 [M+H]⁺.

Step 3: Synthesis of Compound 007 hydrochloride

Compound 007-3 (0.06 g, hydrochloride) was added to N,N-dimethylformamide (1.5 mL). Potassium carbonate (100.53 mg, 727.38 μmol) and cesium fluoride (22.10 mg, 145.48 μmol, 5.36 μL) were added. The mixture was reacted at 60° C. for 16 hours. Additinal potassium carbonate (0.1 g) and cesium fluoride (22 mg) were added, and the mixture was reacted for another 20 hours. 5 mL of water was added to the reaction solution. The mixture was extracted with ethyl acetate (3 mL*2). The combined organic phase was washed with saturated brine (10 mL*3), dried over anhydrous sodium sulfate, and filtered. The filtrate was concentrated and purified by preparative high performance liquid chromatography (column: Phenomenex Luna 80*30 mm*3 μm; mobile phase A: water (0.05% hydrochloric acid); mobile phase B: acetonitrile; running gradientB %: 1%-35%; running time: 8 min) to give compound 007 hydrochloride. LCMS m/z (ESI)=632.2 [M+H]⁺.

Example 8

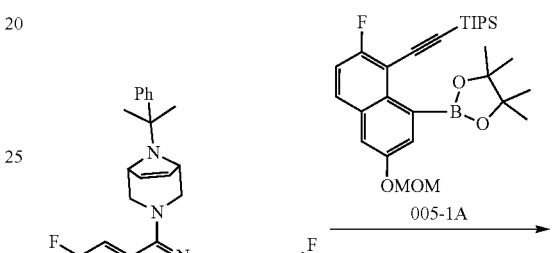

002-3

005-1A 008-1

008-2

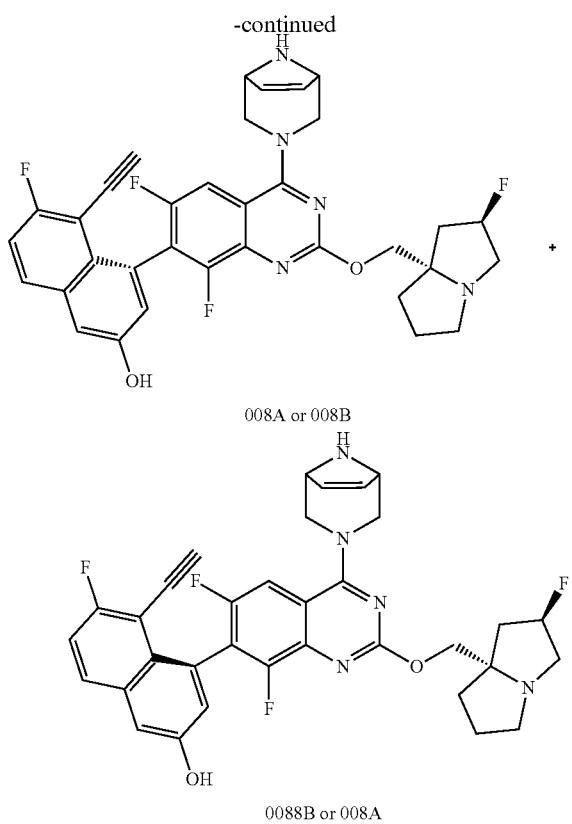

008A or 008B 0088B or 008A

Step 1: Synthesis of Compound 008-1

Compound 002-3 (0.5 g, 795.51 μmol), compound 005-1A (611.59 mg, 1.19 mmol) and potassium phosphate (506.59 mg, 2.39 mmol) were added to anhydrous toluene (5 mL) and water (1 mL). The atmosphere was replaced with nitrogen three times, and chloro [(bis(1-adamantyl)-n-butylphosphine)-2-(2-aminobiphenyl)]palladium (II) (53.19 mg, 79.55 μmol) was added under nitrogen. The mixture was reacted at 80° C. for 16 hours. 10 mL of water was added to the reaction solution, and the mixture was extracted with ethyl acetate (10 mL*2). The combined organic phase was washed with 20 mL of saturated brine, dried over anhydrous sodium sulfate, and filtered. The filtrate was concentrated to give a crude product. The crude product was purified by column chromatography (petroleum ether:ethyl acetate=1:0-0:1) to give compound 008-1. LCMS m/z (ESI)=934.5 [M+H]$^+$. $^1$H NMR (400 MHZ, CDCl$_3$) δ=7.77 (dd, J=5.6, 9.2 Hz, 1H), 7.65 (d, J=7.6 Hz, 2H), 7.50 (d, J=2.4 Hz, 1H), 7.41-7.28 (m, 4H), 7.27-7.24 (m, 1H), 7.20 (d, J=2.0 Hz, 1H), 6.20-5.91 (m, 2H), 5.38-5.13 (m, 3H), 4.69-4.59 (m, 1H), 4.23-4.15 (m, 1H), 4.08-3.99 (m, 1H), 3.97-3.90 (m, 1H), 3.88-3.78 (m, 2H), 3.70 (s, 1H), 3.52 (s, 3H), 3.50-3.43 (m, 1H), 3.30-3.20 (m, 2H), 3.15 (br s, 1H), 3.01-2.91 (m, 1H), 2.33-2.11 (m, 3H), 1.99-1.81 (m, 3H), 1.33 (d, J=10.8 Hz, 6H), 0.96-0.76 (m, 18H), 0.63-0.49 (m, 3H).

Step 2: Synthesis of Compound 008-2 hydrochloride

Compound 008-1 (0.4 g, 428.18 μmol) was added to trifluoroacetic acid (5 mL). The mixture was reacted at 70° C. for 1 hour. The reaction solution was concentrated, and 10 mL of ethyl acetate was added to the concentrated reaction solution. The mixture was washed successively with 10 mL of water, 20 mL of saturated sodium bicarbonate, and 10 mL of saturated brine, dried over anhydrous sodium sulfate, and filtered. The filtrate was then concentrated to give compound 008-2 hydrochloride. LCMS m/z (ESI)=772.3 [M+H]$^+$.

Step 3: Synthesis of Compound 008A and Compound 008B

Compound 008-2 (0.35 g, hydrochloride) was added to N,N-dimethylformamide (4 mL). Potassium carbonate (313.32 mg, 2.27 mmol) and cesium fluoride (137.74 mg, 906.78 μmol, 33.43 μL) were added. The mixture was reacted at 60° C. for 8 h. The reaction solution was diluted with 10 mL of ethyl acetate and washed with 10 ml of water. The aqueous phase was extracted with 5 mL of ethyl acetate. The organic phases were combined, washed with saturated brine (10 mL*3), dried over anhydrous sodium sulfate, and filtered. The filtrate was concentrated, and the crude product was purified by preparative high performance liquid chromatography (column: Phenomenex Luna 80*30 mm*3 μm; mobile phase A: water (0.05% hydrochloric acid); mobile phase B: acetonitrile; running gradient: B: 1%-30%; running time: 8 min). The fraction solution was adjusted to a pH of 7 by adding ammonia water, and then purified by supercritical fluid chromatography (SFC) (column: DAICEL CHIRALPAK IG (250 mm*30 mm, 10 μm); mobile phase: A (supercritical CO$_2$) and B (isopropyl alcohol with 0.1% ammonia); running gradient: 50%-50%; running time: 17 min) to give compounds 008A and 008B.

The analysis and characterization of compound 008A were as follows:

SFC analysis method (column: Chiralpak IG-3, 50×4.6 mm I.D., 3 μm; mobile phase: A (supercritical CO$_2$), B: (ethanol with 0.1% isopropylamine); gradient: B %=5~50%, 3 min; flow rate: 3.4 mL/min; wavelength: 220 nm; pressure: 1800 psi, Rt=1.449 min, enantiomeric excess: 100%. LCMS: MS m/z (ESI)=616.2 [M+H]$^+$. $^1$H NMR (400 MHZ, CD$_3$OD) δ=7.84 (dd, J=6.0, 9.2 Hz, 1H), 7.50 (dd, J=1.6, 10.0 Hz, 1H), 7.35-7.30 (m, 2H), 7.10 (d, J=2.8 Hz, 1H), 6.32-6.25 (m, 2H), 5.41-5.23 (m, 1H), 4.53-4.36 (m, 2H), 4.30-4.14 (m, 2H), 4.05-3.95 (m, 2H), 3.84-3.68 (m, 2H), 3.39-3.33 (m, 1H), 3.29-3.19 (m, 3H), 3.09-3.00 (m, 1H), 2.41-2.10 (m, 3H), 2.06-1.85 (m, 3H).

The analysis and characterization of compound 008B were as follows:

SFC analysis method (column: Chiralpak IG-3, 50×4.6 mm I.D., 3 μm; mobile phase: A (supercritical CO$_2$), B: (ethanol with 0.1% isopropylamine); gradient: B %=5~50%, 3 min; flow rate: 3.4 mL/min; wavelength: 220 nm; pressure: 1800 psi, Rt=2.084 min, enantiomeric excess: 93.62%. LCMS: MS m/z (ESI)=616.2 [M+H]$^+$. $^1$H NMR (400 MHZ, CD$_3$OD) δ=7.84 (dd, J=6.0, 9.2 Hz, 1H), 7.53-7.46 (m, 1H), 7.35-7.27 (m, 2H), 7.10 (d, J=2.0 Hz, 1H), 6.32-6.25 (m, 2H), 5.40-5.20 (m, 1H), 4.51-4.36 (m, 2H), 4.27-4.12 (m, 2H), 4.01-3.95 (m, 2H), 3.83-3.69 (m, 2H), 3.37-3.32 (m, 1H), 3.29-3.15 (m, 3H), 3.07-2.96 (m, 1H), 2.37-2.10 (m, 3H), 2.06-1.87 (m, 3H).

Example 9

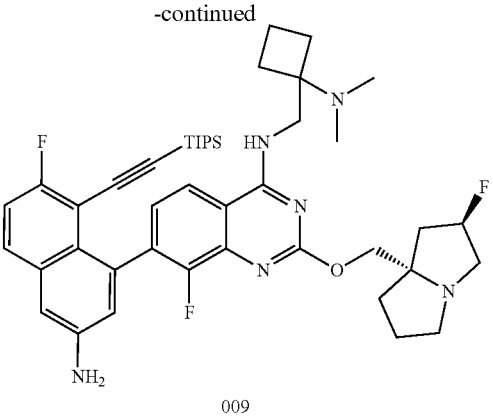
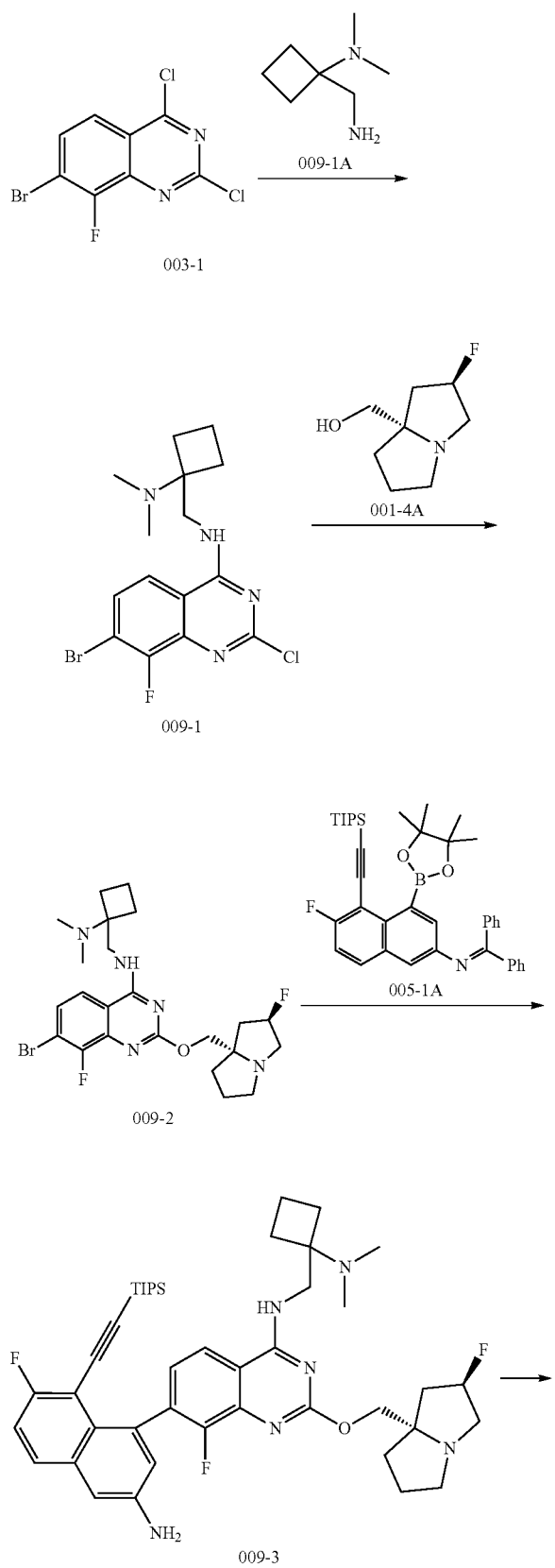

Step 1: Synthesis of Compound 009-1

To a reaction flask were added compound 003-1 (0.5 g, 1.69 mmol), anhydrous dichloromethane (10 mL), triethylamine (512.92 mg, 5.07 mmol, 705.52 µL), and compound 009-1A (170.54 mg, 811.02 µmol). The mixture was stirred at 15° C. for 1 hour. This reaction mixture was combined with the 0.1 g batch of compound 003-1 for work-up. Water (10 mL) was added and the mixture was extracted with dichloromethane (10 mL*3). The combined organic phase was dried over anhydrous sodium sulfate, and filtered. The filtrate was concentrated under reduced pressure to give compound 009-1. LCMS m/z=389.0 [M+H]$^+$. $^1$H NMR (400 MHz, CDCl$_3$) δ ppm: 7.55 (dd, J=8.8, 6.0 Hz, 1H), 7.40-7.33 (m, 1H), 7.12-6.90 (m, 1H), 3.85-3.71 (m, 2H), 2.42-2.25 (m, 8H), 1.93-1.73 (m, 2H), 1.72-1.60 (m, 2H).

Step 2: Synthesis of Compound 009-2

To a reaction flask were added compound 009-1 (0.4 g, 1.03 mmol) and dioxane (4.0 mL). Compound 001-4A (492.78 mg, 3.10 mmol) and cesium carbonate (1.01 g, 3.10 mmol) were added. The mixture was stirred with microwave at 140° C. for 12 hours. The reaction solution was filtered, and the filter cake was rinsed with 10 mL of ethyl acetate. The filtrate was concentrated under reduced pressure to give a crude product. The crude product was purified by preparative high performance liquid chromatography (column: Phenomenex luna C18 250*50 mm*10 µm; mobile phase A: water (0.05% hydrochloric acid), mobile phase B: acetonitrile; running gradient: B %: 5%-35%, running for 10 min) to give the target compound 009-2. LCMS m/z=510.3 [M+H]$^+$. $^1$H NMR (400 MHZ, CDCl$_3$) δ ppm 7.36-7.31 (m, 1H), 7.30-7.25 (m, 1H), 6.70 (br s, 1H), 5.41-5.11 (m, 1H), 4.37-4.15 (m, 2H), 3.85-3.65 (m, 2H), 3.33-3.19 (m, 2H), 3.18 (s, 1H), 3.07-2.89 (m, 1H), 2.39-2.27 (m, 8H), 2.25-2.17 (m, 2H), 2.01-1.59 (m, 8H).

Step 3: Synthesis of Compound 009-3

To a reaction flask were added compound 009-2 (130 mg, 254.69 µmol), anhydrous tetrahydrofuran (2.6 mL), water (0.65 mL), anhydrous potassium phosphate (162.19 mg, 764.08 µmol), and compound 001-5A (482.67 mg, 764.08 µmol). The atmosphere was replaced with nitrogen three times, and [n-butylbis(1-adamantyl)phosphine](2-amino-1, 1'-biphenyl-2-yl) palladium (II) mesylate (18.55 mg, 25.47 µmol) was added. The atmosphere was replaced with nitrogen three times again, and the mixture was heated to 60° C. and stirred for 16 h. Additional compound 001-5A (18.55 mg, 25.47 μmol) was added. The atmosphere was replaced with nitrogen three times, and the mixture was stirred at 60° C. for 16 h. The reaction mixture was cooled down to room temperature, and concentrated under reduced pressure to remove the solvent. The residue was dissolved with 10 mL of ethyl acetate and washed once with 10 ml of water. To the organic phase was added 1N hydrogen chloride solution (10 mL). The mixture was stirred for 10 min. The aqueous phase was collected, and adjusted to a pH of about 9 with sodium carbonate. The mixture was extracted with dichloromethane (10 mL*2), dried over anhydrous sodium sulfate, and filtered. The filtrate was concentrated to give compound 009-3. LCMS m/z=771.4 [M+H]$^+$.

Step 4: Synthesis of Compound 009

Compound 009-3 (178 mg) was added to N,N-dimethylformamide (2 mL). Anhydrous potassium carbonate (159.53 mg, 1.15 mmol) and cesium fluoride (175.34 mg, 1.15 mmol, 42.56 μL) were added. The mixture was stirred at 65° C. for 4 h. This reaction mixture was combined with the 24 mg batch of compound 009-3 for work-up. The reaction solution was cooled down to room temperature, and then filtered. The filter cake was rinsed with 20 mL of ethyl acetate. The mother liquor was washed with saturated brine (20 mL*3), dried over anhydrous sodium sulfate, and filtered. The filtrate was concentrated to give a crude product, and the crude product was purified by preparative high performance liquid chromatography (column: Phenomenex Luna 80*30 mm*3 μm; mobile phase: [water (0.05% hydrochloric acid)-acetonitrile]; acetonitrile %: 1%-30%, 8 min). The obtained fraction was adjusted to a pH of about 9 by adding ammonia water, concentrated, and purified by preparative high performance liquid chromatography (column: Waters Xbridge BEH C18 100*30 mm*10 μm; mobile phase: [water (10 mM ammonium bicarbonate)-acetonitrile]; acetonitrile %: 35%-60%, 8 min) to give compound 009. LCMS m/z=615.5 [M+H]$^+$. $^1$H NMR (400 MHZ, CDCl$_3$) δ ppm 7.66 (dd, J=8.8, 5.6 Hz, 1H), 7.46-7.33 (m, 1H), 7.24-7.13 (m, 2H), 7.08 (d, J=2.4 Hz, 1H), 6.94 (d, J=2.0 Hz, 1H), 6.71 (br s, 1H), 5.40-5.18 (m, 1H), 4.38-4.16 (m, 2H), 3.90 (s, 2H), 3.80 (br s, 2H), 3.31-3.22 (m, 2H), 3.19 (br s, 1H), 3.07-2.91 (m, 1H), 2.78 (s, 1H), 2.56-2.26 (m, 8H), 2.25 (br s, 2H), 2.01-1.61 (m, 8H).

Example 10

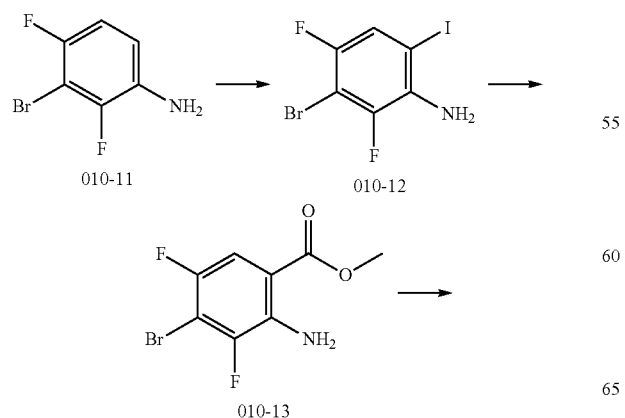

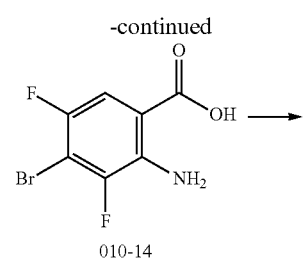
010-14

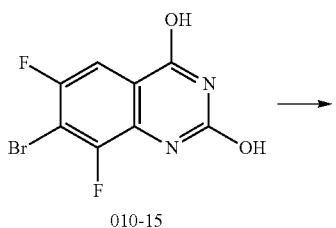
010-15

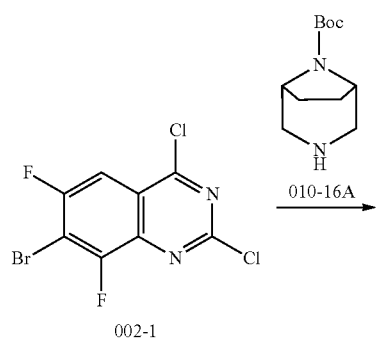
002-1

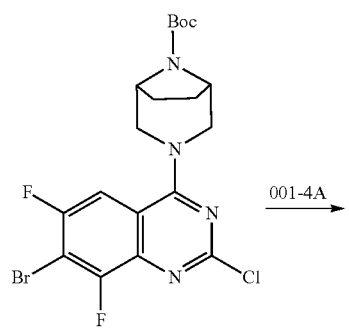
010-17

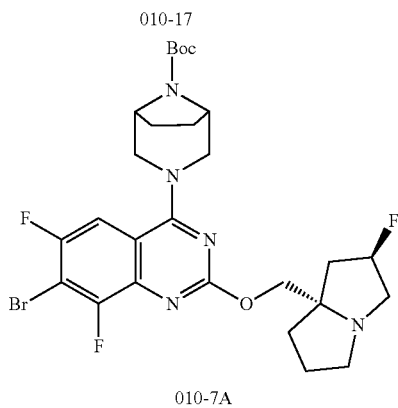
010-7A

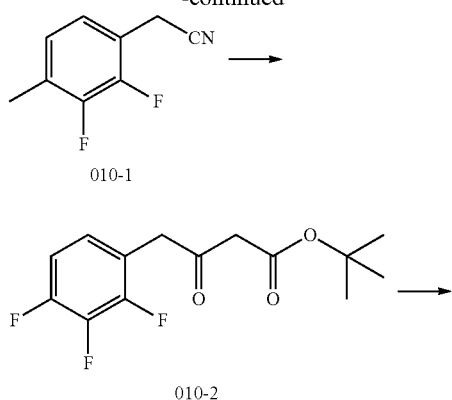
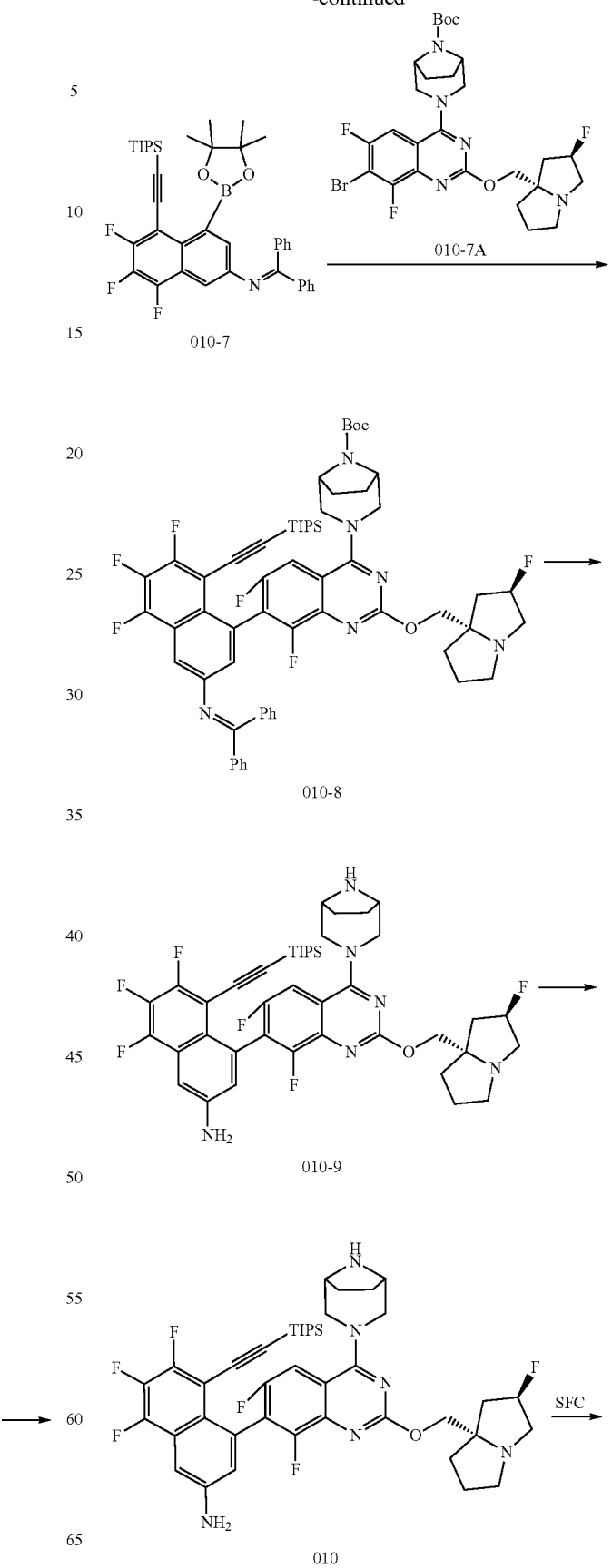

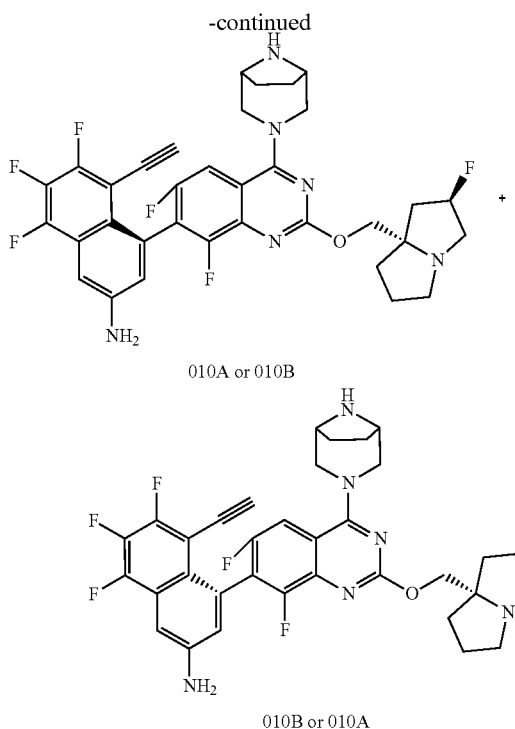

010A or 010B 010B or 010A

Step 1: Synthesis of Compound 010-12

Compound 010-11 (30 g, 144.23 mmol) and silver sulfate (44.97 g, 144.23 mmol, 24.44 mL) were dissolved in ethanol (300 mL). Then iodine (40.27 g, 158.65 mmol, 31.96 mL) was added. The mixture was stirred at 25° C. for 2 h. After the reaction was completed, the reaction solution was filtered, and the filtrate was concentrated under reduced pressure. The crude product was purified on silica gel column (gradient elution:petroleum ether: ethyl acetate=100:1-20:1) to give compound 010-12.

Step 2: Synthesis of Compound 010-13

Compound 010-12 (22 g, 65.89 mmol) and 1, 1'-bis(diphenylphosphino) ferrocene]palladium dichloride dichloromethane (5.38 g, 6.59 mmol) were dissolved in methanol (100 mL) under a carbon monoxide environment at a pressure of 50 Psi and a temperature of 30° C. The mixture was stirred for 5 min, and then triethylamine (46.67 g, 461.22 mmol, 64.20 mL) was added. The mixture was stirried for another 24 h. After the reaction was completed, the mixture was filtered and the filtrate was concentrated under reduced pressure. The crude product was purified on silica gel column (gradient elution:petroleum ether:ethyl acetate=20:1-5:1) to give compound 010-13. LCMS: (ESI) m/z=265.8 [M+H]$^+$.

Step 3: Synthesis of Compound 010-14

Compound 010-13 (15 g, 56.38 mmol) was dissolved in methanol (50 mL). A solution of sodium hydroxide (9.02 g, 225.53 mmol) in water (50 mL) was added. The mixture was stirred at 25° C. for 2 h. After the reaction was completed, the reaction solution was concentrated under reduced pressure and adjusted to a pH of 5 using 2 mol/L hydrochloric acid. A white solid was precipitated and filtered by suction under reduced pressure to give compound 010-14. LCMS: (ESI) m/z=251.8 [M+H]$^+$.

Step 4: Synthesis of Compound 010-15

Compound 010-14 (12 g, 47.62 mmol) and urea (85.79 g, 1.43 mol, 76.60 mL) were added to a reaction flask. The mixture was reacted at 200° C. for 4 h. The reaction solution was cooled to room temperature. 200 mL of water was added and the mixture was stirred. The mixture was filtered by suction under reduced pressure to give a filter cake, which was compound 010-15. LCMS: (ESI) m/z=276.9 [M+H]$^+$.

Step 5: Synthesis of Compound 002-1

N,N-diisopropylethylamine (11.66 g, 90.25 mmol, 15.72 mL) was added dropwise to phosphorus oxychloride (82.50 g, 538.05 mmol, 50 mL) at 0° C., and then compound 010-15 (5 g, 18.05 mmol) was added in batches. After the addition was completed, the mixture was refluxed at 80° C. for 20 h, and then concentrated under reduced pressure. The crude product was purified on silica gel column (gradient elution:petroleum ether:ethyl acetate=20:1-10:1) to give compound 002-1. LCMS: (ESI) m/z=312.9 [M+H]$^+$.

Step 6: Synthesis of Compound 010-17

Compound 010-16A (1.2 g, 3.82 mmol) was dissolved in N,N-dimethylformamide (2 mL). Compound 002-1 (811.51 mg, 3.82 mmol) and N,N-diisopropylethylamine (1.48 g, 11.47 mmol, 2.00 mL) were added. The mixture was stirred to react at 25° C. for 2 h. The reaction solution was poured into 50 mL of water, and a solid was precipitated. The solid was washed with water (3*20 mL) to give compound 010-17. LCMS: (ESI) m/z=489.0 [M+H]$^+$.

Step 7: Synthesis of Compound 010-7A

Compound 010-17 (1.6 g, 3.27 mmol) was dissolved in N,N-dimethylformamide (10 mL) and tetrahydrofuran (10 mL). Then cesium carbonate (3.19 g, 9.80 mmol), compound 001-4A (780.17 mg, 4.90 mmol), and triethylenediamine (36.65 mg, 326.70 μmol, 35.93 μL) were added. The mixture was stirred to react at 25° C. for 18 h. After the reaction was completed, the mixture was extracted with 40 mL of ethyl acetate, and washed with water (15 mL) and saturated brine (15 mL). The organic phase was dried over anhydrous sodium sulfate, and filtered. The filtrate was concentrated to give a crude product. The crude product was purified on silica gel column (gradient elution:petroleum ether:ethyl acetate=20:1-10:1) to give compound 010-7A. LCMS: (ESI) m/z=612.2 [M+H]$^+$.

Step 8: Synthesis of Compound 010-2

To a pre-dried reaction flask were added anhydrous tetrahydrofuran (200 mL) and zinc powder (22.47 g, 343.62 mmol). Trimethylchlorosilane (2.49 g, 22.91 mmol, 2.91 mL) was added under nitrogen with stirring, and the mixture was then warmed up to 45° C. A solution of tert-butyl bromoacetate (37.98 g, 194.72 mmol, 28.77 mL) in anhydrous tetrahydrofuran (60 mL) was added dropwise, and then compound 010-1 (19.6 g, 114.54 mmol) was added under nitrogen. The mixture was stirred at 45° C. for 2 hours. The reaction solution was cooled down to room temperature, and filtered through diatomaceous earth. The filter caker was rinsed with 200 mL of tetrahydrofuran. 200 mL of 1 M hydrochloric acid solution was added to the mother liquor and the mixture was stirred for 2 h. Then the mixture was concentrated under reduced pressure to remove tetrahydrofuran, and the residue was extracted with 50 mL of ethyl acetate. The organic phase was dried over anhydrous sodium sulfate, and filtered. The filtrate was concentrated to give the compound 010-2. $^1$H NMR (400 MHZ, CDCl$_3$) δ ppm 7.08-6.85 (m, 2H), 3.89 (s, 2H), 3.55-3.40 (m, 2H), 1.48 (s, 9H).

Step 9: Synthesis of Compound 010-3

To a pre-dried reaction flask were added compound 010-2 (26.8 g, 92.97 mmol) and trifluoromethanesulfonic acid (455.60 g, 3.04 mol, 268.00 mL). The mixture was stirred at 80° C. for 4 h. The reaction solution was cooled down to room temperature, and then slowly poured into 4 L of saturated aqueous sodium bicarbonate solution. Ice was added to control the temperature to less than 10° C. The mixture was quenched, then stirred for 10 min (aqueous phase pH=7~8), extracted with ethyl acetate (1 L*2), dried over anhydrous sodium sulfate, and filtered. The filtrate was concentrated to give a crude product. The crude product was purified by silica gel column chromatography (gradient elution:petroleum ether:ethyl acetate=100:0~90:10). The fractions were concentrated to dryness, and 100 mL of petroleum ether was added. The mixture was stirred overnight, and then the supernatant was removed. The mixture was dried to give compound 010-3. LCMS m/z=213.0 [M–H]$^-$. $^1$H NMR (400 MHZ, DMSO-d$_6$) δ ppm 10.63 (s, 1H), 9.99 (s, 1H), 7.72-7.56 (m, 1H), 6.65 (d, J=2.0 Hz, 1H), 6.59 (d, J=2.0 Hz, 1H).

Step 10: Synthesis of Compound 010-4

To a pre-dried reaction flask were added compound 010-3 (15 g, 70.05 mmol), (2-bromoethynyl)triisopropylsilane (20.13 g, 77.05 mmol), dioxane (150 mL), and potassium acetate (13.75 g, 140.09 mmol). The atmosphere was replaced with nitrogen three times, and bis(4-methylisopropylphenyl) ruthenium (II) dichloride (6.43 g, 10.51 mmol) was added. The atmosphere was replaced with nitrogen three times, and the mixture was heated to 110° C. and stirred for 2 h. The reaction solution was cooled down to room temperature. This reaction mixture was combined with the batch of compound 010-3 (1.0 g) for work-up. The mixture was cooled down to room temperature, and filtered. The filter cake was rinsed with 200 mL of ethyl acetate. The mother liquor was concentrated under reduced pressure to remove the solvent and then dissolved with 200 mL of ethyl acetate. The solution was washed twice with 100 ml of water and twice with 100 mL of saturated brine, dried over anhydrous sodium sulfate, and filtered. The filtrate was concentrated to give a crude product. The crude compound was purified by silica gel column chromatography (gradient elution:petroleum ether:ethyl acetate=100:0~90:10) to give compound 010-4. LCMS m/z=393.2 [M–H]$^-$. $^1$H NMR (400 MHZ, DMSO-d$_6$) δ ppm 10.53 (s, 1H), 10.08 (s, 1H), 6.67 (d, J=2.0 Hz, 1H), 6.63 (d, J=2.0 Hz, 1H), 1.11 (s, 21H).

Step 11: Synthesis of Compound 010-5

To a pre-dried reaction flask were added compound 010-4 (15 g, 38.02 mmol), anhydrous dichloromethane (300 mL) and N,N-diisopropylethylamine (19.66 g, 152.09 mmol, 26.49 mL). Trifluoromethanesulfonic anhydride (22.53 g, 79.85 mmol, 13.17 mL) was added in three batches and the mixture was stirred at 0° C. for 0.5 hours. This reaction mixture was combined with the batch of compound 010-4 (1 g) for work-up. 200 mL of saturated ammonium chloride solution was added to the reaction solution. The mixture was stirred for 5 min, washed once with 200 mL of saturated ammonium chloride and then twice with half-saturated saline (200 mL), dried over anhydrous sodium sulfate, and filtered. The filtrate was concentrated to give a crude product. The crude compound was purified by silica gel column chromatography (gradient elution:petroleum ether:ethyl acetate=100:0~95:5) to give compound 010-5. LCMS m/z=657.1 [M–H]$^-$. $^1$H NMR (400 MHZ, DMSO-d$_6$) δ ppm 8.56 (d, J=2.4 Hz, 1H), 8.21 (d, J=2.0 Hz, 1H), 1.29-1.04 (m, 21H).

Step 12: Synthesis of Compound 010-6

To a pre-dried reaction flask were added compound 010-5 (19 g, 28.85 mmol), diphenylmethanimine (6.27 g, 34.62 mmol, 5.81 mL), dioxane (190 mL), 4,5-bis(diphenylphosphino)-9,9-dimethylxanthene (3.34 g, 5.77 mmol) and cesium carbonate (18.80 g, 57.70 mmol). The atmosphere was replaced with nitrogen three times, and tris(dibenzylideneacetone) dipalladium (0) (2.64 g, 2.88 mmol) was added. The atmosphere was replaced with nitrogen three times, and the mixture was stirred at 90° C. for 2 h. The reaction solution was cooled down to room temperature, and then filtered. The filter cake was rinsed with 50 mL of ethyl acetate. The mother liquor was concentrated under reduced pressure to remove the solvent, and the residue was dissolved with 100 mL of ethyl acetate. The solution was washed respectively with 50 mL of water and saturated brine (50 mL*2), dried over anhydrous sodium sulfate, and filtered. The filtrate was concentrated and purified by silica gel column chromatography (petroleum ether:ethyl acetate=20:1) to give a crude product. 60 mL of ethanol was added to the crude product. The mixture was stirred for 48 hours, and then filtered. The filter cake was rinsed with 20 mL of ethanol. The filter cake was collected and dried to give compound 010-6. $^1$H NMR (400 MHZ, CDCl$_3$) δ ppm 7.88-7.70 (m, 2H), 7.55 (t, J=7.0 Hz, 1H), 7.46 (t, J=7.6 Hz, 2H), 7.34-7.21 (m, 5H), 7.17-7.11 (m, 2H), 1.27-1.10 (m, 21H).

Step 13: Synthesis of Compound 010-7

To a pre-dried reaction flask were added compound 010-6 (1 g, 1.45 mmol), dioxane (10 mL), potassium acetate (426.84 mg, 4.35 mmol), bis(pinacolato)diboron (1.10 g, 4.35 mmol, 42.07 μL), and 2-di-tert-butylphosphino-2',4',6'-triisopropylbiphenyl (138.22 mg, 289.95 μmol). The atmosphere was replaced with nitrogen three times, and 1,1-bis(diphenylphosphino) ferrocene palladium chloride (106.08 mg, 144.97 μmol) was added. The atmosphere was replaced with nitrogen three times. The mixture was heated to 120° C. and stirred for 2 h. This reaction mixture was combined with the batches of compound 010-6 (0.5 g and 0.1 g) for work-up. The reaction solution was cooled down to room temperature, and filtered. The mother liquor was concentrated to one-half under reduced pressure. 30 mL of ethyl acetate was added. The mixture was washed with saturated brine (30 mL*2), dried over anhydrous sodium sulfate, and filtered. The filtrate was concentrated to give a crude product. The crude product was separated by column chromatography (1000 mesh silica gel, gradient eluting with ethyl acetate:petroleum ether=0%, 2%, 3%, 4%, 5%) to give compound 010-7. $^1$H NMR (400 MHZ, CDCl$_3$) δ ppm 7.84-7.72 (m, 2H), 7.55-7.39 (m, 2H), 7.32-7.22 (m, 6H), 7.15 (br d, J=6.6 Hz, 2H), 1.35 (s, 12H), 1.21-1.11 (m, 21H).

Step 14: Synthesis of Compound 010-8

To a pre-dried reaction flask were added compound 010-7A (250 mg, 408.18 µmol), anhydrous toluene (6 mL), water (1.25 mL), anhydrous potassium phosphate (259.93 mg, 1.22 mmol) and compound 010-7 (408.80 mg, 612.26 µmol). The atmosphere was replaced with nitrogen three times, and [(bis(1-adamantyl)-n-butylphosphine)-2-(2-aminobiphenyl)]palladium (II) chloride (27.29 mg, 40.82 µmol) was added. The atmosphere was replaced with nitrogen three times, and the mixture was heated to 105° C. and stirred for 24 h. The reaction solution was cooled down to room temperature. This reaction mixture was combined with the batch of compound 010-7A (20 mg) for work-up. The mixture was concentrated under reduced pressure to remove the solvent and the residue was dissolved with 200 mL of ethyl acetate. The organic phase was washed twice with 10 ml of water, dried over anhydrous sodium sulfate, and filtered. The filtrate was concentrated to give a crude product. The crude compound was purified by silica gel column chromatography (gradient elution:petroleum ether:ethyl acetate=100:0~50:50, with 5 parts per thousand of triethylamine in ethyl acetate) to give compound 010-8. LCMS m/z=1073.4 [M+H]$^+$.

Step 15: Synthesis of Compound 010-9 hydrochloride

To compound 010-8 (0.3 g, 279.51 µmol) was added hydrogen chloride/methanol (4 M, 3.75 mL). The mixture was stirred at 15° C. for 1 h. This reaction mixture was combined with the batch of compound 010-8 (40 mg) for work-up. The reaction solution was concentrated to dryness under reduced pressure to give compound 010-9 hydrochloride. LCMS m/z=809.5 [M+H]$^+$.

Step 16: Synthesis of Compound 010A and 010B

To a pre-dried reaction flask were added compound 010-9 (0.28 g, hydrochloride), N,N-dimethylformamide (2.8 mL), anhydrous potassium carbonate (712.40 mg, 5.15 mmol), and cesium fluoride (195.74 mg, 1.29 mmol, 47.51 µL). The mixture was stirred at 65° C. for 4 h. This reaction mixture was combined with the batch of compound 010-9 (50 mg) for work-up. The reaction solution was cooled down to room temperature, and filtered. The filter cake was rinsed with 20 mL of ethyl acetate. The mother liquor was washed with saturated brine (20 mL*3), dried over anhydrous sodium sulfate, and filtered. The filtrate was concentrated to give a crude product. The crude product was purified by preparative high performance liquid chromatography (column: Phenomenex luna C18 OBD 80*40 mm*3 µm; mobile phase A: water (0.05% HCl), mobile phase B: acetonitrile; running gradient: B %: 5%-40%, running for 7 min). The fractions were adjusted to a pH of about 9 by adding ammonia dropwise, and then concentrated under reduced pressure to remove acetonitrile. The residue was extracted twice with 20 mL of ethyl acetate, and concentrated under reduced pressure to give a mixture. The mixture was purified by supercritical fluid chromatography (column: DAICEL CHIRALPAK IC (250 mm*30 mm, 10 µm); mobile phase: A (supercritical CO$_2$) and B (isopropyl alcohol with 0.1% ammonia); gradient: B %=60%-60%, running for 15 min) to give compounds 010A and 010B.

Characterization of compound 010A was as follows:
SFC analysis method: column: Chiralpak IC-3, 3 µm, 50×4.6 mm I.D; mobile phase: A (supercritical CO$_2$) and B (isopropyl alcohol with 0.1% isopropylamine); gradient: AB=60:40, 3 min; flow rate: 4.0 mL/min; wavelength: 220 nm; column temperature: 35° C.; pressure: 1800 psi, Rt=0.881 min, enantiomeric excess: 100%. LCMS m/z=653.3 [M+H]$^+$. $^1$H NMR (400 MHZ, CDCl$_3$) δ ppm 7.31-7.28 (m, 2H), 6.98-6.94 (m, 1H), 5.41-5.19 (m, 1H), 4.43-4.30 (m, 2H), 4.30-4.25 (m, 1H), 4.21-4.04 (m, 3H), 3.67 (s, 2H), 3.62-3.43 (m, 2H), 3.34-3.24 (m, 2H), 3.19 (s, 1H), 3.04-2.95 (m, 1H), 2.79 (s, 1H), 2.31 (s, 1H), 2.26-2.16 (m, 2H), 2.02-1.82 (m, 8H).

Characterization of compound 010B was as follows:
SFC analysis method: column: Chiralpak IC-3, 3 µm, 50×4.6 mm I.D; mobile phase: A (supercritical CO$_2$) and B (isopropyl alcohol with 0.1% isopropylamine); gradient: A:B=60:40, 3 min; flow rate: 4.0 mL/min; wavelength: 220 nm; column temperature: 35° C.; pressure: 1800 psi, Rt=1.364 min, enantiomeric excess: 96.69%. LCMS m/z=653.3 [M+H]$^+$. $^1$H NMR (400 MHZ, CDCl$_3$) δ ppm 7.29 (d, J=2.0 Hz, 2H), 6.96 (d, J=2.0 Hz, 1H), 5.47-5.12 (m, 1H), 4.36 (br t, J=14.0 Hz, 2H), 4.26 (d, J=10.4 Hz, 1H), 4.17 (br d, J=10.4 Hz, 1H), 4.11 (br s, 2H), 3.67 (br s, 2H), 3.53 (br t, J=10.8 Hz, 2H), 3.38-3.24 (m, 2H), 3.24-3.15 (m, 1H), 3.09-2.90 (m, 1H), 2.80 (s, 1H), 2.31 (br s, 1H), 2.27-2.15 (m, 2H), 2.06-1.81 (m, 8H).

Example 11

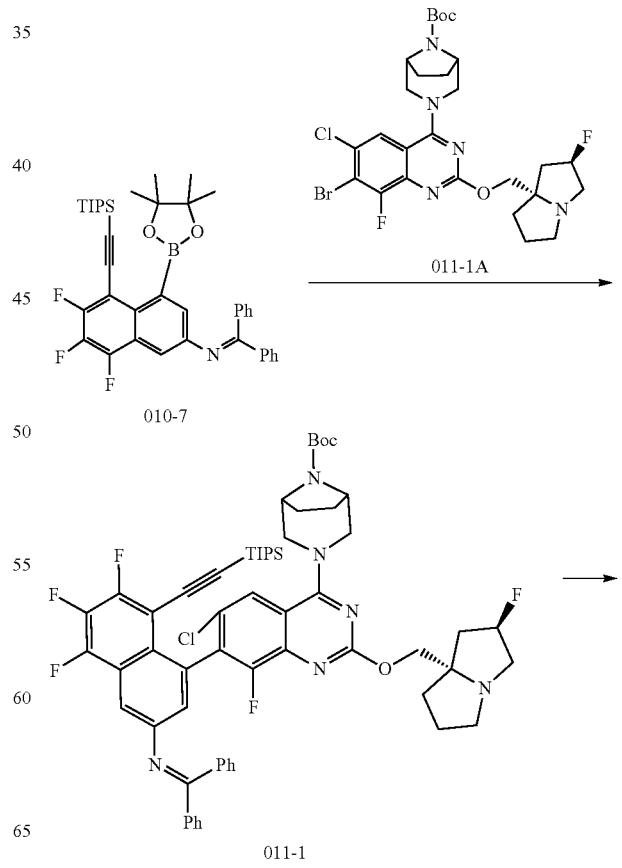

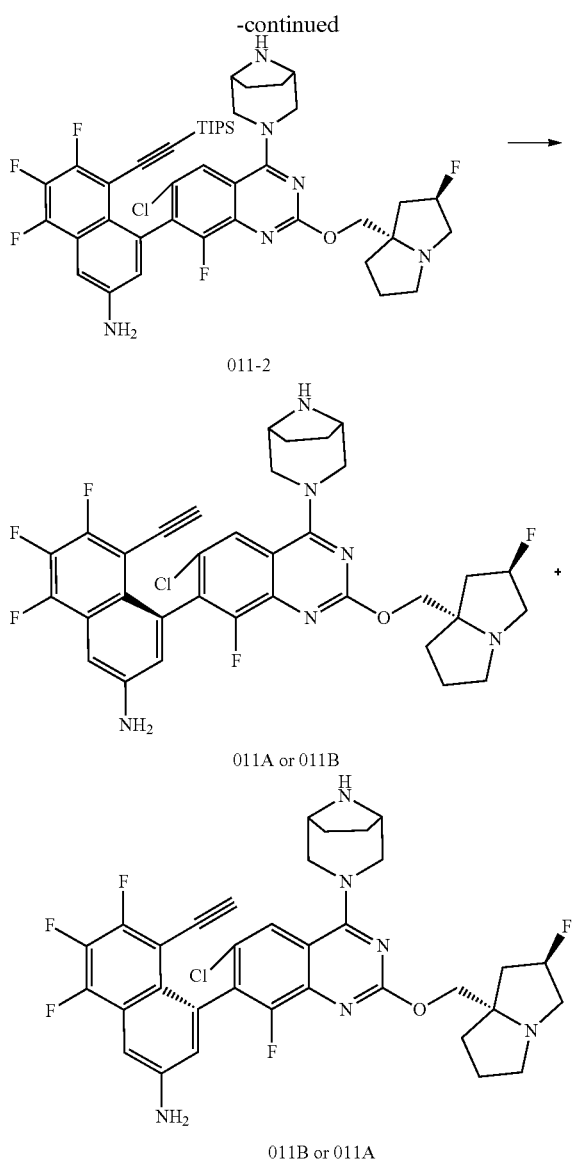

Step 1: Synthesis of Compound 011-1

To a pre-dried reaction flask were added compound 011-1A (0.2 g, 318.00 μmol), anhydrous toluene (5 mL), water (1.25 mL), anhydrous potassium phosphate (202.50 mg, 953.99 μmol), and compound 010-7 (318.48 mg, 477.00 μmol). The atmosphere was replaced with nitrogen three times, and [(bis(1-adamantyl)-n-butylphosphine)-2-(2-aminobiphenyl)]palladium (II) chloride (21.26 mg, 31.80 μmol) was added. The atmosphere was replaced with nitrogen three times, and the mixture was heated to 105° C. and stirred for 24 h. The reaction solution was cooled down to room temperature. This reaction mixture was combined with the batch of compound 011-1A (20 mg) for work-up. The mixture was concentrated under reduced pressure to remove the solvent and the residue was dissolved with 10 mL of ethyl acetate. The organic phase was washed twice with 10 ml of water, dried over anhydrous sodium sulfate, and filtered. The filtrate was concentrated to give a crude product. The crude compound was purified by silica gel column chromatography (gradient elution:petroleum ether:ethyl acetate=100:0~40:60, with 5 parts per thousand of triethylamine in ethyl acetate) to give compound 011-1. LCMS m/z=1089.2 [M+H]$^+$.

Step 2: Synthesis of Compound 011-2 hydrochloride

To compound 011-1 (250 mg, 229.41 μmol) was added hydrogen chloride/methanol (4 M, 6.25 mL). The mixture was stirred at 15° C. for 1 h. This reaction mixture was combined with the batch of compound 011-1 (20 mg) for work-up. The reaction solution was concentrated under reduced pressure to give compound 011-2 hydrochloride. LCMS m/z=825.2 [M+H]$^+$.

Step 3: Synthesis of Compound 011A and Compound 011B

To a pre-dried reaction flask were added compound 011-2 (220 mg, hydrochloride), N,N-dimethylformamide (4 mL), anhydrous potassium carbonate (499.11 mg, 3.61 mmol), and cesium fluoride (137.14 mg, 902.81 μmol, 33.29 μL). The mixture was stirred at 65° C. for 4 h. This reaction mixture was combined with the batch of compound 011-2 (50 mg) for work-up. The reaction solution was cooled down to room temperature, and filtered. The filter cake was rinsed with 20 mL of ethyl acetate. The mother liquor was washed with saturated brine (20 mL*3), dried over anhydrous sodium sulfate, and filtered. The filtrate was concentrated to give a crude product. The crude product was analysized by preparative high performance liquid chromatography (column: Phenomenex luna C18 OBD 80*30 mm*3 μm; mobile phase A: water (0.05% HCl), mobile phase B: acetonitrile; running gradient: B %: 15%-50%, running for 8 min). The fractions were collected, adjusted to a pH of about 9 by adding ammonia dropwise, and then concentrated under reduced pressure to remove acetonitrile. The residue was extracted twice with 20 mL of ethyl acetate, and concentrated under reduced pressure to give a mixture. The mixture was purified by supercritical fluid chromatography (column: DAICEL CHIRALPAK IC (250 mm*30 mm, 10 μm); mobile phase: A (supercritical CO$_2$) and B (isopropyl alcohol with 0.1% ammonia); gradient: B %=50%-50%, running for 15 min) to give compounds 011A and 011B.

Characterization of compound 011A was as follows:
SFC analysis method: column: Chiralpak IC-3, 3 μm, 50×4.6 mm I.D; mobile phase: A (supercritical CO$_2$) and B (isopropyl alcohol with 0.1% isopropylamine); gradient: A:B=50:50, 3 min; flow rate: 3.4 mL/min; wavelength: 220 nm; column temperature: 35° C.; pressure: 1800 psi, Rt=1.656 min, enantiomeric excess: 100%. LCMS m/z=669.3 [M+H]$^+$. $^1$H NMR (400 MHz, CDCl$_3$) δ ppm 7.64 (s, 1H), 7.31 (br s, 1H), 6.90 (s, 1H), 5.42-5.19 (m, 1H), 4.48-4.33 (m, 2H), 4.29 (br d, J=10.4 Hz, 1H), 4.17 (br d, J=10.4 Hz, 1H), 4.11 (s, 2H), 3.68 (br s, 2H), 3.56 (br dd, J=18.2, 12.6 Hz, 2H), 3.38-3.25 (m, 2H), 3.21 (br s, 1H), 3.01 (br s, 1H), 2.76 (s, 1H), 2.32 (br s, 1H), 2.28-2.15 (m, 2H), 2.01-1.79 (m, 8H).

Characterization of compound 011B was as follows:
SFC analysis method: column: Chiralpak IC-3, 3 μm, 50×4.6 mm I.D; mobile phase: A (supercritical CO$_2$) and B (isopropyl alcohol with 0.1% isopropylamine); gradient: A:B=50:50, 3 min; flow rate: 3.4 mL/min; wavelength: 220 nm; column temperature: 35° C.; pressure: 1800 psi, Rt=1.930 min, enantiomeric excess: 96.56%. LCMS m/z=669.3 [M+H]$^+$. $^1$H NMR (400 MHz, CDCl$_3$) δ ppm 7.56 (s, 1H), 7.30-7.28 (m, 1H), 6.81 (d, J=2.0 Hz, 1H), 5.40-5.19 (m, 1H), 4.43 (br d, J=13.0 Hz, 1H), 4.37-4.26 (m, 3H), 4.06 (s, 2H), 3.95-3.82 (m, 3H), 3.69 (br d, J=12.6 Hz, 1H), 3.61-6.41 (m, 2H), 3.32-3.18 (m, 1H), 3.01 (br s, 1H), 2.82-2.66 (m, 1H), 2.41-2.14 (m, 3H), 2.05-1.85 (m, 8H).
Example 12
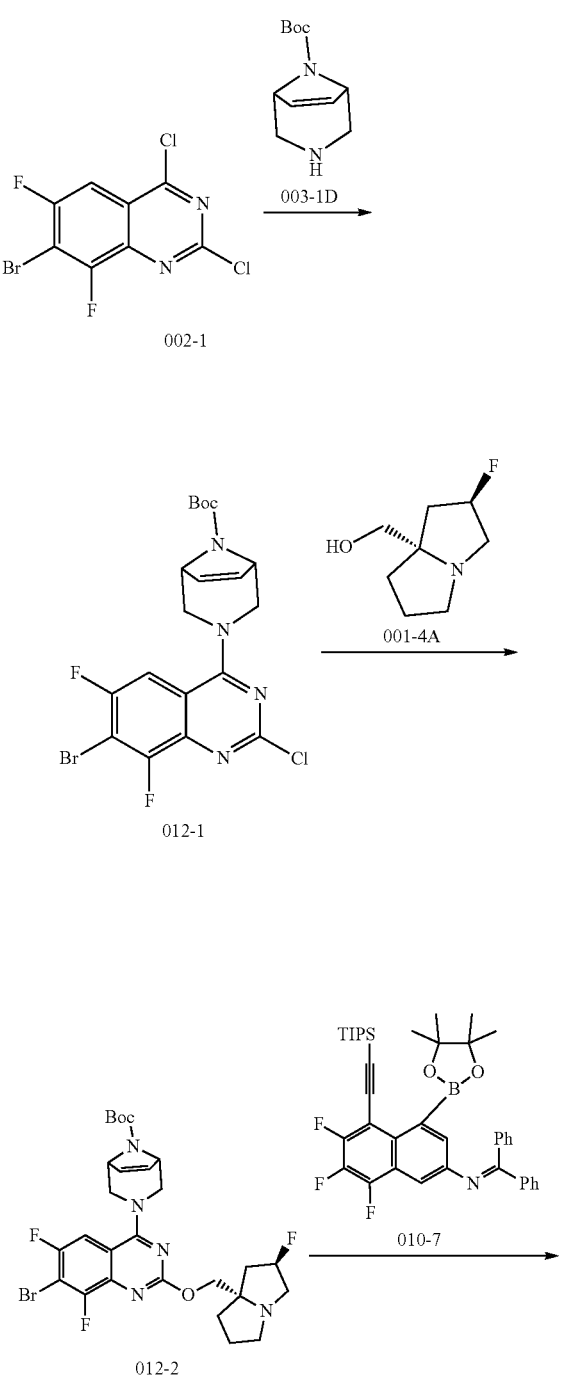
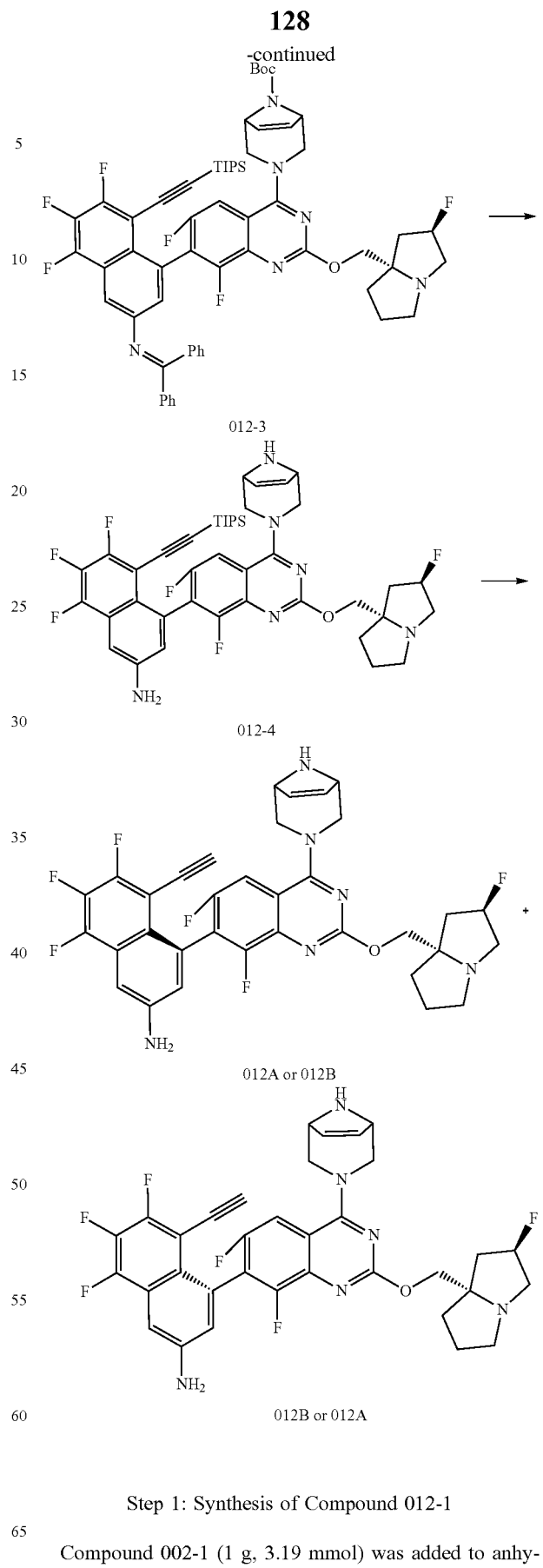
Step 1: Synthesis of Compound 012-1
Compound 002-1 (1 g, 3.19 mmol) was added to anhydrous dichloromethane (10 mL). Compound 003-1D (736.82 mg, 3.50 mmol) and triethylamine (644.70 mg, 6.37 mmol, 886.79 μL) were added. The mixture was reacted at 18° C. for 1 h. The reaction solution was washed successively with saturated ammonium chloride (20 mL*2) and 20 mL of saturated brine, dried over anhydrous sodium sulfate, and filtered. The filtrate was concentrated, and the crude product was stirred with a mixed solvent (petroleum ether:methyl tert-butyl ether=4:1, 20 mL) for 1 h and filtered. The filter cake was rinsed with a mixed solvent at the same ratio (5 mL*2), and dried under reduced pressure to give compound 012-1. LCMS m/z (ESI)=487.0 [M+H]$^+$.

Step 2: Synthesis of Compound 012-2

Compound 012-1 (0.6 g, 1.23 mmol) was added to anhydrous tetrahydrofuran (3 mL) and N,N-dimethylformamide (3 mL). Cesium carbonate (1.20 g, 3.69 mmol), compound 001-4A (235.02 mg, 1.48 mmol) and triethylenediamine (41.40 mg, 369.06 μmol, 40.59 μL) were added. The mixture was reacted at 30° C. for 16 h. The reaction solution was added to 10 mL of methyl tert-butyl ether. The mixture was washed with saturated ammonium chloride (20 mL*2), and the aqueous phase was extracted with 10 mL of methyl tert-butyl ether. The organic phases were combined, washed with saturated brine (20 mL*2), dried over anhydrous sodium sulfate, and filtered. The filtrate was concentrated to give compound 012-2. LCMS m/z (ESI)=610.1 [M+H]$^+$. $^1$H NMR (400 MHZ, CDCl$_3$) δ=7.30-7.28 (m, 1H), 6.20-6.12 (m, 2H), 5.42-5.20 (m, 1H), 4.78-4.58 (m, 2H), 4.40-4.26 (m, 2H), 4.23-4.16 (m, 1H), 4.12-4.02 (m, 1H), 3.81-3.59 (m, 2H), 3.32-3.19 (m, 3H), 3.04-2.96 (m, 1H), 2.31-2.11 (m, 3H), 2.02-1.88 (m, 3H), 1.56 (s, 9H).

Step 3: Synthesis of Compound 012-3

Compound 012-2 (0.25 g, 409.52 μmol), compound 010-7 (300.77 mg, 450.48 μmol) and potassium phosphate (260.79 mg, 1.23 mmol) were added to toluene (3 mL) and water (0.6 mL). The atmosphere was replaced with nitrogen three times, and chloro [(bis(1-adamantyl)-n-butylphosphine)-2-(2-aminobiphenyl)]palladium (II) (54.76 mg, 81.90 μmol) was added under nitrogen. The mixture was reacted at 100° C. for 3 h. 10 mL of water was added to the reaction solution. The mixture was extracted with ethyl acetate (5 mL*2). The layers were separated. The organic phases were combined, washed with 20 mL of saturated brine, dried over anhydrous sodium sulfate, and filtered. The filtrate was concentrated. The crude product was purified by column chromatography (petroleum ether:ethyl acetate=1:0-0:1) to give compound 012-3. LCMS m/z (ESI)=1071.4 [M+H]$^+$.

Step 4: Synthesis of Compound 012-4 hydrochloride

Compound 012-3 (0.2 g, 186.69 μmol) was added to HCl/methanol (4 mL, 4M). The mixture was reacted at 18° C. for 1 h. This reaction mixture was combined with compound 012-3 (50 mg batch) for work-up. The reaction solution was concentrated directly. The crude was stirred with 5 mL of ethyl acetate for 2 h, and then filtered. The filter cake was rinsed with ethyl acetate (2 mL*2) and dried under reduced pressure to give compound 012-4 hydrochloride. LCMS m/z (ESI)=807.3 [M+H]$^+$.

Step 5: Synthesis of Compound 012A and Compound 012B

Compound 012-4 (0.1 g, hydrochloride) was added to N,N-dimethylformamide (2 mL). Potassium carbonate (85.64 mg, 619.61 μmol) and cesium fluoride (37.65 mg, 247.85 μmol, 9.14 μL) were added. The mixture was reacted at 60° C. for 16 hours. This reaction mixture was combined with compound 012-4 (50 mg batch) for work-up. The reaction solution was diluted with 5 mL of ethyl acetate and washed with 10 ml of water. The aqueous phase was extracted with 5 mL of ethyl acetate. The organic phases were combined, washed with saturated brine (10 mL*2), dried over anhydrous sodium sulfate, and filtered. The filtrate was concentrated, and the crude product was purified by preparative high performance liquid chromatography (column: Phenomenex luna C18 80*40 mm*3 μm; mobile phase A: water (0.05% hydrochloric acid); mobile phase B: acetonitrile; running gradient: B: 1%-40%; running time: 7 min). A drop of ammonia was added to the separated solution to give a crude product. The crude product was purified by supercritical fluid chromatography (SFC) (column: DAICEL CHIRALCEL OD (250 mm*30 mm, 10 μm); mobile phase: A (supercritical CO$_2$) and B (ethanol with 0.1% ammonia); gradient: B %=50%-50%, running for 13 min) to give compound 012A and compound 012B.

The analysis and characterization of compound 012A were as follows:

SFC analysis method (column: Chiralcel OD-3, 50×4.6 mm I.D., 3 μm; mobile phase: A (supercritical CO$_2$), B: (ethanol with 0.1% isopropylamine); gradient: B %=5~50%, 3 min; flow rate: 3.4 mL/min; wavelength: 220 nm; pressure: 1800 psi, Rt=1.516 min, 100% ee. LCMS: m/z (ESI)=651.3 [M+H]$^+$. $^1$H NMR (400 MHZ, CD$_3$OD) δ-7.57 (d, J=10.0 Hz, 1H), 7.28 (d, J=2.0 Hz, 1H), 7.07 (d, J=2.0 Hz, 1H), 6.47-6.31 (m, 2H), 5.68-5.45 (m, 1H), 4.72-4.59 (m, 6H), 4.13-3.77 (m, 5H), 3.54-3.40 (m, 2H), 2.80-2.42 (m, 3H), 2.39-2.15 (m, 3H).

The analysis and characterization of compound 012B were as follows:

SFC analysis method (column: Chiralcel OD-3, 50×4.6 mm I.D., 3 μm; mobile phase: A (supercritical CO$_2$), B: (ethanol with 0.1% isopropylamine); gradient: B %=5~50%, 3 min; flow rate: 3.4 mL/min; wavelength: 220 nm; pressure: 1800 psi, Rt=1.751 min, 96.64% ee. LCMS: m/z (ESI)=651.3 [M+H]$^+$. $^1$H NMR (400 MHZ, CD$_3$OD) δ=7.60-7.55 (m, 1H), 7.27 (d, J=2.4 Hz, 1H), 7.06 (d, J=2.4 Hz, 1H), 6.39-6.27 (m, 2H), 5.59-5.38 (m, 1H), 4.66-4.41 (m, 4H), 4.26 (d, J=14.8 Hz, 2H), 3.97-3.65 (m, 5H), 3.42 (s, 1H), 3.37-3.33 (m, 1H), 2.65-2.45 (m, 2H), 2.40-2.16 (m, 3H), 2.11-1.99 (m, 1H).

Example 13

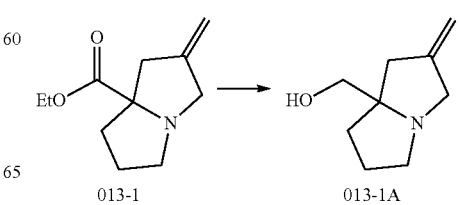

013-1                013-1A

-continued

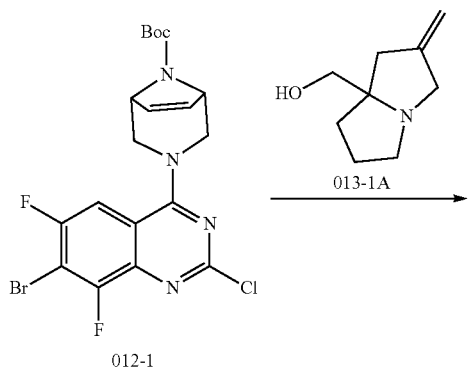

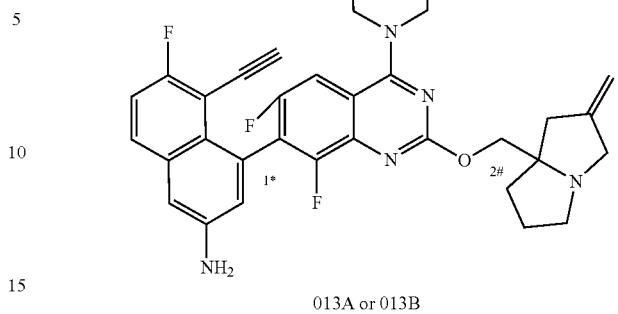

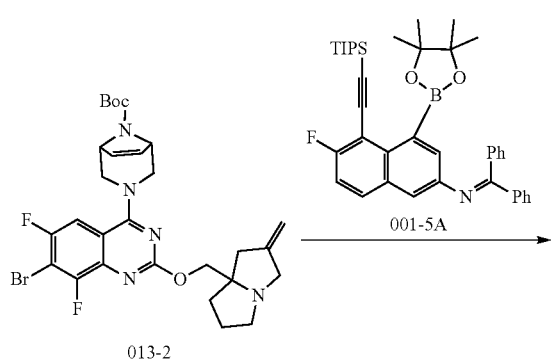

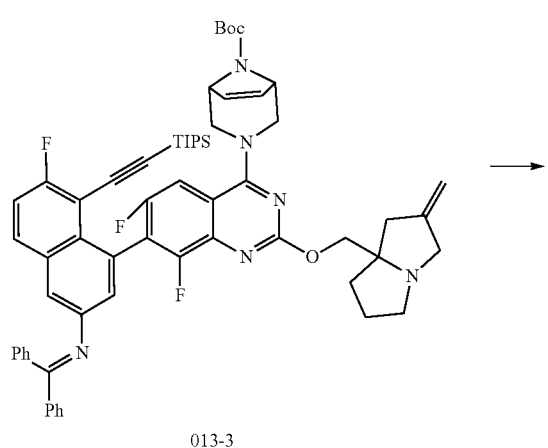

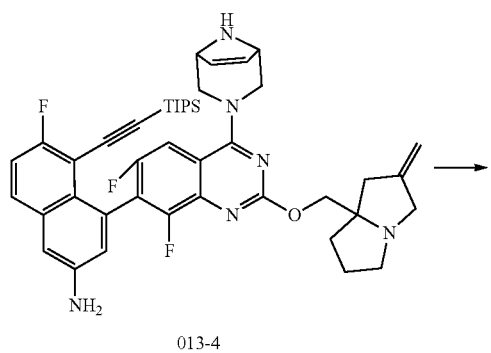

Step 1: Synthesis of Compound 013-1A

Compound 013-1 (1.8 g, 5.57 mmol) was added to anhydrous tetrahydrofuran (20 mL). The atmosphere was replaced with nitrogen three times, and the mixture was cooled down to 10° C. Lithium aluminum hydride (633.94 mg, 16.70 mmol) was added in three portions under nitrogen atmosphere. The reaction mixture was slowly warmed to 20° C. and reacted for 10 min, and then heated to 70° C. and refluxed for 2 h. The mixture was cooled down to 0° C. The reaction mixture was quenched by slowly adding 0.6 mL of water. Then 0.6 mL of 15% sodium hydroxide solution and 1.8 mL of water were added. The mixture was stirred for 5 min, and 5 g of sodium sulfate solid was added. The mixture was stirred for 30 min, and filtered. The filtrate was concentrated to give compound 013-1A. $^1$H NMR (400 MHZ, CDCl$_3$) δ=4.88 (d, J=11.2 Hz, 2H), 3.67-3.55 (m, 1H), 3.32-3.18 (m, 3H), 3.13-2.97 (m, 1H), 2.70-2.58 (m, 1H), 2.51-2.40 (m, 1H), 2.37-2.22 (m, 1H), 1.95-1.54 (m, 5H).

Step 2: Synthesis of Compound 013-2

Compound 012-1 (0.55 g, 1.13 mmol) was added to anhydrous tetrahydrofuran (2.5 mL) and N,N-dimethylformamide (2.5 mL). Cesium carbonate (10 g, 3.38 mmol), compound 013-1A (190.06 mg, 1.24 mmol) and triethylenediamine (37.95 mg, 338.31 μmol, 37.20 μL) were added. The mixture was reacted at 30° C. for 20 h. This reaction mixture was combined with the batch of compound 012-1 (50 mg) for work-up. The reaction solution was added to 10 mL of methyl tert-butyl ether, and washed with saturated ammonium chloride (20 mL*2). The aqueous phase was extracted with 10 mL of methyl tert-butyl ether. The organic phases were combined, washed with saturated brine (20 mL*2), dried over anhydrous sodium sulfate, and filtered. The filtrate was concentrated, and the crude product was purified by column chromatography (petroleum ether:ethyl acetate=100:0-1:4) to give compound 013-2. LCMS: MS m/z (ESI)=604.1 [M+H]$^+$.

Step 3: Synthesis of Compound 013-3

Compound 001-5A (517.29 mg, 818.88 μmol), compound 013-2 (0.45 g, 744.44 μmol) and potassium phosphate (474.06 mg, 2.23 mmol) were added to toluene (5 mL) and water (1 mL). The atmosphere was replaced d with nitrogen three times, and chloro [(bis(1-adamantyl)-n-butylphosphine)-2-(2-aminobiphenyl)]palladium (II) (99.55 mg, 148.89 µmol) was added under nitrogen. The reaction mixture was reacted at 90° C. for 3.5 h. The reaction solution was washed with 10 mL of water, and extracted with ethyl acetate (5 mL*2). The organic phases were combined, washed with 20 mL of saturated brine, dried over anhydrous sodium sulfate, and filtered. The filtrate was concentrated, and the crude product was purified by column chromatography (petroleum ether:ethyl acetate=1:0-0:1) to give compound 013-3. LCMS: MS m/z (ESI)=1029.3 [M+H]$^+$.

Step 4: Synthesis of Compound 013-4 hydrochloride

Compound 013-3 (0.5 g, 485.76 µmol) was added to hydrogen chloride/methanol (10 mL, 4M). The mixture was reacted at 20° C. for 1 h. The reaction solution was concentrated under reduced pressure. 5 mL of ethyl acetate was added to the crude product. The mixture was stirred for 16 h, and then filtered. The filter cake was washed with ethyl acetate (2 mL*2) and dried under reduced pressure to give compound 013-4 hydrochloride. LCMS: MS m/z (ESI)=765.3 [M+H]$^+$ 0.1H NMR (400 MHZ, CD$_3$OD) δ=8.31-8.20 (m, 2H), 7.94-7.84 (m, 1H), 7.75-7.61 (m, 2H), 6.62-6.48 (m, 1H), 6.44-6.28 (m, 1H), 5.36-5.34 (m, 2H), 5.28-5.18 (m, 1H), 4.86-4.75 (m, 2H), 4.72-4.61 (m, 2H), 4.55-4.38 (m, 2H), 4.07-3.91 (m, 2H), 3.91-3.79 (m, 1H), 3.16-3.04 (m, 1H), 2.91-2.84 (m, 1H), 2.58-2.34 (m, 2H), 2.33-2.11 (m, 3H), 1.94-1.72 (m, 1H), 1.03-0.84 (m, 18H), 0.71-0.54 (m, 3H).

Step 5: Synthesis of Compound 013A and Compound 013B

Compound 013-4 (0.42 g, hydrochloride) was added to N,N-dimethylformamide (5 mL). Potassium carbonate (362.14 mg, 2.62 mmol) and cesium fluoride (159.21 mg, 1.05 mmol, 38.64 µL) were added. The mixture was reacted at 60° C. for 15 h. The reaction solution was diluted with 10 mL of ethyl acetate and washed with 20 ml of water. The aqueous phase was extracted with 10 mL of ethyl acetate. The organic phases were combined, washed with saturated brine (20 mL*2), dried over anhydrous sodium sulfate, and filtered. The filtrate was concentrated, and the crude product was purified by preparative high performance liquid chromatography (column: Phenomenex luna C18 75*30 mm*3 µm; mobile phase A: water (0.05% hydrochloric acid); mobile phase B: acetonitrile; running gradient: B %=10%-40%; running time: 8 min). The fractions were adjusted to a pH of ~7 by adding ammonia dropwise to give a crude product. The crude product was purified by supercritical fluid chromatography (SFC) (column: DAICEL DAICEL CHIRALPAK IG (250 mm*30 mm, 10 µm); mobile phase: A (supercritical CO$_2$) and B (ethanol with 0.1% ammonia); gradient: B %=50%-50%, running for 15 min) to give compound 013A and compound 013B. The carbon atoms with "*" and "#" are chiral carbon atoms and exist as a single enantiomer (R) or(S). Compound 013A has a configuration "1S,2R" or "1S,2S" or "1R,2R" or "1R,2S" or "1S" or "1R" or "2S" or "2R"; Compound 013B has a configuration "1S,2R" or "1S,2S" or "1R,2R" or "1R,2S" or "1S" or "1R" or "2S" or "2R".

The analysis and characterization of compound 013A were as follows:

SFC analysis method (column: Chiralpak IG-3, 50×4.6 mm I.D., 3 µm; mobile phase: A (supercritical CO$_2$), B: (ethanol with 0.1% isopropylamine); gradient: B %=50~50%, 6 min; flow rate: 4.0 mL/min; wavelength: 220 nm; pressure: 1800 psi, Rt=0.662 min, 100% ee. LCMS: MS m/z (ESI)=609.1 [M+H]$^+$. $^1$H NMR (400 MHZ, CD$_3$OD) δ=7.74 (dd, J=6.0, 9.2 Hz, 1H), 7.57 (d, J=10.0 Hz, 1H), 7.30-7.17 (m, 2H), 7.04 (s, 1H), 6.42-6.24 (m, 2H), 5.24 (s, 2H), 4.69-4.46 (m, 4H), 4.36-4.14 (m, 3H), 3.96-3.79 (m, 3H), 3.74-3.61 (m, 1H), 3.28-3.12 (m, 2H), 3.06-2.88 (m, 1H), 2.82-2.71 (m, 1H), 2.41-2.28 (m, 1H), 2.23-2.04 (m, 3H).

The analysis and characterization of compound 013B were as follows:

SFC analysis method (column: Chiralpak IG-3, 50×4.6 mm I.D., 3 µm; mobile phase: A (supercritical CO$_2$), B: (ethanol with 0.1% isopropylamine); gradient: B %=50~50%, 6 min; flow rate: 4.0 mL/min; wavelength: 220 nm; pressure: 1800 psi, Rt=1.152 min, 99.38% ee. LCMS: MS m/z (ESI)=609.1 [M+H]$^+$. $^1$H NMR (400 MHz, CD$_3$OD) δ=7.74 (dd, J=5.6, 9.2 Hz, 1H), 7.57 (d, J=10.4 Hz, 1H), 7.29-7.16 (m, 2H), 7.05-7.02 (m, 1H), 6.34-6.26 (m, 2H), 5.18 (s, 2H), 4.57-4.40 (m, 4H), 4.20-4.09 (m, 1H), 4.07-4.03 (m, 2H), 3.87-3.79 (m, 1H), 3.78-3.69 (m, 2H), 3.62-3.52 (m, 1H), 3.28-3.24 (m, 1H), 3.15-3.03 (m, 1H), 3.01-2.90 (m, 1H), 2.76-2.63 (m, 1H), 2.40-2.24 (m, 1H), 2.19-1.98 (m, 3H).

Example 14

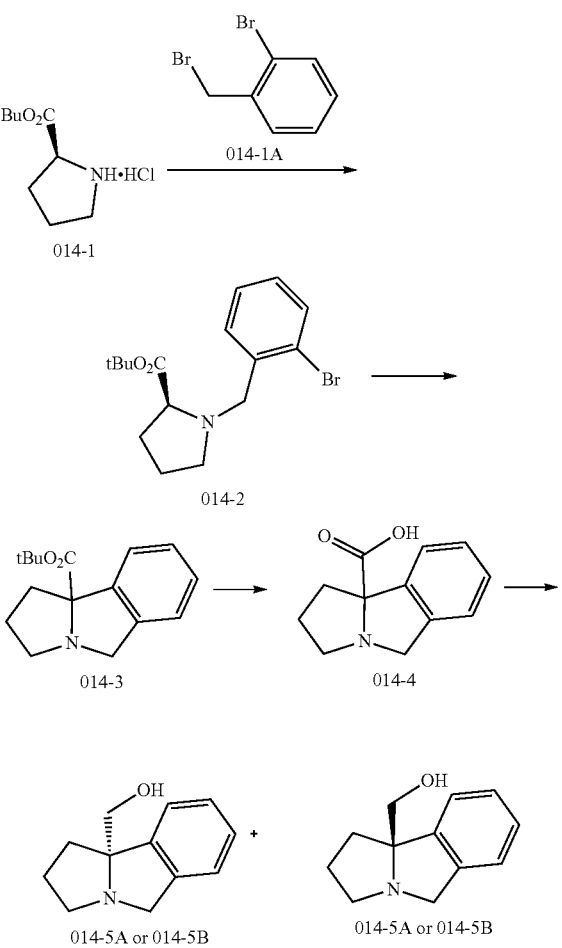

135
-continued
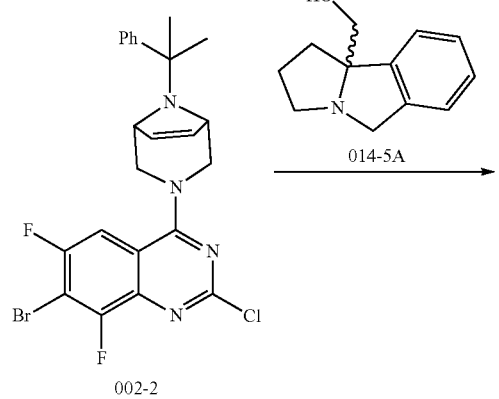
002-2
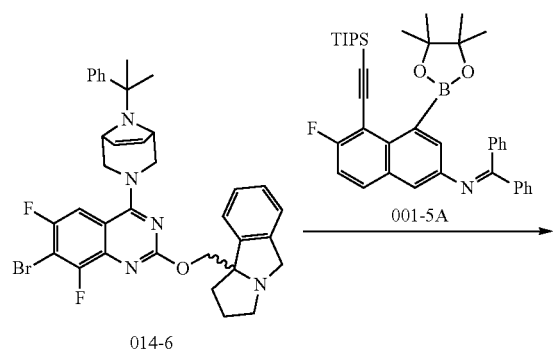
014-6
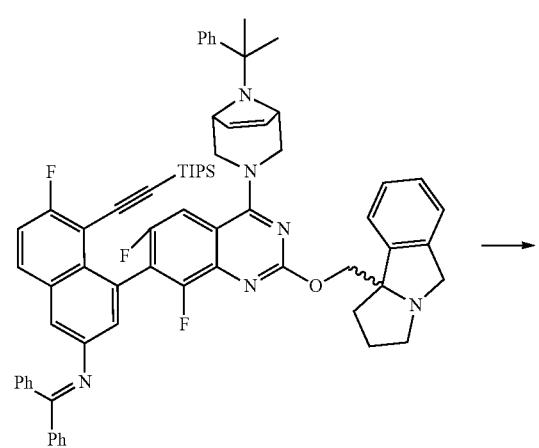
014-7
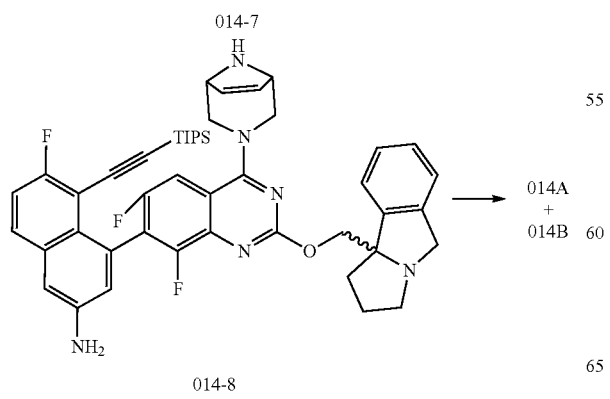
014-8
136
-continued
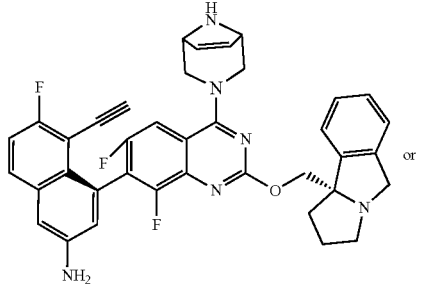
014A
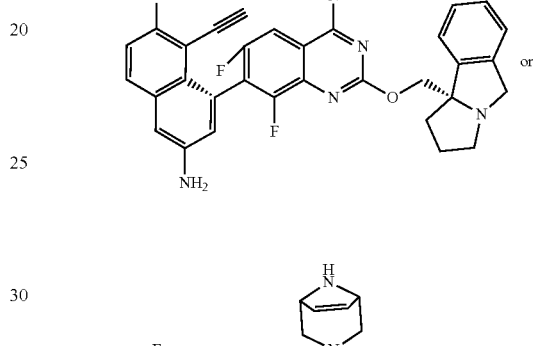
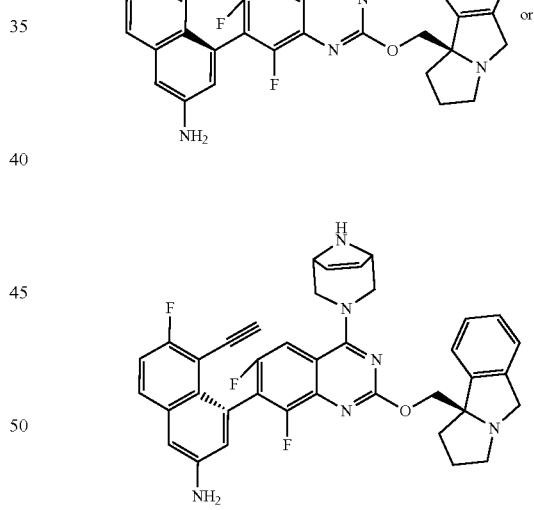
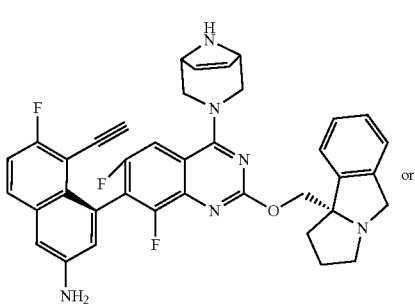

-continued

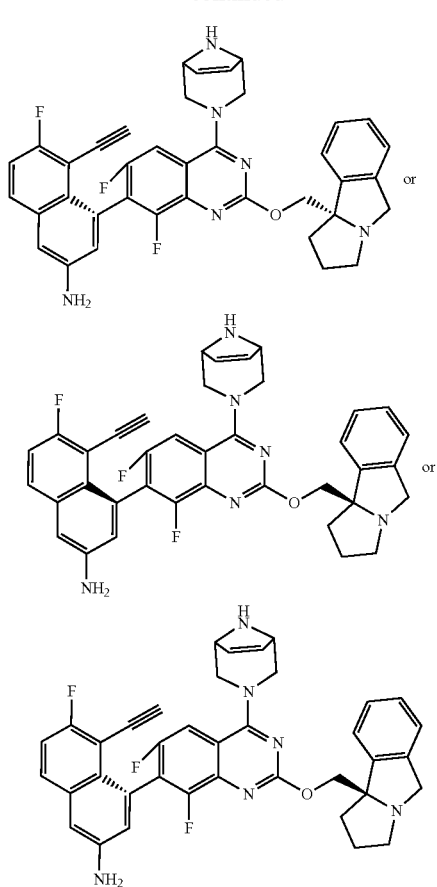

014B

Step 1: Synthesis of Compound 014-2

Compound 014-1 (3.00 g, 17.52 mmol) was added to N,N-dimethylformamide (30 mL). Potassium carbonate (3.63 g, 26.28 mmol) and compound 014-1A (4.47 g, 17.87 mmol) were added. The mixture was reacted at 20° C. for 2 hours. 30 mL of water was added to the reaction solution, and the mixture was extracted with methyl tert-butyl ether (20 mL*2). The organic phases were combined, washed with saturated brine (50 mL), dried over anhydrous sodium sulfate, and filtered. The filtrate was concentrated, and the crude product was purified by column chromatography (petroleum ether:ethyl acetate=100:0-10:1) to give compound 014-2. LCMS: MS m/z (ESI)=340.1 [M+H]$^+$.

Step 2: Synthesis of Compound 014-3

Lithium tert-butoxide (1.18 g, 14.69 mmol, 1.32 mL), tris(dibenzylideneacetone) dipalladium (134.56 mg, 146.95 μmol) and 2-dicyclohexylphosphino-2-(N,N-dimethylamino)-biphenyl (144.58 mg, 367.37 μmol) were added to 1,4-dioxane (35 mL). The atmosphere was replaced with argon three times, and the mixture was stirred for 5 min. Dodecane (1.25 g, 7.35 mmol, 1.67 mL) and compound 014-2 (2.5 g, 7.35 mmol) were added. The atmosphere was replaced with argon three times, and the mixture was reacted at 85° C. under argon atmospherefor 16 h. 50 ml of water was added to the reaction solution, and the mixture was extracted with ethyl acetate (20 mL*2). The organic phase was washed with 30 mL of saturated brine, dried over anhydrous sodium sulfate, and filtered. The filtrate was concentrated. The concentrated organic phase was purified by column chromatography (petroleum ether:ethyl acetate=100:0-0:1) to give compound 014-3. LCMS: MS m/z (ESI)=260.1 [M+H]$^+$.

Step 3: Synthesis of Compound 014-4 trifluoroacetate

Compound 014-3 (1 g, 3.86 mmol) was added to trifluoroacetic acid (5 mL). The mixture was reacted at 20° C. for 3 h. The reaction solution was concentrated under reduced pressure to give compound 014-4 trifluoroacetate. LCMS: MS m/z (ESI)=204.2 [M+H]$^+$.

Step 4: Synthesis of Compound 014-5A and Compound 014-5B

Compound 014-4 (2.5 g, 7.88 mmol, trifluoroacetate) was added to anhydrous tetrahydrofuran (30 mL). The mixture was cooled down to 10° C. Lithium aluminum hydride (897.14 mg, 23.64 mmol) was added. The mixture was reacted at 20° C. for 2 h. The reaction mixture was quenched by the addition of 1 mL of water to the reaction solution, followed by the addition of 1 mL of 15% sodium hydroxide solution and 3 mL of water. The mixture was stirred for 5 min. 5 g of sodium sulfate solid was added and the mixture was stirred for 30 min. The mixture was filtered, and the filtrate was concentrated to give a crude product. The crude product was purified by high performance liquid chromatography (column: Phenomenex luna C18 250*50 mm*10 μm; mobile phase A: water (0.05% hydrochloric acid); mobile phase B: acetonitrile; running gradient: B %=1%-30%; running time: 10 min). The racemate was purified by supercritical fluid chromatography (SFC) (column: Phenomenex-Cellulose-2 (250 mm*30 mm, 5 μm); mobile phase: A (supercritical CO$_2$) and B (ethanol with 0.1% ammonia); gradient: B %=35%-35%, running for 9 min) to give compound 14-5A and compound 14-5B.

The analysis and characterization of compound 14-5A were as follows:

SFC analysis method (column: Lux Cellulose-2, 100×4.6 mm I.D., 3 μm; mobile phase: A (supercritical CO$_2$), B: (ethanol with 0.1% isopropylamine); gradient: B %=40~60%, 3 min; flow rate: 4.0 mL/min; wavelength: 220 nm; pressure: 1800 psi, Rt=1.118 min, 99.44% ee. LCMS: MS m/z (ESI)=190.2 [M+H]$^+$.

The analysis and characterization of compound 14-5B were as follows:

SFC analysis method (column: Lux Cellulose-2, 100×4.6 mm I.D., 3 μm; mobile phase: A (supercritical CO$_2$), B: (ethanol with 0.1% isopropylamine); gradient: B %=40~60%, 3 min; flow rate: 4.0 mL/min; wavelength: 220 nm; pressure: 1800 psi, Rt=2.285 min, 100% ee. LCMS: MS m/z (ESI)=190.2 [M+H]$^+$.

Step 5: Synthesis of Compound 014-6

Compound 002-2 (0.2 g, 395.43 μmol) was added to anhydrous tetrahydrofuran (1.0 mL) and N,N-dimethylformamide (1.0 mL). Cesium carbonate (386.51 mg, 1.19 mmol), compound 014-5A (82.32 mg, 434.97 μmol) and triethylenediamine (13.31 mg, 118.63 μmol, 13.05 μL) were added. The mixture was reacted at 30° C. for 20 h. This reaction mixture was combined with compound 002-2 (30 mg batch) for work-up. The reaction solution was added to 10 mL of methyl tert-butyl ether, and washed with saturated ammonium chloride (20 mL*2). The aqueous phase was extracted with 10 mL of methyl tert-butyl ether. The organic phases were combined, washed with saturated brine (20 mL*2), dried over anhydrous sodium sulfate, and filtered. The filtrate was concentrated, and the crude product was purified by column chromatography (petroleum ether:ethyl acetate=100:0-1:4) to give compound 014-6. LCMS: MS m/z (ESI)=658.1 [M+H]$^+$.

Step 6: Synthesis of Compound 014-7

Compound 001-5A (158.27 mg, 250.54 μmol), compound 014-6 (0.15 g, 227.76 μmol) and potassium phosphate (145.04 mg, 683.29 μmol) were added to toluene (2 mL) and water (0.4 mL). The atmosphere was replaced with nitrogen three times, and chloro [(bis(1-adamantyl)-n-butylphosphine)-2-(2-aminobiphenyl)]palladium (II) (30.46 mg, 45.55 μmol) was added under nitrogen. The reaction mixture was reacted at 90° C. for 8 h. The reaction solution was washed with 10 ml of water, and extracted with ethyl acetate (5 mL*2). The organic phases were combined, washed with 10 mL of saturated brine, dried over anhydrous sodium sulfate, and filtered. The filtrate was concentrated, and the crude product was purified by column chromatography (petroleum ether:ethyl acetate=1:0-0:1) to give compound 014-7. LCMS: MS m/z (ESI)=1083.3 [M+H]$^+$. $^1$H NMR (400 MHZ, CDCl$_3$) δ=7.81-7.74 (m, 2H), 7.69-7.59 (m, 3H), 7.56-7.46 (m, 2H), 7.45-7.31 (m, 5H), 7.30-7.28 (m, 1H), 7.26-7.07 (m, 10H), 6.95-6.86 (m, 1H), 6.11-6.01 (m, 1H), 5.94-5.91 (m, 1H), 4.59 (d, J=12.0 Hz, 1H), 4.53-4.43 (m, 1H), 4.34-4.29 (m, 1H), 3.98-3.86 (m, 2H), 3.83-3.81 (m, 1H), 3.79-3.72 (m, 1H), 3.67 (s, 1H), 3.49-3.39 (m, 1H), 3.37-3.26 (m, 1H), 2.73-2.43 (m, 2H), 2.04-1.94 (s, 2H), 1.87-1.79 (m, 1H), 1.7-1.61 (m, 1H), 1.35-1.29 (m, 6H), 0.92-0.74 (m, 18H), 0.58-0.44 (m, 3H).

Step 7: Synthesis of Compound 014-8

Compound 014-7 (0.15 g, 138.45 μmol) was added to trifluoroacetic acid (2 mL). The mixture was heated to 70° C. and reacted for 1 h. The reaction solution was concentrated and diluted with 5 mL of ethyl acetate. The mixture was washed with 10 mL of water, washed with 10 mL of saturated sodium bicarbonate solution, and washed with 20 mL of 1M hydrochloric acid solution. The aqueous phase was extracted with 10 mL of ethyl acetate, and the organic phase was discarded. The aqueous phases were collected, slowly adjusted to a pH of 9 using sodium carbonate solid, and extracted with ethyl acetate (10 mL*2). The organic phases were combined, washed with 10 mL of saturated brine, dried over anhydrous sodium sulfate, and filtered. The filtrate was concentrated to give compound 014-8. LCMS: MS m/z (ESI)=801.5 [M+H]$^+$.

Step 8: Synthesis of Compound 014A and Compound 014B

Compound 014-8 (0.08 g, 95.52 μmol) was added to N,N-dimethylformamide (1.5 mL). Potassium carbonate (66.01 mg, 477.62 μmol) and cesium fluoride (29.02 mg, 191.05 μmol, 7.04 μL) were added. The mixture was reacted at 60° C. for 15 h. The reaction solution was diluted with 5 mL of ethyl acetate and washed with 10 ml of water. The aqueous phase was extracted with 5 mL of ethyl acetate. The organic phases were combined, washed with saturated brine (10 mL*2), dried over anhydrous sodium sulfate, and filtered. The filtrate was concentrated, and the crude product was purified by preparative high performance liquid chromatography (column: Phenomenex Luna C18 75*30 mm*3 μm; mobile phase A: water (0.05% hydrochloric acid); mobile phase B: acetonitrile; running gradient: B %=13%-43%; running time: 8 min). The fraction solution was adjusted to a pH of 7 by adding ammonia water, and then purified by supercritical fluid chromatography (SFC) (column: DAICEL CHIRALCEL AD (250 mm*30 mm, 10 μm); mobile phase: A (supercritical CO$_2$) and B (ethanol with 0.1% ammonia); gradient: B %=50%-50%, running for 15 min) to give compound 014A and compound 014B.

The analysis and characterization of compound 014A were as follows:

SFC analysis method (column: Chiralpak AD-3, 50×4.6 mm I.D., 3 μm; mobile phase: A (supercritical CO$_2$), B: (ethanol with 0.1% isopropylamine); gradient: B %=5~50%, 3 min; flow rate: 3.4 mL/min; wavelength: 220 nm; pressure: 1800 psi, Rt=1.533 min, 100% ee. LCMS: MS m/z (ESI)=645.2 [M+H]$^+$. $^1$H NMR (400 MHZ, CD$_3$OD) δ=7.74 (dd, J=6.0, 9.2 Hz, 1H), 7.55-7.42 (m, 2H), 7.42-7.30 (m, 3H), 7.28-7.16 (m, 2H), 7.07-7.00 (m, 1H), 6.33-6.22 (m, 2H), 4.80-4.76 (m, 1H), 4.70-4.55 (m, 2H), 4.53-4.46 (m, 1H), 4.45-4.31 (m, 2H), 4.15-4.07 (m, 2H), 3.87-3.72 (m, 2H), 3.68-3.63 (m, 1H), 3.21 (s, 1H), 3.17-3.06 (m, 1H), 2.63-2.49 (m, 1H), 2.33-2.21 (m, 1H), 2.17-2.05 (m, 1H), 2.03-1.93 (m, 1H).

The analysis and characterization of compound 014B were as follows:

SFC analysis method (column: Chiralpak AD-3, 50×4.6 mm I.D., 3 μm; mobile phase: A (supercritical CO$_2$), B: (ethanol with 0.1% isopropylamine); gradient: B %=5~50%, 3 min; flow rate: 3.4 mL/min; wavelength: 220 nm; pressure: 1800 psi, Rt=1.794 min, 100% ee. LCMS: MS m/z (ESI)=645.2 [M+H]$^+$. $^1$H NMR (400 MHZ, CD$_3$OD) δ=7.63 (dd, J=6.0, 9.2 Hz, 1H), 7.41-7.31 (m, 2H), 7.24-7.16 (m, 3H), 7.15-7.10 (m, 1H), 7.07 (d, J=2.4 Hz, 1H), 6.93 (d, J=2.0 Hz, 1H), 6.21-6.10 (m, 2H), 4.66-4.44 (m, 3H), 4.40-4.24 (m, 3H), 4.05 (d, J=15.2 Hz, 1H), 3.91 (d, J=10.4 Hz, 2H), 3.72-3.57 (m, 2H), 3.42-3.31 (m, 1H), 2.84-2.72 (m, 1H), 2.45-2.32 (m, 1H), 2.13-2.01 (m, 1H), 1.99-1.86 (m, 1H), 1.85-1.73 (m, 1H).

Example 15

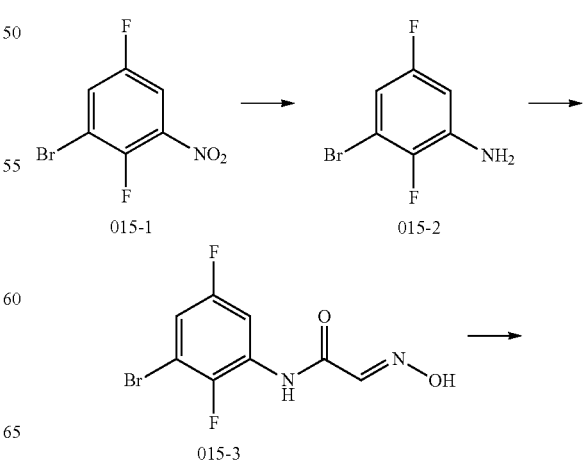

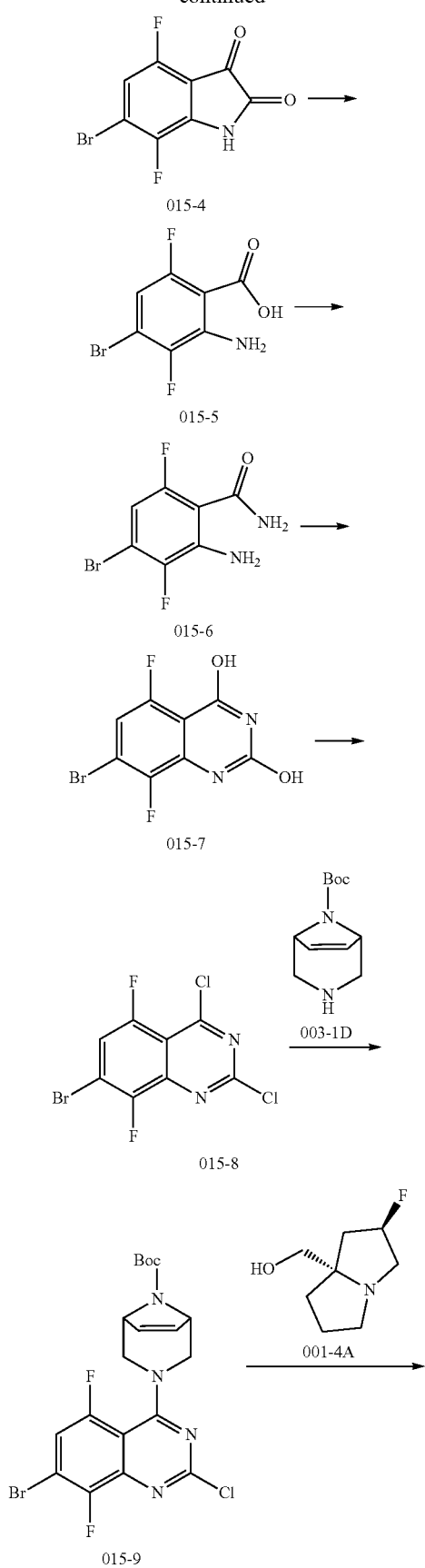
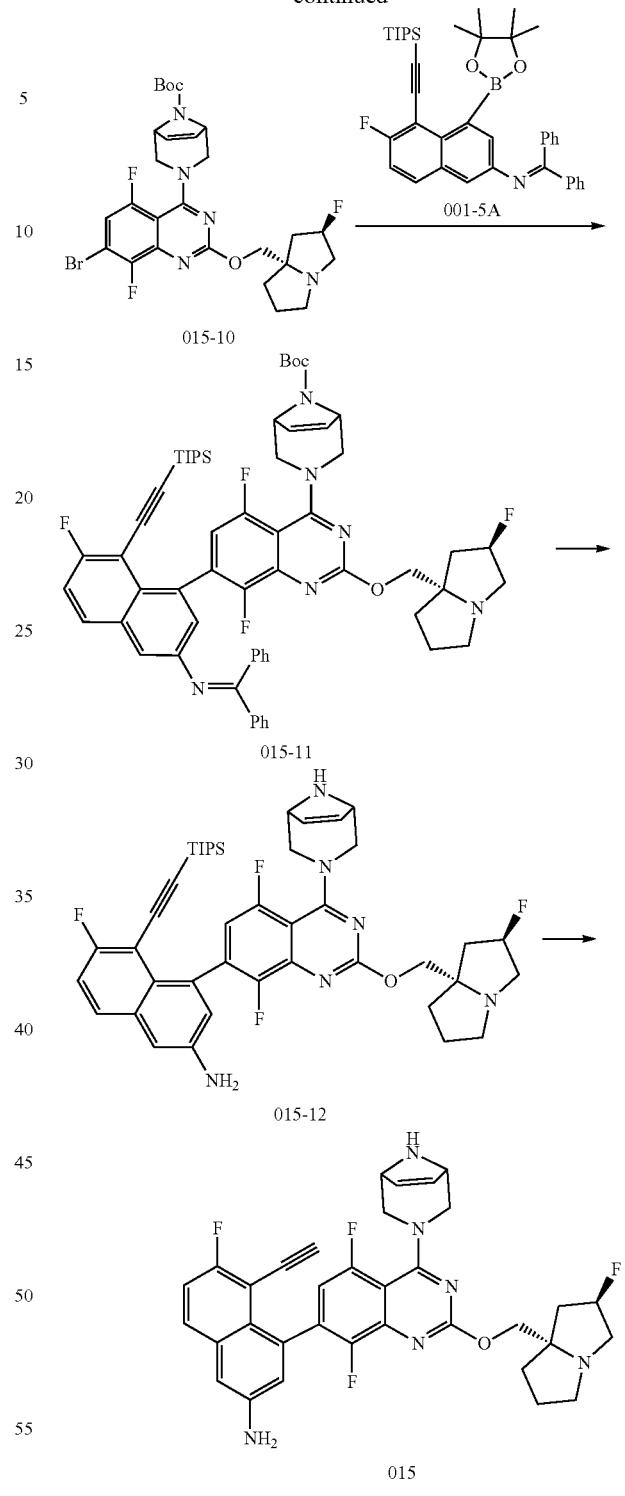
Step 1: Synthesis of Compound 015-2
Iron powder (11.73 g, 210.10 mmol) and ammonium chloride (224.76 mg, 4.20 mmol) were added to water (10 mL) and acetic acid (5 mL). The mixture was heated to 80° C. A solution of compound 015-1 (10 g, 42.02 mmol) in ethanol (100 mL) was added slowly. The mixture was reacted for 0.5 h. This reaction mixture was combined with 015-1 (1 g batch) for work-up. The mixture was filtered, and the filter cake was rinsed using ethyl acetate (100 mL*3). The filtrate was concentrated, and then 100 mL of ethyl acetate was added. The mixture was washed successively with 100 mL of saturated sodium bicarbonate and 200 mL of saturated brine, dried over anhydrous sodium sulfate, and filtered. The filtrate was concentrated to give compound 015-2. LCMS: MS m/z (ESI)=249.0 [M+42]+.

Step 2: Synthesis of Compound 015-3

Compound trichloroacetaldehyde hydrate (11.93 g, 72.11 mmol, 9.39 mL), sodium sulfate (54.63 g, 384.61 mmol, 39.02 mL) and hydroxylamine hydrochloride (11.69 g, 168.27 mmol) were added to water (200 mL). A solution of compound 015-2 (10 g, 48.08 mmol) in ethanol (30 mL) and hydrochloric acid (12 M, 8.41 mL) was added. The mixture was reacted at 70° C. for 20 hours. This reaction mixture was combined with compound 015-2 (1 g batch) for work-up. The reaction solution was filtered and the filter cake was dried to give compound 015-3. LCMS: MS m/z (ESI)=278.9 [M+H]+. $^1$H NMR (400 MHZ, CD$_3$OD) δ=8.01-7.97 (m, 1H), 7.61 (s, 1H), 7.24-7.19 (m, 1H).

Step 3: Synthesis of Compound 015-4

Compound 015-3 (7 g, 25.09 mmol) was added to concentrated sulfuric acid (35 mL). The mixture was reacted at 90° C. for 1 h. The reaction solution was added to 100 mL of ice water and the mixture was extracted with ethyl acetate (50 mL*2). The organic phases were combined, washed with 100 mL of saturated brine, dried over anhydrous sodium sulfate, and filtered. The filtrate was concentrated to give compound 015-4.

Step 4: Synthesis of Compound 015-5

Compound 015-4 (6.7 g, 25.57 mmol) was added to sodium hydroxide (2 M, 115.07 mL). Hydrogen peroxide (11.50 g, 101.44 mmol, 9.75 mL, 30% content) was added. The mixture was reacted at 18° C. for 1 hour. This reaction mixture was combined with compound 015-4 (0.5 g batch) for work-up. The reaction solution was added to 100 mL of sodium thiosulfate solution, and the mixture was extracted with 50 mL of ethyl acetate to remove impurities. The aqueous phase was collected, and adjusted to a pH of 6 with 1 M hydrochloric acid. After a starch-KI paper test was negative, the pH was further adjusted to 3 with hydrochloric acid. A solid was precipitated. The mixture was extracted with ethyl acetate (50 mL*2). The organic phases were combined, washed with 150 mL of saturated brine, dried over anhydrous sodium sulfate, and filtered. The filtrate was concentrated to give compound 015-5. LCMS: MS m/z (ESI)=251.9 [M+H]+. $^1$H NMR (400 MHZ, CD$_3$OD) δ=6.54 (dd, J=5.2, 10.4 Hz, 1H).

Step 5: Synthesis of Compound 015-6

Compound 015-5 (2.5 g, 9.92 mmol) was added to N,N-dimethylformamide (20 mL). N,N-diisopropylethylamine (1.54 g, 11.90 mmol, 2.07 mL), 1-(3-dimethylaminopropyl)-3-ethylcarbodiimide (2.28 g, 11.90 mmol), 1-hydroxybenzotriazole (1.61 g, 11.90 mmol) and ammonia/methanol (7 M, 1.98 mL) were added. The mixture was reacted at 18° C. for 20 hours. The reaction mixture was heated to 30° C. and reacted for 4 h. 40 mL of water was added to the reaction solution, and the mixture was extracted with ethyl acetate (20 mL*3). The organic phases were combined, washed with saturated brine (50 mL*3), dried over anhydrous sodium sulfate, and filtered. The filtrate was concentrated to give compound 015-6. LCMS: MS m/z (ESI)=250.9 [M+H]+. $^1$H NMR (400 MHz, DMSO-d$_6$) δ=8.28-8.05 (m, 2H), 7.20-7.09 (m, 1H), 6.78 (s, 2H).

Step 6: Synthesis of Compound 015-7

Compound 015-6 (2 g, 7.97 mmol) was added to anhydrous tetrahydrofuran (20 mL). Carbonyl diimidazole (1.94 g, 11.95 mmol) and 1.8-diazabicyclo [5.4.0]undec-7-ene (2.43 g, 15.93 mmol, 2.40 mL) were added. The mixture was reacted at 18° C. for 1 hour. 30 mL of water was added to the reaction solution and the mixture was reacted at 50° C. for 2 h. The mixture was extracted with methyl tert-butyl ether (15 mL*2), and the organic phase was discarded. The aqueous phase was adjusted to pH 2-3 with 1 M hydrochloric acid solution. A solid was precipitated. The mixture was filtered. The filter cake was rinsed with water (5 mL*2), and then dried under reduced pressure to give compound 015-7. LCMS: MS m/z (ESI)=276.9 [M+H]+. $^1$H NMR (400 MHZ, DMSO-d$_6$) δ=11.75-11.40 (m, 2H), 7.50-7.35 (m, 1H).

Step 7: Synthesis of Compound 015-8

Compound 015-7 (1.5 g, 5.41 mmol) was added to phosphorus oxychloride (15 mL). N,N-diisopropylethylamine (3.50 g, 27.05 mmol, 4.72 mL) was added. The mixture was reacted at 100° C. for 2 hours. The reaction solution was concentrated. The concentrated product was diluted with 30 mL of ethyl acetate, and slowly added to 50 mL of iced sodium bicarbonate solution. The layers were separated. The aqueous phase was extracted with 20 mL of ethyl acetate. The organic phases were combined, washed successively with 50 mL of saturated ammonium chloride and 50 mL of saturated brine, dried over anhydrous sodium sulfate, and filtered. The filtrate was concentrated to give compound 015-8.

Step 8: Synthesis of Compound 015-9

Compound 015-8 (0.5 g, 1.59 mmol) was added to anhydrous dichloromethane (5 mL). Compound 003-1D (368.41 mg, 1.75 mmol) and triethylamine (322.35 mg, 3.19 mmol, 443.40 μL) were added. The reaction was reacted at 18° C. for 2 h. The reaction solution was washed successively with saturated ammonium chloride (20 mL*2) and 20 mL of saturated brine, dried over anhydrous sodium sulfate, and filtered. The filtrate was concentrated, and the crude product was purified by column chromatography (petroleum ether:ethyl acetate=100:0-1:1) to give compound 015-9. LCMS: MS m/z (ESI)=487.0 [M+H]+0.1H NMR (400 MHZ, CDCl$_3$) δ=7.51 (d, J=6.0 Hz, 1H), 6.09-5.90 (m, 2H), 4.77-4.42 (m, 3H), 4.02-3.46 (m, 3H), 1.51 (s, 9H).

Step 9: Synthesis of Compound 015-10

Compound 015-9 (0.48 g, 984.16 μmol) was added to anhydrous tetrahydrofuran (2.5 mL) and N,N-dimethylformamide (2.5 mL). Cesium carbonate (961.98 mg, 2.95 mmol), compound 001-4A (188.02 mg, 1.18 mmol) and triethylenediamine (33.12 mg, 295.25 μmol, 32.47 μL) were added. The mixture was reacted at 20° C. for 20 h. The reaction solution was added to 10 mL of methyl tert-butyl ether. The mixture was washed with saturated ammonium chloride (20 mL*2), and the aqueous phase was extracted with 10 mL of methyl tert-butyl ether. The organic phases were combined, washed with saturated brine (20 mL*2), dried over anhydrous sodium sulfate, and filtered. The filtrate was concentrated to give compound 015-10. LCMS: MS m/z (ESI)=610.2 [M+H]⁺. ¹H NMR (400 MHZ, CDCl₃) δ=7.03-6.92 (m, 1H), 6.07 (d, J=4.0 Hz, 2H), 5.42-5.14 (m, 1H), 4.70-4.54 (m, 2H), 4.23-4.12 (m, 2H), 4.08-3.99 (m, 2H), 3.68-3.53 (m, 2H), 3.35-3.24 (m, 2H), 3.20-3.08 (m, 1H), 3.04-2.90 (m, 1H), 2.28-2.12 (m, 3H), 1.96-1.85 (m, 3H), 1.51 (s, 9H).

Step 10: Synthesis of Compound 015-11

Compound 001-5A (284.57 mg, 450.48 μmol), compound 015-10 (0.25 g, 409.52 μmol) and potassium phosphate (260.79 mg, 1.23 mmol) were added to toluene (3 mL) and water (0.6 mL). The atmosphere was replaced with nitrogen three times, and chloro [(bis(1-adamantyl)-n-butylphosphine)-2-(2-aminobiphenyl)]palladium (II) (54.76 mg, 81.90 μmol) was added under nitrogen. The mixture was reacted at 90° C. for 3 h. 10 mL of water was added to the reaction solution. The mixture was extracted with ethyl acetate (5 mL*2). The layers were separated. The organic phases were combined, washed with 20 mL of saturated brine, dried over anhydrous sodium sulfate, and filtered. The filtrate was concentrated. The crude product was purified by column chromatography (petroleum ether:ethyl acetate=1:0-0:1) to give compound 015-11. LCMS: MS m/z (ESI)=1035.3 [M+H]⁺. ¹H NMR (400 MHZ, CDCl₃) δ=7.81-7.76 (m, 2H), 7.68-7.63 (m, 1H), 7.54-7.47 (m, 1H), 7.46-7.39 (m, 2H), 7.37-7.28 (m, 3H), 7.25-7.19 (m, 2H), 7.17-7.10 (m, 2H), 6.90-6.82 (m, 1H), 6.66-6.56 (m, 1H), 6.25-6.03 (m, 2H), 5.39-5.16 (m, 1H), 4.80-4.40 (m, 3H), 4.25-4.17 (m, 1H), 4.09-3.94 (m, 1H), 3.87-3.55 (m, 2H), 3.52-3.32 (m, 1H), 3.31-3.08 (m, 3H), 3.03-2.91 (m, 1H), 2.36-2.10 (m, 3H), 2.00-1.85 (m, 3H), 1.62-1.39 (m, 9H), 0.95-0.77 (m, 18H), 0.61-0.48 (m, 3H).

Step 11: Synthesis of Compound 015-12 hydrochloride

Compound 015-11 (0.2 g, 193.18 μmol) was added to HCl/methanol (4 mL, 4M). The mixture was reacted at 18° C. for 1 h. The reaction solution was concentrated directly. The crude was stirred with 5 mL of ethyl acetate for 2 h, and then filtered. The filter cake was rinsed with ethyl acetate (2 mL*2) and concentrated under reduced pressure to give compound 015-12 hydrochloride. LCMS: MS m/z (ESI)=771.3 [M+H]⁺.

Step 12: Synthesis of Compound 015

Compound 015-12 (0.1 g, hydrochloride) was added to N,N-dimethylformamide (2 mL). Potassium carbonate (85.59 mg, 619.25 μmol) and cesium fluoride (37.63 mg, 247.70 μmol, 9.13 μL) were added. The mixture was reacted at 60° C. for 5 hours. This reaction mixture was combined with compound 015-12 (50 mg batch) for work-up. The reaction solution was diluted with 5 mL of ethyl acetate and washed with 10 ml of water. The aqueous phase was extracted with 5 mL of ethyl acetate. The organic phases were combined, washed with saturated brine (10 mL*2), dried over anhydrous sodium sulfate, and filtered. The filtrate was concentrated, and the crude product was purified by preparative high performance liquid chromatography (column: Phenomenex luna C18 150*40 mm*10 μm; mobile phase A: water (10 mM ammonium bicarbonate); mobile phase B: acetonitrile; running gradient B %=50%-80%; running time: 8 min) to give compound 015. LCMS: MS m/z (ESI)=615.2 [M+H]⁺. ¹H NMR (400 MHZ, CD₃OD) δ=7.71 (dd, J=6.0, 9.2 Hz, 1H), 7.22 (t, J=8.8 Hz, 1H), 7.14 (d, J=2.4 Hz, 1H), 7.02 (d, J=2.4 Hz, 1H), 6.90 (dd, J=5.2, 11.6 Hz, 1H), 6.27-6.18 (m, 2H), 5.41-5.22 (m, 1H), 4.30-4.07 (m, 4H), 3.95-3.90 (m, 2H), 3.77-3.64 (m, 2H), 3.29-3.18 (m, 4H), 3.07-2.97 (m, 1H), 2.40-2.10 (m, 3H), 2.07-1.85 (m, 3H).

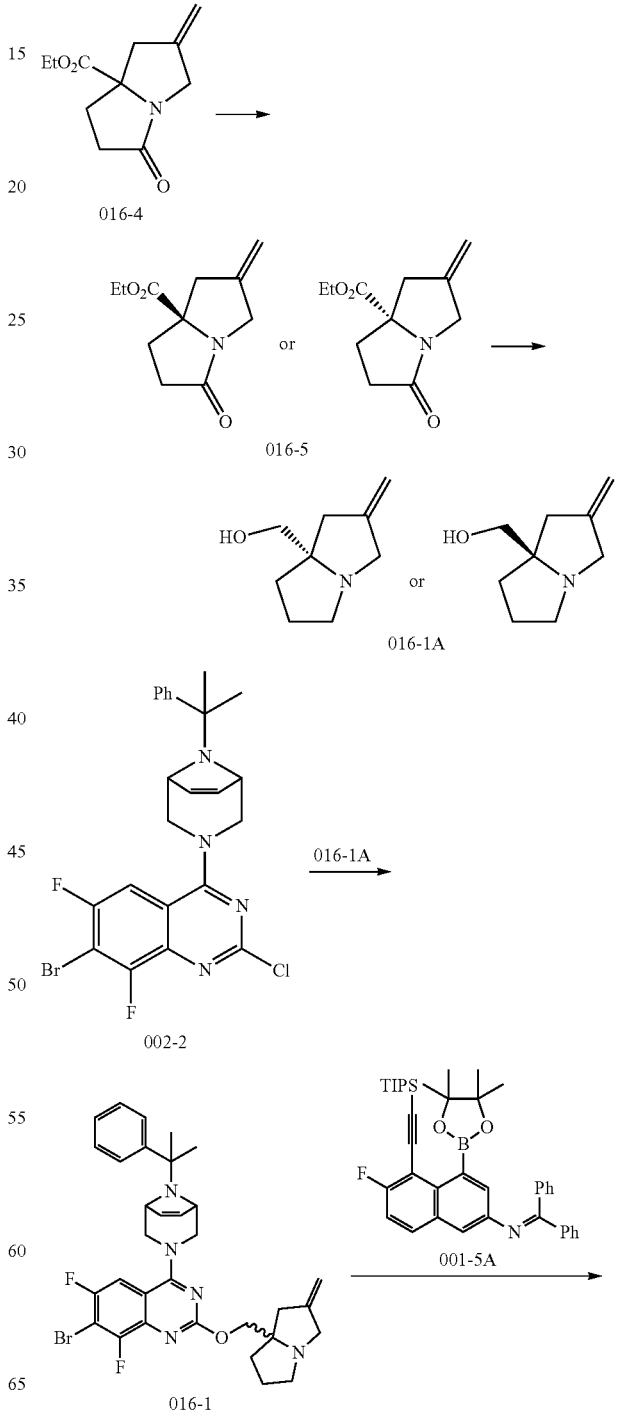

147
-continued
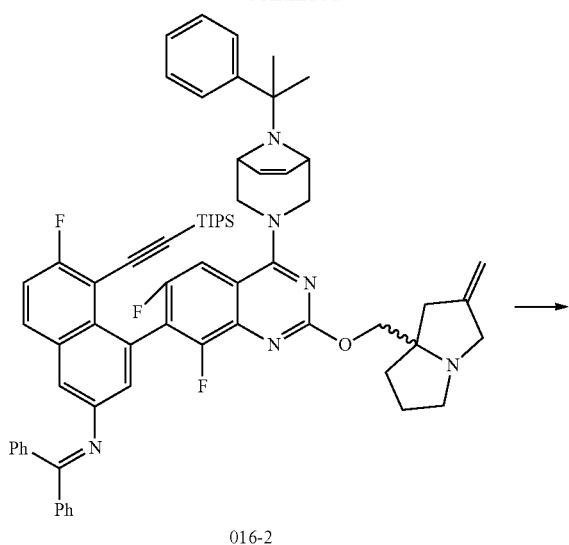
016-2
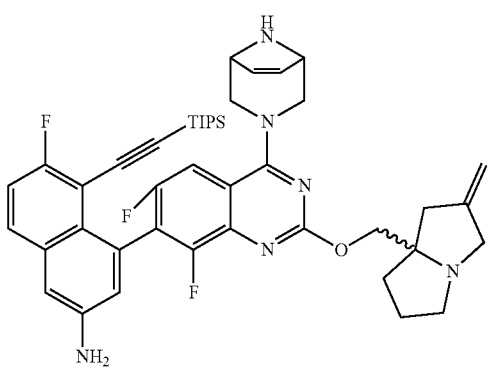
016-3
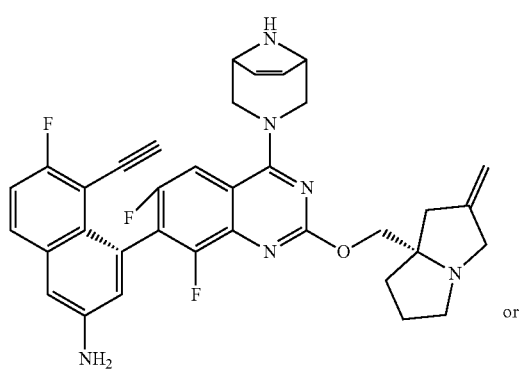
016A
148
-continued
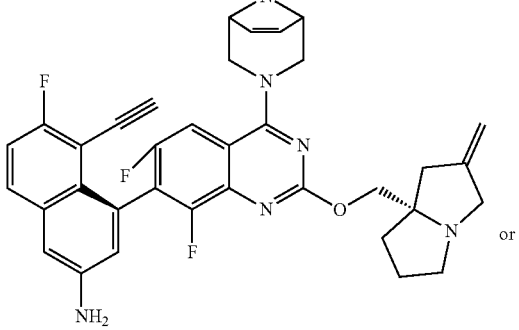
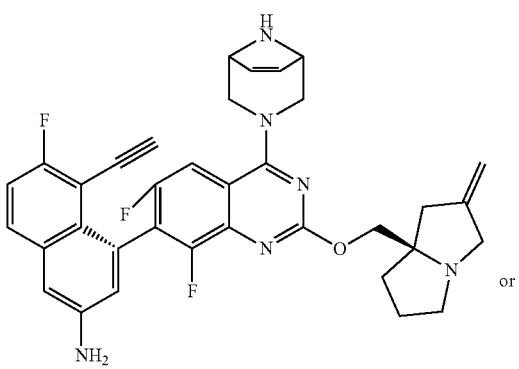
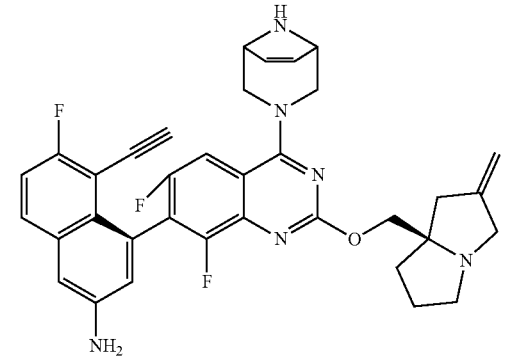
016A + 016B
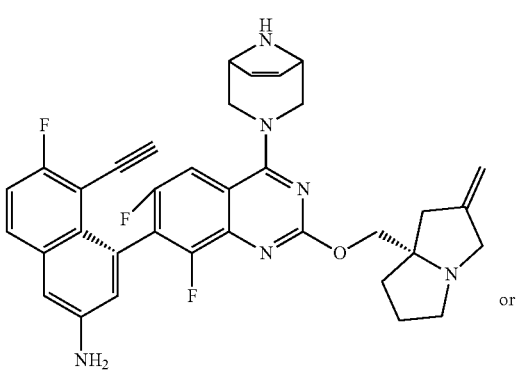
016B

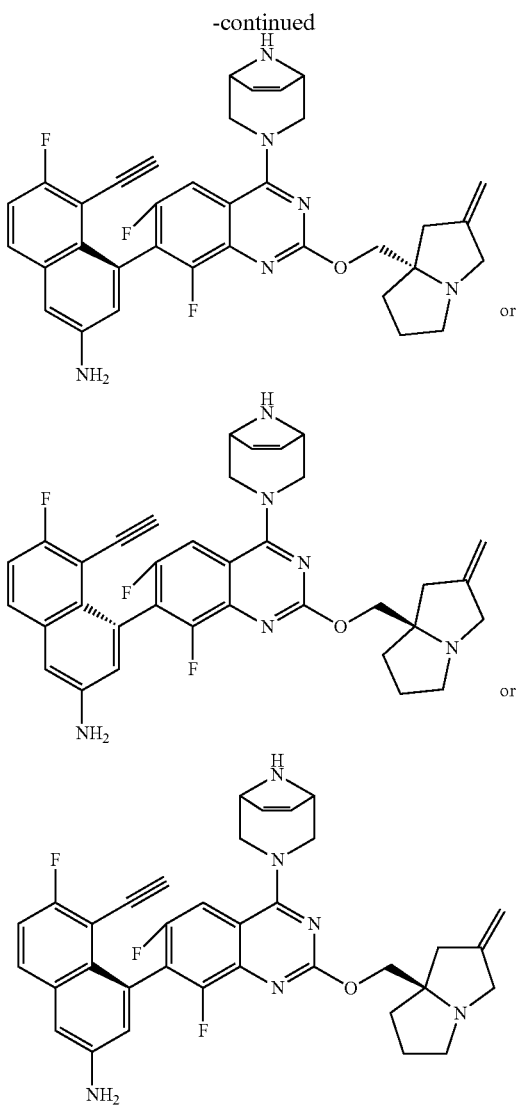

Step 1: Synthesis of Compound 016-5

Compound 016-4 (15 g) was purified by supercritical fluid chromatography (column: ChiralPak IH, 250*50 mm, 10 μm; mobile phase: A (supercritical CO$_2$), B: [0.1% ammonia-ethanol]; B %: 20%-20%) to give compound 016-5. SFC analysis method (column: Chiralpak IH-3,100×4.6 mm I.D., 3 μm; mobile phase: A (supercritical CO$_2$) and B (EtOH with 0.1% isopropylamine); gradient: B %=10~50%, 4 min; flow rate: 3.4 mL/min; wavelength: 220 nm; pressure: 2000 psi), Rt=1.489 min, ee=98.82%. $^1$H NMR (400 MHZ, CDCl$_3$) δ=4.99-4.86 (m, 2H), 4.26-3.95 (m, 3H), 3.59 (m, 1H), 3.00-2.88 (m, 1H), 2.87-2.12 (m, 4H), 1.91 (s, 1H), 1.20-1.08 (m, 3H).

Step 2: Synthesis of Compound 016-1A

Lithium tetrahydroaluminum (1.55 g, 40.15 mmol, 98% purity) was dissolved in anhydrous tetrahydrofuran (30 mL). The solution was cooled down to 0° C. A solution of compound 016-5 (2.8 g, 13.38 mmol) in anhydrous tetrahydrofuran (2 mL) was added under nitrogen, and the mixture was heated to 70° C. and reacted for 1 hour. After the reaction was completed, 1.5 mL of water was added at 0° C. 1.5 mL of 15% NaOH solution was added, and 4.5 mL of water was added. The mixture was stirred for 20 min. The reaction solution was filtered, and the filter cake was washed with 10 mL of tetrahydrofuran. The filtrate was concentrated to give compound 016-1A. $^1$H NMR (400 MHZ, CDCl$_3$) δ=4.99-4.86 (m, 2H), 4.26-3.95 (m, 3H), 3.59 (m, 1H), 3.00-2.88 (m, 1H), 2.74-2.27 (m, 4H), 1.91 (s, 1H), 1.20-1.08 (m, 3H).

Step 3: Synthesis of Compound 016-1

Compound 002-2 (0.6 g, 1.19 mmol) was added to anhydrous tetrahydrofuran (3 mL) and N,N-dimethylformamide (3 mL). Cesium carbonate (1.16 g, 3.56 mmol), compound 016-1A (199.94 mg, 1.30 mmol) and triethylenediamine (39.92 mg, 355.88 μmol, 39.14 μL) were added. The mixture was reacted at 25° C. for 16 h. The reaction solution was added to 10 mL of methyl tert-butyl ether. The mixture was washed with 20 ml of water. The aqueous phase was extracted with 10 mL of methyl tert-butyl ether. The organic phases were combined, washed with saturated brine (20 mL×2), dried over anhydrous sodium sulfate, and filtered. The filtrate was concentrated, and the crude product was purified by column chromatography (petroleum ether:ethyl acetate=100:0-1:4) to give compound 016-1. MS m/z (ESI)=622.2 [M+H]$^+$.

Step 4: Synthesis of Compound 016-2

Compound 001-5A (639.26 mg, 1.01 mmol), compound 016-1 (0.42 g, 674.65 μmol) and potassium phosphate (429.62 mg, 2.02 mmol) were added to a mixed solution of toluene (5 mL) and water (1 mL). The atmosphere was replaced with nitrogen three times, and chloro [(bis(1-adamantyl)-n-butylphosphine)-2-(2-aminobiphenyl)]palladium (II) (90.22 mg, 134.93 μmol) was added under nitrogen. The reaction mixture was heated to 90° C. and reacted for 3 h. The reaction solution was washed with 10 mL of water, and extracted with ethyl acetate (5 mL×2). The layers were separated. The organic phases were combined, washed with 10 mL of saturated brine, dried over anhydrous sodium sulfate, and filtered. The filtrate was concentrated, and the crude product was purified by column chromatography (petroleum ether:ethyl acetate=1:0-0:1) to give compound 016-2. MS m/z (ESI)=1047.3 [M+H]$^+$.

Step 5: Synthesis of Compound 016-3

Compound 016-2 (250.00 mg, 238.69 μmol) was added to trifluoroacetic acid (2 mL). The mixture was heated to 70° C. and reacted for 0.5 h. The reaction solution was concentrated and diluted with 5 mL of ethyl acetate. The mixture was washed with 10 mL of water and washed with 10 mL of saturated sodium bicarbonate solution. The organic phase was washed with 1 M hydrochloric acid solution (8 mL×2). The aqueous phase was extracted with 10 mL of ethyl acetate, and the organic phase was discarded. The aqueous phases were collected, slowly adjusted to a pH of 9 using sodium carbonate solid, and extracted with ethyl acetate (10 mL×2). The organic phases were combined, washed with 10 mL of saturated brine, dried over anhydrous sodium sulfate, and filtered. The filtrate was concentrated to give compound 016-3. MS m/z (ESI)=765.3 [M+H]$^+$.

Step 6: Synthesis of Compound 016A and Compound 016B

Compound 016-3 (80 mg, 104.58 μmol) was dissolved in N,N-dimethylformamide (2 mL). Potassium carbonate (72.27 mg, 522.88 µmol) and cesium fluoride (47.66 mg, 313.73 µmol, 11.57 µL) were added. The mixture was stirred at 60° C. for 5 h. The mixture was filtered, and the filtrate was purified by preparative high performance liquid chromatography (column: Phenomenex luna C18 80*40 mm*3 µm; mobile phase: [water (0.05% HCl)-acetonitrile]; acetonitrile %: 10%-45%, 7 min). The fraction solution was added to saturated sodium bicarbonate solution (5 mL). The mixture was concentrated. Acetonitrile was removed, and the residue was extracted with ethyl acetate (5 mL×3). The organic phases were combined and concentrated to give a crude product, which was purified by supercritical fluid chromatography (SFC) (column: DAICEL CHIRALPAK IG (250 mm*30 mm, 10 µm); mobile phase: A (supercritical $CO_2$), mobile phase:B [0.1% ammonia-ethanol]; B %:50%-50%, 16 min) to give compounds 016A and 016B.

The analysis and characterization of 016A were as follows:

LCMS: m/z (ESI)=609.3 [M+H]$^+$.

The analysis and characterization of 016B were as follows:

SFC analysis method (column: Chiralpak IG-3, 50×4.6 mm I.D., 3 µm; mobile phase: A (supercritical $CO_2$) and B (EtOH with 0.1% isopropylamine); gradient: B %=50~40%, running for 3 min; flow rate: 4.0 mL/min; wavelength: 220 nm; pressure: 1800 psi), Rt=1.25 min, ee=98.2%. LCMS: m/z (ESI)=609.3 [M+H]$^+$. $^1$H NMR (400 MHZ, CDCl$_3$) δ ppm 7.63-7.74 (m, 1H), 7.20-7.27 (m, 2H), 7.11-7.16 (m, 1H), 6.95-7.02 (m, 1H), 6.20-6.38 (m, 2H), 4.94-5.06 (m, 2H), 4.32-4.48 (m, 2H), 4.16-4.28 (m, 2H), 3.90-4.04 (m, 4H), 3.69-3.88 (m, 3H), 3.29-3.42 (m, 2H), 2.84-2.94 (m, 1H), 2.65-2.81 (m, 2H), 2.38-2.50 (m, 1H), 2.20-2.31 (m, 1H), 1.93-2.03 (m, 2H).

Example 17

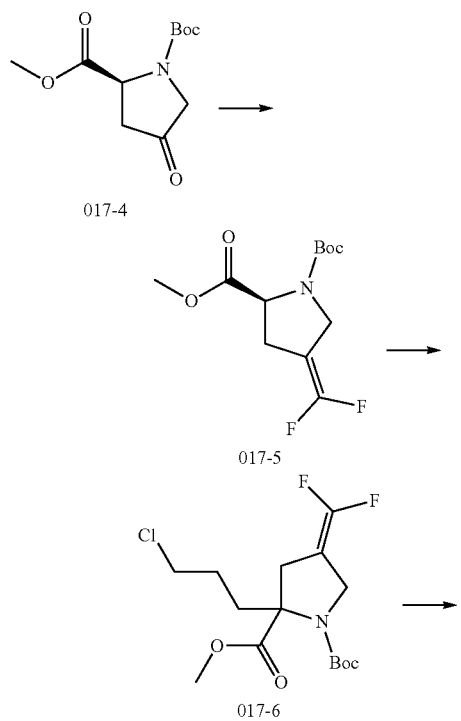

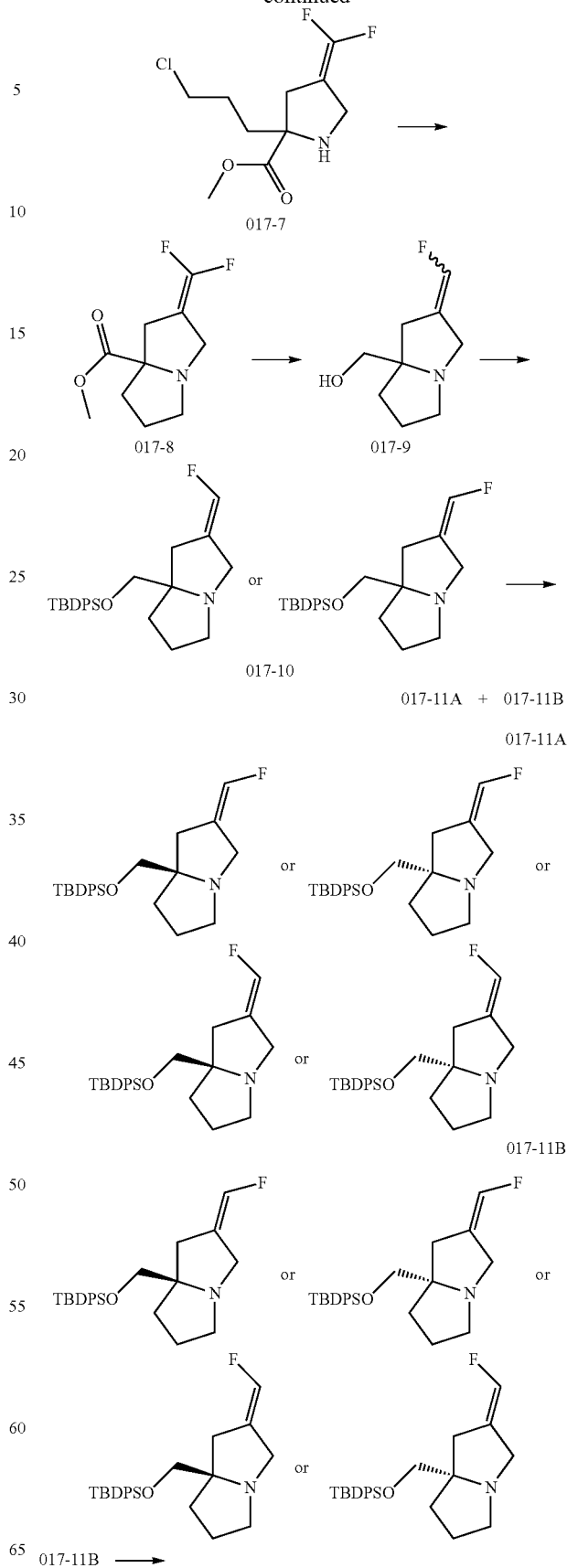

-continued
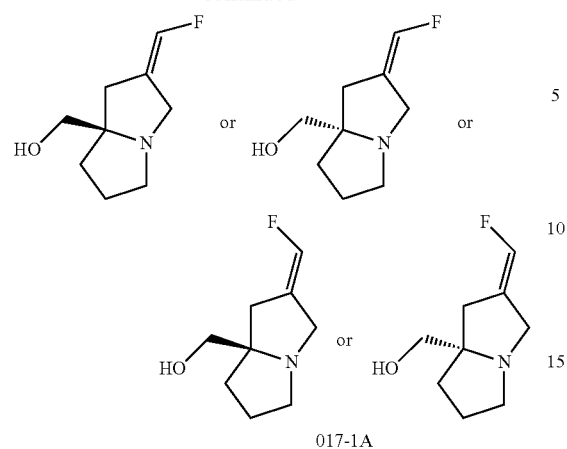
017-1A
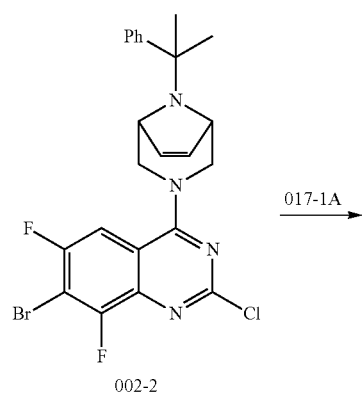
002-2
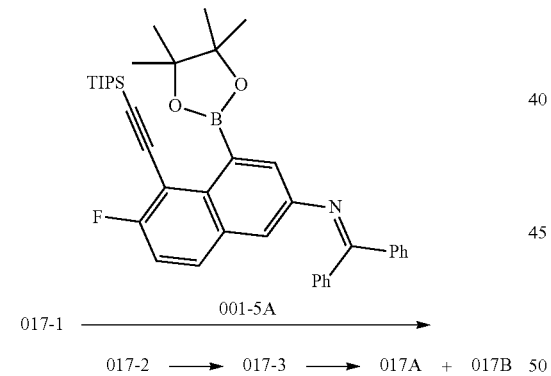
017-1 →<sup>001-5A</sup> 017-2 → 017-3 → 017A + 017B
017-1
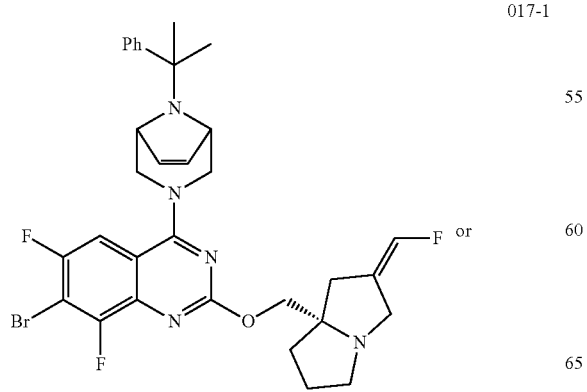
-continued
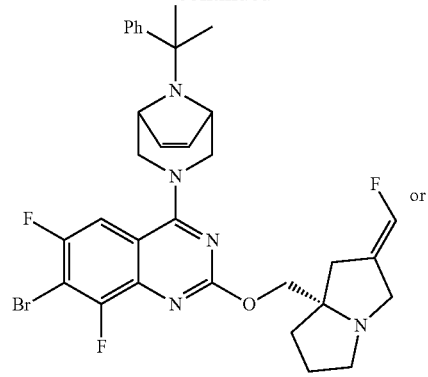
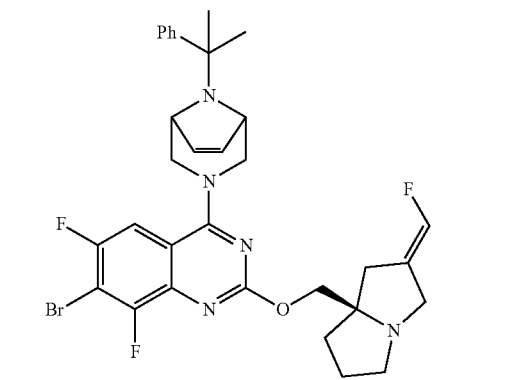
017-2
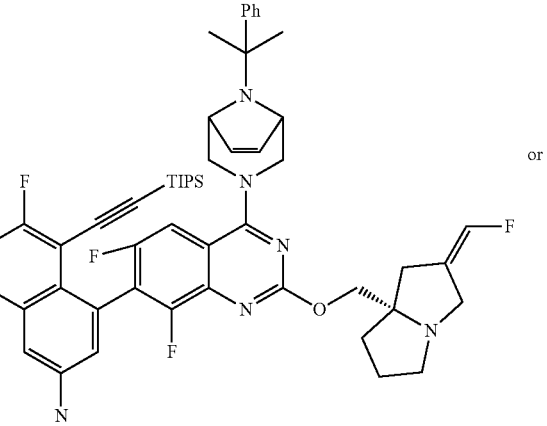

155
-continued
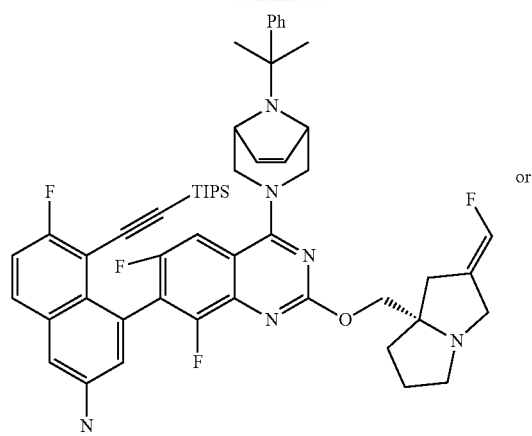
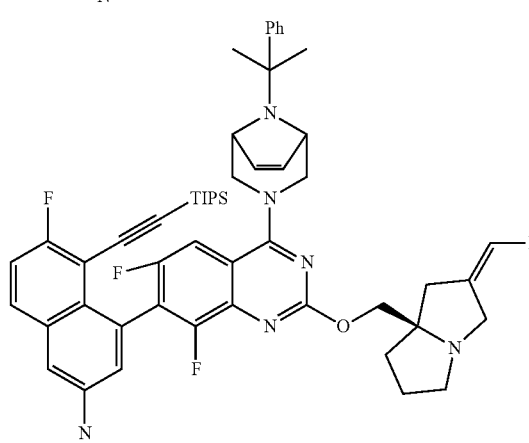
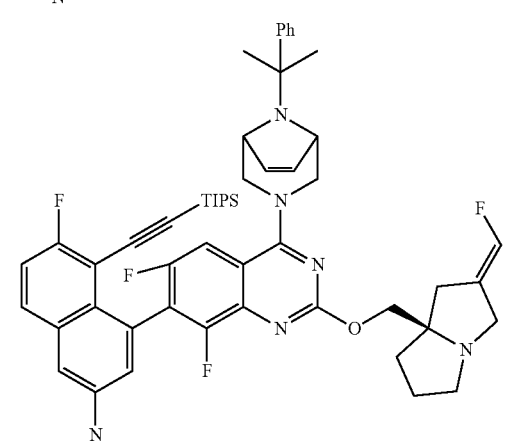
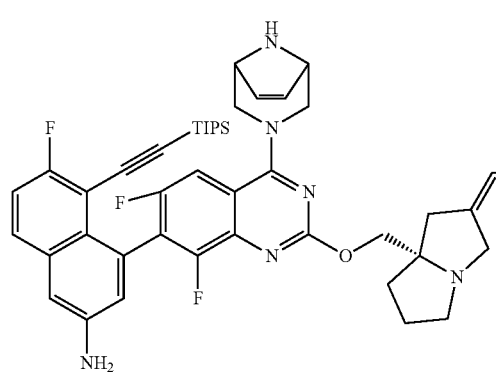
156
-continued
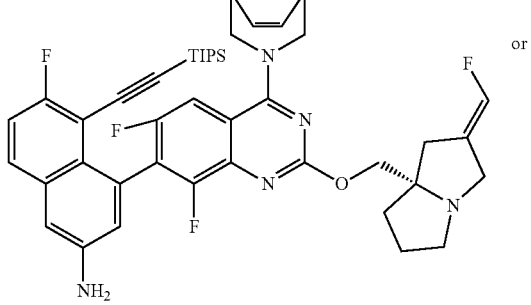
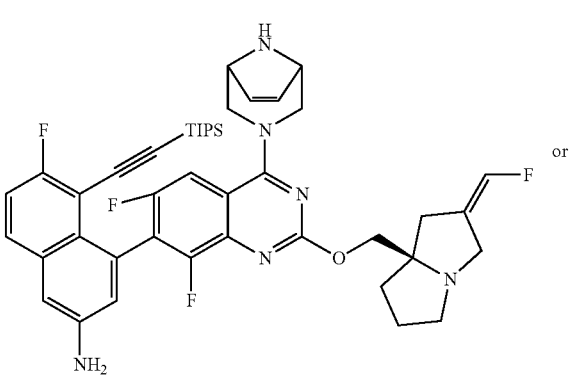
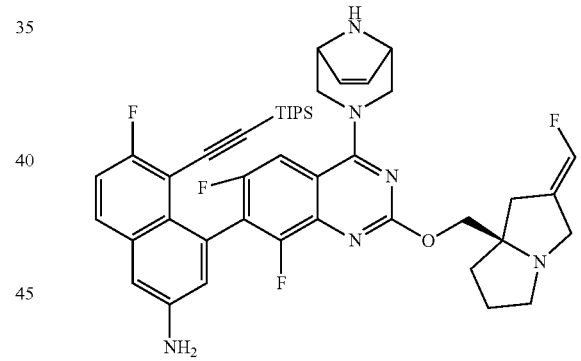
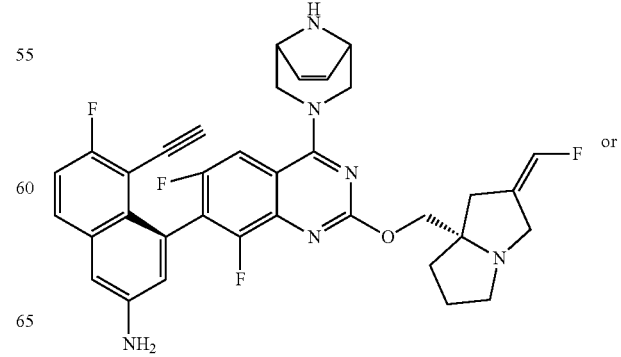

157                                                                 158
-continued                                                       -continued
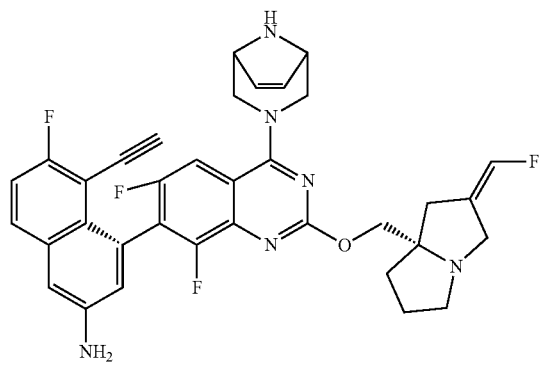
or
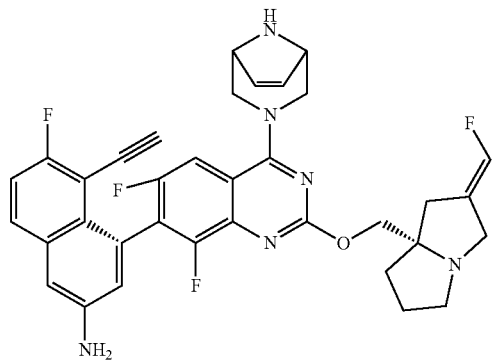
or
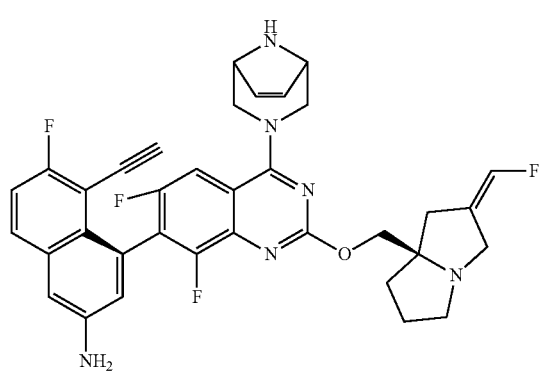
or
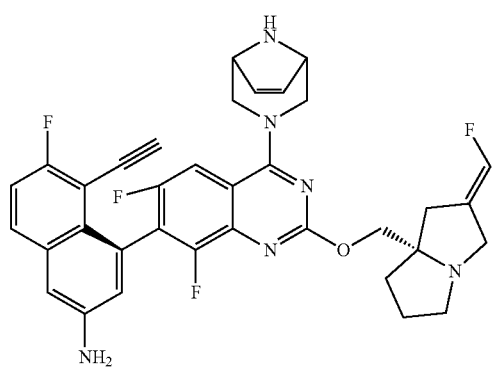
or
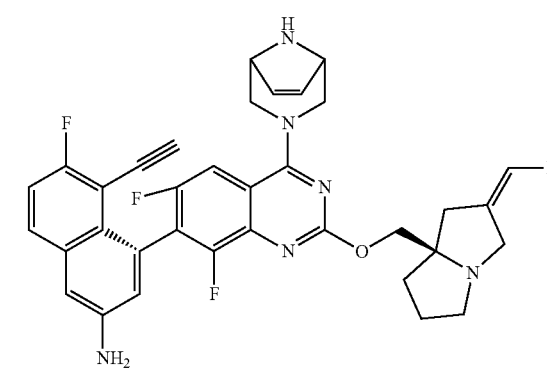
or
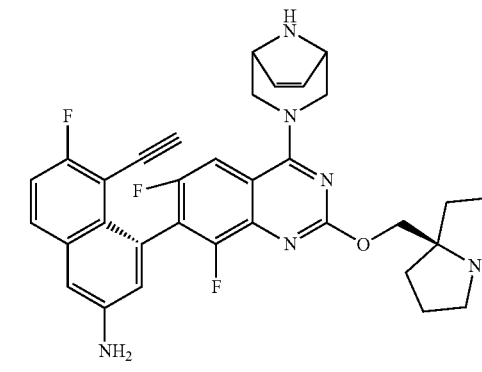
or
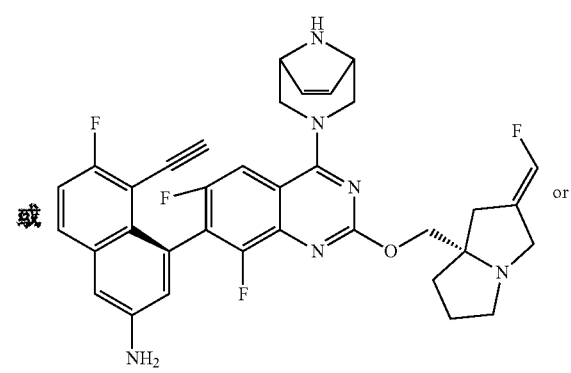
or
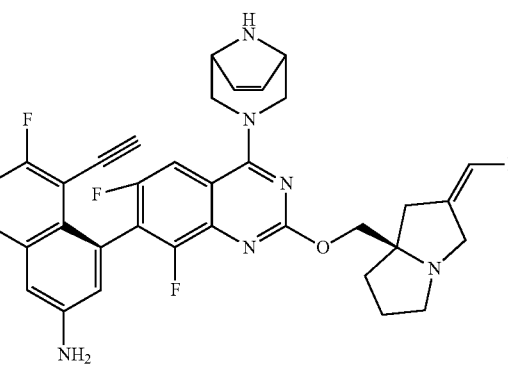
or 159
-continued

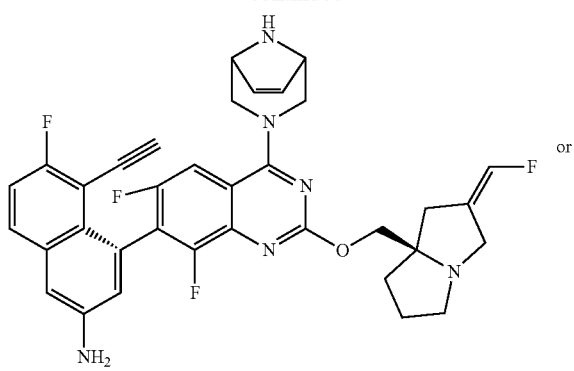

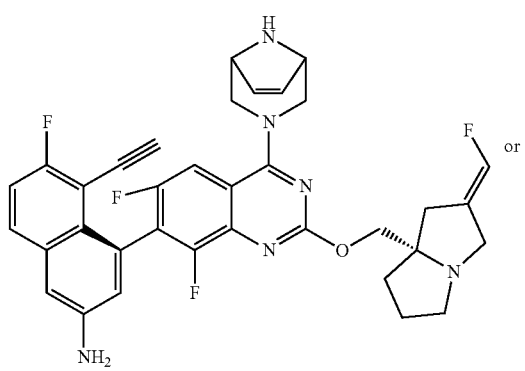

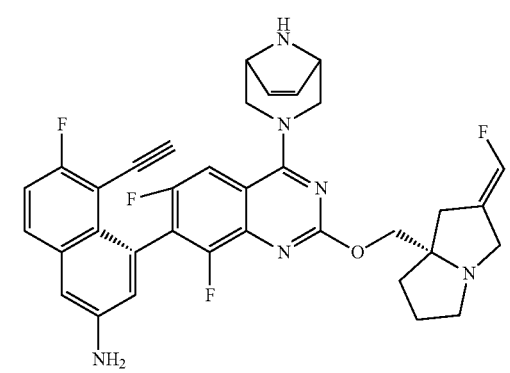

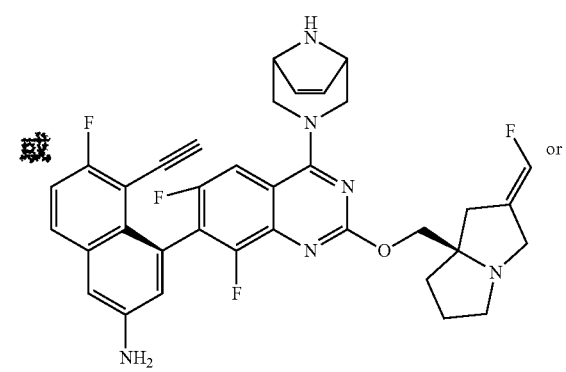

160
-continued

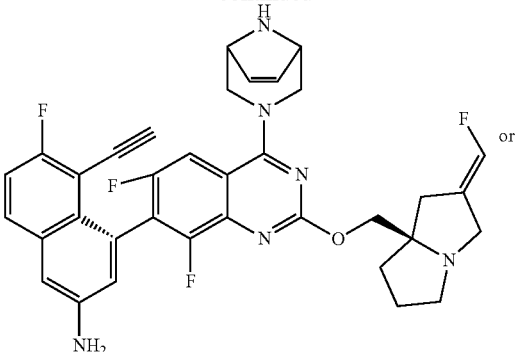

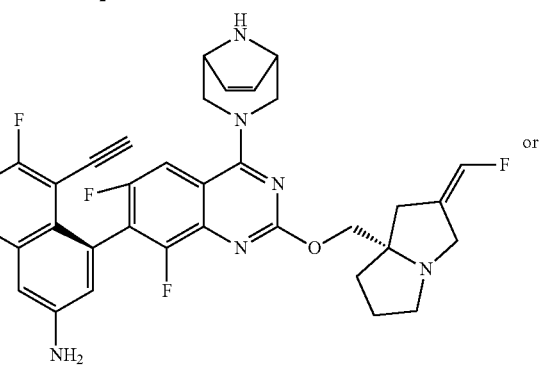

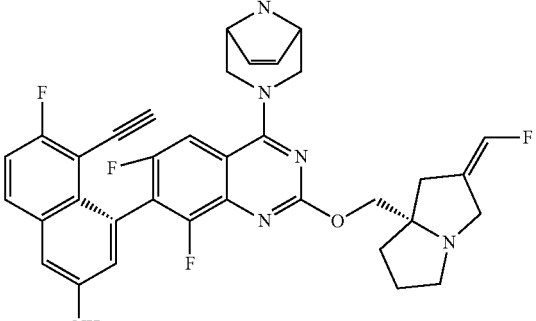

Step 1: Synthesis of Compound 017-5

Compound 017-4 (1.0 g, 4.11 mmol) was dissolved in anhydrous tetrahydrofuran (30 mL) under nitrogen, and the mixture was cooled down to 0° C. Dibromodifluoromethane (1.90 g, 9.04 mmol, 835.93 µL) was slowly added dropwise to the reaction solution, and hexamethylphosphoramide (2.95 g, 18.09 mmol, 3.29 mL) was slowly added dropwise to the reaction solution. The mixture was allowed to warm up to 25° C., and stirred for 14 hours. The reaction solution was cooled down to room temperature, and filtered. Water (10 mL) was added to the filtrate, and the mixture was extracted with ethyl acetate (5 mL). The layers were separated. The organic layer was washed with saturated brine (5 mL×2), dried over anhydrous sodium sulfate, and filtered. The filtrate was concentrated to give a crude product. The crude product was purified by silica gel column chromatography (petroleum ether/ethyl acetate=20/1-1/1) to give compound 017-5. $^1$H NMR (400 MHZ, CDCl$_3$) δ ppm 4.41-4.62 (m, 1H), 4.04-4.22 (m, 2H), 3.67-3.88 (m, 3H), 2.82-3.03 (m, 1H), 2.60-2.73 (m, 1H), 1.37-1.55 (m, 9H).

Step 2: Synthesis of Compound 017-6

Compound 017-5 (2 g, 7.21 mmol) was dissolved in anhydrous tetrahydrofuran (20 mL) under nitrogen, and the mixture was cooled down to −60° C. Lithium hexamethyldisilazide (1 M, 7.93 mL) was added and the mixture was stirred for 10 min. 1-Chloro-3-iodopropane (2.21 g, 10.82 mmol, 1.16 mL) was added dropwise to the reaction solution. The mixture was allowed to warm up to room temperature (30° C.) and stirred for 10 hours. The reaction solution was filtered, and water (10 mL) was added. The mixture was extracted with ethyl acetate (5 mL), washed with saturated brine (5 mL×2), dried over anhydrous sodium sulfate, and filtered. The filtrate was concentrated to give a crude product. The crude product was purified by silica gel column chromatography (petroleum ether/ethyl acetate=50/1~0/1) to give compound 017-6. $^1$H NMR (400 MHZ, $CDCl_3$) δ ppm 4.03-4.36 (m, 2H), 3.74 (s, 3H), 3.47-3.64 (m, 2H), 2.61-2.93 (m, 2H), 2.33-2.49 (m, 1H), 1.93-2.14 (m, 1H), 1.71-1.84 (m, 2H), 1.44 (m, 9H).

Step 3: Synthesis of Compound 017-7 hydrochloride

Compound 017-6 (20 g, 56.53 mmol) was dissolved in hydrochloric acid/ethyl acetate (4 M, 120 mL). The mixture was reacted at 25° C. for 2 h, and then the reaction solution was concentrated to give compound 017-7 hydrochloride, which was used directly in the next step.

Step 4: Synthesis of Compound 017-8

Compound 017-7 (20 g, 56.5 mmol, hydrochloride) was dissolved in N,N-dimethylformamide (65 mL). Potassium carbonate (14.2 g, 102 mmol) was added. The mixture was reacted at 25° C. for 12 hours. The reaction solution was diluted with 500 mL of ethyl acetate, washed successively with water (300 mL×2) and 300 mL of brine, dried over anhydrous sodium sulfate, and filtered. The filtrate was concentrated to give a crude product. The crude product was purified by silica gel column chromatography (petroleum ether/ethyl acetate=100/1~0/1) to give 017-8.

Step 5: Synthesis of Compound 017-9

Compound 017-8 (1.5 g, 6.91 mmol) was added to anhydrous tetrahydrofuran (15 mL). The mixture was cooled down to 0° C. The atmosphere was replaced with nitrogen three times, and a solution of vitride in toluene (3.5 M, 7.89 mL) was added dropwise under nitrogen. The mixture was slowly heated up to 25° C. and reacted for 16 hours. The mixture was cooled down to 0° C., and 10 mL of ethyl acetate was slowly added to the reaction solution, followed by addition of 1 mL of water, 1 mL of 15% sodium hydroxide solution, 3 mL of water, and sodium sulfate solid. The mixture was stirred for 1 h, and filtered. The filter cake was dispersed in 20 mL of ethyl acetate, and the mixture was stirred for 0.5 h, and filtered. The procedure was repeated twice until the filtrate was free of product. The filtrate was concentrated to give compound 017-9.

Step 6: Synthesis of Compound 017-10

Compound 017-9 (2 g, 11.68 mmol) was added to anhydrous dichloromethane (20 mL). The mixture was cooled down to 0° C. Imidazole (1.19 g, 17.52 mmol) and tert-butyldiphenylchlorosilane (3.85 g, 14.02 mmol, 3.60 mL) were added and the mixture was reacted at 25° C. for 1 hour. The reaction solution was washed with 20 mL of water, washed with 20 mL of saturated saline, dried over anhydrous sodium sulfate, and filtered. The filtrate was concentrated, and the crude product was purified by column chromatography (petroleum ether:ethyl acetate=100:0-10:1) to isolate the upper point to give compound 017-10. LCMS: m/z (ESI)=410.2 $[M+H]^+$.

Step 7: Synthesis of Compound 017-11B and Compound 017-11A

Compound 017-10 (0.6 g) was purified by supercritical fluid chromatography (SFC). (column: DAICEL CHIRALCEL OZ 250*25 mm I.D. 10 μm; mobile phase: A (supercritical $CO_2$), mobile phase: B [0.1% ammonia-methanol]; B %: 30%-30%) to give compounds 017-11A and 017-11B.

The analysis and characterization of 017-11A were as follows:

SFC analysis method (column: Lux Cellulose-2, 100×4.6 mm I.D., 3 μm; mobile phase: A (supercritical $CO_2$) and B (MeOH with 0.1% isopropylamine); gradient: B %=10~50%, running for 4 min; flow rate: 3.4 mL/min; wavelength: 220 nm; pressure: 2000 psi), Rt=1.546 min, ee=96.74%. $^1$H NMR (400 MHZ, $CDCl_3$) δ ppm 7.63-7.69 (m, 4H), 7.35-7.44 (m, 6H), 6.27-6.55 (m, 1H), 3.69-3.88 (m, 1H), 3.30-3.48 (m, 2H), 2.53-2.69 (m, 2H), 2.14-2.28 (m, 1H), 1.96-2.08 (m, 1H), 1.79-1.90 (m, 2H), 1.57-1.72 (m, 3H), 1.08 (s, 9H).

The analysis and characterization of 017-11B were as follows:

SFC analysis method (column: Lux Cellulose-2, 100×4.6 mm I.D., 3 μm; mobile phase: A (supercritical $CO_2$) and B (MeOH with 0.1% isopropylamine); gradient: B %=10~50%, running for 4 min; flow rate: 3.4 mL/min; wavelength: 220 nm; pressure: 2000 psi), Rt=1.865 min, ee=99.83%. $^1$H NMR (400 MHZ, $CDCl_3$) δ ppm 7.62-7.69 (m, 4H), 7.33-7.46 (m, 6H), 6.26-6.53 (m, 1H), 3.70-3.78 (m, 1H), 3.42 (d, J=3.10 Hz, 2H), 3.29-3.38 (m, 1H), 3.02-3.13 (m, 1H), 2.52-2.65 (m, 2H), 2.16-2.24 (m, 1H), 1.97-2.04 (m, 1H), 1.69-1.91 (m, 2H), 1.58-1.69 (m, 1H), 1.07 (s, 9H).

Step 8: Synthesis of Compound 017-1A hydrochloride

Compound 017-11B (1.2 g, 2.93 mmol) was dissolved in 24 mL of 1,4-dioxane. Concentrated hydrochloric acid (12 M, 7.20 mL) was added. The mixture was reacted at 95° C. for 12 h. The reaction solution was cooled, diluted with 10 mL of water, and washed with 10 mL of ethyl acetate to give compound 017-1A hydrochloride. $^1$H NMR (400 MHZ, $D_2O$) δ ppm 6.53-6.90 (m, 1H), 4.22 (br d, J=15.04 Hz, 1H), 3.97 (br d, J=15.04 Hz, 1H), 3.69-3.79 (m, 1H), 3.55-3.67 (m, 2H), 3.14-3.24 (m, 1H), 2.67-2.76 (m, 1H), 2.54-2.64 (m, 1H), 1.94-2.19 (m, 4H).

Step 9: Synthesis of Compound 017-1

To a pre-dried reaction flask were added compound 002-2 (500 mg, 988.56 μmol), N,N-dimethylformamide (5 mL), compound 017-1A (220.03 mg, 1.29 mmol, hydrochloride), anhydrous tetrahydrofuran (5 mL), triethylenediamine (33.27 mg, 296.57 μmol, 32.61 μL), anhydrous cesium carbonate (966.28 mg, 2.97 mmol), and 4A molecular sieve (100 mg). The mixture was stirred at 25° C. for 16 hours, and then warmed up to 45° C. and stirred for 24 hours. The mixture was cooled down to room temperature, and then filtered. The filter cake was rinsed with 20 mL of ethyl acetate, washed with saturated brine (20 mL×2), dried over anhydrous sodium sulfate, and filtered. The filtrate was concentrated to give a crude product. The crude compound was purified by silica gel column chromatography (petroleum ether:ethyl acetate (with 5 parts per thousand of triethylamine)=100:0~70:30) to give compound 017-1. LCMS m/z=640.1 [M+H]$^+$.

Step 10: Synthesis of Compound 017-2

To a pre-dried reaction flask were added compound 017-1 (140 mg, 218.57 μmol), compound 001-5A (207.10 mg, 327.85 μmol), anhydrous toluene (3.5 mL), anhydrous potassium phosphate (139.19 mg, 655.70 μmol), and water (0.7 mL). The atmosphere was replaced with nitrogen three times, and [(n-butylbis(1-adamantyl)phosphine)-2-(2-aminobiphenyl)]palladium (II) chloride (14.61 mg, 21.86 μmol) was added. The mixture was heated to 105° C. and stirred for 10 h. The reaction solution was filtered and then concentrated under reduced pressure to give a crude product. The crude product was purified by silica gel column chromatography (petroleum ether:ethyl acetate (with 0.5% triethylamine)=100:0~70:30), then dissolved with 20 mL of ethyl acetate, and extracted with 2N hydrochloric acid (15 mL×2). The aqueous phase was extracted once with 20 mL of methyl tertiary-butyl ether, and then adjusted to a pH of about 8 by adding sodium carbonate solid. The mixture was extracted with ethyl acetate (20 mL×2), dried over anhydrous sodium sulfate, and filtered. The filtrate was concentrated to give compound 017-2. LCMS m/z=901.3 [M+H]$^+$.

Step 11: Synthesis of Compound 017-3 trifluoroacetate

To a pre-dried reaction flask were added compound 017-2 (0.2 g, 221.94 μmol) and trifluoroacetic acid (3.08 g, 27.01 mmol, 2 mL). The mixture was stirred at 70° C. for 1 hour. The reaction solution was concentrated under reduced pressure to give compound 017-3 trifluoroacetate. LCMS m/z=783.3 [M+H]$^+$.

Step 12: Synthesis of Compound 017A and Compound 017B

To a pre-dried reaction flask were added compound 017-3 (0.2 g, 222.96 μmol, trifluoroacetate), N,N-dimethylformamide (0.5 mL), anhydrous potassium carbonate (308.16 mg, 2.23 mmol), and cesium fluoride (169.34 mg, 1.11 mmol, 41.10 μL). The mixture was stirred at 65° C. for 12 h. The reaction solution was cooled down to room temperature, and filtered. The filter cake was rinsed with 20 mL of ethyl acetate, washed with saturated brine (20 mL×3), dried over anhydrous sodium sulfate, and filtered. The filtrate was concentrated to give a crude product. The crude product was purified by preparative high performance liquid chromatography (column: Phenomenex luna C18 OBD 80*40 mm*3 μm; mobile phase A: water (0.05% hydrochloric acid), mobile phase B: acetonitrile; running gradient: B %: 5%-30%, running for 7 min). The fractions were adjusted to a pH of ~7 by adding ammonia, and purified by supercritical fluid chromatography (column: DAICEL CHIRALPAK IG (250 mm*30 mm, 10 μm); mobile phase: A (supercritical CO$_2$), mobile phase B: [0.1% ammonia-ethanol]; B %: 50%-50%, 13 min) to give compounds 017A and 017B. The analysis and characterization of compound 017A were as follows:

SFC analysis method (column: Chiralpak IC-3, 3 μm, 50×4.6 mm I.D; mobile phase: A (supercritical CO$_2$) and B (EtOH with 0.1% isopropylamine); gradient: A:B=50:50, 3 min; flow rate: 3.4 mL/min; wavelength: 220 nm; column temperature: 35° C.; pressure: 1800 psi), Rt=1.723 min, ee=100%. LCMS m/z=627.2 [M+H]$^+$.

The analysis and characterization of compound 017B were as follows:

SFC analysis method (column: Chiralpak IC-3, 3 μm, 50×4.6 mm I.D; mobile phase: A (supercritical CO$_2$) and B (EtOH with 0.1% isopropylamine); gradient: A:B=50:50, 3 min; flow rate: 3.4 mL/min; wavelength: 220 nm; column temperature: 35° C.; pressure: 1800 psi), Rt=2.128 min, ee=98.10%. LCMS m/z=627.2 [M+H]$^+$. $^1$H NMR (400 MHZ, CD$_3$OD) δ ppm 7.73 (dd, J=9.0, 5.8 Hz, 1H), 7.48 (dd, J=10.0, 1.6 Hz, 1H), 7.23 (t, J=8.8 Hz, 1H), 7.17 (d, J=2.4 Hz, 1H), 7.03 (d, J=2.4 Hz, 1H), 6.78-6.51 (m, 1H), 6.33-6.25 (m, 2H), 4.43 (br t, J=14.2 Hz, 2H), 4.26-4.15 (m, 2H), 3.98 (br dd, J=8.8, 2.0 Hz, 2H), 3.84 (br d, J=14.9 Hz, 1H), 3.81-3.70 (m, 2H), 3.46 (br d, J=14.8 Hz, 1H), 3.25 (s, 1H), 3.19-3.12 (m, 1H), 2.76-2.66 (m, 2H), 2.43 (br d, J=15.8 Hz, 1H), 2.18-2.06 (m, 1H), 2.04-1.79 (m, 3H).

Example 18

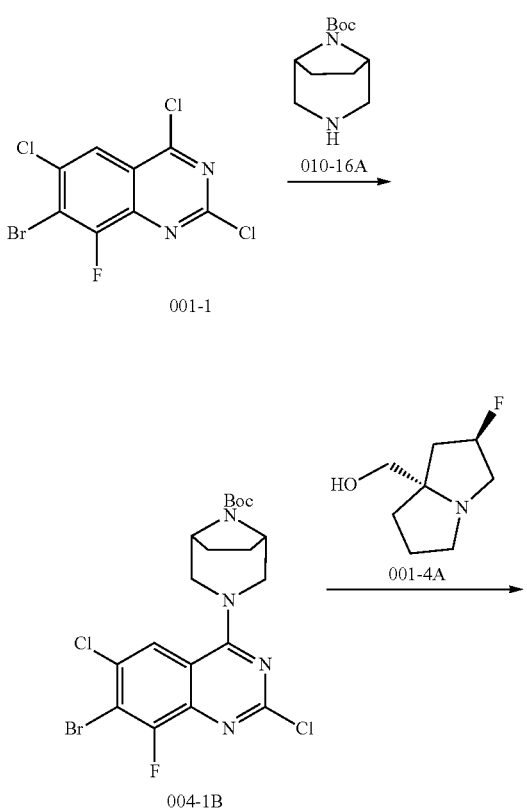

-continued
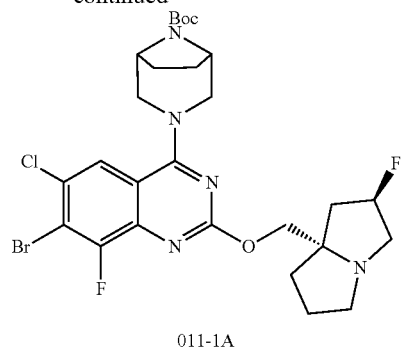
011-1A
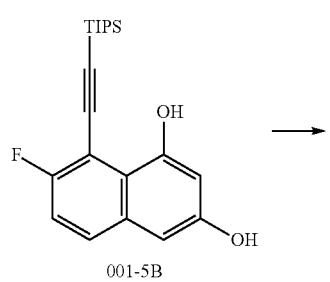
001-5B
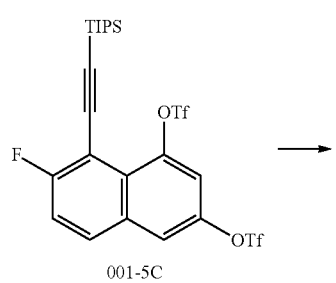
001-5C
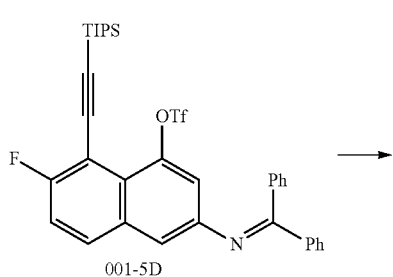
001-5D
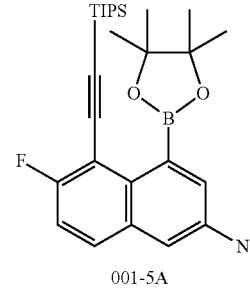
001-5A
-continued
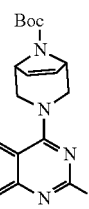
011-1A
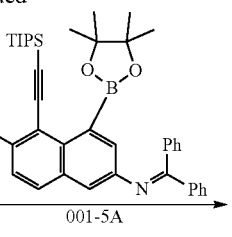
001-5A
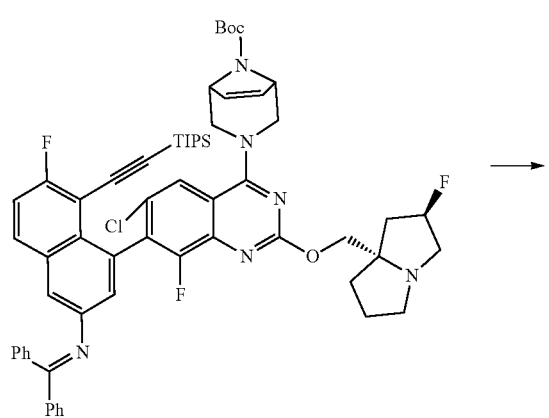
018-2
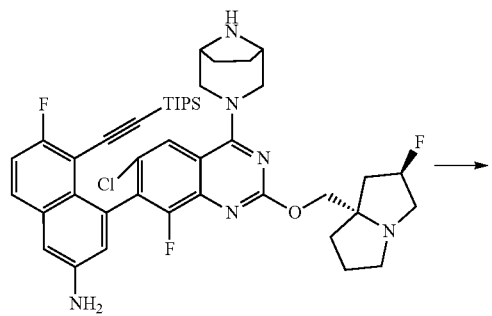
018-3
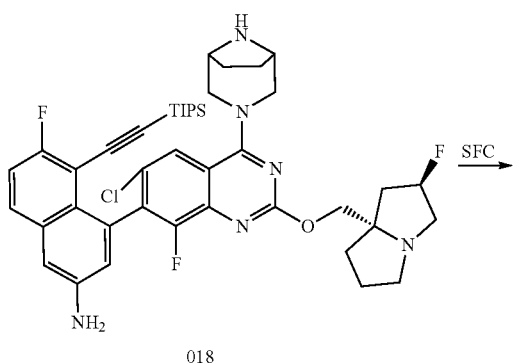
018

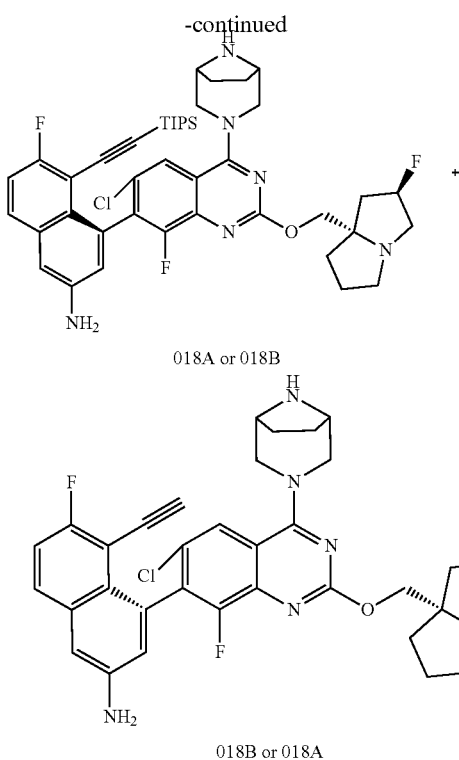

018A or 018B 018B or 018A

Step 1: Synthesis of Compound 004-1B

Compound 001-1 (3.95 g, 11.96 mmol, 1 eq) and compound 010-16A (2.54 g, 11.96 mmol, 1 eq) were dissolved in N,N-dimethylformamide (100 mL). Diisopropylethylamine (3.87 g, 29.91 mmol, 5.21 mL, 2.5 eq) was added. The mixture was reacted at 20° C. for 16 h. 200 ml of water was added and the mixture was extracted with ethyl acetate 3 times, 100 mL each time. The organic phases were combined, dried over anhydrous sodium sulfate, and rotary-evaporated to dryness to give a crude product. The crude product was separated on silica gel column (petroleum ether:ethyl acetate=20:1-10:1-5:1) to give compound 004-1B. LCMS: (ESI) m/z: 506.8 [M+H]+.

Step 2: Synthesis of Compound 011-1A

Compound 004-1B (1.5 g, 2.96 mmol, 1 eq) was dissolved in tetrahydrofuran (6 mL) and N,N-dimethylformamide (6 mL). 001-4A (707.64 mg, 4.44 mmol, 1.5 eq), cesium carbonate (2.90 g, 8.89 mmol, 3 eq) and triethylenediamine (33.24 mg, 296.33 µmol, 32.59 µL, 0.1 eq) were added sequentially under nitrogen. After the addition was completed, the mixture was reacted at 20° C. for 16 h. To the reaction solution was added water, and the mixture was extracted with ethyl acetate (10 mL*3). The organic phase was washed with water and concentrated by rotary-evaporation to dryness to give a crude product. The crude product was purified by column chromatography (PE:EA=10:1) to give compound 011-1A. LCMS: (ESI) m/z: 628.1 [M+H]+.

Step 3: Synthesis of Compound 001-5C

To a pre-dried reaction flask were added compound 001-5B (2 g, 5.58 mmol, 1 eq), dichloromethane (40 mL), and N,N-diisopropylethylamine (4.33 g, 33.47 mmol, 5.83 mL, 6 eq). Trifluoromethanesulfonic anhydride (6.30 g, 22.31 mmol, 3.68 mL, 4 eq) was added at 0° C. The mixture was stirred at 0° C. for 1 hr. After the reaction was completed, water (5 mL) was added. The mixture was extracted with dichloromethane (5 mL×4). The combined organic phase was washed with saturated brine (5 mL), dried over anhydrous sodium sulfate, and filtered. The filtrate was concentrated under reduced pressure, and the crude product was purified by silica gel column chromatography (gradient elution:petroleum ether:ethyl acetate=10:1) to give compound 001-5C.

Step 4: Synthesis of Compound 001-5D

To the reaction flask were added compound 001-5C (3.2 g, 5.14 mmol, 1 eq), diphenylimine (1.86 g, 10.28 mmol, 1.72 mL, 2 eq), and anhydrous toluene (64 mL), followed by cesium carbonate (5.02 g, 15.42 mmol, 3 eq) and 4,5-bis(diphenylphosphino)-9,9-dimethylxanthene (594.75 mg, 1.03 mmol, 0.2 eq) under nitrogen. Tris(dibenzylideneacetone) dipalladium (470.62 mg, 513.94 µmol, 0.1 eq) was added and the mixture was stirred at 100° C. for 2 hr. After the reaction was completed, the reaction solution was cooled to room temperature and concentrated under reduced pressure. The crude product was purified by column chromatography (gradient elution: petroleum ether: ethyl acetate=10:1) to give compound 001-5D. LCMS: (ESI) m/z=654.2 [M+H]+. 1H NMR (400 MHz, CDCl3) δ ppm 7.83~7.78 (m, 5H), 7.60~7.49 (m, 9H), 1.20~1.16 (m, 21H).

Step 5: Synthesis of Compound 001-5A

Compound 001-5D (2.4 g, 3.67 mmol, 1 eq), bis(pinacolato)diboron (1.86 g, 7.34 mmol, 2 eq), and potassium acetate (1.08 g, 11.01 mmol, 3 eq) were dissolved in anhydrous toluene (48 mL). 1,1'-Bis(diphenylphosphino)ferrocene palladium dichloride (537.20 mg, 734.17 µmol, 0.2 eq) was added. Under nitrogen, the mixture was stirred at 130° C. for 12 h.

After the reaction was completed, the mixture was concentrated under reduced pressure and the crude product was purified by column chromatography (gradient elution:petroleum ether:ethyl acetate=10:1) to give compound 001-5A. LCMS: (ESI) m/z=632.3 [M+H]+. 1H NMR (400 MHZ, DMSO) δ ppm 7.80-7.87 (m, 1H), 7.68-7.74 (m, 2H), 7.55-7.62 (m, 1H), 7.47-7.53 (m, 2H), 7.39-7.47 (m, 1H), 7.27-7.35 (m, 4H), 7.18-7.23 (m, 2H), 7.10-7.15 (m, 1H), 1.26 (s, 12H), 1.07-1.15 (m, 21H).

Step 6: Synthesis of Compound 018-2

Compound 011-1A (0.15 g, 238.50 µmol, 1 eq), compound 001-5A (225.99 mg, 357.75 µmol, 1.5 eq) and potassium phosphate (151.88 mg, 715.50 µmol, 3 eq) were added to toluene (4 mL) and water (1 mL). The atmosphere was replaced with nitrogen three times. Chloro [(bis(1-adamantyl)-n-butylphosphine)-2-(2-aminobiphenyl)]palladium (II) (15.95 mg, 23.85 µmol, 0.1 eq) was added under nitrogen. The atmosphere was replaced with nitrogen three times. The mixture was reacted at 100° C. for 1.5 h. After the reaction was completed, the reaction solution was cooled down to room temperature and 20 mL of ethyl acetate and 10 mL of water were added. The mixture was left to stand, and the layers were separated. The aqueous phase was extracted once with 10 mL of ethyl acetate. The organic phases were combined, dried over anhydrous sodium sulfate, and filtered.

The filtrate was concentrated and purified by silica gel column chromatography (gradient elution:petroleum ether: ethyl acetate=100:0~60:40, 5 parts per thousand of triethylamine was added to ethyl acetate) to give compound 018-2. LCMS: (ESI) m/z=1053.6 [M+H]$^+$.

$^1$H NMR (400 MHZ, CD$_3$OD) δ ppm 7.83 (dd, J=9.2, 5.6 Hz, 1H), 7.77-7.71 (m, 3H), 7.55-7.48 (m, 1H), 7.47-7.40 (m, 2H), 7.38-7.24 (m, 5H), 7.17-7.12 (m, 2H), 6.81 (d, J=2.0 Hz, 1H), 5.30-5.23 (m, 1H), 4.73 (br t, J=14.0 Hz, 1H), 4.44-4.33 (m, 2H), 4.30-4.22 (m, 1H), 4.19-4.04 (m, 3H), 3.76 (s, 1H), 3.37-3.16 (m, 4H), 3.06-2.97 (m, 1H), 2.34-1.82 (m, 9H), 1.52 (s, 9H), 0.95-0.81 (m, 18H), 0.61-0.43 (m, 3H).

Step 7: Synthesis of Compound 018-3

Compound 018-2 (0.15 g, 142.35 μmol, 1 eq) was added to hydrogen chloride/methanol (4 M, 4 mL, 112.40 eq). The mixture was reacted at 15° C. for 2 h. After the reaction was completed, the reaction solution was concentrated to dryness under reduced pressure, and then the residue was purified by slurring with 4 mL of ethyl acetate overnight, and filtered. The filter cake was collected and dried under vacuum to give compound 018-3. LCMS: (ESI) m/z=789.5 [M+H]$^+$.

Step 8: Synthesis of Compound 018

Compound 018-3 (0.1 g, 115.96 μmol, 1 eq) was added to N,N-dimethylformamide (1 mL). Potassium carbonate (256.42 mg, 1.86 mmol, 16 eq) and cesium fluoride (2.84 mg, 347.88 μmol, 3 eq) were added. The mixture was stirred at 65° C. for 3 h. After the reaction was completed, the mixture was cooled down to room temperature, and then filtered. The filter cake was rinsed with 10 mL of ethyl acetate. Then the mother liquor was washed with saturated brine (20 mL*3), dried over anhydrous sodium sulfate, and filtered. The filtrate was concentrated to give a crude product. The crude product was purified by preparative high performance liquid chromatography (HPLC) with the following method: column: Phenomenex Luna 80*30 mm*3 μm; mobile phase: [water (hydrochloric acid)-acetonitrile]; acetonitrile %: 1%-40%, 8 min. The obtained fraction was adjusted to a pH of about 8 by adding ammonia dropwise, and then concentrated under reduced pressure to remove acetonitrile. The residue was extracted twice with 20 mL of ethyl acetate, dried over anhydrous sodium sulfate, and filtered. The filtrate was concentrated to give the product 018. The product was purified by SFC chromatographic column: DAICEL CHIRALPAK IC (250 mm*30 mm, 10 μm); mobile phase: [0.1% ammonia-isopropanol]; isopropanol %: 60%-60%, 16 min, and then concentrated under reduced pressure to remove the solvent to give compound 018A and compound 018B.

The analysis and characterization of compound 018A were as follows:

SFC analysis method: column: Chiralpak IC-3, 3 μm, 50×4.6 mm I.D; mobile phase: A (CO$_2$) and B (IPA with 0.1% isopropylamine); gradient: B %=5~50%, 5 min; flow rate: 4.0 mL/min; wavelength: 220 nm; pressure: 124.14 bar, Rt=1.13 min, enantiomeric excess: 100%. LCMS: (ESI) m/z=633.3 [M+H]$^+$. $^1$H NMR (400 MHZ, CD$_3$OD) δ ppm 7.81 (s, 1H), 7.73 (dd, J=8.8, 5.6 Hz, 1H), 7.23 (t, J=8.8 Hz, 1H), 7.17 (d, J=2.2 Hz, 1H), 6.97 (d, J=2.2 Hz, 1H), 5.24-5.42 (m, 1H), 4.54 (d, J=12.8 Hz, 1H), 4.43 (d, J=12.8 Hz, 1H), 4.33 (d, J=10.4 Hz, 1H), 4.23 (d, J=10.8 Hz, 1H), 3.73-3.66 (m, 3H), 3.60 (d, J=12.4 Hz, 1H), 3.35-3.23 (m, 3H), 3.21-3.19 (m, 1H), 3.10-3.02 (m, 1H), 2.44-2.13 (m, 3H), 2.06-1.98 (m, 2H), 1.94-1.81 (m, 5H).

The analysis and characterization of compound 018B were as follows:

SFC analysis method: column: Chiralpak IC-3, 3 μm, 50×4.6 mm I.D; mobile phase: A (CO$_2$) and B (IPA with 0.1% isopropylamine); gradient: B %=5~50%, 5 min; flow rate: 4.0 mL/min; wavelength: 220 nm; pressure: 124.14 bar, Rt=2.20 min, enantiomeric excess: 97.76%. LCMS: (ESI) m/z=633.3 [M+H]$^+$ 0.1H NMR (400 MHZ, CD$_3$OD) δ ppm 7.80 (s, 1H), 7.73 (dd, J=8.8, 6.0 Hz, 1H), 7.23 (t, J=9.0 Hz, 1H), 7.17 (d, J=2.2 Hz, 1H), 6.97 (d, J=2.4 Hz, 1H), 5.39-5.25 (m, 1H), 4.54-4.40 (m, 2H), 4.26 (dd, J=23.2 Hz, 10.4 Hz, 2H), 3.70-3.59 (m, 4H), 3.29-3.19 (m, 4H), 3.08-3.01 (m, 1H), 2.40-2.13 (m, 3H), 2.06-1.96 (m, 2H), 1.92-1.82 (m, 5H).

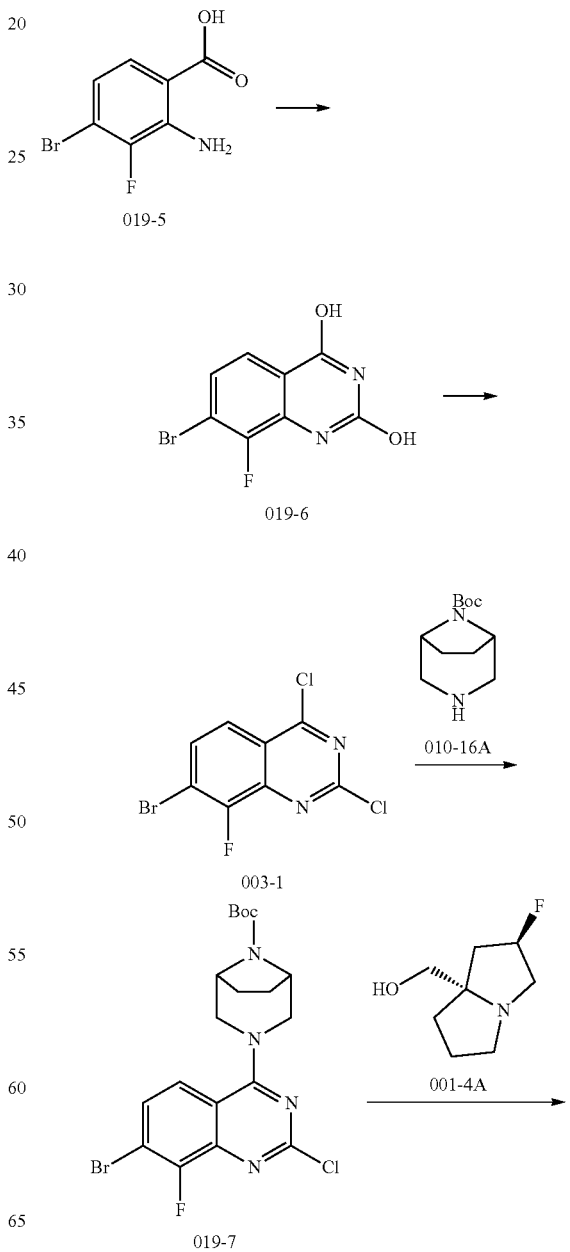

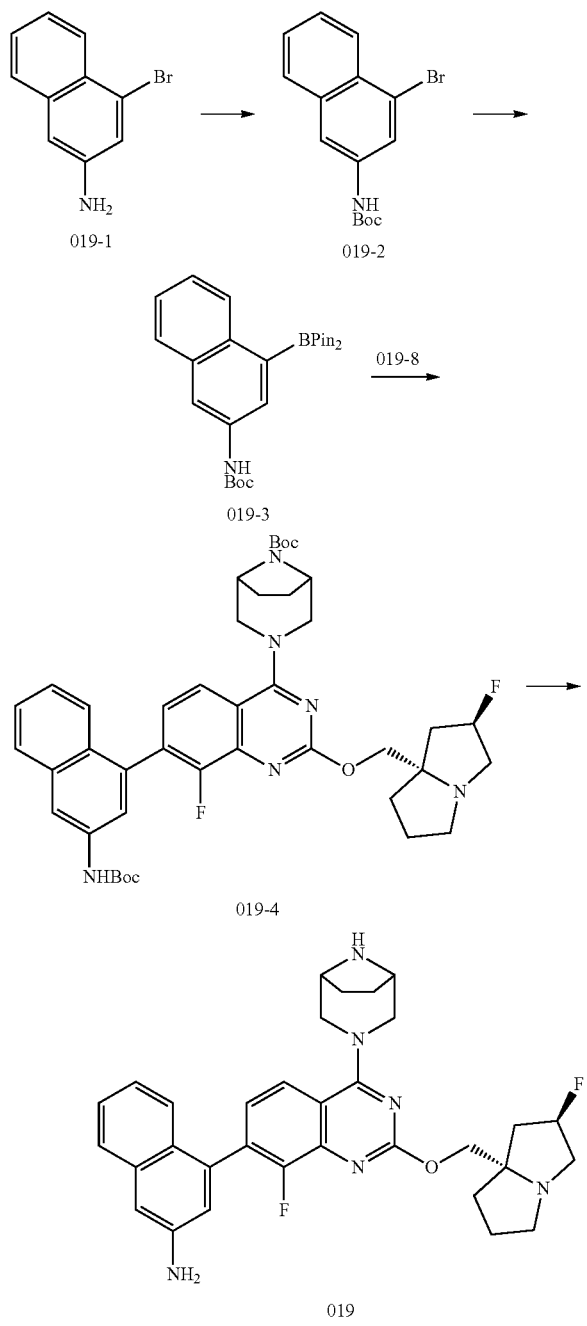

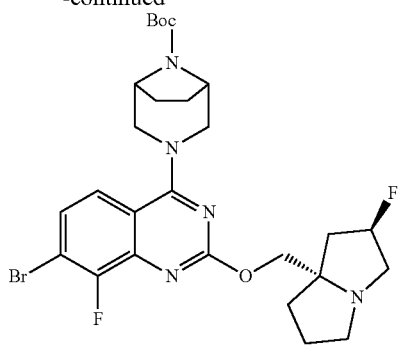

Step 1: Synthesis of Compound 019-6

Compound 019-5 (4 g, 17.09 mmol, 1 eq) and urea (10.27 g, 170.92 mmol, 9.17 mL, 10 eq) were added to a flask. The mixture was reacted at 200° C. for 1.5 h. After the reaction was completed, the reaction was cooled down to room temperature. The reaction solid was slurried with 30 mL of ethyl acetate for 1 h and filtered. The filter cake was concentrated by rotary-evaporation to dryness, then slurried with 30 mL of water for 1 h, and filtered. The filter cake was rotary-evaporated to dryness to give compound 019-6. $^1$H NMR (400 MHZ, DMSO-$d_6$) δ=11.45-11.06 (m, 2H), 7.67-7.56 (m, 1H), 7.45-7.35 (m, 1H).

Step 2: Synthesis of Compound 003-1

Compound 019-6 (2.5 g, 9.65 mmol, 1 eq) was added to phosphorus oxychloride (20 mL). Diisopropylethylenediamine (3.74 g, 28.95 mmol, 5.04 mL, 3 eq) was added. The mixture was reacted at 100° C. for 3 h. After the reaction was completed, the reaction solution was concentrated directly. The concentrated product was slowly added to 20 mL of ice water and extracted with 10 mL*2 of ethyl acetate. The organic phases were combined, washed respectively with 20 mL of saturated ammonium chloride and saturated brine, dried over anhydrous sodium sulfate, and filtered. The filtrate was concentrated to give compound 003-1. $^1$H NMR (400 MHZ, DMSO-$d_6$) δ=8.81-8.59 (m, 2H); LCMS: (ESI) m/z: 296.8 [M+H]$^+$.

Step 3: Synthesis of Compound 019-7

Compound 003-1 (1.5 g, 5.07 mmol, 1 eq) was added to anhydrous dichloromethane (20 mL). Triethylamine (1.54 g, 15.21 mmol, 2.12 mL, 3 eq) and compound 010-16A (1.29 g, 6.08 mmol, 1.2 eq) were added. The mixture was reacted at 20° C. for 2 h. After the reaction was completed, the crude product was purified using a column (petroleum ether:ethyl acetate=100:0-1:1) to give compound 019-7. $^1$H NMR (400 MHZ, DMSO-$d_6$) δ=7.83 (d, J=0.8 Hz, 1H), 7.71-7.63 (m, 1H), 4.42-4.30 (m, 2H), 4.23 (s, 2H), 3.58 (d, J=1.2 Hz, 2H), 1.84-1.74 (m, 2H), 1.68-1.59 (m, 2H), 1.45 (s, 9H); LCMS: (ESI) m/z: 473.0 [M+H]$^+$.

Step 4: Synthesis of Compound 019-8

Compound 019-7 (0.7 g, 1.48 mmol, 1 eq) was added to N,N-dimethylformamide (7 mL) and anhydrous tetrahydrofuran (7 mL). Compound 001-4A (354.34 mg, 2.23 mmol, 1.5 eq), cesium carbonate (1.45 g, 4.45 mmol, 3 eq), and triethylenediamine (16.64 mg, 148.38 μmol, 16.32 μL, 0.1 eq) were added. The mixture was reacted at 20° C. for 20 h. After the reaction was completed, 20 mL of water was added to the reaction solution, and the mixture was extracted with 10 mL*2 of ethyl acetate. The organic phases were combined, washed with 20 mL of saturated saline, dried over anhydrous sodium sulfate, and filtered. The filtrate was concentrated, and the crude product was purified using a column (dichloromethane:methanol=100:0-10:1) to give compound 019-8. $^1$H NMR (400 MHZ, CDCl$_3$) δ=7.45-7.39 (m, 1H), 7.32-7.28 (m, 1H), 5.40-5.13 (m, 1H), 4.45-4.28 (m, 4H), 4.26-4.21 (m, 1H), 4.18-4.05 (m, 1H), 3.69-3.42 (m, 2H), 3.33-3.10 (m, 3H), 3.05-2.92 (m, 1H), 2.30-2.07 (m, 3H), 2.00-1.84 (m, 5H), 1.81-1.70 (m, 2H), 1.52 (s, 9H); LCMS: (ESI) m/z: 594.1 [M+H]$^+$.

Step 5: Synthesis of Compound 019-2

Compound 019-1 (0.27 g, 1.22 mmol, 1 eq) was dissolved in THF (10 mL). Di-tert-butyl dicarbonate (318.41 mg, 1.46 mmol, 335.16 µL, 1.2 eq) was slowly added. The mixture was reacted at 80° C. for 12 h. After the reaction was completed, the mixture was directly rotary-evaporated to dryness and the crude product was purified on silica gel column (gradient elution:petroleum ether:ethyl acetate=10: 1-5:1) to give compound 019-2.

Step 6: Synthesis of Compound 019-3

Compound 019-2 (0.35 g, 1.09 mmol, 1 eq), bis(pinacolato)diboron (413.78 mg, 1.63 mmol, 1.5 eq), 1,1'-bis(diphenylphosphino) ferrocene palladium (II) dichloride (79.48 mg, 108.63 µmol, 0.1 eq), and potassium acetate (159.92 mg, 1.63 mmol, 1.5 eq) were dissolved in 1,4-dioxane (10 mL) under nitrogen. The mixture was reacted at 80° C. for 16 h. After the reaction was completed, the mixture was directly rotary-evaporated to dryness. The crude product was purified on silica gel column (gradient elution:petroleum ether:ethyl acetate=50:1-20:1) to give compound 019-3.

Step 7: Synthesis of Compound 019-4

Compound 019-3 (100 mg, 270.81 µmol, 1 eq), 1,1'-bis (diphenylphosphino) ferrocene palladium (II) dichloride (19.82 mg, 27.08 µmol, 0.1 eq), potassium carbonate (74.86 mg, 541.62 µmol, 2 eq), and compound 019-8 (160.99 mg, 270.81 µmol, 1 eq) were dissolved in 1,4-dioxane (2.5 mL) and water (0.5 mL) under nitrogen. The mixture was reacted at 95° C. for 16 h. After the reaction was completed, the mixture was directly rotary-evaporated to dryness and the crude product was purified on silica gel column (gradient elution:petroleum ether: ethyl acetate=50:1-20:1) to give compound 019-4.

Step 8: Synthesis of Compound 019

Compound 019-4 (49.93 mg, 65.97 µmol, 1 eq) was dissolved in 1,4-dioxane (2 mL). Hydrochloric acid (48.11 mg, 1.32 mmol, 47.17 µL, 20 eq) was added. The mixture was reacted at 25° C. for 4 hr. After the reaction was completed, the mixture was directly rotary-evaporated to dryness to give compound 019 hydrochloride, LCMS: (ESI) m/z=557.3 [M+H]$^+$.

$^1$H NMR (400 MHZ, CD$_3$OD) δ=8.11 (br d, J=7.3 Hz, 1H), 8.05-8.00 (m, 1H), 7.68-7.49 (m, 5H), 5.58-5.46 (m, 1H), 4.43-3.71 (m, 7H), 3.62-3.56 (m, 2H), 3.44-3.32 (m, 1H), 2.78-2.50 (m, 2H), 2.48-2.38 (m, 1H), 2.34-1.96 (m, 7H).

Example 20

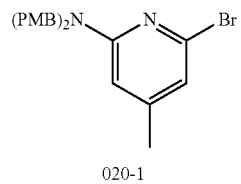

020-1

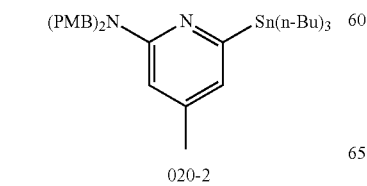

020-2

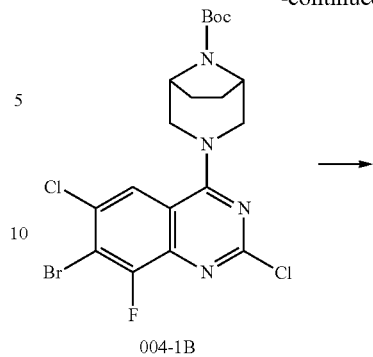

004-1B

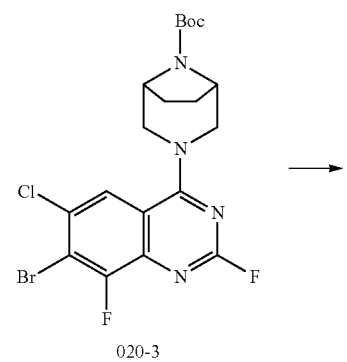

020-3

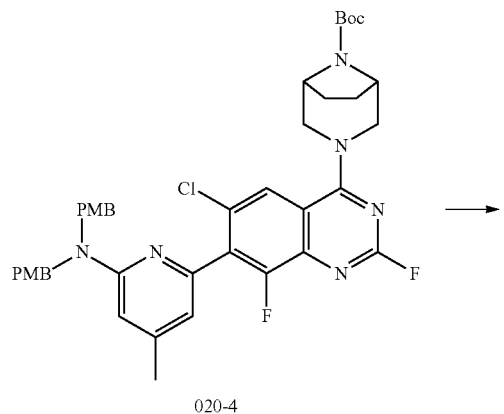

020-4

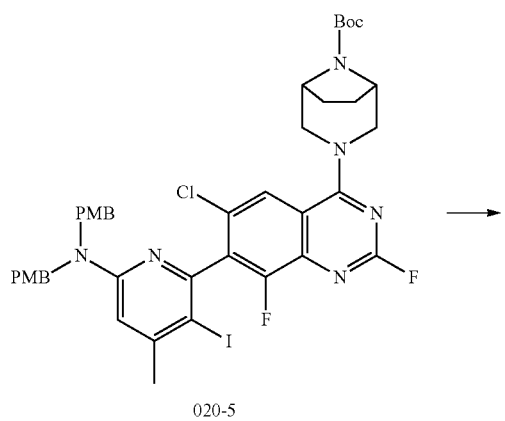

020-5

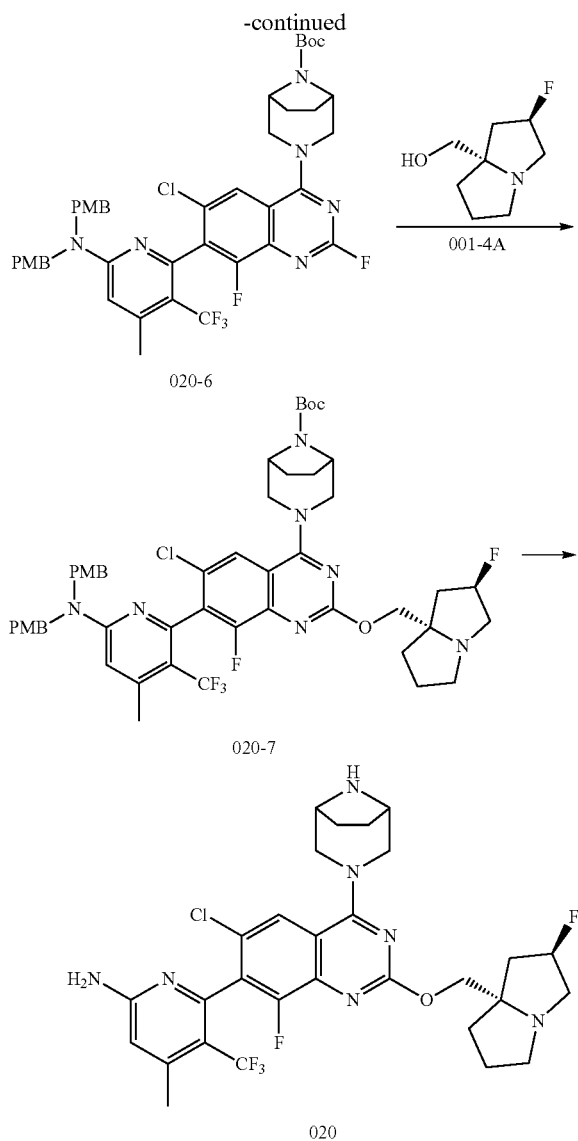

Step 1: Synthesis of Compound 020-2

Under nitrogen, compound 020-1 (5 g, 11.70 mmol, 1 eq), hexa-n-butyltin (20.36 g, 35.10 mmol, 17.55 mL, 3 eq), tris(dibenzylideneindenylacetone) dipalladium (1.07 g, 1.17 mmol, 0.1 eq), tricyclohexylphosphine (656.23 mg, 2.34 mmol, 758.64 µL, 0.2 eq), lithium chloride (2.48 g, 58.50 mmol, 1.20 mL, 5 eq) and 1,4-dioxane (50 mL) were stirred at 110° C. for 2 h. After the reaction was completed, the mixture was rotary-evaporated to dryness and the crude product was purified on silica gel column (gradient elution: petroleum ether: ethyl acetate=100:1) to give compound 020-2. LCMS: (ESI) m/z=639.3 [M+H]$^+$.

Step 2: Synthesis of Compound 020-3

Compound 004-1B (2.5 g, 4.94 mmol, 1 eq) was dissolved in N,N-dimethylacetamide (30 mL). Potassium fluoride (5.74 g, 98.78 mmol, 2.31 mL, 20 eq) was added. The mixture was reacted at 120° C. for 18 h. After the reaction was completed, water was added and the mixture was extracted with 100 mL of ethyl acetate. The organic phase was dried over anhydrous sodium sulfate, and rotary-evaporated to dryness. The crude product was purified on silica gel column (gradient elution:petroleum ether:ethyl acetate=20:1-10:1) to give compound 020-3. LCMS: (ESI) m/z=489.1 [M+H]$^+$.

Step 3: Synthesis of Compound 020-4

Compound 020-3 (384.12 mg, 784.34 µmol, 1 eq), compound 020-2 (0.5 g, 784.34 µmol, 1 eq), tetrakis(triphenylphosphine) palladium (90.63 mg, 78.43 µmol, 0.1 eq), cuprous iodide (22.41 mg, 117.65 µmol, 0.15 eq) and lithium chloride (39.90 mg, 941.20 µmol, 19.28 µL, 1.2 eq) were dissolved in 1,4-dioxane (10 mL). The mixture was reacted at 120° C. for 18 h. After the reaction was completed, the mixture was directly rotary-evaporated to dryness. The crude product was purified on silica gel column (gradient elution:petroleum ether: ethyl acetate=20:1-2:1) to give compound 020-4, LCMS: (ESI) m/z=757.3 [M+H]$^+$.

Step 4: Synthesis of Compound 020-5

Compound 020-4 (0.1 g, 132.05 µmol, 1 eq) was dissolved in N,N-dimethylformamide (5 mL). N-iodosuccinimide (44.57 mg, 198.08 µmol, 1.5 eq) was added. The mixture was reacted at 25° C. for 1 h. After the reaction was completed, water was added. The mixture was extracted with 100 mL of ethyl acetate. The organic phase was dried over anhydrous sodium sulfate and rotary-evaporated to dryness. The crude product was purified on silica gel column (gradient elution:petroleum ether:ethyl acetate=20:1-5:1) to give compound 020-5. LCMS: (ESI) m/z=883.2 [M+H]$^+$.

Step 5: Synthesis of Compound 020-6

Compound 020-5 (0.1 g, 113.23 µmol, 1 eq) was dissolved in N,N-dimethylformamide (2 mL). Cuprous iodide (64.69 mg, 339.69 µmol, 3 eq) and hexamethylphosphoramide (202.91 mg, 1.13 mmol, 198.93 µL, 10 eq) were then added. Under nitrogen, methyl fluorosulfonyldifluoroacetate (217.53 mg, 1.13 mmol, 144.06 µL, 10 eq) was then added and the mixture was reacted at 90° C. for 2 h. After the reaction was completed, water was added. The mixture was extracted with 100 mL of ethyl acetate. The organic phase was dried over anhydrous sodium sulfate and rotary-evaporated to dryness. The crude product was purified on silica gel column (gradient elution:petroleum ether:ethyl acetate=20:1-5:1) to give compound 020-6.

Step 6: Synthesis of Compound 020-7

001-4A (28.94 mg, 181.76 µmol, 3 eq) was dissolved in THF (2 mL). Sodium hydride (14.54 mg, 363.52 µmol, 60% content, 6 eq) was added at 0° C. After the addition was completed, the mixture was heated to 25° C. and stirred for 1 h. Then 020-6 (0.05 g, 60.59 µmol, 1 eq) was added and the mixture was stirred for 1 h. After the reaction was completed, methanol (0.5 mL) was added to quench the reaction. The mixture was concentrated to dryness to remove the solvent, and the crude product was purified on silica gel column (gradient elution:petroleum ether:ethyl acetate=50:1-20:1) to give compound 020-7.

Step 7: Synthesis of Compound 020

Compound 020-7 (0.05 g, 51.84 µmol, 1 eq) was dissolved in trifluoroacetic acid (2 mL). The mixture was stirred at 50° C. for 5 h. The mixture was rotary-evaporated to dryness and purified by preparative HPLC column: Welch Xtimate C18 100*40 mm*3 μm; mobile phase: [water (0.1% trifluoroacetic acid)-acetonitrile]; acetonitrile %: 7%-37%, 8 min, to give compound 020 trifluoroacetate, LCMS: (ESI) m/z=624.3 [M+H]⁺. ¹H NMR (400 MHZ, CD₃OD) δ ppm 2.01-2.27 (m, 5H) 2.30-2.41 (m, 2H) 2.45 (br d, J=8.78 Hz, 1H) 2.52 (br s, 3H) 2.55-2.85 (m, 2H) 3.41-3.58 (m, 1H) 3.80-4.12 (m, 5H) 4.26 (br s, 2H) 4.60-4.80 (m, 4H) 5.53 (br s, 1H) 5.67 (br d, J=3.51 Hz, 1H) 6.64-6.89 (m, 1H) 6.80 (s, 1H) 7.97 (s, 1H).

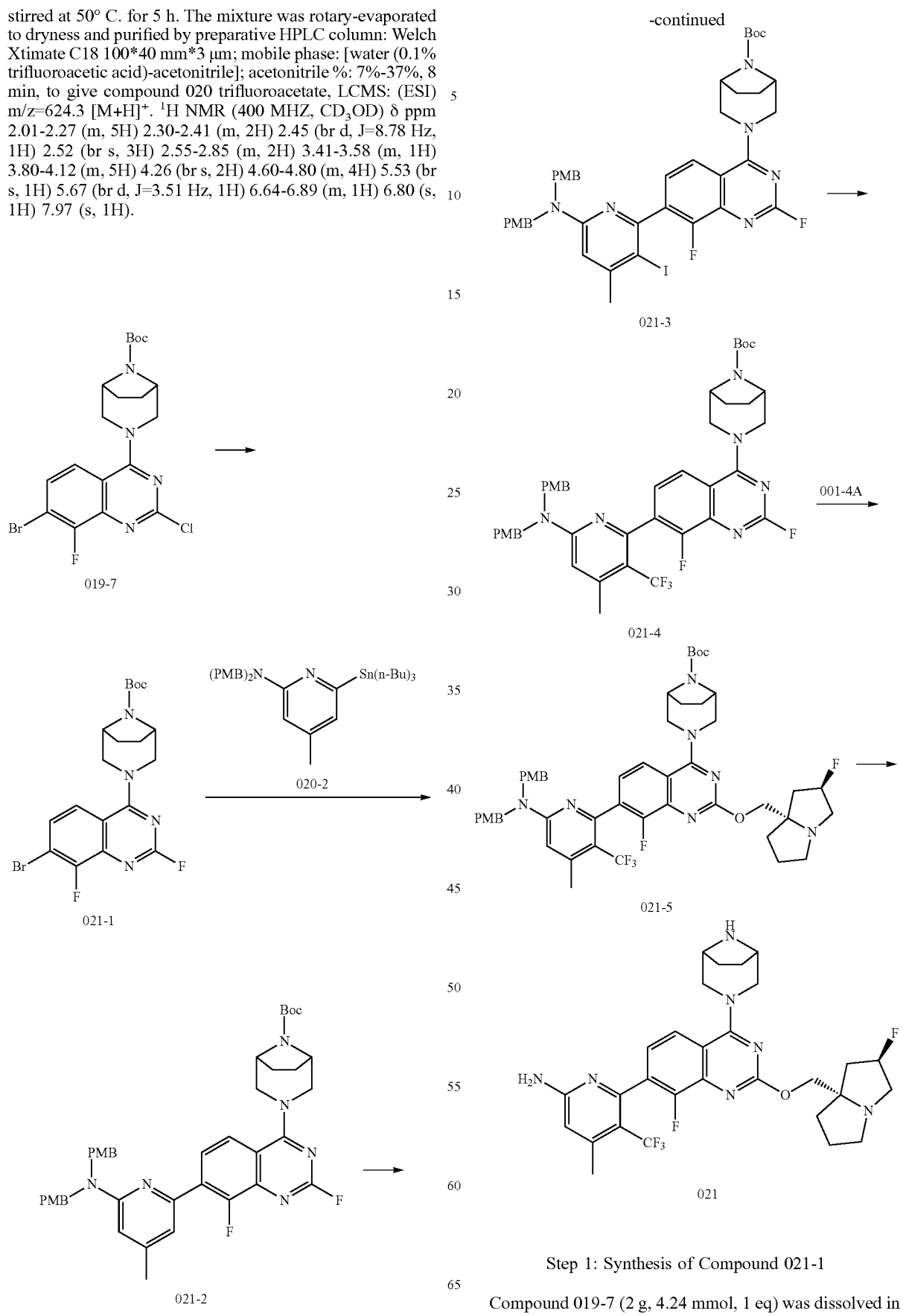

Step 1: Synthesis of Compound 021-1

Compound 019-7 (2 g, 4.24 mmol, 1 eq) was dissolved in N,N-dimethylacetamide (30 mL). Potassium fluoride (1.23 g, 21.20 mmol, 496.58 μL, 5 eq) was added. The mixture was reacted at 120° C. for 24 h. After the reaction was completed, water was added and the mixture was extracted with 100 mL of ethyl acetate. The organic phase was dried over anhydrous sodium sulfate and rotary-evaporated to dryness. The crude product was purified on silica gel column (gradient elution:petroleum ether:ethyl acetate=20:1-10:1) to give compound 021-1, LCMS: (ESI) m/z=455.0 [M+H]+.

Step 2: Synthesis of Compound 021-2

Compound 021-1 (220 mg, 483.20 μmol, 1 eq), compound 020-2 (308.03 mg, 483.20 μmol, 1 eq), tetrakis(triphenylphosphine) palladium (55.84 mg, 48.32 μmol, 0.1 eq), cuprous iodide (13.80 mg, 72.48 μmol, 0.15 eq) and lithium chloride (20.48 mg, 483.20 μmol, 9.90 μL, 1 eq) were dissolved in 1,4-dioxane (10 mL). The mixture was reacted at 120° C. for 18 h. After the reaction was completed, the mixture was directly rotary-evaporated to dryness. The crude product was purified on silica gel column (gradient elution:petroleum ether:ethyl acetate=20:1-2:1) to give compound 021-2, LCMS: (ESI) m/z=723.3 [M+H]+.

Step 3: Synthesis of Compound 021-3

Compound 021-2 (200 mg, 276.69 μmol, 1 eq) was dissolved in N,N-dimethylformamide (5 mL). Then N-iodosuccinimide (186.75 mg, 830.08 μmol, 3 eq) was added. The mixture was reacted at 25° C. for 5 h. After the reaction was completed, water was added and the mixture was extracted with 100 mL of ethyl acetate. The organic phase was dried over anhydrous sodium sulfate, and filtered. The filtrate was concentrated and the crude product was purified on silica gel column (gradient elution:petroleum ether:ethyl acetate=20:1-5:1) to give compound 021-3. LCMS: (ESI) m/z=849.2 [M+H]+.

Step 4: Synthesis of Compound 021-4

Compound 021-3 (120 mg, 141.39 μmol, 1 eq) was dissolved in N,N-dimethylformamide (2 mL). Cuprous iodide (53.86 mg, 282.78 μmol, 2 eq) and hexamethylphosphoramide (126.69 mg, 706.95 μmol, 124.20 μL, 5 eq) were then added. Under nitrogen, methyl fluorosulfonyldifluoroacetate (135.81 mg, 706.95 μmol, 89.94 μL, 5 eq) was then added and mixture was reacted at 80° C. for 18 h. After the reaction was completed, water was added. The mixture was extracted with 100 mL of ethyl acetate. The organic phase was dried over anhydrous sodium sulfate, and filtered. The filtrate was concentrated to give a crude product. The crude product was purified on silica gel column (gradient elution: petroleum ether:ethyl acetate=20:1-5:1) to give compound 021-4. LCMS: (ESI) m/z=791.3 [M+H]+.

Step 5: Synthesis of Compound 021-5

Compound 021-4 (200 mg, 252.90 μmol, 1 eq) was dissolved in tetrahydrofuran (2 mL) and N,N-dimethylformamide (2 mL). Then cesium carbonate (164.80 mg, 505.80 μmol, 2 eq) and triethylenediamine (14.18 mg, 126.45 μmol, 13.91 μL, 0.5 eq) were added. Finally, 001-4A (80.52 mg, 505.80 μmol, 2 eq) was added and the mixture was reacted at 25° C. for 28 h. After the reaction was completed, water was added and the mixture was extracted with 100 mL of ethyl acetate. The organic phase was dried over anhydrous sodium sulfate, and filtered. The filtrate was concentrated to give a crude product. The crude product was purified on silica gel column (gradient elution:petroleum ether:ethyl acetate=50:1-20:1) to give compound 021-5. LCMS: (ESI) m/z=930.7 [M+H]+.

Step 6: Synthesis of Compound 021

Compound 021-5 (100 mg, 107.53 μmol, 1 eq) was dissolved in trifluoroacetic acid (1.54 g, 13.51 mmol, 1 mL, 125.61 eq). The mixture was reacted at 55° C. for 4 hr, and separated by preparative HPLC (column: Phenomenex C18 150*40 mm*5 μm; mobile phase: [water (0.05% hydrochloric acid)-acetonitrile]; acetonitrile %: 5%-35%, 10 min) to give compound 021 hydrochloride. LCMS: (ESI) m/z=590.5 [M+H]+. 1H NMR (400 MHZ, CD3OD) δ=8.09 (d, J=8.8 Hz, 1H), 7.57 (t, J=7.5 Hz, 1H), 7.05 (s, 1H), 5.69-5.56 (m, 1H), 4.86-4.75 (m, 4H), 4.31 (br s, 2H), 4.16-3.84 (m, 5H), 3.55-3.44 (m, 1H), 2.86-2.56 (m, 5H), 2.51 (br s, 1H), 2.43-2.32 (m, 2H), 2.31-2.13 (m, 5H).

Example 22

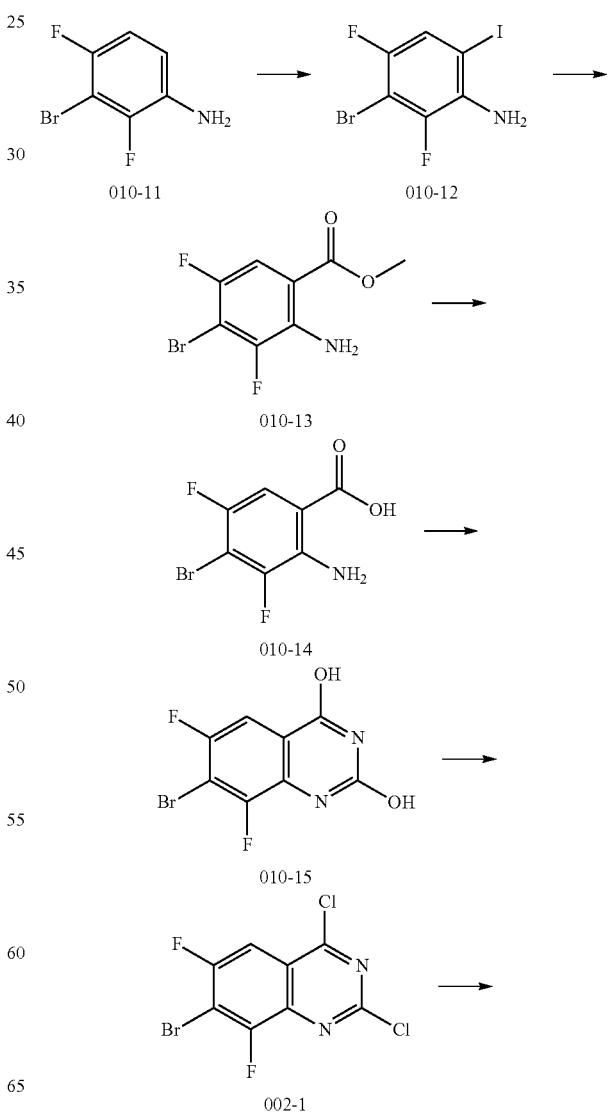

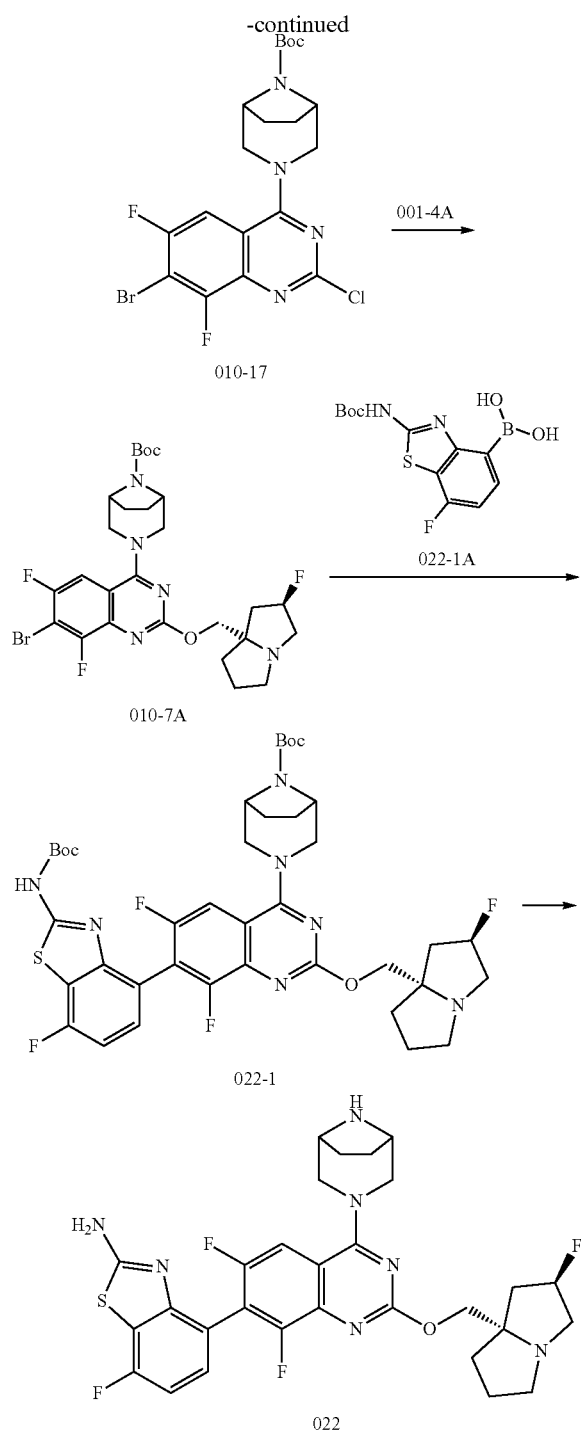

Step 1: Synthesis of Compound 010-12

Compound 010-11 (30 g, 144.23 mmol, 1 eq) and silver sulfate (44.97 g, 144.23 mmol, 24.44 mL, 1 eq) were dissolved in ethanol (300 mL). Then iodine (40.27 g, 158.65 mmol, 31.96 mL, 1.1 eq) was added. The mixture was stirred at 25° C. for 2 h. After the reaction was completed, the reaction solution was filtered, and the filtrate was evaporated to dryness. The crude product was purified on silica gel column (gradient elution:petroleum ether: ethyl acetate=100:1-20:1) to give compound 010-12. $^1$H NMR (400 MHZ, CDCl$_3$) δ:5.08 (d, J=7.8 Hz, 1H), 4.30-4.24 (m, 1H), 1.63-1.53 (m, 2H), 1.32 (s, 9H), 0.70-0.58 (m, 1H), 0.42-0.32 (m, 2H), 0.05-0.05 (m, 2H).

Step 2: Synthesis of Compound 010-13

Compound 010-12 (22 g, 65.89 mmol, 1 eq) and 1,1'-bis(diphenylphosphino) ferrocene]palladium dichloride dichloromethane (5.38 g, 6.59 mmol, 0.1 eq) were dissolved in methanol (100 mL) under a carbon monoxide environment at a pressure of 50 Psi and a temperature of 30° C. The mixture was stirred for 5 min, and then triethylamine (46.67 g, 461.22 mmol, 64.20 mL, 7 eq) was added. The mixture was stirried for another 24 h. After the reaction was completed, the mixture was filtered and the filtrate was evaporated to dryness. The crude product was purified on silica gel column (gradient elution:petroleum ether:ethyl acetate=20:1-5:1) to give compound 010-13. LCMS: (ESI) m/z=265.8 [M+H]$^+$.

Step 3: Synthesis of Compound 010-14

Compound 010-13 (15 g, 56.38 mmol, 1 eq) was dissolved in methanol (50 mL). A solution of sodium hydroxide (9.02 g, 225.53 mmol, 4 eq) in water (50 mL) was added. The mixture was stirred at 25° C. for 2 h. After the reaction was completed, the reaction solution was concentrated and adjusted to a pH of 5 using 2 mol/L hydrochloric acid. A white solid was precipitated and filtered by suction to give compound 010-14. LCMS: (ESI) m/z=251.8 [M+H]$^+$.

Step 4: Synthesis of Compound 010-15

Compound 010-14 (12 g, 47.62 mmol, 1 eq) and urea (85.79 g, 1.43 mol, 76.60 mL, 30 eq) were added to a reaction flask. The mixture was reacted at 200° C. for 4 h. The reaction solution was cooled to room temperature and slurried using 200 ml of water. The mixture was filtered by suction to give compound 010-15. LCMS: (ESI) m/z=276.9 [M+H]$^+$.

Step 5: Synthesis of Compound 002-1

N,N-diisopropylethylamine (11.66 g, 90.25 mmol, 15.72 mL, 5 eq) was added dropwise to phosphorus oxychloride (82.50 g, 538.05 mmol, 50 mL, 29.81 eq) at 0° C., and then compound 010-15 (5 g, 18.05 mmol, 1 eq) was added in batches. After the addition was completed, the mixture was refluxed at 80° C. for 20 h. The phosphorus oxychloride was evaporated. The crude product was purified on silica gel column (gradient elution:petroleum ether:ethyl acetate=20:1-10:1) to give compound 002-1. LCMS: (ESI) m/z=312.9 [M+H]$^+$.

Step 6: Synthesis of Compound 010-17

Compound 010-16A (1.2 g, 3.82 mmol, 1 eq) was dissolved in N,N-dimethylformamide (2 mL). Compound 002-1 (811.51 mg, 3.82 mmol, 1 eq) and N,N-diisopropylethylamine (1.48 g, 11.47 mmol, 2.00 mL, 3 eq) were added. The mixture was stirred to react at 25° C. for 2 h. The reaction solution was poured into 50 ml of water, and a solid was precipitated. The solid was washed with water (3*20 mL) to give compound 010-17. LCMS: (ESI) m/z=489.0 [M+H]$^+$.

Step 7: Synthesis of Compound 010-7A

Compound 010-17 (1.6 g, 3.27 mmol, 1 eq) was dissolved in N,N-dimethylformamide (10 mL) and THF (10 mL).

Then cesium carbonate (3.19 g, 9.80 mmol, 3 eq), compound 001-4A (780.17 mg, 4.90 mmol, 1.5 eq), and triethylenediamine (36.65 mg, 326.70 μmol, 35.93 μL, 0.1 eq) were added. The mixture was stirred to react at 25° C. for 18 h. After the reaction was completed, the mixture was extracted with 40 mL of ethyl acetate, and washed with water and saturated brine. The organic phase was dried over anhydrous sodium sulfate, and filtered. The filtrate was concentrated to give a crude product. The crude product was purified on silica gel column (gradient elution:petroleum ether:ethyl acetate=20:1-10:1) to give compound 010-7A. LCMS: (ESI) m/z=612.2 [M+H]$^+$.

Step 8: Synthesis of Compound 022-1

Compound 010-7A (0.2 g, 408.38 μmol, 1 eq) and compound 022-1A (127.47 mg, 408.38 μmol, 1 eq) were dissolved in 1,4-dioxane (2 mL) and water (2 mL). 1,1'-Bis(di-tert-butylphosphino) ferrocene palladium dichloride (26.62 mg, 40.84 μmol, 0.1 eq), and potassium phosphate (130.03 mg, 612.57 μmol, 1.5 eq) were added. The mixture was reacted under nitrogen at 90° C. for 18 h. After the reaction was completed, the reaction solution was rotary-evaporated to dryness and the crude product was purified on silica gel column (gradient elution:petroleum ether:ethyl acetate=20:1-10:1) to give compound 022-1. LCMS: (ESI) m/z=800.3 [M+H]$^+$.

Step 9: Synthesis of Compound 022

Compound 022-1 (25 mg, 31.25 μmol, 1 eq) was dissolved in acetonitrile (1 mL) and hydrochloric acid/1,4-dioxane (1 mL). The mixture was reacted at 25° C. for 12 h. After the reaction was completed, the mixture was rotary-evaporated to dryness to remove the solvent and separated by preparative column: Phenomenex C18 150*40 mm*5 μm; mobile phase: [water (0.2% formic acid)-acetonitrile]; acetonitrile %: 1%-30%, 10 min, to give compound 022 formate. LCMS: (ESI) m/z=600.1 [M+H]$^+$.

Example 23

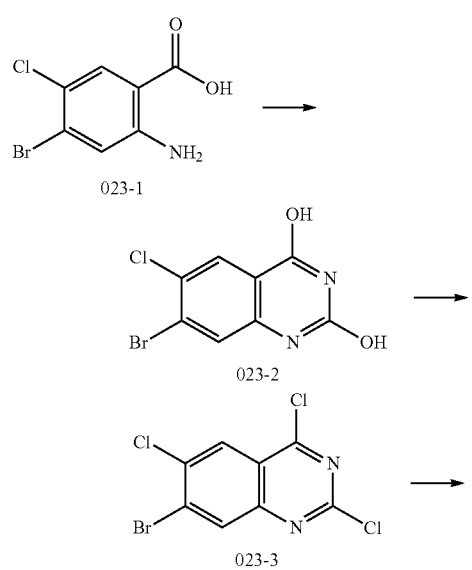

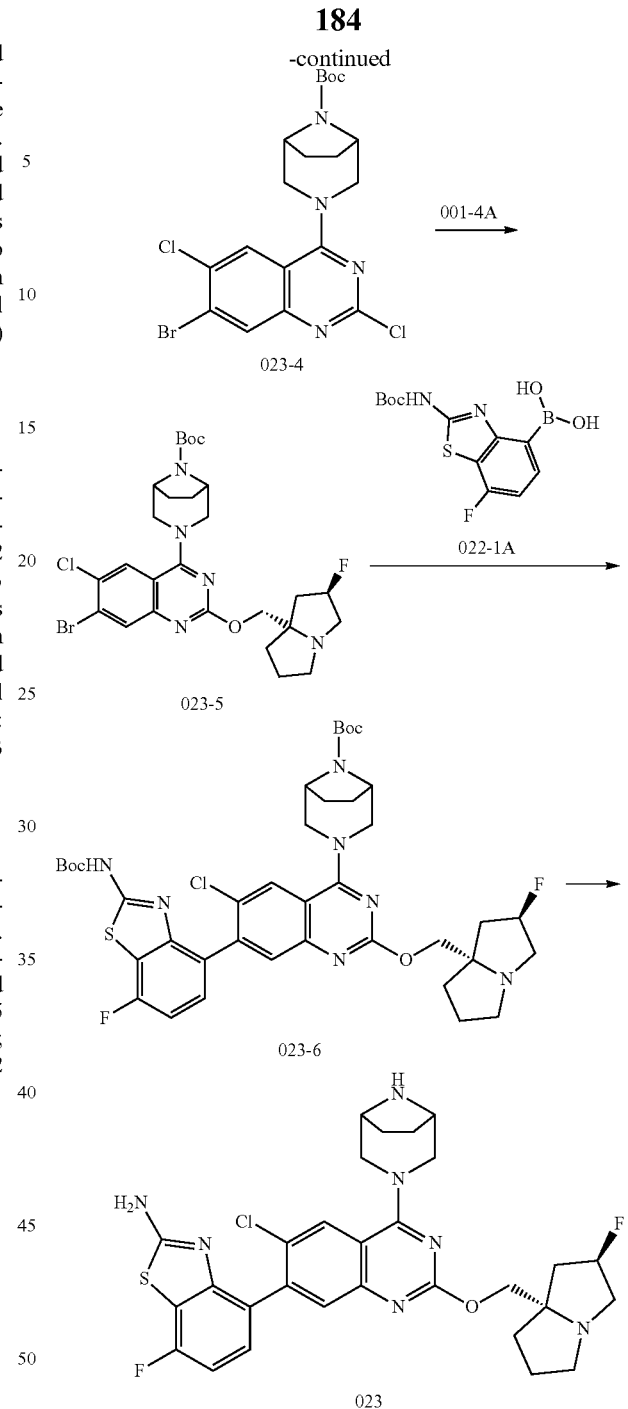

Step 1: Synthesis of Compound 023-2

Compound 023-1 (15 g, 59.89 mmol, 1 eq) was added to a reaction flask and then urea (60 g, 999.08 mmol, 53.57 mL, 16.68 eq) was added. The mixture was heated to 200° C. to reflux for 4 h. The mixture was cooled to room temperature and slurried with hot water to give compound 023-2. LCMS: (ESI) m/z=274.9 [M+H]$^+$.

Step 2: Synthesis of Compound 023-3

N,N-diisopropylethylamine (11.73 g, 90.75 mmol, 15.81 mL, 5 eq) was added to phosphorus oxychloride (82.50 g, 538.05 mmol, 50 mL, 29.64 eq) at 0° C. After the addition was completed, 023-2 (5 g, 18.15 mmol, 1 eq) was added in batches, and then the mixture was reacted at 100° C. After the reaction was completed, the reaction solution was evaporated to dryness, and phosphorus trichloride was removed. The crude product was purified on silica gel column (gradient elution:petroleum ether:ethyl acetate=20:1-10:1) to give compound 023-3. $^1$H NMR (400 MHZ, DMSO-d$_6$) δ ppm 8.50 (s, 1H) 8.58 (s, 1H).

Step 3: Synthesis of Compound 023-4

023-3 (3 g, 9.60 mmol, 1 eq) and 010-16A (2.04 g, 9.60 mmol, 1 eq) were dissolved in N,N-dimethylformamide (10 mL). N,N-diisopropylethylamine (3.72 g, 28.81 mmol, 5.02 mL, 3 eq) was added. The mixture was stirred at 25° C. for 4 h. The reaction solution was poured into 200 mL of water and filtered to give a solid. The solid was washed three times with 20 mL of water to give compound 023-4. LCMS: (ESI) m/z=487.0 [M+H]$^+$.

Step 4: Synthesis of Compound 023-5

023-4 (1.5 g, 3.07 mmol, 1 eq) was dissolved in N,N-dimethylformamide (10 mL) and THF (10 mL). Then cesium carbonate (3.00 g, 9.22 mmol, 3 eq), 001-4A (733.71 mg, 4.61 mmol, 1.5 eq), and triethylenediamine (34.46 mg, 307.25 μmol, 33.79 μL, 0.1 eq) were added. The mixture was stirred at 25° C. for 18 h. After the reaction was completed, the mixture was extracted with 50 mL of ethyl acetate, washed three times with water, and washed with saturated brine. The organic phases were combined, dried over anhydrous sodium sulfate, and filtered. The filtrate was concentrated, and the crude product was purified on silica gel column (gradient elution:petroleum ether:ethyl acetate=100:1-20:1) to give compound 023-5. LCMS: (ESI) m/z=610.2 [M+H]$^+$.

Step 5: Synthesis of Compound 023-6

023-5 (0.4 g, 654.72 μmol, 1 eq) and 022-1A (204.36 mg, 654.72 μmol, 1 eq) were dissolved in 1,4-dioxane (6 mL) and water (6 mL). 1,1'-Bis(di-tert-butylphosphino) ferrocene palladium dichloride (42.67 mg, 65.47 μmol, 0.1 eq) and potassium phosphate (208.47 mg, 982.09 μmol, 1.5 eq) were added. The mixture was reacted at 90° C. under nitrogen for 18 h. After the reaction was completed, the reaction solution was rotary-evaporated to dryness and the crude product was purified on silica gel column (gradient elution: dichloromethane: methanol=100:1-20:1) to give compound 023-6. LCMS: (ESI) m/z=798.3 [M+H]$^+$.

Step 6: Synthesis of Compound 023

023-6 (0.1 g, 125.26 μmol, 1 eq) was dissolved in acetonitrile (2 mL). Hydrogen chloride/1,4-dioxane (2 mL) was added. The mixture was reacted at 25° C. for 15 h. After the reaction was completed, the reaction solution was evaporated to dryness and separated by preparative HPLC: column: Phenomenex C18 150*40 mm*5 μm; mobile phase: [water (0.2% formic acid)-acetonitrile]; acetonitrile %: 7%-37%, 10 min, to give compound 023 formate. $^1$H NMR (400 MHZ, DMSO-d$_6$) δ ppm 1.67-1.95 (m, 8H) 1.96-2.06 (m, 2H) 2.10-2.19 (m, 1H) 2.79-2.87 (m, 1H) 2.99-3.15 (m, 3H) 3.63 (br d, J=13.30 Hz, 1H) 3.87 (br s, 2H) 3.96-4.12 (m, 2H) 4.32 (br d, J=12.80 Hz, 2H) 5.17-5.38 (m, 1H) 7.03 (t, J=8.78 Hz, 1H) 7.22 (dd, J=8.28, 5.77 Hz, 1H) 7.54 (s, 1H) 7.87 (s, 2H) 7.98 (s, 1H) 8.22 (s, 1H).

Example 24

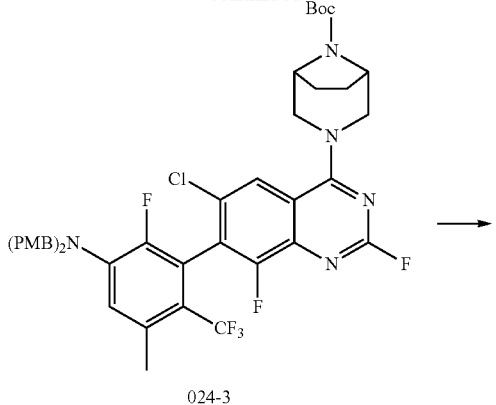

Step 1: Synthesis of Compound 024-1

020-3 (1.8 g, 3.68 mmol, 1 eq) and 024-1A (1.50 g, 3.68 mmol, 1 eq) were dissolved in 1,4-dioxane (2 mL) and water (2 mL). 1,1'-Bis(di-tert-butylphosphino) ferrocene palladium dichloride (479.09 mg, 735.08 μmol, 0.2 eq) and potassium phosphate (1.17 g, 5.51 mmol, 1.5 eq) were added. The mixture was reacted at 90° C. under nitrogen for 18 h. After the reaction was completed, the mixture was extracted twice with 30 mL of ethyl acetate. The organic phases were combined, dried over anhydrous sodium sulfate, and filtered. The filtrate was concentrated and the crude product was purified by silica gel column (gradient elution: dichloromethane:methanol=100:1-20:1) to give compound 024-1. LCMS: (ESI) m/z=774.3 [M+H]$^+$.

Step 2: Synthesis of Compound 024-2

024-1 (1.3 g, 1.68 mmol, 1 eq) was dissolved in N,N-dimethylformamide (2 mL). N-iodosuccinimide (1.13 g, 5.04 mmol, 3 eq) was added. The mixture was reacted at 25° C. for 2 h. After the reaction was completed, the mixture was extracted twice with 30 mL of ethyl acetate. The organic phases were combined, dried over anhydrous sodium sulfate, and filtered. The filtrate was concentrated and the crude product was purified on silica gel column (gradient elution: petroleum ether:ethyl acetate=100:1-10:1) to give compound 024-2. LCMS: (ESI) m/z=900.2 [M+H]$^+$.

Step 3: Synthesis of Compound 024-3

024-2 (100 mg, 111.09 μmol, 1 eq) was dissolved in N-methylpyrrolidone (2 mL). Then methyl fluorosulfonyldifluoroacetate (3.02 g, 15.72 mmol, 2 mL, 141.50 eq) and cuprous iodide (105.79 mg, 555.45 μmol, 5 eq) were added. Under nitrogen, hexamethylphosphoramide (99.54 mg, 555.45 μmol, 97.59 μL, 5 eq) was added. The mixture was refluxed at 80° C. for 18 hours. After the reaction was completed, the mixture was extracted twice with 20 mL of ethyl acetate. The organic phases were combined, dried over anhydrous sodium sulfate, and filtered. The filtrate was concentrated and the crude product was purified on silica gel column (gradient elution:petroleum ether:ethyl acetate=100:1-10:1) to give the compound 024-3. LCMS: (ESI) m/z=842.3 [M+H]$^+$.

Step 4: Synthesis of Compound 024-4

024-3 (70 mg, 83.11 μmol, 1 eq) was dissolved in tetrahydrofuran (1 mL) and N,N-dimethylformamide (1 mL). Then cesium carbonate (27.08 mg, 83.11 μmol, 1 eq), 001-4A (15.88 mg, 99.73 μmol, 1.2 eq), and triethylenediamine (932.23μ, 8.31 μmol, 9.14e-1 μL, 0.1 eq) were added. The mixture was reacted at 25° C. for 18 h. After the reaction was completed, water was added and the mixture was extracted with 100 mL of ethyl acetate. The organic phase was dried over anhydrous sodium sulfate, and filtered. The filtrate was concentrated, and the crude product was purified on silica gel column (gradient elution: dichloromethane:methanol=100:1-20:1) to give compound 024-4. LCMS: (ESI) m/z=981.4 [M+H]$^+$.

Step 5: Synthesis of Compound 024

024-4 (50 mg, 50.94 μmol, 1 eq) was dissolved in trifluoroacetic acid (5.81 mg, 50.94 μmol, 3.77 μL, 1 eq). The mixture was stirred at 25° C. for 2 h. After the reaction was completed, the mixture was rotary-evaporated to dryness to remove the solvent and separated by preparative column: Phenomenex C18 150*40 mm*5 μm; mobile phase: [water (0.2% formic acid)-acetonitrile]; acetonitrile %: 5%-35%, 10 min, to give compound 024 formate. LCMS: (ESI) m/z=641.2 [M+H]$^+$.

Example 25

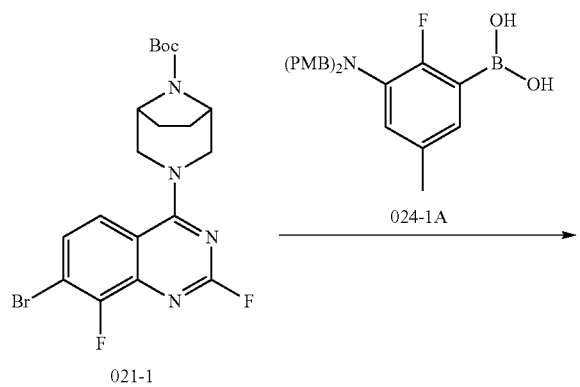

021-1

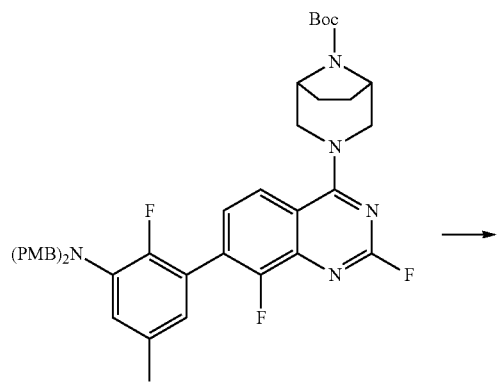

025-1

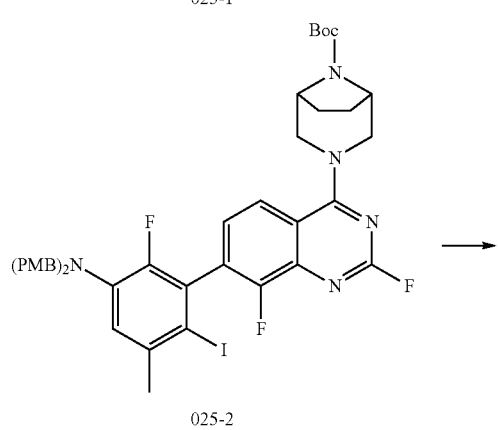

025-2

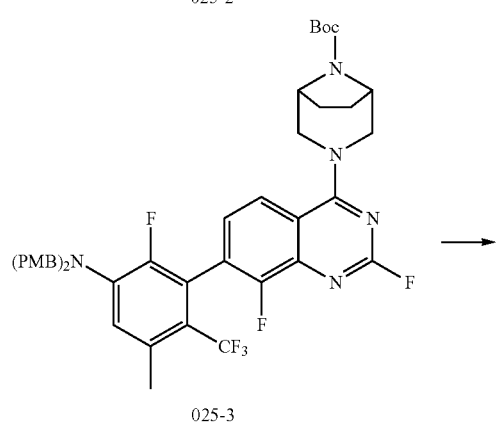

025-3

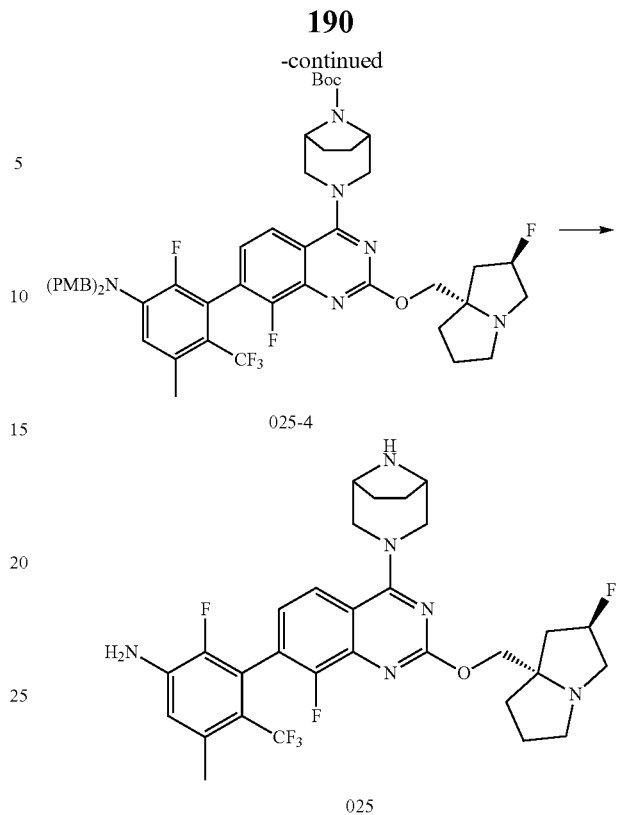

025-4

025

Step 1: Synthesis of Compound 025-1

021-1 (1.1 g, 2.42 mmol, 1 eq) and 024-1A (988.77 mg, 2.42 mmol, 1 eq) were dissolved in 1,4-dioxane (2 mL) and water (2 mL). 1,1'-Bis(di-tert-butylphosphino) ferrocene palladium dichloride (314.93 mg, 483.20 µmol, 0.2 eq) and potassium phosphate (769.27 mg, 3.62 mmol, 1.5 eq) were added. The mixture was reacted under nitrogen at 90° C. for 18 hours. After the reaction was completed, the mixture was extracted twice with 30 mL of ethyl acetate. The organic phases were combined, dried over anhydrous sodium sulfate, and filtered. The filtrate was concentrated and the crude product was purified by silica gel column (gradient elution: petroleum ether/ethyl acetate=10:1-5:1) to give compound 025-1. LCMS: (ESI) m/z=740.3 [M+H]$^+$.

Step 2: Synthesis of Compound 025-2

025-1 (1.1 g, 1.49 mmol, 1 eq) was dissolved in N,N-dimethylformamide (2 mL). N-iodosuccinimide (501.77 mg, 2.23 mmol, 1.5 eq) was added. The mixture was reacted at 25° C. for 2 h. After the reaction was completed, the mixture was extracted twice with 30 mL of ethyl acetate. The organic phases were combined, dried over anhydrous sodium sulfate, and filtered. The filtrate was concentrated to give a crude product. The crude product was purified on silica gel column (gradient elution:petroleum ether:ethyl acetate=10:1-5:1) to give compound 025-2. LCMS: (ESI) m/z=866.2 [M+H]$^+$.

Step 3: Synthesis of Compound 025-3

025-2 (1.1 g, 1.27 mmol, 1 eq) was dissolved in N,N-dimethylformamide (2 mL). Methyl fluorosulfonyldifluoroacetate (1.22 g, 6.35 mmol, 808.29 µL, 5 eq), hexamethylphosphoramide (1.14 g, 6.35 mmol, 1.12 mL, 5 eq), and cuprous iodide (483.98 mg, 2.54 mmol, 2 eq) were added. The mixture was refluxed at 80° C. under nitrogen for 18 h. After the reaction was completed, the mixture was extracted twice with 20 mL of ethyl acetate. The organic phases were combined, dried over anhydrous sodium sulfate, and filtered. The filtrate was concentrated, and the crude product was purified on silica gel column (gradient elution:petroleum ether:ethyl acetate=10:1-5:1) to give compound 025-3. LCMS: (ESI) m/z=866.2 [M+H]$^+$.

Step 4: Synthesis of Compound 025-4

025-3 (118.24 mg, 742.74 μmol, 1 eq) was dissolved in tetrahydrofuran (2 mL) and N,N-dimethylformamide (2 mL). Cesium carbonate (242.00 mg, 742.74 μmol, 1 eq), triethylenediamine (8.33 mg, 74.27 μmol, 8.17 μL, 0.1 eq) and 001-4A (0.6 g, 742.74 μmol, 1 eq) were added. The mixture was reacted at 25° C. for 18 h. After the reaction was completed, water was added and the mixture was extracted with 100 mL of ethyl acetate. The organic phase was dried over anhydrous sodium sulfate, and filtered. The filtrate was concentrated and the crude product was purified on silica gel column (gradient elution: dichloromethane: methanol=100: 1-20:1) to give compound 025-4. LCMS: (ESI) m/z=947.4 [M+H]$^+$.

Step 5: Synthesis of Compound 025

025-4 (60 mg, 63.36 μmol, 1 eq) was dissolved in trifluoroacetic acid (7.22 mg, 63.36 μmol, 4.69 μL, 1 eq) and the solution was stirred at 25° C. for 1 h. After the reaction was completed, the mixture was rotary-evaporated to dryness to remove the solvent and separated by preparative column: Phenomenex C18 150*40 mm*5 μm; mobile phase: [water (0.2% formic acid)-acetonitrile]; acetonitrile %: 5%-35%, 10 min, to give compound 025 formate. LCMS: (ESI) m/z=607.2 [M+H]$^+$; $^1$H NMR (400 MHZ, DMSO-d$_6$) δ ppm 1.68-1.80 (m, 6H) 2.00-2.17 (m, 3H) 2.36 (br s, 3H) 2.83 (br d, J=5.25 Hz, 2H) 2.95-3.14 (m, 3H) 3.66 (br s, 2H) 3.98-4.12 (m, 2H) 4.27 (br d, J=11.76 Hz, 2H) 5.18-5.39 (m, 1H) 6.00 (br s, 2H) 6.80 (br d, J=8.75 Hz, 1H) 7.10 (br t, J=7.63 Hz, 1H) 7.80 (br d, J=8.76 Hz, 1H) 8.24 (s, 1H).

Example 26

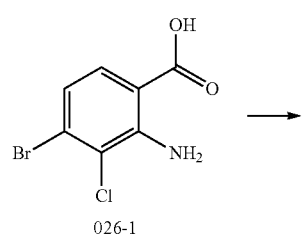

026-1

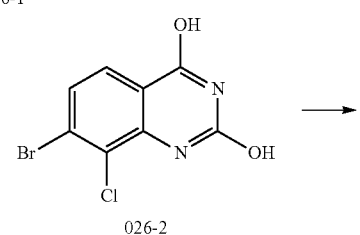

026-2

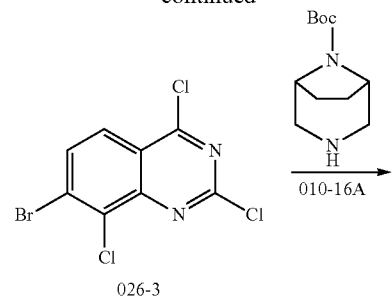

026-3

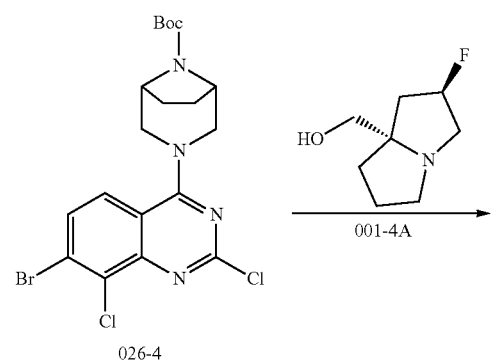

026-4

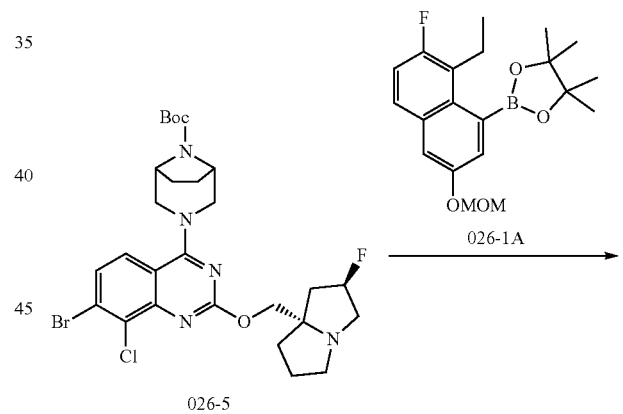

026-5

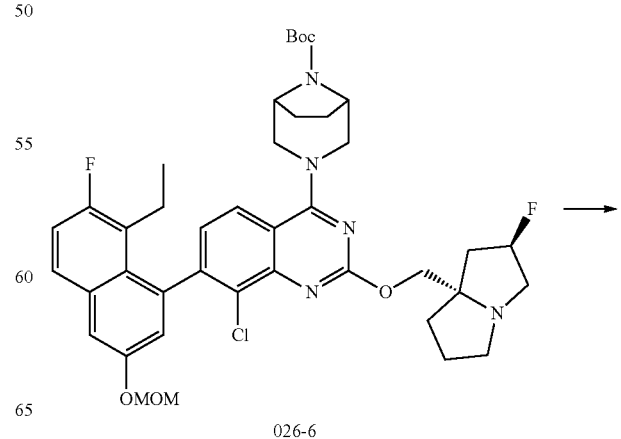

026-6

-continued

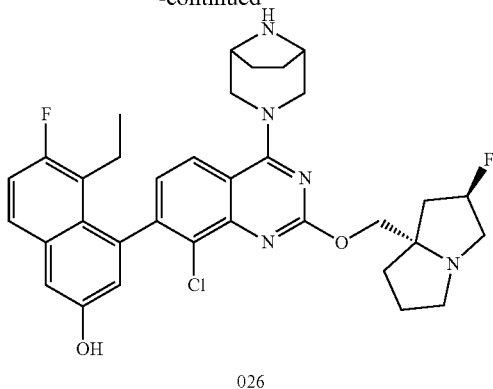

026

Step 1: Synthesis of Compound 026-2

026-1 (4.8 g, 19.16 mmol, 1 eq) and urea (69.06 g, 1.15 mol, 61.66 mL, 60 eq) were added to a reaction flask and the mixture was stirred to react at 200° C. for 2 h. After the reaction was completed, the mixture was cooled down to room temperature, and 200 mL of water was added. The mixture was filtered by suction to give compound 026-2. LCMS: (ESI) m/z=274.9 [M+H]$^+$.

Step 2: Synthesis of Compound 026-3

N,N-diisopropylethylamine (11.13 g, 86.12 mmol, 15.00 mL, 11.86 eq) was added dropwise to phosphorus oxychloride (50 mL) at 0° C. 026-2 (2 g, 7.26 mmol, 1 eq) was added in batches and the mixture was refluxed at 80° C. for 20 h. After the reaction was completed, the reaction solution was evaporated to dryness to remove phosphorus trichloride. The crude product was purified on silica gel column (gradient elution:petroleum ether:ethyl acetate=10:1-3:1) to give compound 026-3. LCMS: (ESI) m/z=310.8 [M+H]$^+$.

Step 3: Synthesis of Compound 026-4

026-3 (1 g, 3.20 mmol, 1 eq) was dissolved in N,N-dimethylformamide (2 mL). 010-16A (679.59 mg, 3.20 mmol, 1 eq) and N,N-diisopropylethylamine (1.24 g, 9.60 mmol, 1.67 mL, 3 eq) were added. The mixture was stirred to react at 25° C. for 2 h. After the reaction was completed, the reaction solution was poured into 200 mL of water and a solid was precipitated. The solid was washed with 60 mL of water to give compound 026-4. LCMS: (ESI) m/z=487.0 [M+H]$^+$.

Step 4: Synthesis of Compound 026-5

026-4 (1.3 g, 2.66 mmol, 1 eq) was dissolved in N,N-dimethylformamide (10 mL) and tetrahydrofuran (10 mL). Then cesium carbonate (867.60 mg, 2.66 mmol, 1 eq), 001-4A (635.88 mg, 3.99 mmol, 1.5 eq), and triethylenediamine (29.87 mg, 266.28 μmol, 29.28 μL, 0.1 eq) were added. The mixture was stirred to react at 25° C. for 18 h. After the reaction was completed, the mixture was extracted with 50 mL of ethyl acetate, and washed with saturated brine. The organic phases were combined, dried over anhydrous sodium sulfate, and filtered. The filtrate was concentrated, and the crude product was purified on silica gel column (gradient elution:petroleum ether:ethyl acetate=100:1-20:1) to give compound 026-5. LCMS: (ESI) m/z=610.2 [M+H]$^+$.

Step 5: Synthesis of Compound 026-6

026-5 (0.2 g, 327.36 μmol, 1 eq) and compound 026-1A (91.03 mg, 327.36 μmol, 1 eq) were dissolved in 1,4-dioxane (1 mL) and water (0.2 mL). [1,1-bis(diphenylphosphino)ferrocene]palladium dichloride (21.34 mg, 32.74 μmol, 0.1 eq) and potassium phosphate (104.23 mg, 491.04 μmol, 1.5 eq) were added. The mixture was reacted at 90° C. under nitrogen for 18 h. After the reaction was completed, the reaction solution was evaporated to dryness and the crude product was purified on silica gel column (gradient elution: petroleum ether:ethyl acetate=100:1-20:1) to give compound 026-6. LCMS: (ESI) m/z=764.3 [M+H]$^+$.

Step 6: Synthesis of Compound 026

026-6 (100 mg, 130.84 μmol, 1 eq) was dissolved in hydrochloric acid/1,4-dioxane (2 mL). Acetonitrile (2 mL) was added. The mixture was stirred to react at 25° C. for 15 h. The reaction solution was rotary-evaporated to dryness and separated by preparative HPLC: column: Phenomenex C18 150*40 mm*5 μm; mobile phase: [water (0.2% formic acid)-acetonitrile]; acetonitrile %: 1%-30%, 10 min, to give compound 026 formate. 1H NMR (400 MHZ, DMSO-d$_6$) δ ppm 0.71 (br s, 3H) 1.69-1.91 (m, 8H) 2.04 (br d, J=18.89 Hz, 2H) 2.23 (br s, 1H) 2.83 (br s, 2H) 3.01 (br s, 2H) 3.09 (br s, 3H) 3.92-4.20 (m, 4H) 4.23-4.35 (m, 2H) 5.20-5.38 (m, 1H) 6.83 (br s, 1H) 7.25-7.39 (m, 3H) 7.74 (br s, 1H) 7.95 (br d, J=7.25 Hz, 1H) 8.28 (br s, 1H).

Example 27

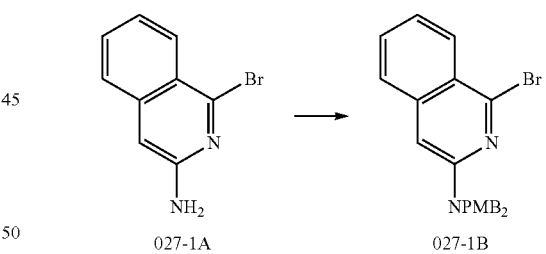

027-1A                    027-1B

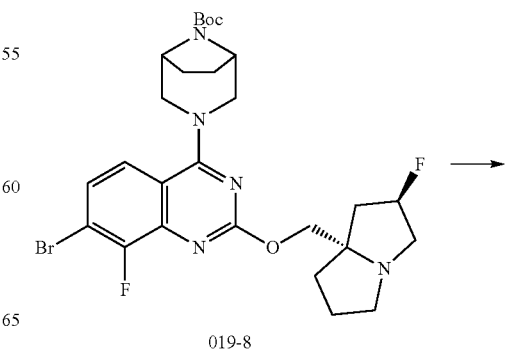

019-8

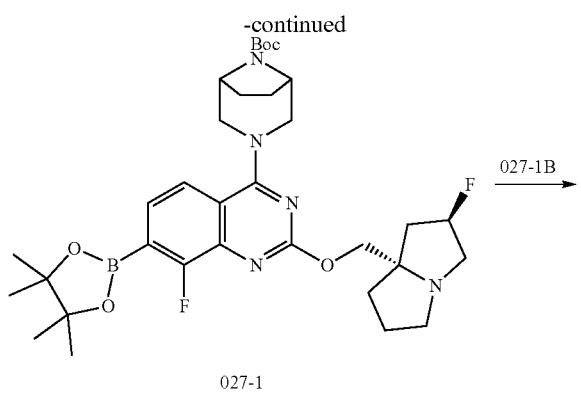

027-1

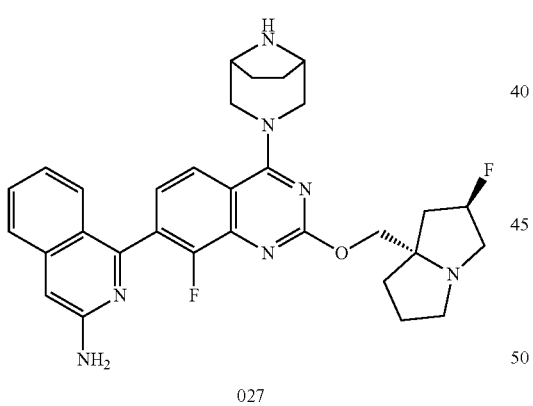

027-2

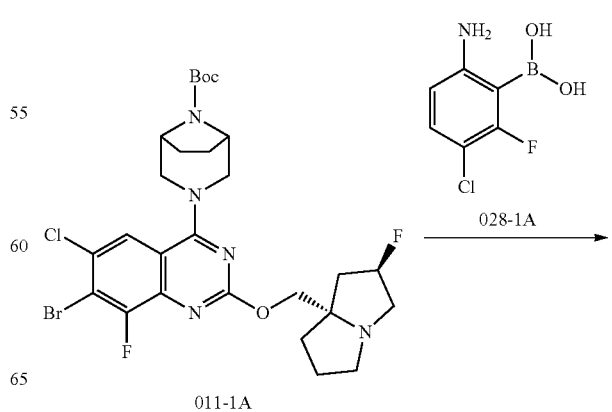

027

Step 1: Synthesis of Compound 027-1B 027-1A (0.9 g, 4.03 mmol, 1 eq) was dissolved in N-methylpyrrolidone (5 mL). Potassium carbonate (1.39 g, 10.09 mmol, 2.5 eq), potassium iodide (669.76 mg, 4.03 mmol, 1 eq) and p-methoxybenzyl chloride (1.58 g, 10.09 mmol, 1.37 mL, 2.5 eq) were added. The mixture was reacted at 25° C. for 15 h. After the reaction was completed, the mixture was extracted twice with 20 mL of ethyl acetate. The organic phases were combined, dried over anhydrous sodium sulfate, and filtered. The filtrate was concentrated and the crude product was purified on silica gel column (gradient elution: petroleum ether:ethyl acetate=100:1-10:1) to give compound 027-1B. LCMS: (ESI) m/z=463.1 [M+H]$^+$.

Step 2: Synthesis of Compound 027-1

019-8 (0.6 g, 1.01 mmol, 1 eq) was dissolved in 1,4-dioxane (10 mL). Bis(pinacolato)diboron (384.44 mg, 1.51 mmol, 1.5 eq), bis(diphenylphosphino) ferrocene palladium dichloride (73.85 mg, 100.93 μmol, 0.1 eq), and potassium acetate (148.58 mg, 1.51 mmol, 1.5 eq) were added. The mixture was refluxed at 105° C. for 15 h. After the reaction was completed, the reaction solution was rotary-evaporated to dryness and separated by preparative HPLC: column: Phenomenex C18 150*40 mm*5 μm; mobile phase: [water (formic acid)-acetonitrile]; acetonitrile %: 10%-40%, 10 min, to give compound 027-1 (110 mg, 171.46 μmol, 16.99% yield). LCMS: (ESI) m/z=560.3 [M−82+H]$_+$.

Step 3: Synthesis of Compound 027-2

027-1 (82.83 mg, 178.76 μmol, 1 eq) and 027-1B (100 mg, 178.76 μmol, 1 eq) were dissolved in 1,4-dioxane (2 mL) and water (0.4 mL). Potassium phosphate (56.92 mg, 268.14 μmol, 1.5 eq) and 1,1-bis(tert-butylphosphine) ferrocene palladium chloride (11.65 mg, 17.88 μmol, 0.1 eq) were added. The mixture was reacted at 80° C. under nitrogen for 15 h. After the reaction was completed, the reaction solution was directly evaporated to dryness and the crude product was purified on silica gel column (gradient elution:petroleum ether:ethyl acetate=100:1-30:1) to give compound 027-2. LCMS: (ESI) m/z=898.4 [M+H]$^+$.

Step 4: Synthesis of Compound 027

027-2 (100 mg, 111.35 μmol, 1 eq) was dissolved in trifluoroacetic acid (2 mL). The solution was stirried at 25° C. for 2 h. After the reaction was completed, the reaction mixture was rotary-evaporated to dryness to remove the solvent and separated by preparative HPLC: column: Phenomenex C18 150*40 mm*5 μm; mobile phase: [water (0.2% formic acid)-acetonitrile]; acetonitrile %: 55%-85%, 10 min, to give compound 027 formate. LCMS: (ESI) m/z=558.3 [M+H]$^+$.

Example 28

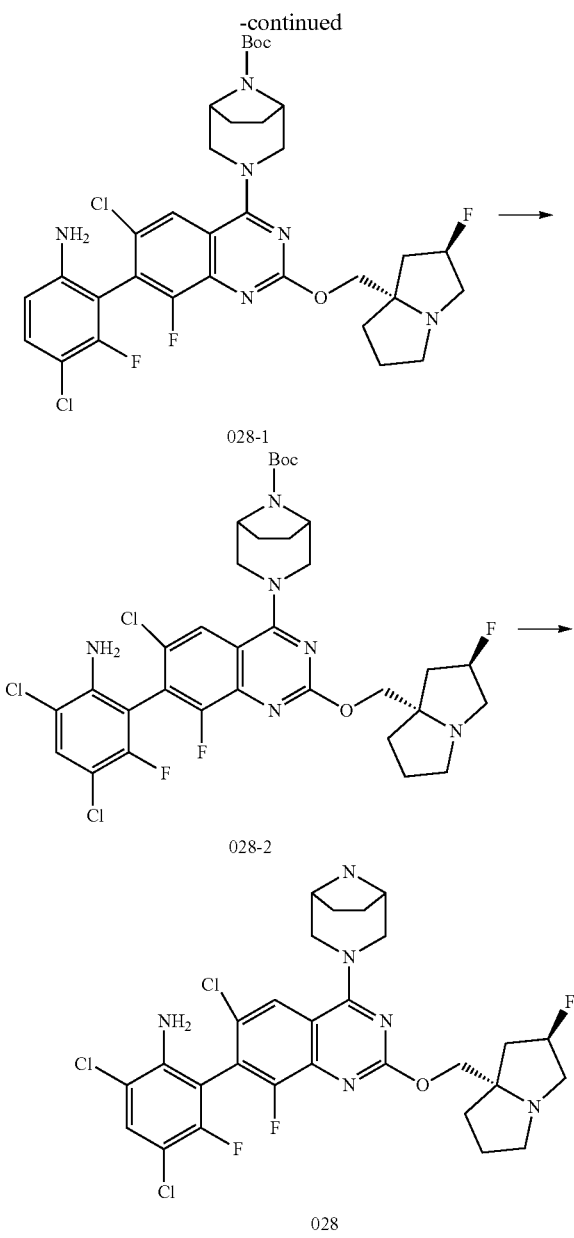

Step 1: Synthesis of Compound 028-1

Compound 011-1A (0.30 g, 477.00 μmol, 1 eq), compound 028-1A (180.67 mg, 953.99 μmol, 2 eq) and anhydrous potassium phosphate (506.25 mg, 2.38 mmol, 5 eq) were added to 1,4-dioxane (15 mL). The atmosphere was replaced with nitrogen three times, and (2-dicyclohexylphosphino-2,4,6-triisopropyl-1,1-biphenyl) [2-(2-amino-1,1-biphenyl)]palladium (II) chloride (37.53 mg, 47.70 μmol, 0.1 eq) was added under nitrogen. The atmosphere was replaced with nitrogen three times. The mixture was reacted at 100° C. for 16 h. After the reaction was completed, the reaction solution was cooled down to room temperature, and 20 mL of water and 20 mL of ethyl acetate were added to the reaction solution. The reaction solution was stirred for 5 min and then left to stand. The layers were separated. The aqueous phase was extracted once with 20 mL of ethyl acetate. The organic phases were combined, washed three times with 20 mL of saturated brine, then dried over anhydrous sodium sulfate, and filtered. The filtrate was concentrated to give a crude product, which was purified using a column (petroleum ether:ethyl acetate=100:0-0:100) to give compound 028-1. LCMS: (ESI) m/z=693.2 [M+H]; $^1$H NMR (400 MHz, CDCl$_3$) δ ppm 7.7 (s, 1H) 7.30-7.23 (m, 1H), 6.67-6.48 (m, 1H), 5.37-5.24 (m, 1H), 4.43-4.21 (m, 6H), 3.79-3.48 (m, 3H), 3.39 (s, 2H), 3.33-3.15 (m, 2H), 3.11-2.93 (m, 1H), 2.43-2.16 (m, 3H), 2.01-1.94 (m, 5H), 1.85-1.76 (m, 2H), 1.53 (s, 9H).

Step 2: Synthesis of Compound 028-2

Compound 028-1 (110 mg, 158.60 μmol, 1 eq) was added to N,N-dimethylformamide (2 mL). N-chlorosuccinimide (23.30 mg, 174.46 μmol, 1.1 eq) was added. The mixture was reacted at 70° C. for 3 h. After the reaction was completed, 10 mL of ethyl acetate and 5 mL of water were added to the reaction solution and the mixture was stirred for 5 min. The mixture was left to stand and the layers were separated. The aqueous phase was extracted once with 10 mL of ethyl acetate. The organic phases were combined, washed twice with 20 mL saturated brine, dried over anhydrous sodium sulfate, and filtered. The filtrate was concentrated to give a crude product, which was purified by silica gel column (dichloromethane:methanol (with 1% ammonia added dropwise)=20:1) to give compound 028-2. LCMS: (ESI) m/z=727.1 [M+H]$^+$. 1HNMR (400 MHZ, CDCl$_3$) δ ppm 7.77 (s, 1H), 7.42 (d, J=7.25 Hz, 1H), 5.34-5.20 (m, 1H), 4.40-4.27 (m, 5H), 3.7-3.5 (s, 3H), 3.32-3.21 (m, 2H), 3.15-3.19 (m, 1H) 2.93-3.04 (m, 2H), 2.32-2.10 (m, 4H), 2.00-1.76 (m, 7H), 1.52 (s, 9H).

Step 3: Synthesis of Compound 028

Compound 028-2 (40 mg, 54.94 μmol, 1 eq) was added to anhydrous dichloromethane (2 mL). Trifluoroacetic acid (308.00 mg, 2.70 mmol, 200.00 μL, 49.16 eq) was added. The mixture was reacted at 25° C. for 2 h. Solid was precipitated. After the reaction was completed, the reaction solution was concentrated to dryness under reduced pressure and the crude product was purified by preparative chromatography (column: Phenomenex Luna 80*30 mm*3 μm; mobile phase: [water (0.05% hydrochloric acid)-acetonitrile]; acetonitrile %: 15%-35%, 7 min) to give compound 028 hydrochloride. $^1$H NMR (400 MHZ, CD$_3$OD) THANOL-d MHz, a 80*30 mm*3.00 J=7.25 Hz, 1H), 5.34-5.20 (m, 1H), 4.40-4.27 (m, 5H), 3.7-3.5 (s, 3H), 3.32-3.21 (m, 2H), 3.15-3.19m, 2H), 3.84-4.04 (m, 3H), 3.42-3.59 (m, 1H), 2.56-2.82 (m, 2H), 2.44-2.54 (m, 1H), 2.31-2.42 (m, 2H), 2.29-2.14 (m, 5H).

Example 29

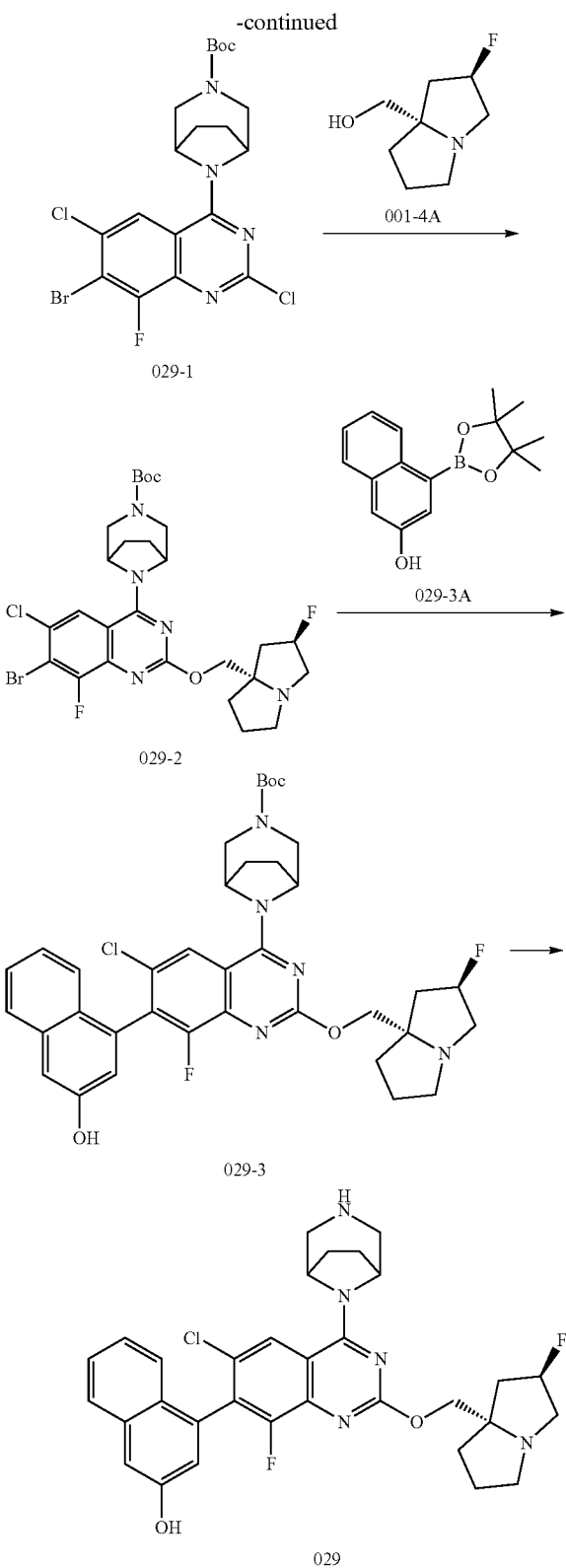

Step 1: Synthesis of Compound 029-1

Compound 001-1 (400 mg, 1.21 mmol, 1 eq) was dissolved in anhydrous N,N-dimethylformamide (10 mL) at 20° C., and N,N-diisopropylethylamine (391.21 mg, 3.03 mmol, 527.24 μL, 2.5 eq) and 029-1A (257.03 mg, 1.21 mmol, 1 eq) were added. The mixture was stirred for 0.5 h. After the reaction was completed, the mixture was diluted with ethyl acetate (150 mL), washed with saturated brine (30 mL), and dried over anhydrous sodium sulfate. The organic phase was separated and dried. The organic solvent was removed under reduced pressure to give a crude product 029-1. $^1$H NMR (400 MHZ, CDCl$_3$) δ=7.79 (d, J=2.0 Hz, 1H), 4.93 (br d, J=12.8 Hz, 1H), 5.00-4.87 (m, 1H), 4.15-3.90 (m, 2H), 3.42-3.20 (m, 2H), 2.06-1.85 (m, 4H), 1.50 (s, 9H).

Step 2: Synthesis of Compound 029-2

Compound 029-1 (600 mg, 1.19 mmol, 1 eq) was dissolved in tetrahydrofuran (3 mL) and N,N-dimethylformamide (3 mL). 001-4A (284.17 mg, 1.78 mmol, 1.5 eq), cesium carbonate (1.16 g, 3.57 mmol, 3 eq) and triethylenediamine (13.35 mg, 119.00 μmol, 13.09 μL, 0.1 eq) were added sequentially under nitrogen. The reaction solution was stirred at 20° C. for another 16 h. After the reaction was completed, 100 mL of ethyl acetate was added to the reaction solution. The organic phase was washed with saturated brine (10 mL), dried over anhydrous sodium sulfate, filtered, and dried. The organic solvent was removed under reduced pressure, and the resulting crude product was separated by silica gel column chromatography (eluent: ethyl acetate:petroleum ether=0~80%) to give compound 029-2. $^1$H NMR (400 MHZ, CDCl$_3$) δ=7.73 (d, J=2.0 Hz, 1H), 5.38-5.20 (m, 1H), 4.89-4.75 (m, 2H), 4.29-4.21 (m, 1H), 4.19-4.13 (m, 1H), 4.04 (br d, J=12.0 Hz, 1H), 3.91 (br d, J=12.0 Hz, 1H), 3.43-3.16 (m, 5H), 3.03-2.97 (m, 1H), 2.34-2.11 (m, 3H), 2.01-1.76 (m, 8H), 1.65 (br s, 1H), 1.50 (s, 9H).

Step 3: Synthesis of Compound 029-3

Under nitrogen protection, 029-2 (50 mg, 79.50 μmol, 1 eq), 029-3A (25.77 mg, 95.40 μmol, 1.2 eq) and sodium carbonate (25.28 mg, 238.50 μmol, 3 eq) were dissolved in 1,4-dioxane (2 mL) and water (1 mL). [1,1'-bis(diphenylphosphino) ferrocene]palladium dichloride dichloromethane complex (6.49 mg, 7.95 μmol, 0.1 eq) was added. After the addition was completed, the mixture was reacted at 100° C. for 3 h. After the reaction was completed, the mixture was cooled and the organic solvent was removed under reduced pressure. The resulting crude product was purified by a preparative silica gel plate (developing agent: dichloromethane:methanol=10:1) to give compound 029-3. LCMS: (ESI) m/z=692.2 [M+H]$^+$.

Step 4: Synthesis of Compound 029

Compound 029-3 (40 mg, 57.79 μmol, 1 eq) was dissolved in dichloromethane (2 mL) at 20° C. Trifluoroacetic acid (770.00 mg, 6.75 mmol, 0.5 mL, 116.86 eq) was added and the reaction solution was stirred for 1 h. After the reaction was completed, the reaction solution was rotary-evaporated to dryness and the resulting crude product was purified by preparative chromatography (column: Phenomenex Synergi C18 150*30 mm*4 μm; mobile phase: [water (0.05% hydrochloric acid)-acetonitrile]; acetonitrile %:

20%-50%, 9 min) to give compound 029 hydrochloride. LCMS: (ESI) m/z=592.1 [M+H]+.

Example 30

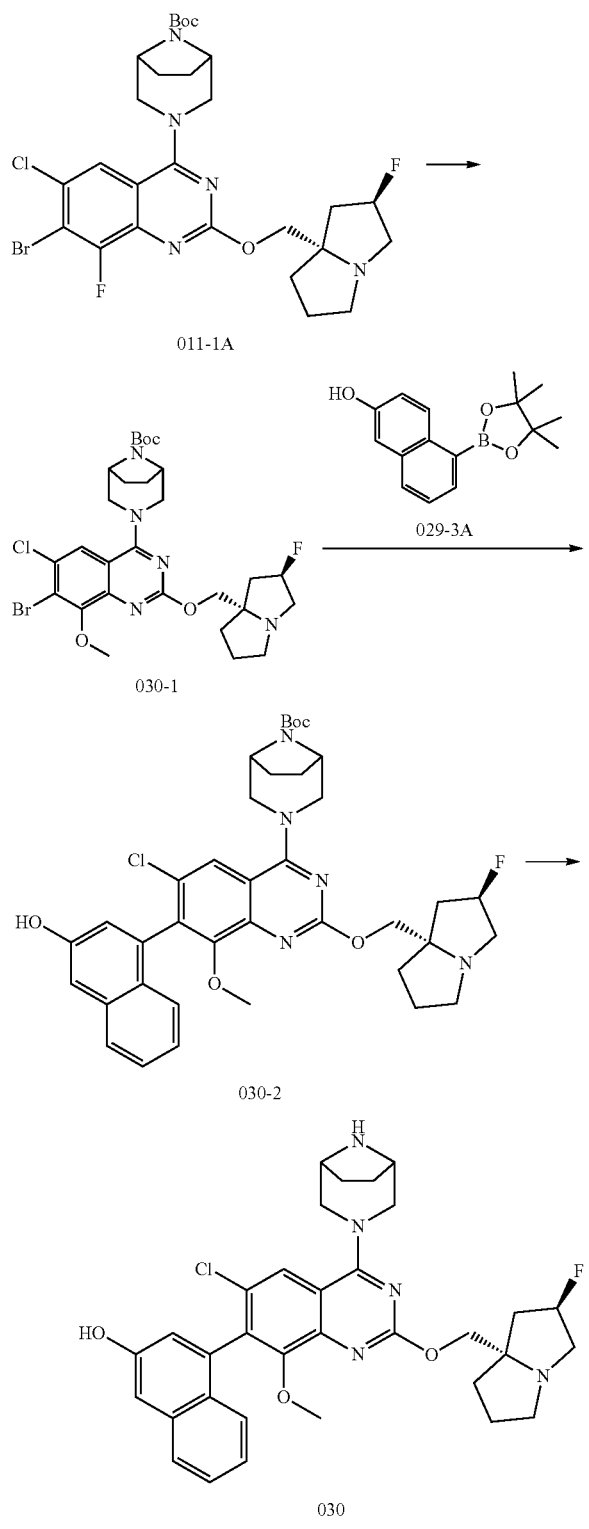

Step 1: Synthesis of Compound 030-1

Compound 011-1A (500 mg, 794.99 μmol, 1 eq) was dissolved in tetrahydrofuran (5 mL) at 20° C., and sodium methanol (85.90 mg, 1.59 mmol, 2 eq) was added. The reaction solution was heated to 70° C. and stirred for 48 h. After the reaction was completed, the mixture was rotary-evaporated to dryness to remove the solvent and the resulting crude product was purified by a preparative silica gel plate (developing agent: ethyl acetate/petroleum ether=0~100%) to give compound 030-1. $^1$H NMR (400 MHZ, CDCl$_3$) δ=7.65 (s, 1H), 5.37 (br s, 1H), 5.24 (br s, 1H), 4.28 (br d, J=7.3 Hz, 6H), 4.15-4.12 (m, 3H), 3.54 (br s, 2H), 3.37-3.17 (m, 3H), 3.01 (br s, 1H), 2.34-2.10 (m, 3H), 2.01-1.88 (m, 5H), 1.81 (br d, J=8.0 Hz, 2H), 1.52 (s, 9H).

Step 2: Synthesis of Compound 030-2

Compound 030-1 (50 mg, 78.01 μmol, 1 eq), 029-3A (25.29 mg, 93.61 μmol, 1.2 eq) and cesium carbonate (76.25 mg, 234.02 μmol, 3 eq) were dissolved in 1,4-dioxane (5 mL) and water (1 mL) under nitrogen, and Pd(PPh$_3$)$_4$ (9.01 mg, 7.80 μmol, 0.1 eq) was added. After the addition was completed, the mixture was reacted at 100° C. for 16 h. After the reaction was completed, the mixture was rotary-evaporated to dryness to remove the solvent and the resulting crude product was purified by a preparative silica gel plate (developing agent: dichloromethane:methanol=10:1) to give compound 030-2, LCMS: (ESI) m/z=704.3 [M+H]+.

Step 3: Synthesis of Compound 030

Compound 030-2 (20.00 mg, 28.40 μmol, 1 eq) was dissolved in dichloromethane (3 mL) at 20° C. and trifluoroacetic acid (1.54 g, 13.51 mmol, 1 mL, 475.58 eq) was added. The reaction solution was stirred for another 16 h. After the reaction was completed, the mixture was rotary-evaporated to dryness to remove the solvent and purified by preparative chromatography (column: Welch Xtimate C18 100*40 mm*3 μm; mobile phase: [water (0.1% trifluoroacetic acid)-acetonitrile]; acetonitrile %: 15%-45%, 8 min) to give compound 030 trifluoroacetate. LCMS: (ESI) m/z=604.5 [M+H]+.

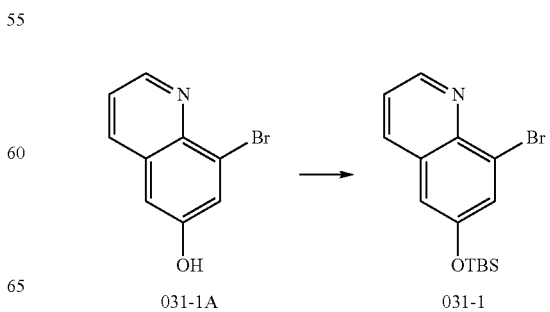

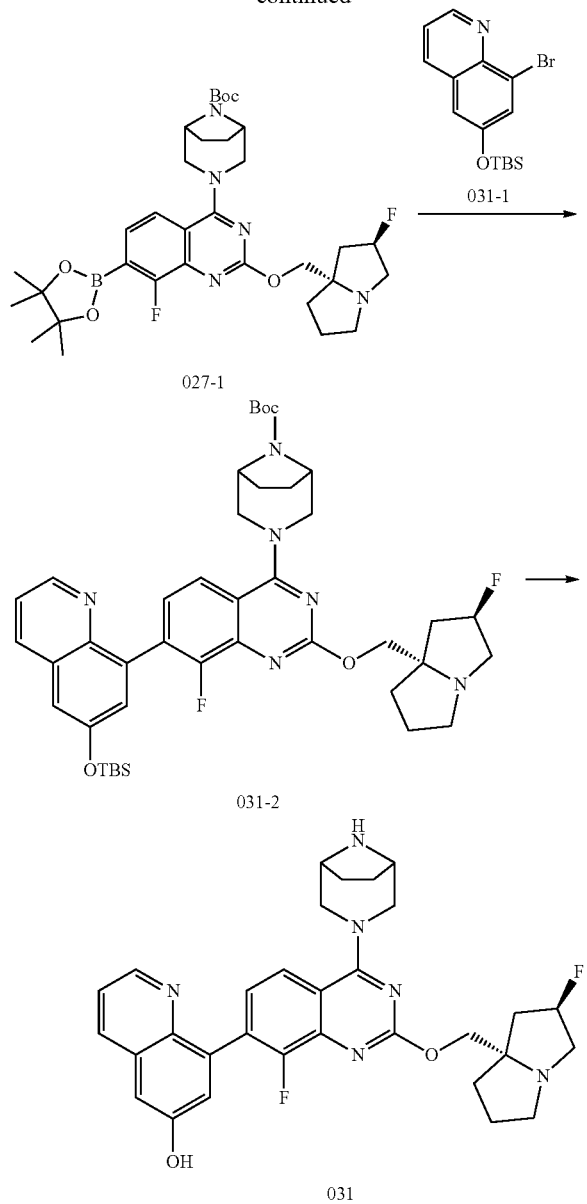

chromatography (gradient elution:petroleum ether: ethyl acetate=10:0-1:10) to give compound 031-1. LCMS: (ESI) m/z=338.0 [M+H]⁺.

Step 2: Synthesis of Compound 031-2

Compound 027-1 (0.2 g), compound 031-1 (43.54 mg, 128.71 μmol, 1.2 eq) and sodium carbonate (34.10 mg, 321.77 μmol, 3 eq) were added to 1,4-dioxane (4 mL) and water (0.8 mL). The atmosphere was replaced with nitrogen three times. [1,1-Bis(diphenylphosphino) ferrocene]palladium dichloride (7.85 mg, 10.73 μmol, 0.1 eq) was added under nitrogen. The mixture was reacted at 100° C. for 2 h. After the reaction was completed, 5 mL of ethyl acetate was added to the reaction solution. The organic phase was washed with 10 mL of saturated brine, dried over anhydrous sodium sulfate, and filtered. The filtrate was concentrated, and the crude product was purified by preparative high performance liquid chromatography (column: Phenomenex luna C18 80*40 mm*3 μm; mobile phase A: water (0.05% HCl), mobile phase B: acetonitrile; running gradient: acetonitrile %: 40%-70%, running time: 7 min) to give compound 031-2. LCMS: (ESI) m/z=773.3 [M+H]⁺.

Step 3: Synthesis of Compound 031

Compound 031-2 (0.035 g, 45.28 μmol, 1 eq) was added to acetonitrile (2 mL). Hydrochloric acid/1,4-dioxane (4 M, 226.39 μL, 20 eq) was added. The mixture was reacted at 25° C. for 2 h. After the reaction was completed, the reaction solution was added to 5 mL of water. The mixture was extracted twice using 3 mL of ethyl acetate and the aqueous phase was concentrated to give compound 031. LCMS: (ESI) m/z=559.3 [M+H]⁺. ¹H NMR (400 MHZ, CD₃OD) δ=8.47-8.43 (m, 1H), 8.15-8.10 (m, 1H), 7.81 (d, J=8.8 Hz, 1H), 7.43-7.27 (m, 3H), 7.14 (d, J=2.4 Hz, 1H), 5.40-5.22 (m, 1H), 4.57-4.50 (m, 2H), 4.33-4.17 (m, 2H), 3.66-3.57 (m, 4H), 3.26-3.13 (m, 3H), 3.03-2.95 (m, 1H), 2.42-2.27 (m, 1H), 2.41-2.09 (m, 2H), 1.94 (s, 2H), 1.89 (s, 2H), 1.84 (s, 3H).

Step 1: Synthesis of Compound 031-1

Compound 031-1A (0.22 g, 981.91 μmol, 1 eq) and imidazole (147.07 mg, 2.16 mmol, 2.2 eq) were dissolved in anhydrous dichloromethane (4 mL). The solution was cooled down to 0° C. Tert-butyldimethylchlorosilane (162.79 mg, 1.08 mmol, 132.35 μL, 1.1 eq) was added dropwise. The atmosphere was replaced with nitrogen. The reaction system was slowly warmed up to 20° C. and stirred for 3 hours. After the reaction was completed, the reaction system was diluted by adding 5 mL of dichloromethane and 10 mL of water. The layers were separated. The organic phase was collected and the aqueous phase was extracted with 30 mL of dichloromethane. The organic phases were combined, washed with saturated brine, dried over anhydrous sodium sulfate, and concentrated under reduced pressure to give a crude product, which was purified by column

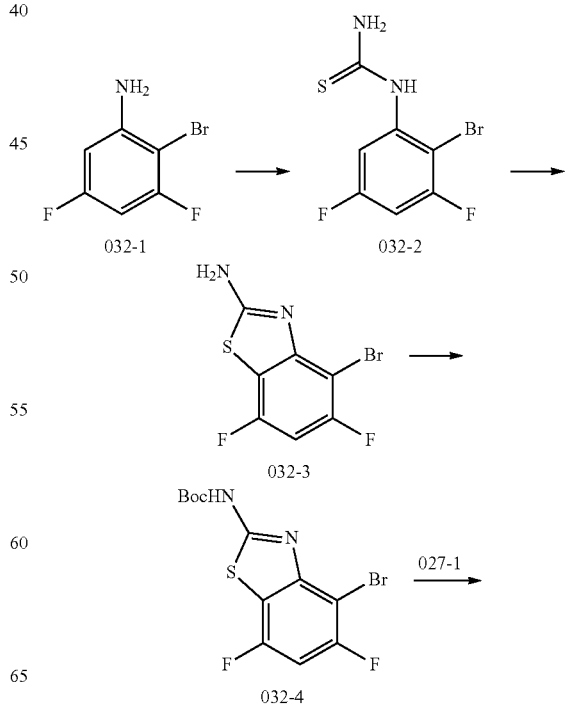

-continued

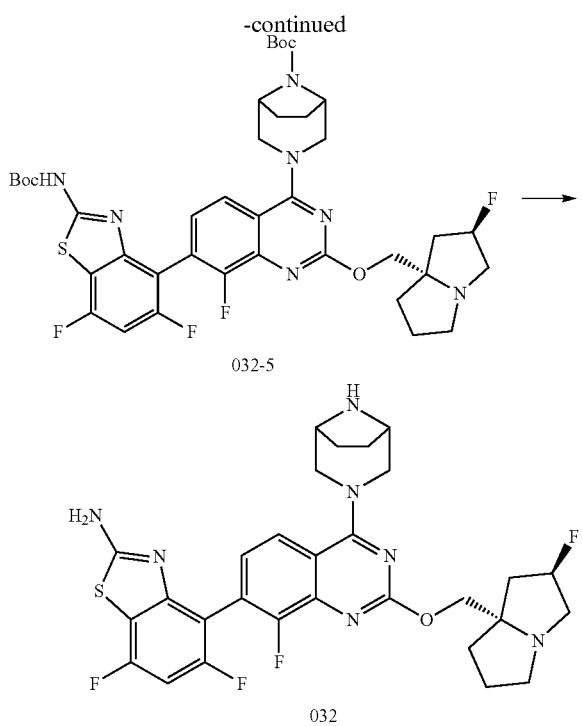

Step 1: Synthesis of Compound 032-2

Ammonium thiocyanate (2.38 g, 31.25 mmol, 2.38 mL, 1.3 eq) was added to acetone (50 mL). Benzoyl chloride (3.38 g, 24.04 mmol, 2.79 mL, 1 eq) were added. The mixture was reacted at 70° C. for 0.5 h. The mixture was cooled down to 50° C., and a solution of compound 032-1 (5 g, 24.04 mmol, 1 eq) in acetone (7 mL) was added in batches. The mixture was reacted at 70° C. for 0.5 h. Sodium hydroxide (2 M, 42.07 mL, 3.5 eq) was added and the mixture was refluxed for another 0.5 h. After the reaction was completed, the reaction solution was cooled down to room temperature. The reaction solution was adjusted to pH 5 with hydrochloric acid, and then adjusted to pH 8 with ammonia. The mixture was stirred for 0.5 h, and then extracted twice with 30 mL of ethyl acetate. The organic phases were combined, dried over anhydrous sodium sulfate, and filtered. The filtrate was concentrated to give a crude product, and the crude product was slurried and stirred with 30 mL of dichloromethane for 1 h. The mixture was filtered to give compound 032-2. LCMS: (ESI) m/z=266.9 [M+H]$^+$.

Step 2: Synthesis of Compound 032-3

Compound 032-2 (2 g, 7.49 mmol, 1 eq) was added to dichloroethane (20 mL). A solution of bromine (2.39 g, 14.98 mmol, 772.04 µL, 2 eq) in dichloroethane (2 mL) was added. The mixture was reacted at 95° C. for 2 h. After the reaction was completed, the reaction solution was filtered and the filter cake was rinsed with 20 mL of 1,2-dichloroethane to give compound 032-3. LCMS: (ESI) m/z=264.8 [M+H]$^+$.

Step 3: Synthesis of Compound 032-4

Compound 032-3 (1.0 g, 3.77 mmol, 1 eq) was added to anhydrous tetrahydrofuran (15 mL). N,N-diethylisopropylamine (1.22 g, 9.43 mmol, 1.64 mL, 2.5 eq) and 4-dimethylaminopyridine (46.09 mg, 377.25 µmol, 0.1 eq) were added. Di-tert-butyl dicarbonate (988.01 mg, 4.53 mmol, 1.04 mL, 1.2 eq) was added under nitrogen to the reaction solution. The mixture was reacted at 20° C. for 19 h. After the reaction was completed, 20 mL of water was added to the reaction solution. The mixture was extracted twice using 10 mL of ethyl acetate. The organic phases were combined, washed with 20 mL of saturated brine, dried over anhydrous sodium sulfate, and filtered. The filtrate was concentrated to give a crude product. The crude product was slurried with 10 mL of dichloromethane for 1 h, and filtered to give compound 032-4. LCMS: (ESI) m/z=308.8 [M−55].

Step 4: Synthesis of Compound 032-5

Compound 027-1 (0.2 g), compound 032-4 (47.00 mg, 128.71 µmol, 1.2 eq) and sodium carbonate (34.10 mg, 321.77 µmol, 3 eq) were added to 1,4-dioxane (4 mL) and water (0.8 mL). The atmosphere was replaced three times with nitrogen.

[1,1-Bis(diphenylphosphino) ferrocene]palladium dichloride (7.85 mg, 10.73 µmol, 0.1 eq) was added under nitrogen. The mixture was reacted at 100° C. for 2 h. After the reaction was completed, 5 mL of ethyl acetate was added to the reaction solution. The mixture was washed using 8 mL of water and saturated brine, dried over anhydrous sodium sulfate, and filtered. The filtrate was concentrated to give a crude product. The crude product was purified by preparative high performance liquid chromatography (column: Phenomenex luna C18 80*40 mm*3 µm; mobile phase A: water (0.05% hydrochloric acid), mobile phase B: acetonitrile; running gradient: acetonitrile %: 40%-70%, running time: 7 min) to give compound 032-5. LCMS: (ESI) m/z=800.3 [M+H]$^+$.

Step 5: Synthesis of Compound 032

Compound 032-5 (0.025 g, 31.25 µmol, 1 eq) was added to acetonitrile (1 mL). Hydrochloric acid/1,4-dioxane (4 M, 156.27 µL, 20 eq) was added. The mixture was reacted at 25° C. for 7 h. After the reaction was completed, the reaction solution was added to 5 mL of water. The mixture was extracted twice with 3 mL of ethyl acetate, and the crude product was purified by preparative high performance liquid chromatography (column: Phenomenex luna C18 80*40 mm*3 µm; mobile phase A: water (0.05% hydrochloric acid), mobile phase B: acetonitrile; running gradient: acetonitrile %: 10%-35%, running time: 7 min) to give compound 032 hydrochloride. LCMS: (ESI) m/z=600.2 [M+H]$^+$; $^1$H NMR (400 MHZ, CD$_3$OD) δ=8.09-7.97 (m, 1H), 7.73-7.62 (m, 1H), 7.04-6.93 (m, 1H), 5.70-5.52 (m, 1H), 4.34-4.27 (m, 2H), 4.17-4.03 (m, 3H), 4.00-3.85 (m, 3H), 3.52-3.43 (m, 3H), 2.91-2.57 (m, 3H), 2.54-2.45 (m, 1H), 2.42-2.32 (m, 2H), 2.28-2.21 (m, 1H), 2.19-2.09 (m, 4H).

Example 33

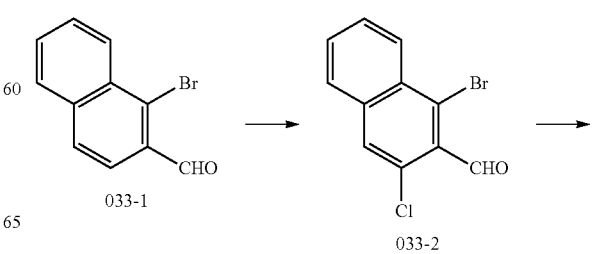

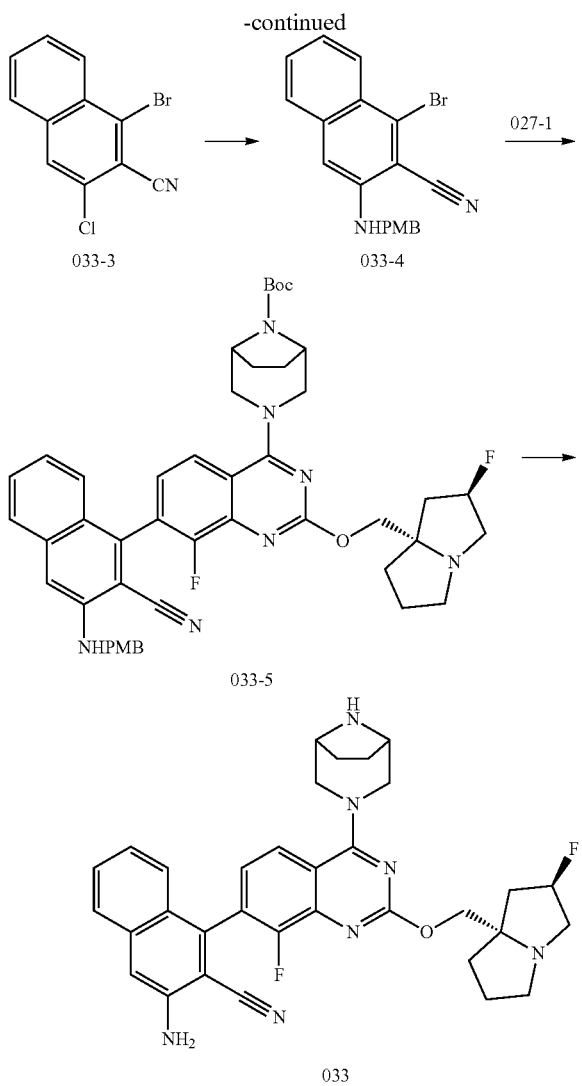

Step 1: Synthesis of Compound 033-2

Compound 033-1 (5 g, 21.27 mmol, 1 eq), N-chlorosuccinimide (4.26 g, 31.90 mmol, 1.5 eq), 4-nitro-2-(trifluoromethyl) phenol (1.32 g, 6.38 mmol, 0.3 eq) and 4-trifluoromethylaniline (342.71 mg, 2.13 mmol. 263.62 μL, 0.1 eq) were dissolved in dichloroethane (20 mL). Trifluoroacetic acid (24.25 g, 212.70 mmol, 15.75 mL, 10 eq) and palladium acetate (77.53 mg, 2.13 mmol, 0.1 eq) were added under nitrogen. The mixture was reacted at 80° C. for 16 h. After the reaction was completed, the reaction solution was cooled down to room temperature. 20 mL of water was added to the reaction solution and the mixture was extracted twice with 20 mL of dichloromethane. The organic phases were combined, dried over anhydrous sodium sulfate and concentrated to give a crude product, which was purified using a column (petroleum ether:ethyl acetate=10:1) to give compound 033-2. LCMS: (ESI) m/z=268.9 [M+H]⁺.

Step 2: Synthesis of Compound 033-3

Compound 033-2 (3 g, 11.13 mmol, 1 eq) was added to dimethyl sulfoxide (10 mL). Then hydroxylamine hydrochloride (1.55 g, 22.26 mmol, 2 eq) was added. The mixture was reacted at 95° C. for 6 h. After the reaction was completed, 30 mL of water was added to the reaction solution. The mixture was extracted 3 times using 30 mL of methyl tert-butyl ether. The organic phases were combined, washed with 20 mL of saturated brine, dried over anhydrous sodium sulfate and concentrated to give compound 033-3. ¹H NMR (400 MHZ, CD₃OD) δ=8.31-8.26 (m, 1H), 7.97-7.91 (m, 1H), 7.83-7.81 (m, 1H), 7.78-7.50 (m, 2H).

Step 3: Synthesis of Compound 033-4 p-Methoxybenzylamine (617.64 mg, 4.50 mmol, 582.68 μL, 1.2 eq) and compound 033-3 (1 g, 3.75 mmol, 1 eq) were added to N,N-dimethylformamide (5 mL). Then potassium carbonate (1.04 g, 7.50 mmol, 2 eq) was added. The mixture was reacted at 80° C. for 16 h. After the reaction was completed, 30 mL of water was added to the reaction solution. The mixture was extracted twice using 20 mL of methyl tert-butyl ether. The organic phases were combined, washed with 30 mL of saturated brine, dried over anhydrous sodium sulfate and concentrated. The crude product was purified by silica gel column chromatography (petroleum ether: ethyl acetate=1:0-1:1) to give compound 033-4. ¹H NMR (400 MHZ, CD₃OD) δ=7.78-7.73 (m, 1H), 7.61 (d, J=8.4 Hz, 1H), 7.58-7.50 (m, 1H), 7.40 (d, J=7.2 Hz, 1H), 7.30-7.24 (m, 3H), 6.85-6.78 (m, 1H).

Step 4: Synthesis of Compound 033-5

Compound 033-4 (70.90 mg, 193.06 μmol, 1.2 eq) and sodium bicarbonate (27.03 mg, 321.77 μmol, 12.51 μL, 2 eq) were added to 1,4-dioxane (5 mL) and water (3 mL). The atmosphere was replaced with nitrogen three times. [1,1-Bis(diphenylphosphino) ferrocene]palladium dichloride (11.77 mg, 16.09 μmol, 0.1 eq) was added under nitrogen. The mixture was heated to 100° C., and compound 027-1 (0.09 g, 160.88 μmol, 1 eq) was added. The atmosphere was replaced with nitrogen three times, and the mixture was reacted under nitrogen at 100° C. for 1 h. After the reaction was completed, the reaction solution was poured into 30 mL of water, and the mixture was extracted three times with 20 mL of ethyl acetate. The organic phases were combined, washed with 20 ml of saturated brine, then dried over anhydrous sodium sulfate and concentrated. The crude product was purified by preparative high performance liquid chromatography (column: Phenomenex luna C18 80*40 mm*3 μm; mobile phase A: water (0.05% hydrochloric acid), mobile phase B: acetonitrile; running gradient: acetonitrile %: 34%-54%, running time: 7 min) to give compound 033-5. LCMS: (ESI) m/z=802.2 [M+H]⁺.

Step 5: Synthesis of Compound 033

Compound 033-5 (0.002 g, 2.49 μmol, 1 eq) was added to anhydrous dichloromethane (0.25 mL) and trifluoroacetic acid (0.05 mL). The mixture was reacted at 25° C. for 5 h. After the reaction was completed, the mixture was rotary-evaporated to dryness to remove the solvent and the crude product was purified by preparative high performance liquid chromatography (column: Phenomenex luna C18 80*40 mm*3 μm; mobile phase A: water (0.04% hydrochloric acid), mobile phase B: acetonitrile; running gradient: acetonitrile %: 10%-30%, running time: 8 min) to give compound 033 hydrochloride. LCMS: (ESI) m/z=582.3 [M+H]⁺.

Assay Example 1: Assay of SOS1-Mediated Binding Ability of $KRAS^{G12D}$ to Effector Protein c-Raf 1. Purpose Compounds that can effectively inhibit the binding of $KRAS^{G12D}$ to the downstream effector protein c-Raf of the MAPK pathway were screened out by a TR-FRET method.

2. Assay Steps 2.1 Preparation of 1× Enzymatic Reaction Buffer:

TABLE 1

Reaction Buffer

| 1× Buffer | Stock Concentration | Dilution Folds | Assay Concentration. |
|---|---|---|---|
| Hepes pH 7.4 | 1M | 40 | 25 mM |
| $NaCl_2$ | 5M | 40 | 125 mM |
| $MgCl_2$ | 1M | 200 | 5 mM |
| Tween20 | 1% | 100 | 0.01% |
| BSA | 7.50% | 75 | 0.10% |
| DTT | 1M | 1000 | 1 mM |
| $H_2O$ | | / | |
| Total | | / | |

2.2 Preparation of KRAS G12D Enzyme (2×):

TABLE 2

KRAS G12D Enzyme
$KRAS^{G12D}$ Solution

| Reagents | Stock Concentration | 2 Assay Concentration | Assay Concentration |
|---|---|---|---|
| KRAS G12D | 41.667 μM | 200 nM | 100 nM |
| 1× Assay buffer | / | / | / |

2.3 Preparation of Substrate and Antibody Mixture (2×):

TABLE 3

Substrate and Antibody Mixture
2× c-Raf/SOS1/GTP/MAb Anti 6HIS-d2/MAb Anti GST-Eu

| Reagents | Stock Concentration | 2× Assay Concentration | Assay Concentration |
|---|---|---|---|
| SOS1 | 14 μM | 50 nM | 25 nM |
| c-Raf | 13 μM | 50 nM | 25 nM |
| GTP | 50 mM | 100 μM | 50 μM |
| MAb Anti 6HIS-d2 | 200× | / | / |
| MAb Anti-GST-Eu cryptate | 200× | / | / |
| 1× Detection buffer | | / | |

3. Compound Screening:
1) The compounds were serially diluted 5-fold with DMSO in a dilution plate to a final starting concentration of 10 μM.
2) The compounds were transferred with Echo to a 384 reaction plate with 100 μL per well.
3) 5 μL of KRAS G12D enzyme was added to each well of the reaction plate.
4) The plates were sealed with a sealing film and centrifuged at 1000 g for 30 seconds, and then incubated at room temperature for 15 minutes.
5) 2× cRaf/SOS1/GTP/MAb Anti 6HIS-d2/MAb Anti GST-Eu mixture was prepared with 1× enzyme reaction buffer, and 5 μL of the mixture was added to the reaction plate.
6) The mixture was centrifuged at 1000 g for 30 seconds and reacted at room temperature for 2 hours.
7) The fluorescence signals at 615 nm (Cryptate) and 665 nm (XL665) were read with a BMG microplate reader.
8) Data analysis was performed using Graphpad 7.0 software to give $IC_{50}$.

4. Assay Results

The results are shown in Table 4:

TABLE 4

$IC_{50}$ Values of Compounds for $KRAS^{G12D}$ Activity

| Compound Nos. | $IC_{50}$ (nM) |
|---|---|
| Compound 001B | 18.9 |
| Compound 002 | 22.49 |
| Compound 002A | 23.7 |
| Compound 003 | 20.4 |
| Compound 005 | 12.3 |
| Compound 006 | 37.4 |
| Compound 013B | 15.9 |
| Compound 017B | 18.2 |
| Compound 018B | 6.23 |

Assay conclusion: The compounds of the present disclosure can significantly inhibit $KRAS^{G12D}$ activity.

Assay Example 2. Anti-Cell Proliferation Effects of Compounds in Tumor Cell Line AsPC-1

1. Research Purpose

In this assay, the inhibitory effects of compounds on cell proliferation were studied by detecting the effects of compounds on the in vitro cell activity in the tumor cell line AsPC-1.

2. Assay Materials

TABLE 5

Cell Line

| Cell Line | Tumor Type | Growth Characteristic | Culture Method |
|---|---|---|---|
| AsPC-1 | pancreatic cancer | adherent growth | RPMI 1640 + 10% FBS |

Ultra Low Cluster-96 well plate (Corning-7007)
Greiner CELLSTAR 96-well plate (#655090)
Promega CellTiter-Glo 3D Luminescence Cell Viability Detection Kit (Promega-G9683)
2104-10 En Vision Plate Reader, PerkinElmer
RPMI 1640, DMEM, PBS (phosphate buffered solution), FBS (fetal bovine serum), Antibiotic-antimycotic, L-glutamine, DMSO (dimethyl sulfoxide)

3. Assay Methods and Steps

Cell Culture

The tumor cell line was cultured in a 37° C., 5% $CO_2$ incubator according to the culture conditions indicated in the culture method. The cells were periodically passaged, and cells in logarithmic growth phase were taken for plating.

Cell Plating

Cells were stained with trypan blue and viable cells were counted.

The cell concentration was adjusted to an appropriate concentration.

TABLE 6

Cell Line

| Cell Line | Density (per well) |
|---|---|
| AsPC-1 | 7000 cells |

135 μL of cell suspension was added to each well of the ULA culture plate, and the same volume of culture medium without cells was added to the blank control well.

Immediately after plating, the ULA plate was centrifuged at 1000 rpm for 10 minutes at room temperature. Note: After centrifugation, be careful not to cause unnecessary shocks in subsequent operations.

The plate was incubated overnight in an incubator at 37° C., 5% $CO_2$, and 100% relative humidity.

Preparation of 10× Compound Working Solution and Treatment of Cells with Compounds (Day 1)

After preparing the 10× compound working solution (10× working solution in DMSO), 15 μL of the 10× compound working solution was added to the ULA culture plate, and 15 μL of DMSO-cell culture solution mixture was added to the vehicle control and blank control, respectively.

The 96-well cell plate was placed back into the incubator and cultured for 120 hours.

Cell spheroidization was observed every day until the end of the assay.

CellTiter-Glo Luminescence Assay for Cell Viability Detection (Day 5)

The following steps were performed according to the instructions of the Promega CellTiter-Glo 3D Luminescence Cell Viability Dectection Kit (Promega #G9683).

150 μL (equivalent to the volume of cell medium in each well) of CellTiter-Glo 3D reagent was added to each well. The cell plate was wrapped in aluminum foil to be protected from light.

The culture plate was shaken on an orbital shaker for 5 minutes.

The mixture in wells was mixed well by carefully pipetting up and down 10 times. Ensure that the cell spheres were sufficiently detached before proceeding to the next step.

The solution in the ULA culture plate was then transferred to a black bottom culture plate (#655090) and left at room temperature for 25 minutes to stabilize the luminescence signal.

Luminescence signals were detected with a 2104 EnVision plate reader.

4. Data Analysis

The inhibition rate (IR) of the assayed compound was calculated by the following formula: IR (%)=(1−(RLU of compound−RLU of blank control)/(RLU of vehicle control−RLU of blank control))*100%. The inhibition rates of different concentrations of compounds were calculated in Excel, and then the GraphPad Prism software was used to plot the inhibition curves and calculate the relevant parameters, including the minimum inhibition rate, the maximum inhibition rate, and IC50.

4. Assay Results
The results are shown in Table 7:

TABLE 7

Anti-proliferation Activity of Compounds against $KRAS^{G12D}$ Mutated AsPC-1 Cells

| Compound Nos. | $IC_{50}$ (nM) |
|---|---|
| Compound 002A | 17.7 |
| Compound 013B | 14.2 |
| Compound 016B | 14.2 |
| Compound 017B | 6.5 |

Assay conclusion: The compounds of the present disclosure have a significant anti-proliferation activity against $KRAS^{G12D}$ Mutated AsPC-1 Cells.

Assay Example 3. Inhibitory Effect of Compounds on Phospho-ERK in GP2D Cells

1. Research Purpose
In this assay, the inhibitory effect of the assayed compounds on the phosphorylation of ERK protein downstream of the KRAS (121) signaling pathway in human colon cancer GP2D cells was analyzed.

2. Reagents, Consumables and Instruments

TABLE 8

Assay Materials

| Reagents, Consumables | Manufacturers | Item Nos. | Batch Nos. |
|---|---|---|---|
| GP2D | Cobioer | CBP60010 | / |
| DMEM medium | Gibco | 11995-065 | AH29755233 |
| FBS | AusGenex | FBS500-S | FBA01221-1 |
| 0.25% Trypsin-EDTA (1X) | Gibco | 25200-072 | 2360195 |
| Penicillin-streptomycin | Gibco | 15140-122 | 2321148 |
| IRDye 800CW Goat anti-Rabbit IgG (H + L) (0.5 mg) | LI-COR | 926-32211 | D11103-05 |
| IRDye 680RD Goat anti Mouse IgG (H + L) (0.5 mg) | LI-COR | 926-68070 | D10901-15 |
| phospho-p44/42 MAPK(T202/Y204) Rabbit mAb | CST | 4370S | 28 |
| GAPDH (D4C6R) Mouse mAb | CST | 97166S | 6 |
| T75 Flask | Corning | 430641 | / |
| 384-well Flat Bottom | Corning | 354663 | / |
| 384-well Clear, Flat Bottom | Labcyte | PP-0200 | / |
| DMSO | Sigma | BCCG0991 | 814O032 |
| PBS | Solarbio | P1020 | 20220609 |
| 8% fixative solution | Solarbio | P1112 | 20211231 |
| 10 × PBST | Solarbio | P1033 | 20220501 |
| Blocking buffer | LI-COR | 927-70001 | 220301 |
| Methanol | psaitong | 67-56-1 | / |
| Sealing Film For 96 Well Plates | BioTSS | SF-800 | / |

TABLE 9

Assay Instruments

| Instruments | Manufacturers | Model Nos. |
|---|---|---|
| $CO_2$ Incubator | ESCO | CLM-240B-8-CN |
| Echo 655 Liquid Handler | Labcyte | Echo 655 |
| Odyssey CLx | LI-COR | Odyssey CLx |
| Centrifuge | Eppendorf | 5810R |

TABLE 9-continued

Assay Instruments

| Instruments | Manufacturers | Model Nos. |
|---|---|---|
| Multi-channel pipettes Apricot Tips (125 μL) | Eppendorf/Sartorius Apricot Designs | / 050-384-EZ-NS |
| S2-PIPETTE | Apricot Designs | SP2-384-0125-03 |

3. Assay Process
1. Cell Culture
  1) GP2D cells were cultured in a cell culture 75 flask at 37° C., 5% $CO_2$, and the medium was DMEM medium (added with 10% FBS and 1% P/S).
  2) After cultivation for 2 days, the medium was removed and the sterile PBS buffer was used to wash once.
  3) 3 mL of trypsin was added and the cells were digested in a 37° C. incubator for 2 to 3 minutes until cells fell off.
  4) 9 mL of fresh culture medium was added to neutralize the digestion; the cells were aspirated into a centrifuge tube and centrifuged at 1000 rpm at room temperature for 5 minutes.
  5) The supernatant was removed, and 3 mL of fresh culture medium was added to resuspend the cells; the cells were counted by a cell counter.
2. Compound Screening
  1) 7000 cells per well were plated in a 384-cell culture plate with 40 μL of culture medium, and cultured overnight in a 37° C. and 5% $CO_2$ incubator.
  2) The Echo655 instrument was used to add 40 nL of serially diluted compounds (the initial concentration of the compound was 1000 nM, and the compound was serially diluted 3-fold. The final concentration of DMSO was 0.1%), and the plate was incubated in a 37° C. and 5% $CO_2$ incubator for 1 hour. EGF stimulating factor (the final concentration was 0.1 ng/mL) was added and incubated in a 37° C. and 5% $CO_2$ incubator for 15 minutes.
  3) 40 μL of 8% paraformaldehyde fixative was added and incubated at room temperature for 20 minutes.
  4) PBS buffer was added to wash twice, 40 μL of pre-cooled methanol was added, and the mixture was incubated at room temperature for 20 minutes.
  5) PBS buffer was added to wash twice, 20 μL of blocking solution was added, and the plate was blocked at room temperature for 1 hour.
  6) The blocking solution was removed, the primary antibody mixture (phospho-p44/42 MAPK (T202/Y204) Rabbit mAb diluted 1000 times, GAPDH ($D4C_6R$) Mouse mAb diluted 2000 times) was added, and the mixture was incubated overnight in a 4° C. refrigerator.
  7) PBST (0.05% Tween 20) buffer was added to wash for three times, the secondary antibody mixture (IRDye 680RD Goat anti Mouse IgG (H+L) diluted 2000 times, IRDye 800CW Goat anti-Rabbit IgG (H+L) diluted 2000 times) was added, and the mixture was incubated at room temperature in the dark for 1 hour.
  8) PBST (0.05% Tween 20) buffer was added to wash for three times; the plate was centrifuged upside down at 1000 rpm for 1 minute, and dried in the dark; the Odyssey CLx instrument was used to scan the plate.
4. Data Analysis
1) Data Analysis:

Relative Signal=Signal Value(total channel 800)/Signal Value(total channel 700)

H=Ave (dimethyl sulfoxide), L=Ave (compound), SD (H)=STDEV (dimethyl sulfoxide); SD (L)=STDEV (compound)

CV % (H)=100*(SD_H/Ave_H),CV % (L)=100*SD_L/Ave_L

Z'=1-3*(SD_H+SD_L)/(Ave_H-Ave_L)

Inhibition=(Ave_H-Sample)/(Ave_H-Ave_L)*100

2) Fit the cpd IC50 from non-linear regression equation:

Y=Bottom+(Top-Bottom)/(1+10^((Log IC50-X)*HillSlope))

X: Log of cpd concentration, Y: Inhibition
Top and Bottom: Plateaus in same units as Y; logIC50: same log units as X; HillSlope: Slope factor or Hill slope 5. Assay Results
The results are shown in Table 10:

TABLE 10

Inhibitory effects of compounds on intracellular phospho-ERK

| Compound Nos. | $IC_{50}$ (nM) |
|---|---|
| Compound 002A | 0.15 |
| Compound 013B | 0.12 |
| Compound 017B | 0.069 |

Assay conclusion: The compounds of the present disclosure have a significant inhibitory effect on phospho-ERK in GP2D cells.

Assay Example 4. Assay of the Activity of Inhibiting $KRAS^{G12D}$

1. Purpose
Compounds that can effectively inhibit the binding of KRAS to GTP were screened out by a TR-FRET method.

2. Consumables and Instruments

TABLE 11

Consumables and Instruments

| Name | Suppliers | Item Nos. |
|---|---|---|
| HEPES (4-(2-hydroxyethyl)-1-piperazine ethanesulfonic acid) pH 7.3 | Thermo Fisher Scientific | BP299-500 |
| sodium chloride | Promega | V4221 |
| EDTA (ethylenediaminetetraacetic acid) | EMD Millipore | 324506 |
| Tween 20 | Bio-Rad | 1706531 |
| magnesium chloride | MP Biomedicals | 191421 |
| Bodipy GDP (guanosine 5'-diphosphate, BODIPY ™ FL 2'-(or -3')-O—(N-(2-aminoethyl)urethane), bis(triethylammonium) salt) | Invitrogen | G22360 |
| GTP (guanine-5'-triphosphate) | Sigma | G8877 |
| Tb-SA (terbium labeled streptavidin) | Invitrogen | PV3576 |
| SOS (son of sevenless) protein | | |
| $KRAS^{G12D}$ (Kirsten rat sarcoma viral oncogene) protein | | |
| compound plate | Labcyte | LP-0200 |
| assay plate | Perkin Elmer | 6008269 |
| 15 mL centrifuge tube | Corning | 430791 |
| 1.5 mL centrifuge tube | Axygen | MCT-150-C |
| Dragonfly autosampler | TTP | |
| Bravo | Agilent | |
| Echo 550 | Labcyte | |
| Envision | Perkin Elmer | |

3. Preparation of Reagent a. Stock Reagents:

1) KRAS Nucleotide Exchange Buffer 20 mL of 1000 mM HEPES, 20 mL of 500 mM EDTA, 10 mL of 5 M sodium chloride, 0.1 mL of 100% Tween 20, and 949.9 mL of water were weighed and formulated to 1 L of solution. The solution was sterilized by filtration and stored at 4° C.

2) KRAS Assay Buffer 20 mL of 1000 mM HEPES, 10 mL of 1000 mM magnesium chloride, 30 mL of 5 M sodium chloride, 0.05 mL of 100% Tween 20, and 939.95 mL of water were weighed and formulated to 1 L of solution. The solution was sterilized by filtration and stored at 4° C.

3) KRAS/Bodipy GDP/Tb-SA Mixture 9.5 μL of 95 μM KRAS$^{G12D}$ protein and 440.5 μL of KRAS nucleotide exchange buffer were weighed and mixed. The mixture was incubated at room temperature for 1 hour and formulated to 1 L of solution together with 8.4 μL of 17.9 μM Tb-SA, 1.8 μL of 5 mM Bodipy GDP and 9539.8 μL of KRAS assay buffer. After mixing, the solution was left to stand at room temperature for 6 hours, and stored at −80° C.

b. Assay Reagents:

1) KRAS Enzyme Solution 73.3 μL of KRAS/Bodipy GDP/Tb-SA mixture and 2126.7 μL of KRAS assay buffer were weighed and formulated to 2200 μL of solution.

2) SOS/GTP Mixture 1.59 μL of 166 μM SOS protein, 198 μL of 100 mM GTP and 2000.41 μL of KRAS assay buffer were weighed and formulated to 2200 μL of solution.

4. Assay Process

1) The concentration of a stock solution of the control compound was 1 mM, and the concentration of a stock solution of compounds to be assayed was 10 mM. 9 μL of the control compound and compounds to be assayed were transferred to a 384-LDV plate;

2) The compounds on the LDV plate were serially diluted 3-fold with Bravo to 10 concentrations;

3) 9 nL of the compounds on the LDV plate were transferred to an assay plate using ECHO;

4) 3 μL of 3 nM Kras/0.5 nM TB-SA/30 nM BodipyGDP mixture and 3 μL of Ras buffer were sequentially added to each well of the assay plate using a Dragonfly autosampler, and the assay plate was centrifuged at 1000 rpm/min for 1 minute;

5) The assay plate was incubated at room temperature for 1 hour;

6) 3 μL of 120 nM SOS/9 mM GTP mixture was added to each well of the assay plate using a Dragonfly autosampler, and the assay plate was centrifuged at 1000 rpm/min for 1 minute;

7) The assay plate was incubated at room temperature for 1 hour;

8) The plate was read with Envision and data were recorded;

9) The data were analyzed using Excel and Xlfit, and IC$_{50}$ of the compounds to be assayed were calculated.

5 Assay Results

The results are shown in Table 12.

TABLE 12

| IC$_{50}$ values of compounds on inhibiting KRAS$^{G12D}$ enzyme | |
|---|---|
| Compound Nos. | KRAS$^{G12D}$ IC$_{50}$ (nM) |
| Compound 022 formate | 6.6 |
| Compound 029 hydrochloride | 38.6 |

Assay conclusion: The compounds of the present disclosure have significant inhibitory effect on KRAS$^{G12D}$ enzyme.

Assay Example 5. Assay of p-ERK Inhibition in GP2D Cells

1. Purpose

Compounds that can effectively inhibit p-ERK in GP2D cells were screened out by a HTRF method.

2. Assay Process

1) GP2D cells were inoculated in a transparent 96-well cell culture plate, and each well contained 80 μL of cell suspension and 8000 cells. The cell plate was inoculated in a carbon dioxide incubator at 37° C. overnight;

2) 2 μL of the compound was weighed and added to 78 μL of the cell medium. After the mixture was mixed thoroughly, 20 μL of the solution of compound was weighed and added to the corresponding well of the cell plate. The cell plate was placed back to the carbon dioxide incubator and incubated for another 1 hour;

3) After completion of the incubation, the cell supernatant was discarded. 50 μL of 1× cell lysate was added to each well. The mixture was incubated with shaking at room temperature for 30 minutes;

4) Phospho-ERK 1/2 Eu Cryptate antibody and Phospho-ERK1/2 d2 antibody were diluted 20-fold with detection buffer;

5) 16 μL of cell lysate supernatant was weighed and added into each well of a new 384 white microwell plate, and then 2 μL of the diluted solution of Phospho-ERK1/2 Eu Cryptate antibody and 2 μL of the diluted solution of Phospho-ERK1/2 d2 antibody were added. The mixture was incubated at room temperature for at least 4 hours;

6) After completion of the incubation, HTRF was read with multi-label analyzer: excitation: 320 nm, emission: 615 nm, 665 nm;

7). IC$_{50}$ of the compounds to be assayed were calculated.

3. Assay Results

The results are shown in Table 13.

TABLE 13

| IC$_{50}$ values of compounds on inhibiting p-ERK in GP2D cells | |
|---|---|
| Compound Nos. | GP2D p-ERK IC$_{50}$ (nM) |
| Compound 018B | 0.67 |
| Compound 020 trifluoroacetate | 1.6 |
| Compound 021 hydrochloride | 21.4 |
| Compound 024 formate | 11.6 |
| Compound 026 formate | 4.4 |

Assay conclusion: The compounds of the present disclosure have significant inhibitory effect on p-ERK in GP2D cells.

Assay Example 6. Assay of Inhibition of GP2D Cell Proliferation

1. Purpose of Assay:
The aim of this assay was to verify the inhibitory effect of the compounds of the present disclosure on the proliferation of KRAS G12D mutated GP2D human pancreatic cancer cells.

2. Assay Materials:
Cell line GP2D, DMEM medium, and penicillin/streptomycin antibiotics were purchased from Wisent; fetal bovine serum was purchased from Biosera; and CellTiter-Glo® 3D Cell Viability Assay (3D cell viability chemiluminescence assay reagent) reagent was purchased from Promega.

3. Assay Method:
GP2D cells were seeded in a 96-well U-bottom cell culture plate. Each well contained 80 μL of cell suspension containing 2000 GP2D cells. The cell plate was incubated overnight in a $CO_2$ incubator. The compounds to be assayed were serially diluted 5-fold with a pipette to the 8th concentration, i.e. diluted from 200 μM to 2.56 nM. A double replicate well assay was set up. 78 μL of medium was added to the middle plate, and then 2 μL per well of the serial dilution compound was transferred to the middle plate according to the corresponding position. The mixture was mixed well and 20 μL per well was transferred to the cell plate. The concentration of compound transferred to the cell plate ranged from 1 μM to 0.0128 nM. The cell plate was incubated in a $CO_2$ incubator for 5 days. At the end of the incubation of the cell plate with compounds added, 100 μL of cell viability chemiluminescence assay reagent was added to each well of the cell plate. The cell plate was incubated at room temperature for 10 minutes to stabilize the luminescence signal. Data were read using a multi-label analyzer.

4. Data Analysis:
The raw data were converted into an inhibition rate by using an equation (Sample-Min)/(Max-Min)*100%. IC50 value can be obtained by curve fitting with four parameters ("log (inhibitor) vs. response—Variable slope" model in GraphPad Prism).

5. Assay Results
The results are shown in Table 14.

TABLE 14

$IC_{50}$ value of compound on the inhibition of GP2D cell proliferation

| Compound No. | GP2D $IC_{50}$ (nM) |
| --- | --- |
| Compound 026 formate | 16 |

Assay conclusion: The compound of the present disclosure has a significant inhibitory effect on GP2D cell proliferation.

Assay Example 7: Pharmacokinetic Study In Vivo

The intravenous injection vehicle and formulation of compound 002A: the compound to be assayed was mixed with a solution of 5% dimethyl sulfoxide/95% (10% aqueous solution of hydroxypropyl-β-cyclodextrin), and the mixture was adjusted to a clear solution of 0.40 mg/mL. The oral vehicle and formulation: the compound to be assayed was mixed with a solution of 5% dimethyl sulfoxide/95% (10% aqueous solution of hydroxypropyl-β-cyclodextrin); the mixture was stirred until visually uniform; and the mixture was adjusted to 3 mg/mL. The intravenous injection vehicle and formulation of Compound 013B and Compound 017B: the compound to be assayed was mixed with 5% dimethyl sulfoxide/10% polyethylene glycol-15 hydroxystearate/85% water; the mixture was adjusted to 0.4 mg/mL; and the mixture was stirred until clear. The oral vehicle and formulation: the compound to be assayed was mixed with a solution of 5% dimethyl sulfoxide/95% (10% aqueous solution of hydroxypropyl-β-cyclodextrin); the mixture was stirred until visually uniform; and the mixture was adjusted to 5 mg/mL. Male $C_{57}BL/6J$ mice aged 7 to 10 weeks were selected, and administered candidate compound solutions intravenously or orally. Whole blood was collected for a certain period of time. Plasma was prepared. Drug concentration was analyzed by LC-MS/MS method. Pharmacokinetic parameters were calculated using Certara WinNonlin software (Certara Company, USA). The assay results are shown in Table 15:

TABLE 15

Results of Pharmacokinetics of Assayed Compounds

| Route of Administration | Parameters of Pharmacokinetics | Compound 002A | Compound 013B | Compound 017B |
| --- | --- | --- | --- | --- |
| intravenous administration | dose (mg/kg) | 1.74 | 1.81 | 1.94 |
| | half-life $T_{1/2}$ (h) | 7.12 | 20.3 | 10.7 |
| | clearance rate CL (ml/min/kg) | 189 | 106 | 95.7 |
| | apparent volume of distribution $Vd_{ss}$ (L/kg) | 56.3 | 94.2 | 51.4 |
| | area under plasma concentration-time curve $AUC_{0-last}$ (nM · h) | 267 | 405 | 488 |
| oral administration | dose (mg/kg) | 28.2 | 51.0 | 47.0 |
| | peak time $T_{max}$ (h) | 1.13 | 0.25 | 0.25 |
| | peak concentration $C_{max}$ (nM) | 345 | 1955 | 1385 |
| | area under plasma concentration-time curve $AUC_{0-last}$ (nM · h) | 637 | 3146 | 2409 |
| | bioavailability F (%) | 16.1 | 31.0 | 19.1 |

Assay conclusion: The PK study shows that each compound has good plasma exposure and oral bioavailability in mice.

What is claimed is:

1. A compound, or a pharmaceutically acceptable salt thereof, wherein the compound is selected from the group consisting of:

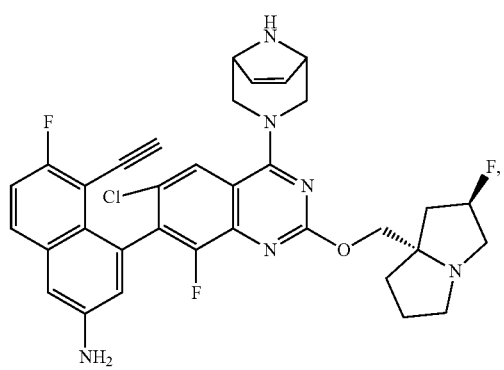

219
-continued

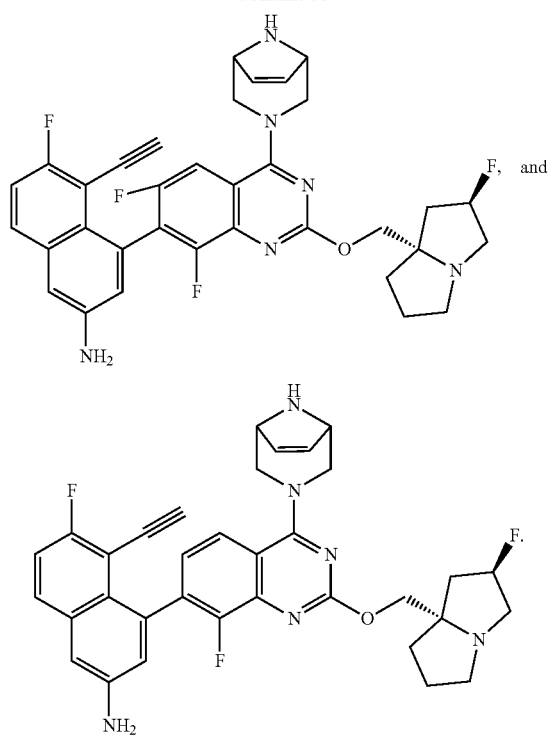

2. The compound or pharmaceutically acceptable salt of claim 1, wherein the compound is selected from the group consisting of:

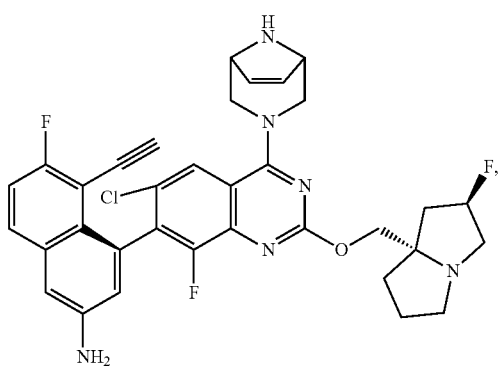

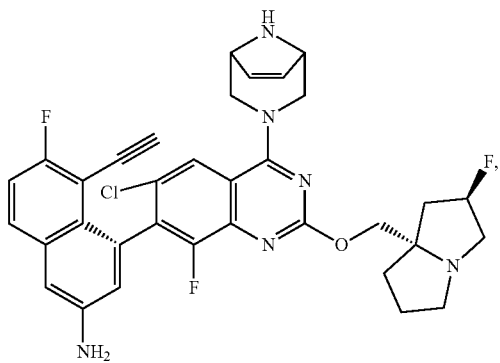

220
-continued

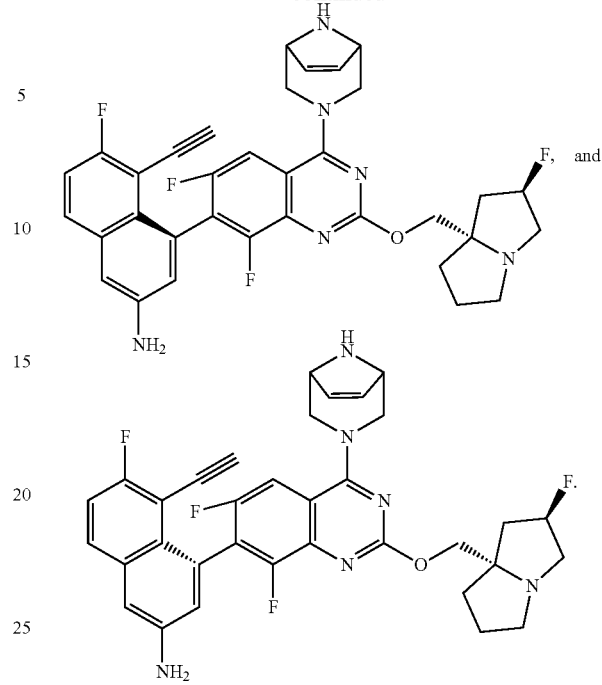

3. The compound or pharmaceutically acceptable salt of claim 1 that is or a pharmaceutically acceptable salt thereof.
4. The compound of claim 3.
5. The pharmaceutically acceptable salt of claim 3.
6. The compound or pharmaceutically acceptable salt of claim 1 that is or a pharmaceutically acceptable salt thereof.

7. The compound of claim 6.
8. The pharmaceutically acceptable salt of claim 6.
9. The compound or pharmaceutically acceptable salt of claim 1 that is

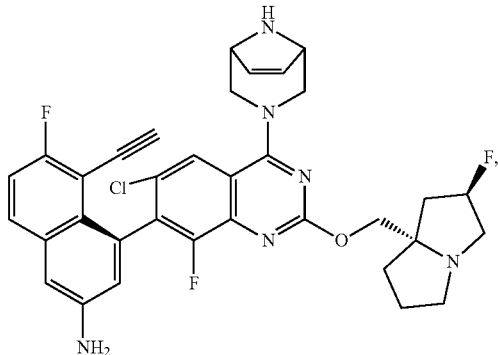

or a pharmaceutically acceptable salt thereof.
10. The compound of claim 9.
11. The pharmaceutically acceptable salt of claim 9.

12. The compound of pharmaceutically acceptable salt of claim 1 that is

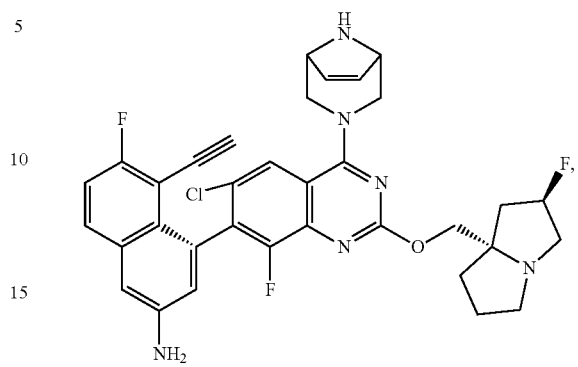

or a pharmaceutically acceptable salt thereof.
13. The compound of claim 12.
14. The pharmaceutically acceptable salt of claim 12.

* * * * *